(12) United States Patent
Chabrier De Lassauniere et al.

(10) Patent No.: US 7,291,641 B2
(45) Date of Patent: *Nov. 6, 2007

(54) DERIVATIVES OF HETEROCYCLES WITH 5 MEMBERS, THEIR PREPARATION AND THEIR USE AS MEDICAMENTS

(75) Inventors: Pierre-Etienne Chabrier De Lassauniere, Paris (FR); Jermiah Harnett, Gif-sur Yvette (FR); Dennis Bigg, Gif-sur-Yvette (FR); Ann-Marie Liberatore, Auffargis (FR); Jacques Pommier, Paris (FR); Jacques Lannoy, Bievres (FR); Christophe Thurieau, Paris (FR); Zheng Xin Dong, Holliston, MA (US)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 30 days.

This patent is subject to a terminal disclaimer.

(21) Appl. No.: 10/915,001

(22) Filed: Aug. 10, 2004

(65) Prior Publication Data

US 2005/0038087 A1    Feb. 17, 2005

Related U.S. Application Data

(63) Continuation-in-part of application No. 10/681,002, filed on Oct. 8, 2003, which is a continuation of application No. PCT/FR02/01218, filed on Apr. 9, 2002, which is a continuation-in-part of application No. 10/089,993, filed as application No. PCT/FR00/02805 on Oct. 10, 2000.

(30) Foreign Application Priority Data

Oct. 11, 1999  (FR) ................................... 99 12643
Aug. 1, 2000  (FR) ................................... 00 10151
Sep. 1, 2000  (FR) ................................... 00 11169
Apr. 10, 2001  (FR) ................................... 01 04943
Feb. 14, 2002  (FR) ................................... 02 01811

(51) Int. Cl.
*A61K 31/417* (2006.01)
*C07D 233/61* (2006.01)
(52) U.S. Cl. ................ 514/400; 548/335.5; 548/338.1
(58) Field of Classification Search ............ 548/335.5, 548/338.1; 514/400
See application file for complete search history.

(56) References Cited

U.S. PATENT DOCUMENTS

2004/0132788 A1 * 7/2004 Chabrier De Lassauniere et al. ........................ 514/365

FOREIGN PATENT DOCUMENTS

WO    WO 02/10140 A2 *  2/2002

* cited by examiner

*Primary Examiner*—Rebecca Anderson
(74) *Attorney, Agent, or Firm*—Charles A. Muserlian

(57) ABSTRACT

Thiaxozle, oxazole, imidazole, isoxazole and isoxazoline compounds of the formula

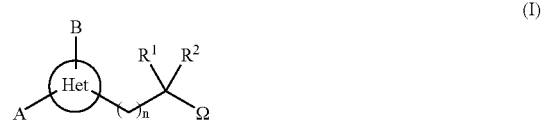

(I)

wherein Het is thiazole, oxazole, imidazole, isoxazole or isoxazoline, n is an integer from 0 to 6, A is selected from the various optionally substituted aromatic radicals defined in the specification, B is hydrogen, alkyl or phenyl, $R^1$ and $R^2$ are independently hydrogen, alkyl or cycloalkyl or $R^1$ and $R^2$ taken together with the carbon atom which carries them, form a carbocycle with 3 to 7 members and $\Omega$ is —$NH^{46}R^{47}$ or —$OR^{48}$, $R^{46}$ and $R^{47}$ are independently hydrogen, alkyl, cycloalkyl or —$(CH_2)_k COOR^{51}$, $R^{51}$ is alkyl or haloalkyl and $R^{48}$ is hydrogen or alkyl having advantageous pharmacological properties which allow their use in therapeutics, for treating neurodegenerative disorders or pain.

6 Claims, No Drawings

DERIVATIVES OF HETEROCYCLES WITH 5 MEMBERS, THEIR PREPARATION AND THEIR USE AS MEDICAMENTS

PRIOR APPLICATIONS

This application is a Continuation-in-Part of U.S. patent application Ser. No. 10/681,002 filed Oct. 8, 2003 which is a Continuation of PCT/FR02/01218 filed Apr. 9, 2002 which is a Continuation-in-Part of U.S. patent application Ser. No. 10/089,993 filed Apr. 4, 2002 which is a 371 of PCT/FR00/02805 filed Oct. 10, 2000.

The present invention relates to the use of compounds of general formula (I) for preparing a medicament intended to inhibit monoamine oxydases (MAO) and/or lipidic peroxidation and/or to act as modulators of the sodium channels. A subject of the invention is also, as medicaments, the compounds of general formula (II) defined hereafter. Moreover it relates to new compounds of general formula (III).

The compounds mentioned above often present 2 or 3 of the activities mentioned above, which confer advantageous pharmacological properties on them.

In fact, taking into account the potentiel role of the MAO's and ROS's ("reactive oxygen species", at the origin of lipidic peroxidation) in physiopathology, the new described derivatives corresponding to general formula (I) can produce beneficial or favorable effects in the treatment of pathologies where these enzymes and/or these radicular species are involved. In particular:

disorders of the central or peripheral nervous system such as for example neurological diseases where Parkinson's disease, cerebral or spinal cord traumatisms, cerebral infarction, sub arachnoid hemorrhage, epilepsy, ageing, senile dementia, Alzheimer's disease, Huntington's chorea, amyotrophic lateral sclerosis, peripheral neuropathies, pain can in particular be mentioned;

schizophrenia, depressions, psychoses;
disorders of the memory and the humour;
pathologies such as for example migraine;
behavioural disorders, bulimia and anorexia;
auto-immune and viral diseases such as for example lupus, AIDS, parasitic and viral infections, diabetes and its complications, multiple sclerosis.
addiction to toxic substances;
proliferative and inflammatory pathologies;
and more generally all the pathologies characterised by an excessive production of ROS's and/or participation of MAO's.

In all of these pathologies, experimental evidence exists which demonstrates the involvement of ROS's (*Free Radic. Biol. Med.* (1996) 20, 675-705; *Antioxid. Health. Dis.* (1997) 4 (Handbook of Synthetic Antioxidants), 1-52) as well as the involvement of MAO's (Goodman & Gilman's: *The pharmacological basis of therapeutics*, 9th ed., 1995, 431-519).

The advantage of a combination of the inhibitory activities of MAO and inhibition of lipidic peroxidation is for example well illustrated in Parkinson's disease. This pathology is characterized by a loss of dopaminergic neurons of the nigrostriatal route the cause of which would in part be linked to an oxidizing stress due to ROS's. The exogenic dopamine from L Dopa is used in therapeutics in order to maintain sufficient levels of dopamine. MAO inhibitors are also used with L Dopa to avoid its metabolic degradation but do not act on the ROS's. Compounds which act both on MAO's and ROS's will therefore have a certain advantage.

Moreover, the character of the modulator of the sodium channels is very useful for therapeutic indications such as:
the treatment or prevention of pain, and in particular:
post-operative pain,
migraine,
neuropathic pain such as trigeminal neuralgia, post-herpetic pain, diabetic neuropathies, glossopharyngeal neuralgias, secondary radiculopathies and neuropathies associated with metastatic infiltrations, adiposis dolorosa and pain associated with burns,
central pain as a result of vascular cerebral accidents, thalamic lesions and multiple sclerosis, and
chronic inflammatory pain or pain linked to a cancer;
the treatment of epilepsy;
the treatment of disorders linked to neurodegeneration, and in particular:
vascular cerebral accidents,
cerebral traumatism, and
neurodegenerative diseases such as Alzheimer's disease, Parkinson's disease and amyotrophic lateral sclerosis;
the treatment of bipolar disorders and irritable colon syndrome.

The concrete advantages of the presence in a compound of at least one of these activities is therefore clearly apparent from the above.

The European Patent Application EP 432 740 describes derivatives of hydroxyphenylthiazoles, which can be used in the treatment of inflammatory diseases, in particular rheumatic diseases. These derivatives of hydroxyphenylthiazoles show properties of trapping free radicals and inhibitors of the metabolism of arachidonic acid (they inhibit lipoxygenase and cyclooxygenase).

Other derivatives of hydroxyphenylthiazoles or hydroxyphenyloxazoles are described in the PCT Patent Application WO 99/09829. These have analgesic properties.

A certain number of derivatives of imidazoles with close or identical structures to those of the compounds corresponding to general formula (I) according to the invention have moreover been described by the Applicant in the PCT Patent Application WO 99/64401 as agonists or antagonists of somatostatin. However, said derivatives of imidazoles have therapeutic properties in fields different from those indicated above (suppression of the growth hormone and the treatment of acromegalia, treatment of the recurrence of stenosis, inhibition of the secretion of gastric acid and prevention of gastro-intestinal bleeding in particular).

Moreover, the compounds of general formula (A1)

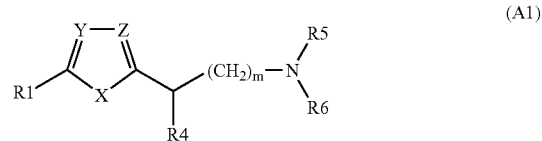

(A1)

in which

R1 represents one of the aryl, heteroaryl, aralkyl or cycloalkyl radicals optionally substituted by one to three substituents chosen independently from a halogen atom, the $CF_3$, CN, OH, alkyl or alkoxy radical, $SO_2R9$ with R9 representing $NH_2$ or $NHCH_3$;

X represents NR2, R2 representing H or alkyl;

Y represents N or CR3;

Z represents CR3 or N;

on the condition however that Y and Z are not both CR3 or N at the same time;

R3 represents H, alkyl, halogen, hydroxyalkyl or phenyl optionally substituted by 1 to 3 substituents chosen from H, $CF_3$, CN, $SO_2NH_2$, OH, alkyl or alkoxy;

m represents 0, 1 or 2;

R4 represents H or alkyl;

when Z represents CR3, then R3 and R4 can also represent together —$(CH_2)_{n1}$— with n1 an integer from 2 to 4 or R2 and R4 can also represent together —$(CH_2)_{n2}$— with n2 an integer from 2 to 4;

R5 and R6 represent independently H, alkyl, alkoxy, aryl or aralkyl;

NR5R6 can also represent together (in particular):
the optionally substituted 2-(1,2,3,4-tetrahydroquinolyl) radical,
a

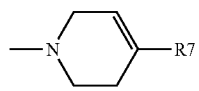

radical in which R7 represents one of the phenyl, benzyl or phenethyl radicals in which the phenyl ring can be substituted;
a

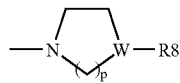

radical in which p is an integer from 1 to 3,

W is N and R8 represents H, $CF_3$, one of the phenyl, pyridyl or pyrimidinyl radicals optionally substituted once to twice by radicals chosen from halogen, OH, alkyl or alkoxy, or W is CH and R8 represents phenyl optionally substituted or aralkyl optionally substituted on the aryl group;

have been described in the PCT Patent Application WO 96/16040 as partial agonists or antagonists of the dopamine sub-receptors of the brain or as prodrug forms of such partial agonists or antagonists. Therefore these compounds would have useful properties in the diagnosis and treatment of affective disorders such as schizophrenia and depression as well as certain disorders of movement such as Parkinson's disease.

It has also been described in the PCT Patent Application WO 98/27108 that certain amides of general formula (A2)

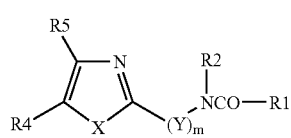

in which:

R1 represents in particular an alkyl, optionally substituted phenyl or optionally substituted heterocyclic aryl radical;

R2 represents H or phenylalkyl;

R4 represents H, quinolyl, 3-4-methylenedioxyphenyl or one of the phenyl or pyridyl radicals optionally substituted, by a radical or radicals chosen in particular from alkyl, alkoxy, alkylthio, optionally protected hydroxy, amino, alkylamino, dialkylamino;

R5 represents H or an imidazolyl, phenyl, nitrophenyl, phenylalkyl radical, or also a —CO—N(R7)(R8) radical, in which R7 and R8 represent independently H, phenyl, phenylalkyl, alkyl or alkoxy;

or R4 and R5 in combination form a group of formula —CH=CH—CH=CH—;

Y is a phenylene radical substituted by a phenyl, phenoxy or phenylalkoxy radical, or a group of formula —CH(R3)—, in which R3 represents H or a radical of formula —$(CH_2)_n$—R6, in which R6 represents an optionally protected hydroxy, acyl, carboxy, acylamino, alkoxy, phenylalkoxy, alkylthio, optionally substituted phenyl, optionally substituted pyridyl, pyrazinyl, pyrimidinyl, furyl, imidazolyl, naphthyl, N-alkylindolyl or 3,4-methylenedioxyphenyl radical and n is an integer from 0 to 3;

R2 and R3 taken together with the carbon atoms which carry them can form a phenyl group;

X represents S or NR9;

R9 representing H, an alkyl or cycloalkyl radical, or also a benzyl radical optionally substituted once on its phenyl part by H, alkyl or alkoxy;

are inhibitors of the NO synthases and can be used to treat diseases which include in particular cardiovascular or cerebral ischemia, cerebral hemorrhage, disorders of the central nervous system, Alzheimer's disease, multiple sclerosis, diabetes, hepatitis, migraine, rheumatoid arthritis and osteoporosis.

In a different field, the Applicant has itself previously described in the PCT Patent Application WO 98/58934 derivatives of amidines having the ability to inhibit NO synthases and/or lipidic peroxidation.

The Applicant has now unexpectedly discovered that certain intermediates of the first stages of synthesis of the amidines described in the PCT Patent Application WO 98/58934, and more generally certain derivatives of heterocycles with five members, namely the products of general formula (I) defined hereafter, have at least one of the three properties chosen from the following properties (and often even two of these three properties even sometimes all three at the same time):

MAO inhibition properties;

lipidic peroxidation inhibition properties; and properties of modulating the sodium channels.

These advantageous properties offer the advantage of opening up numerous uses for such compounds, in particular in the treatment of neurodegenerative diseases, and in particular those indicated previously, of pain or of epilepsy.

According to the invention, the compounds corresponding to general formula $(I)_G$

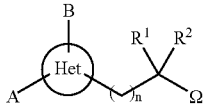 $(I)_G$ in racemic, enantiomeric form or any combination of these forms, in which Het is a heterocycle with 5 members comprising 2 heteroatoms and such that general formula $(I)_G$ corresponds exclusively to one of the following sub-formulae:

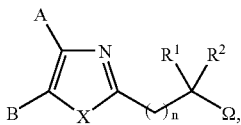 $(I)_{G1}$

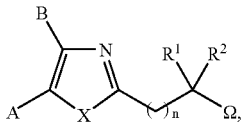 $(I)_{G2}$

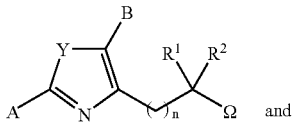 $(I)_{G3}$ and

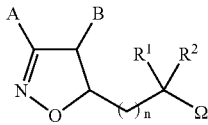 $(I)_{G4}$ in which

A represents either a

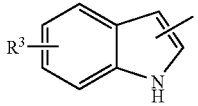

radical in which $R^3$ represents a hydrogen atom, the OH group or an alkoxy or alkyl radical, or a

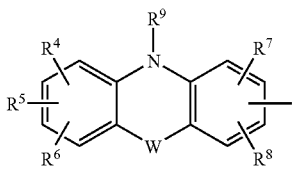

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^9$ represents a hydrogen atom, an alkyl radical or a —$COR^{15}$ group, $R^{15}$ representing a hydrogen atom or an alkyl, alkoxy or $NR^{16}R^{17}$ radical, $R^{16}$ and $R^{17}$ representing, independently, a hydrogen atom or an alkyl radical, or $R^{16}$ and $R^{17}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and W doesn't exist, or represents a bond, or —O—, —S— or —$NR^{18}$—, in which $R^{18}$ represents a hydrogen atom or an alkyl radical;

either a

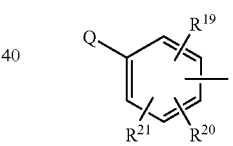

radical in which Q represents H, —$OR^{22}$, —$SR^{22}$, —$NR^{23}R^{24}$, a phenyl radical optionally substituted by one or more substituents chosen independently from a halogen atom, an OH, cyano, nitro, alkyl, haloalkyl, alkoxy, alkylthio or —$NR^{10}R^{11}$ radical and a group with two substituents representing together a methylenedioxy or ethylenedioxy radical, or also Q represents a —$COPh$, —$SO_2Ph$ or —$CH_2Ph$ radical, said —$COPh$, —$SO_2Ph$ or —$CH_2Ph$ radical being optionally substituted on its aromatic part by one or more of the substituents chosen independently from an alkyl or alkoxy radical and a halogen atom, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom, an alkyl or alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{22}$ representing a hydrogen atom, an alkyl radical or an aryl radical optionally substituted by one or more substituents chosen from the alkyl, OH, halogen, nitro and alkoxy radicals, $R^{23}$ and $R^{24}$ representing, independently, a hydrogen atom, an alkyl radical or a —CO—$R^{25}$ radical, $R^{25}$ representing an alkyl radical, and $R^{19}$, $R^{20}$ and $R^{21}$ represent, independently, a hydrogen, a halogen, the OH or $SR^{26}$ group, or an alkyl, cycloalkyl, alkenyl, alkoxy, cyano, nitro, —$SO_2NHR^{49}$, —$CONHR^{55}$, —$S(O)_qR^{56}$, —$NH(CO)R^{57}$, —$CF_3$, —$OCF_3$ or $NR^{27}R^{28}$ radical, $R^{26}$ representing a hydrogen atom or an alkyl radical, $R^{27}$ and $R^{28}$ representing, independently, a hydrogen atom, an alkyl radical or a —$COR^{29}$ group, or $R^{27}$ and $R^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, $R^{29}$ representing a hydrogen atom, an alkyl, alkoxy or —$NR^{30}R^{31}$ radical, $R^{30}$ and $R^{31}$ representing, independently, a hydrogen atom or an alkyl radical, or $R^{30}$ and $R^{31}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, or a

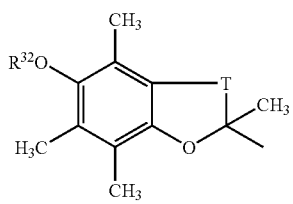

radical in which $R^{32}$ represents a hydrogen atom or an alkyl radical, and T represents a —$(CH_2)_m$— radical with m=1 or 2, or finally a

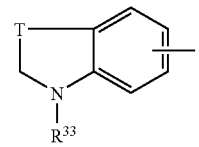

radical in which $R^{33}$ represents a hydrogen atom or an alkyl, —Σ—$NR^{34}R^{35}$ or —Σ—$CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or $NR^{10}R^{11}$ radicals, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and T represents a —$(CH_2)_m$— radical with m=1 or 2, or also A represents an alkyl, cycloalkyl or cycloalkylalkyl radical;

X represents S or $NR^{38}$, $R^{38}$ representing a hydrogen atom or an alkyl, cyanoalkyl, aralkyl, alkylcarbonyl or aralkylcarbonyl radical, Y represents O or S;

$R^1$ represents a hydrogen atom, an alkyl, aminoalkyl, alkoxyalkyl, cycloalkyl, cycloalkylalkyl, trifluoromethylalkyl, alkenyl, allenyl, allenylalkyl, alkynyl, cyanoalkyl, —$(CH_2)_g$-$Z^1R^{39}$, —$(CH_2)_g$—$COR^{40}$, —$(CH_2)_g$—NH-$COR^{70}$, aryl, aralkyl, arylcarbonyl, heteroarylalkyl or aralkylcarbonyl radical, the aryl group of the aryl, aralkyl, arylcarbonyl, heteroarylalkyl or aralkylcarbonyl radicals itself being optionally substituted by one or more substituents chosen from the group constituted by the alkyl, halogen, alkoxy, nitro, cyano, cyanoalkyl, amino, alkylamino, dialkylamino, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom, an alkyl, aminoalkyl, alkoxyalkyl, cycloalkyl, cycloalkylalkyl, trifluoromethylalkyl or —$(CH_2)_g$—$NHCOR^{71}$ radical, or also one of the aralkyl or heteroarylalkyl radicals optionally substituted on the aryl or heteroaryl group by one or more of the groups chosen independently from the group composed of a halogen atom and an alkyl, alkoxy, hydroxy, cyano, nitro, amino, alkylamino or dialkylamino radical, $R^{70}$ and $R^{71}$ representing independently an alkyl or alkoxy radical;

or $R^1$ and $R^2$, taken together with the carbon atom which carries them, form a carbocycle with 3 to 7 members;

B represents a hydrogen atom, an alkyl radical, a —$(CH_2)_g$-$Z^3R^{44}$ radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, $Z^3$ representing a bond, —O—, —$NR^{45}$— or —S—, $R^{44}$ and $R^{45}$ representing, independently, a hydrogen atom or an alkyl, alkenyl, alkynyl, alkoxy, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —$(CH_2)_g$-$Z^4R^{50}$, —$(CH_2)_k$—$COR^{51}$, —$(CH_2)_k$—$COOR^{51}$, —$(CH_2)_k$—$CONHR^{51}$, —$CSNHR^{51}$ or —$SO_2R^{51}$ radical, or also a radical chosen from the aryl, aralkyl, aryloxyalkyl, arylcarbonyl, arylimino, aralkylcarbonyl, heteroaryl and in particular pyridinyl, pyridinylalkyl or pyridinylcarbonyl radicals, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by one or more substituents chosen independently from halogen, alkyl, alkoxy, hydroxy, nitro, cyano, cyanoalkyl, amino, alkylamino, dialkylamino, —$(CH_2)_k$-$Z^5R^{50}$, —$(CH_2)_k$—$COR^{51}$ and —$(CH_2)_k$—$COOR^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group composed of —$CH(R^{53})$—, —$NR^{54}$—, —O—, —S— and —CO—, said heterocycle being able to be for example an azetidine, a piperazine, a homopiperazine, a 3,5-dioxopiperazine, a piperidine, a pyrrolidine, a morpholine or a thiomorpholine, $R^{50}$ and $R^{52}$, representing, independently each time that they occur, a hydrogen atom or an alkyl, alkenyl, alkynyl, allenyl, allenylalkyl or cyanoalkyl radical, $R^{51}$ representing, independently each time that it occurs, a hydrogen atom, one of the cycloalkyl or cycloalkylalkyl radicals in which the cycloalkyl radical has 3 to 7 carbon atoms, a linear or branched alkyl radical containing 1 to 8 carbon atoms, an alkenyl, alkynyl, allenyl, allenylalkyl, haloalkyl, cyanoalkyl, alkoxyalkyl or $NR^{58}R^{59}$ radical, or also an aryl or aralkyl radical, said aryl or aralkyl radical being able to be substituted by one or more of the substituents chosen independently from a halogen atom and an alkyl or alkoxy radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—$COR^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —$(CH_2)_k$-$Z^8R^{63}$ and —$(CH_2)_k$—$COR^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, —O—, —$NR^{67}$— or —S—, $R^{63}$ and $R^{67}$ representing, independently, a hydrogen atom, an alkyl, allenyl, allenylalkyl, alkenyl, alkynyl or cyanoalkyl radical, $R^{64}$ representing a hydrogen atom, an alkyl, allenylalkyl, alkenyl, allenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, and $R^{48}$ represents a hydrogen atom or an alkyl, alkynyl or cyanoalkyl radical;

g and p, each time that they occur, being independently integers from 1 to 6, and k and n, each time that they occur, being independently integers from 0 to 6;

it being understood that when Het is such that the compound of general formula $(I)_G$ corresponds to general sub-formula $(I)_{G4}$, then:

A represents the 4-hydroxy-2,3-di-tertiobutyl-phenyl radical;

B, $R^1$ and $R^2$ all represent H; and finally

Ω represents OH;

or pharmaceutically acceptable salts of the compounds of general formula $(I)_G$;

can be used for preparing a medicament intended to have at least one of the following three activities:
- to inhibit the monoamine oxydases, in particular monoamine oxydase B,
- to inhibit lipidic peroxidation,
- to have a modulating activity vis-à-vis the sodium channels.

Preferably, the compounds of general formula $(I)_G$ used according to the invention will be compounds of general formula (I)

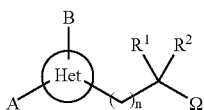
(I)

in racemic, enantiomeric form or any combination of these forms, in which Het is a heterocycle with 5 members comprising 2 heteroatoms and such that general formula (I) corresponds exclusively to one of the following sub-formulae:

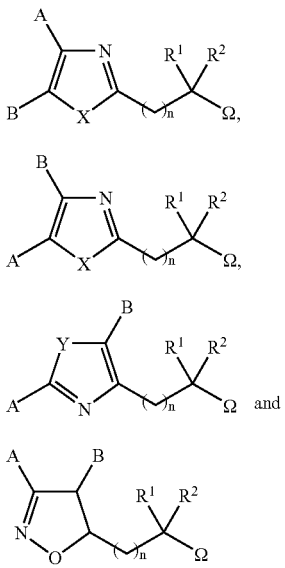

in which

A represents either a

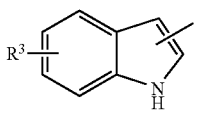

radical in which $R^3$ represents a hydrogen atom, the OH group or an alkoxy or alkyl radical, or a

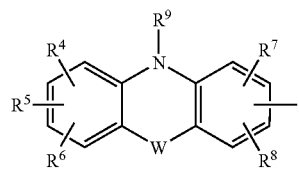

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom, an alkyl radical or a $-COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^9$ represents a hydrogen atom, an alkyl radical or a $-COR^{15}$ group, $R^{15}$ representing a hydrogen atom or an alkyl, alkoxy or $NR^{16}R^{17}$ radical, $R^{16}$ and $R^{17}$ representing, independently, a hydrogen atom or an alkyl radical, or $R^{16}$ and $R^{17}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and W doesn't exist, or represents a bond, or $-O-$, $-S-$ or $-NR^{18}-$, in which $R^{18}$ represents a hydrogen atom or an alkyl radical;

either a

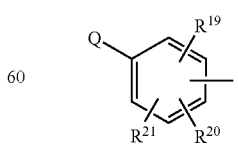

radical in which Q represents H, $-OR^{22}$, $-SR^{22}$, $-NR^{23}R^{24}$, a phenyl radical optionally substituted by one or more substituents chosen independently from a halogen atom, an OH, cyano, nitro, alkyl, alkoxy or —NR$^{10}$R$^{11}$ radical and a group with two substituents representing together a methylenedioxy or ethylenedioxy radical, or also Q represents a —COPh, —SO$_2$Ph or —CH$_2$Ph radical, said —COPh, —SO$_2$Ph or —CH$_2$Ph radical being optionally substituted on its aromatic part by one or more of the substituents chosen independently from an alkyl or alkoxy radical and a halogen atom, R$^{10}$ and R$^{11}$ representing, independently, a hydrogen atom, an alkyl radical or a —COR$^{12}$ group, or R$^{10}$ and R$^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, R$^{12}$ representing a hydrogen atom, an alkyl or alkoxy or NR$^{13}$R$^{14}$ radical, R$^{13}$ and R$^{14}$ representing, independently, a hydrogen atom or an alkyl radical, or R$^{13}$ and R$^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, R$^{22}$ representing a hydrogen atom, an alkyl radical or an aryl radical optionally substituted by one or more substituents chosen from the alkyl, OH, halogen, nitro and alkoxy radicals, R$^{23}$ and R$^{24}$ representing, independently, a hydrogen atom, an alkyl radical or a —CO—R$^{25}$ radical, R$^{25}$ representing an alkyl radical, and R$^{19}$, R$^{20}$ and R$^{21}$ represent, independently, a hydrogen, a halogen, the OH or SR$^{26}$ group, or an alkyl, cycloalkyl, alkenyl, alkoxy, cyano, nitro, —SO$_2$NHR$^{49}$, —CONHR$^{55}$, S(O)$_q$R$^{56}$, —NH(CO)R$^{57}$, —CF$_3$, —OCF$_3$ or NR$^{27}$R$^{28}$ radical, R$^{26}$ representing a hydrogen atom or an alkyl radical, R$^{27}$ and R$^{28}$ representing, independently, a hydrogen atom, an alkyl radical or a —COR$^{29}$ group, or R$^{27}$ and R$^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, R$^{49}$ and R$^{55}$ representing, independently each time that they occur, a hydrogen atom or an alkyl or alkylcarbonyl radical, q representing an integer from 0 to 2, R$^{56}$ and R$^{57}$ representing, independently each time that they occur, a hydrogen atom or an alkyl or alkoxy radical, R$^{29}$ representing a hydrogen atom, an alkyl, alkoxy or —NR$^{30}$R$^{31}$ radical, R$^{30}$ and R$^{31}$ representing, independently, a hydrogen atom or an alkyl radical, or R$^{30}$ and R$^{31}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, or a

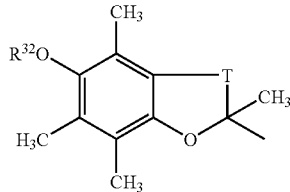

radical in which R$^{32}$ represents a hydrogen atom or an alkyl radical, and T represents a —(CH$_2$)$_m$— radical with m=1 or 2, or finally a

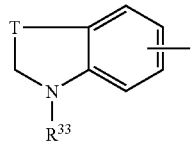

radical in which R$^{33}$ represents a hydrogen atom or an alkyl, —Σ—NR$^{34}$R$^{35}$ or —Σ—CHR$^{36}$R$^{37}$ radical, Σ representing a linear or branched alkylene radical containing 1 to 6 carbon atoms, R$^{34}$ and R$^{35}$ representing, independently, a hydrogen atom or an alkyl radical, R$^{36}$ and R$^{37}$ representing, independently, a hydrogen atom or a carbocyclic or heterocyclic aryl radical optionally substituted by one or more substituents chosen from the alkyl, OH, halogen, nitro, alkoxy or NR$^{10}$R$^{11}$ radicals, R$^{10}$ and R$^{11}$ representing, independently, a hydrogen atom, an alkyl radical or a —COR$^{12}$ group, or R$^{10}$ and R$^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, R$^{12}$ representing a hydrogen atom or an alkyl, alkoxy or NR$^{13}$R$^{14}$ radical, R$^{13}$ and R$^{14}$ representing, independently, a hydrogen atom or an alkyl radical, or R$^{13}$ and R$^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and T represents a —(CH$_2$)$_m$— radical with m=1 or 2, or also A represents an alkyl, cycloalkyl or cycloalkylalkyl radical;

X represents S or NR$^{38}$, $R^{38}$ representing a hydrogen atom or an alkyl, cyanoalkyl, aralkyl, alkylcarbonyl or aralkylcarbonyl radical, Y represents O or S;

$R^1$ represents a hydrogen atom, an alkyl, aminoalkyl, alkoxyalkyl, cycloalkyl, cycloalkylalkyl, trifluoromethylalkyl, alkenyl, allenyl, allenylalkyl, alkynyl, cyanoalkyl, —$(CH_2)_g$-$Z^1R^{39}$, —$(CH_2)_g$—$COR^{40}$, —$(CH_2)_g$—NHCOR$^{70}$, aryl, aralkyl, arylcarbonyl, heteroarylalkyl or aralkylcarbonyl radical, the aryl group of the aryl, aralkyl, arylcarbonyl, heteroarylalkyl or aralkylcarbonyl radicals itself being optionally substituted by one or more substituents chosen from the group constituted by the alkyl, halogen, alkoxy, nitro, cyano, cyanoalkyl, amino, alkylamino, dialkylamino, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom, an alkyl, aminoalkyl, alkoxyalkyl, cycloalkyl, cycloalkylalkyl, trifluoromethylalkyl or —$(CH_2)_g$—NHCOR$^{71}$ radical, or also one of the aralkyl or heteroarylalkyl radicals optionally substituted on the aryl or heteroaryl group by one or more of the groups chosen independently from the group composed of a halogen atom and an alkyl, alkoxy, hydroxy, cyano, nitro, amino, alkylamino or dialkylamino radical, $R^{70}$ and $R^{71}$ representing independently an alkyl or alkoxy radical;

or $R^1$ and $R^2$, taken together with the carbon atom which carries them, form a carbocycle with 3 to 7 members;

B represents a hydrogen atom, an alkyl radical, a —$(CH_2)_g$-$Z^3R^{44}$ radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, $Z^3$ representing a bond, —O—, —$NR^{45}$— or —S—, $R^{44}$ and $R^{45}$ representing, independently, a hydrogen atom or an alkyl, alkenyl, alkynyl, alkoxy, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —$(CH_2)_g$-$Z^4R^{50}$, —$(CH_2)_k$—COR$^{51}$, —$(CH_2)_k$—COOR$^{51}$, —$(CH_2)_k$—CONHR$^{51}$ or —$SO_2R^{51}$ radical, or also a radical chosen from the aryl, aralkyl, aryloxyalkyl, arylcarbonyl, arylimino, aralkylcarbonyl, heteroaryl and in particular pyridinyl, pyridinylalkyl or pyridinylcarbonyl radicals, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by one or more substituents chosen independently from halogen, alkyl, alkoxy, hydroxy, nitro, cyano, cyanoalkyl, amino, alkylamino, dialkylamino, —$(CH_2)_k$-$Z^5R^{50}$, —$(CH_2)_k$—COR$^{51}$ and —$(CH_2)_k$—COOR$^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group composed of —CH($R^{53}$)—, —$NR^{54}$—, —O—, —S— and —CO—, said heterocycle being able to be for example an azetidine, a piperazine, a homopiperazine, a 3,5-dioxopiperazine, a piperidine, a pyrrolidine, a morpholine or a thiomorpholine, $R^{50}$ and $R^{52}$ representing, independently each time that they occur, a hydrogen atom or an alkyl, alkenyl, alkynyl, allenyl, allenylalkyl or cyanoalkyl radical, $R^{51}$ representing, independently each time that they occur, a hydrogen atom, one of the cycloalkyl or cycloalkylalkyl radicals in which the cycloalkyl radical has 3 to 7 carbon atoms, a linear or branched alkyl radical containing 1 to 8 carbon atoms, an alkenyl, alkynyl, allenyl, allenylalkyl, cyanoalkyl, alkoxyalkyl or $NR^{58}R^{59}$ radical, or also an aryl or aralkyl radical, said aryl or aralkyl radical being able to be substituted by one or more of the substituents chosen independently from a halogen atom and an alkyl or alkoxy radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—COR$^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —$(CH_2)_k$-$Z^8R^{63}$ and —$(CH_2)_k$—COR$^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, —O—, —$NR^{67}$— or —S—, $R^{63}$ and $R^{67}$ representing, independently, a hydrogen atom, an alkyl, allenyl, allenylalkyl, alkenyl, alkynyl or cyanoalkyl radical, $R^{64}$ representing a hydrogen atom, an alkyl, allenylalkyl, alkenyl, allenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, and $R^{48}$ represents a hydrogen atom or an alkyl, alkynyl or cyanoalkyl radical;

g and p, each time that they occur, being independently integers from 1 to 6, and k and n, each time that they occur, being independently integers from 0 to 6;

it being understood that when Het is such that the compound of general formula (I) corresponds to general sub-formula (I)$_4$, then:

A represents the 4-hydroxy-2,3-di-tertiobutyl-phenyl radical;

B, R$^1$ and R$^2$ all represent H; and finally

Ω represents OH;

or pharmaceutically acceptable salts of the compounds of general formula (I).

According to preferred variants of the invention, these compounds have at least two of the activities mentioned above. In particular, they inhibit both the MAO's and trap the ROS's or they will have both an antagonist activity vis-à-vis the sodium channels and a trapping activity on the ROS's. In certain cases, the compounds of general formula (I)$_G$ or (I) even combine the three activities.

This allows the compounds of general formula (I)$_G$ or (I) to be of use in the treatment of the diseases mentioned previously such as being linked to MAO'S, to lipidic peroxidation and to the sodium channels.

By alkyl, unless otherwise specified, is meant a linear or branched alkyl radical containing 1 to 6 carbon atoms. By cycloalkyl, when no further detail is given, is meant a monocyclic carbon system containing 3 to 7 carbon atoms. By alkenyl, when no further detail is given, is meant a linear or branched alkyl radical containing 1 to 6 carbon atoms and having at least one unsaturation (double bond). By alkynyl, when no further detail is given, is meant a linear or branched alkyl radical containing 1 to 6 carbon atoms and having at least one double unsaturation (triple bond). By allenyl, is meant the —CH=C=CH$_2$ radical. By carbocyclic or heterocyclic aryl, is meant a carbocyclic system (in particular, the phenyl radical which can be noted Ph in an abbreviated fashion) or heterocyclic system comprising at least one aromatic ring, a system being called heterocyclic when at least one of the rings which comprises it contains a heteroatom (O, N or S). By heterocycle, is meant a mono- or polycyclic system, said system comprising at least one heteroatom chosen from O, N and S and being saturated, partially or totally unsaturated or aromatic. By heteroaryl, is meant a heterocycle as defined previously in which at least one of the rings which comprises it is aromatic. By haloalkyl, is meant an alkyl radical at least one of hydrogen atoms of which (and optionally all) is replaced by a halogen atom.

Moreover, by an optionally substituted radical is meant unless otherwise specified a radical comprising one or more substituents chosen independently from the group composed of a halogen atom and the alkyl and alkoxy radicals.

By alkylthio, alkoxy, haloalkyl, alkoxyalkyl, trifluoromethylalkyl, cycloalkylalkyl, haloalkoxy, aminoalkyl, alkenyl, alkynyl, allenylalkyl, cyanoalkyl and aralkyl radicals, is meant respectively the alkylthio, alkoxy, haloalkyl, alkoxyalkyl, trifluoromethylalkyl, cycloalkylalkyl, haloalkoxy, aminoalkyl, alkenyl, alkynyl, allenylalkyl, cyanoalkyl and aralkyl radicals the alkyl radical (the alkyl radicals) of which have the meaning(s) indicated previously.

By heterocycle, is meant in particular the thiophene, piperidine, piperazine, quinoline, indoline and indole radicals. By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen, is meant the fluorine, chlorine, bromine or iodine atoms.

Preferably, the compounds according to the invention are such that they correspond to general formula (I):

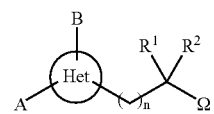

(I)

in racemic, enantiomeric form or any combination of these forms, in which Het is a heterocycle with 5 members comprising 2 heteroatoms and such that general formula (I) corresponds exclusively to one of the following sub-formulae:

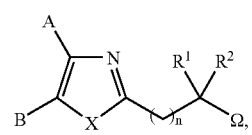

(I)$_1$

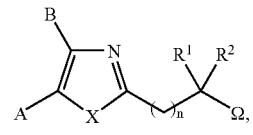

(I)$_2$

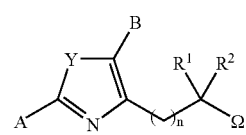

(I)$_3$ and

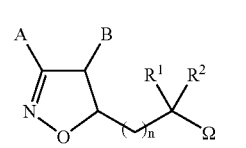

(I)$_4$ in which

A represents either a

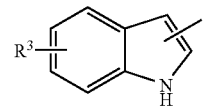

radical in which R$^3$ represents a hydrogen atom, the OH group or an alkoxy or alkyl radical, or a

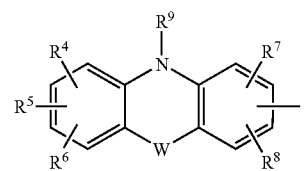

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom or an alkyl radical $R^9$ represents a hydrogen atom or an alkyl radical, and W doesn't exist, or represents a bond, or —O—, —S— or —NR$^{18}$—, in which $R^{18}$ represents a hydrogen atom or an alkyl radical;

or a

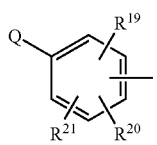

radical in which Q represents H, —OR$^{22}$, —SR$^{22}$, —NR$^{23}$R$^{24}$, a phenyl radical optionally substituted by one or more substituents chosen independently from a halogen atom, an OH, cyano, nitro, alkyl, alkoxy or —NR$^{10}$R$^{11}$ radical and a group with two substituents representing together a methylenedioxy or ethylenedioxy radical, or also Q represents a —COPh, —OPh, —SPh, —SO$_2$Ph or —CH$_2$Ph radical, said —COPh, —OPh, —SPh, —SO$_2$Ph or —CH$_2$Ph radical being optionally substituted on its aromatic part by one or more of the substituents chosen independently from an alkyl or alkoxy radical and a halogen atom, $R^{10}$ and $R^{11}$ representing, independently, a hydrogen atom or an alkyl radical, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{22}$ representing a hydrogen atom, an alkyl radical or an aryl radical optionally substituted by one or more substituents chosen from the alkyl, OH, halogen, nitro and alkoxy radicals, $R^{23}$ and $R^{24}$ representing, independently, a hydrogen atom, an alkyl radical or a —CO—R$^{25}$ radical, $R^{25}$ representing an alkyl radical, and $R^{19}$, $R^{20}$ and $R^{21}$ represent, independently, a hydrogen, a halogen, the OH or SR$^{26}$ group, or an alkyl, cycloalkyl, alkenyl, alkoxy, cyano, nitro, —SO$_2$NHR$^{49}$, —CONHR$^{55}$, —S(O)$_q$R$^{56}$, —NH(CO)R$^{57}$, —CF$_3$, —OCF$_3$ or NR$^{27}$R$^{28}$ radical, $R^{26}$ representing a hydrogen atom or an alkyl radical, $R^{27}$ and $R^{28}$ representing, independently, a hydrogen atom, an alkyl radical or a —COR$^{29}$ group, or $R^{27}$ and $R^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, $R^{29}$ representing a hydrogen atom, an alkyl, alkoxy or —NR$^{30}$R$^{31}$ radical, $R^{30}$ and $R^{31}$ representing, independently, a hydrogen atom or an alkyl radical, or $R^{30}$ and $R^{31}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, or a

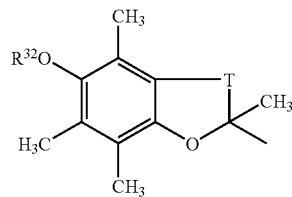

radical in which $R^{32}$ represents a hydrogen atom or an alkyl radical, and T represents a —(CH$_2$)$_m$— radical with m=1 or 2, or finally a

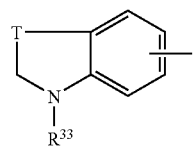

radical in which $R^{33}$ represents a hydrogen atom or an alkyl, —Σ—NR$^{34}$R$^{35}$ or —Σ—CHR$^{36}$R$^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or NR$^{10}$R$^{11}$ radicals, $R^{10}$ and $R^{11}$ representing, independently, a hydrogen atom, an alkyl radical, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and T represents a —$(CH_2)_m$— radical with m=1 or 2, or also A represents an alkyl, cycloalkyl or cycloalkylalkyl radical;

X represents S or $NR^{38}$, $R^{38}$ representing a hydrogen atom or an alkyl, cyanoalkyl, aralkyl, alkylcarbonyl or aralkylcarbonyl radical, Y represents O or S;

$R^1$ represents a hydrogen atom, an alkyl, aminoalkyl, alkoxyalkyl, cycloalkyl, cycloalkylalkyl, trifluoromethylalkyl, alkenyl, allenyl, allenylalkyl, alkynyl, cyanoalkyl, —$(CH_2)_g$-$Z^1R^{39}$, —$(CH_2)_g$—$COR^{40}$, —$(CH_2)_g$—NH-$COR^{70}$, aryl, aralkyl, arylcarbonyl, heteroarylalkyl or aralkylcarbonyl radical, the aryl group of the aryl, aralkyl, arylcarbonyl, heteroarylalkyl or aralkylcarbonyl radicals itself being optionally substituted by one or more substituents chosen from the group constituted by the alkyl, halogen, alkoxy, nitro, cyano, cyanoalkyl, amino, alkylamino, dialkylamino, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom, an alkyl, aminoalkyl, alkoxyalkyl, cycloalkyl, cycloalkylalkyl, trifluoromethylalkyl or —$(CH_2)_g$—$NHCOR^{71}$ radical, or also one of the aralkyl or heteroarylalkyl radicals optionally substituted on the aryl or heteroaryl group by one or more of the groups chosen independently from the group composed of a halogen atom and an alkyl, alkoxy, hydroxy, cyano, nitro, amino, alkylamino or dialkylamino radical, $R^{70}$ and $R^{71}$ representing independently an alkyl or alkoxy radical;

or $R^1$ and $R^2$, taken together with the carbon atom which carries them, form a carbocycle with 3 to 7 members;

B represents a hydrogen atom, an alkyl radical, a —$(CH_2)_g$-$Z^3R^{44}$ radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, $Z^3$ representing a bond, —O—, —$NR^{45}$— or —S—, $R^{44}$ and $R^{45}$ representing, independently, a hydrogen atom or an alkyl, alkenyl, alkynyl, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —$(CH_2)_g$-$Z^4R^{50}$, —$(CH_2)_k$—$COR^{51}$, —$(CH_2)_k$—$COOR^{51}$, —$(CH_2)_k$—$CONHR^{51}$ or —$SO_2R^{51}$ radical, or also a radical chosen from the aryl, aralkyl, aryloxyalkyl, arylcarbonyl, arylimino, aralkylcarbonyl, heteroaryl and in particular pyridinyl, pyridinylalkyl or pyridinylcarbonyl radicals, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by one or more substituents chosen independently from halogen, alkyl, alkoxy, hydroxy, nitro, cyano, cyanoalkyl, amino, alkylamino, dialkylamino, —$(CH_2)_k$-$Z^5R^{50}$, —$(CH_2)_k$—$COR^{51}$ and —$(CH_2)_k$—$COOR^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group composed of —$CH(R^{53})$—, —$NR^{54}$—, —O—, —S— and —CO—, said heterocycle being able to be for example an azetidine, a piperazine, a homopiperazine, a 3,5-dioxopiperazine, a piperidine, a pyrrolidine, a morpholine or a thiomorpholine, $R^{50}$ and $R^{52}$ representing, independently each time that they occur, a hydrogen atom or an alkyl, alkenyl, alkynyl, alkoxy, allenyl, allenylalkyl or cyanoalkyl radical, $R^{51}$ representing, independently each time that they occur, a hydrogen atom, one of the cycloalkyl or cycloalkylalkyl radicals in which the cycloalkyl radical has 3 to 7 carbon atoms, a linear or branched alkyl radical containing 1 to 8 carbon atoms, an alkenyl, alkynyl, allenyl, allenylalkyl, cyanoalkyl, alkoxyalkyl or $NR^{58}R^{59}$ radical, or also an aryl or aralkyl radical, said aryl or aralkyl radical being able to be substituted by one or more of the substituents chosen independently from a halogen atom and an alkyl or alkoxy radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—$COR^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —$(CH_2)_k$-$Z^8R^{63}$ and —$(CH_2)_k$—$COR^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, —O—, —$NR^{67}$— or —S—, $R^{63}$ and $R^{67}$ representing, independently, a hydrogen atom, an alkyl, allenyl, allenylalkyl, alkenyl, alkynyl or cyanoalkyl radical, $R^{64}$ representing a hydrogen atom, an alkyl, allenylalkyl, alkenyl, alkenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, g and p, each time that they occur, being independently integers from 1 to 6, and k and n, each time that they occur, being independently integers from 0 to 6;

and $R^{48}$ represents a hydrogen atom or an alkyl, alkynyl or cyanoalkyl radical;

it being understood that when Het is such that the compound of general formula (I) corresponds to general sub-formula $(I)_4$, then:

A exclusively represents the 4-hydroxy-2,3-di-tertiobutyl-phenyl radical;

B represents H, $R^1$ and $R^2$ both represent H; and finally

Ω represents OH;

or salts of said compounds

According to the invention, there will generally be preferred the compounds of general formula (I) in which at least one of the following radicals is found:

A representing:
either the

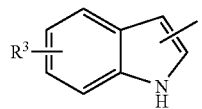

radical in which $R^3$ represents a hydrogen atom, the OH group or an alkoxy or alkyl radical,
or the

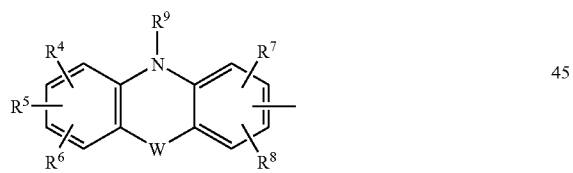

radical in which $R^4$, $R^5$, $R^6$, $R^7$ and $R^8$ represent, independently, a hydrogen atom, the OH group or an alkyl or alkoxy radical, $R^9$ represents a hydrogen atom or an alkyl radical, and W does not exist, or represents a bond, —O—, —S— or —$NR^{18}$—, $R^{18}$ representing a hydrogen atom or an alkyl radical;
or the

radical in which Q represents H, —$OR^{22}$, —$SR^{22}$ or a phenyl radical optionally substituted by one substituent or substituents chosen independently from a halogen atom, an OH, cyano, nitro, alkyl, alkoxy or —$NR^{10}R1$ radical and a group of two substituents together representing a methylenedioxy or ethylenedioxy radical, or also Q represents an —OPh, —SPh, —$SO_2Ph$ or —$CH_2Ph$ radical, said —OPh, —SPh, —$SO_2Ph$ or —$CH_2Ph$ radical being optionally substituted on its aromatic part by a substituent or substituents chosen from an alkyl or alkoxy radical and a halogen atom, $R^{10}$ and $R^{11}$ representing, independently, a hydrogen atom or an alkyl radical;

$R^{22}$ representing a hydrogen atom, an alkyl radical or an aryl radical optionally substituted by one or more substituents chosen from the alkyl, OH, halogen, nitro and alkoxy radicals, and $R^{19}$, $R^{20}$ and $R^{21}$ represent, independently, a hydrogen, a halogen, the OH or $SR^{26}$ group, or an alkyl, cycloalkyl, alkenyl, alkoxy, cyano, nitro, —$SO_2NHR^{49}$, —$CONHR^{55}$, —$S(O)_qR^{56}$, —NH$(CO)R^{57}$, —$CF_3$, —$OCF_3$ or $NR_{27}R^{28}$ radical, $R^{26}$ representing a hydrogen atom or an alkyl radical, $R^{27}$ and $R^{28}$ representing, independently, a hydrogen atom, an alkyl radical or a —$COR^{29}$ group, or also $R^{27}$ and $R^{28}$ forming together with the nitrogen atom which carries them a heterocycle with 5 to 6 members chosen from —$CH_2$—, —NH— and —O—, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, $R^{29}$ representing a hydrogen atom, an alkyl, alkoxy or —$NR^{30}R^{31}$ radical, $R^{30}$ and $R^{31}$ representing, independently, a hydrogen atom or an alkyl radical,
or the

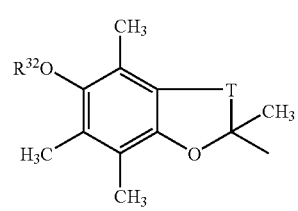

radical in which $R^{32}$ represents a hydrogen atom or an alkyl radical, and T represents the —$(CH_2)_2$— radical
or finally the

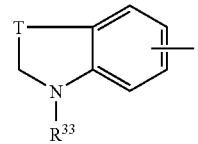

radical in which $R^{33}$ represents a hydrogen atom or an alkyl, —Σ—$NR^{34}R^{35}$ or —Σ—$CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or $NR^{10}R^{11}$ radicals, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, such as for example azetidine, pyrrolidine, piperidine, piperazine, morpholine or thiomorpholine, and T represents the —(CH$_2$)— radical;

Ω representing:

either the $NR^{46}R^{47}$ radical in which $R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —(CH$_2$)$_k$—$COR^{51}$, —$COOR^{51}$ or —$SO_2R^{51}$ radical or also a radical chosen from the aryl, aralkyl, aryloxyalkyl, arylcarbonyl, arylimino, aralkylcarbonyl, heteroaryl radicals and in particular pyridinyl, pyridinylalkyl or pyridinylcarbonyl, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by a substituent or substituents chosen independently from halogen, alkyl, alkoxy, hydroxy, nitro, cyano, cyanoalkyl, amino, alkylamino, dialkylamino, —(CH$_2$)$_k$-$Z^5R^{50}$, —(CH$_2$)$_k$—$COR^{51}$ and —(CH$_2$)$_k$—$COOR^{51}$, $R^{51}$ representing a hydrogen atom or an alkyl, alkenyl, alkynyl or alkoxyalkyl radical or the OH radical;

Moreover, when A represents the

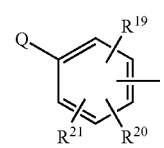

radical, the Q radical is preferably found in para position with respect to the heterocycle Het.

Generally, all the preferences relating to sub-groups of compounds of general formula (I) presented below remain applicable with respect to the use of compounds of general formula (I) as defined previously for the preparation of medicaments intended to inhibit monoamine oxidases, in particular monoamine oxidase B, to inhibit lipidic peroxidation, to have a modulatory activity on the sodium channels or to have two of the three activities or the three activities mentioned previously.

According to a particular variant of the invention, the compounds of general formula (I) or their salts are more especially intended to have an inhibitory activity on MAO's and/or ROS's and they will therefore be preferably such that:

A represents either a

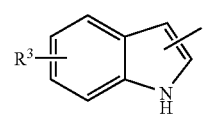

radical in which $R^3$ represents a hydrogen atom, the OH group or an alkoxy or alkyl radical, or a

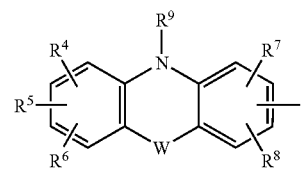

radical in which $R^4$, $R^5$, $R^6$, $R^7$ and $R^8$ represent, independently, a hydrogen atom, a halogen, the OH group or an alkyl, alkoxy or $NR^{10}R^{11}$ radical, $R^{10}$ and $R^{11}$ representing, independently, a hydrogen atom or an alkyl radical, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^9$ represents a hydrogen atom or an alkyl radical, and W doesn't exist, or represents a bond, or —O—, —S— or —$NR^{18}$—, in which $R^{18}$ represents a hydrogen atom or an alkyl radical;

or a

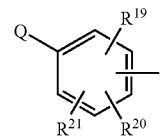

radical in which Q represents —OR$^{22}$, —SR$^{22}$, —NR$^{23}$R$^{24}$, a phenyl radical optionally substituted by one or more of the substituents chosen independently from a halogen atom and an OH, cyano, nitro, alkyl, alkoxy or —NR$^{10}$R$^{11}$ radical, R$^{10}$ and R$^{11}$ representing, independently, a hydrogen atom or an alkyl radical, or R$^{10}$ and R$^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, R$^{22}$ representing a hydrogen atom, an alkyl radical or an aryl radical optionally substituted by one or more substituents chosen from the alkyl, OH, halogen, nitro and alkoxy radicals, R$^{23}$ and R$^{24}$ representing, independently, a hydrogen atom or an alkyl radical, and R$^{19}$, R$^{20}$ and R$^{21}$ represent, independently, a hydrogen, a halogen, the OH or SR$^{26}$ group, or an alkyl, alkenyl, alkoxy or NR$^{27}$R$^{28}$ radical, R$^{26}$ representing a hydrogen atom or an alkyl radical, R$^{27}$ and R$^{28}$ representing, independently, a hydrogen atom or an alkyl radical, or R$^{27}$ and R$^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms; said heterocycle being able to be for example azetidine, pyrrolidine, piperidine, piperazine, morpholine or thiomorpholine, or a

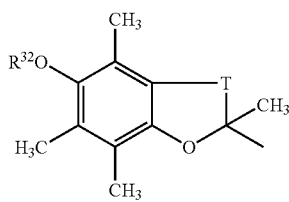

radical in which R$^{32}$ represents a hydrogen atom or an alkyl radical, and T represents a —(CH$_2$)$_m$— radical with m=1 or 2, or finally a

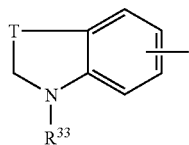

radical in which R$^{33}$ represents a hydrogen atom or an alkyl, —Σ—NR$^{34}$R$^{35}$ or —Σ—CHR$^{36}$R$^{37}$ radical, Σ representing a linear or branched alkylene radical containing 1 to 6 carbon atoms, R$^{34}$ and R$^{35}$ representing, independently, a hydrogen atom or an alkyl radical, R$^{36}$ and R$^{37}$ representing, independently, a hydrogen atom or a carbocyclic or heterocyclic aryl radical optionally substituted by one or more substituents chosen from the alkyl, OH, halogen, nitro, alkoxy or NR$^{10}$R$^{11}$ radicals, R$^{10}$ and R$^{11}$ representing, independently, a hydrogen atom or an alkyl radical, or R$^{10}$ and R$^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and T represents a —(CH$_2$)$_m$— radical with m=1 or 2, X represents S or NR$^{38}$, R$^{38}$ representing a hydrogen atom or an alkyl or cyanoalkyl radical, Y represents O or S;

R$^1$ represents a hydrogen atom, an alkyl, cycloalkyl, alkenyl, allenyl, allenylalkyl, alkynyl, cyanoalkyl, —(CH$_2$)$_g$-Z$^1$R$^{39}$, —(CH$_2$)$_g$—COR$^{40}$, aryl, aralkyl, arylcarbonyl, or aralkylcarbonyl radical, the aryl group of the aryl, aralkyl, arylcarbonyl, or aralkylcarbonyl radicals being itself optionally substituted by a substituent or substituents chosen from the group constituted by the alkyl, halogen, alkoxy, nitro, cyano, cyanoalkyl, —(CH$_2$)$_k$-Z$^2$R$^{39}$ or —(CH$_2$)$_k$—COR$^{40}$ radicals, Z$^1$ and Z$^2$ representing a bond, —O—, —NR$^{41}$— or —S—, R$^{39}$ and R$^{41}$ representing, independently each time that they occur, a hydrogen atom or an alkyl, alkenyl, alkynyl, alkoxy or cyanoalkyl radical, R$^{40}$ representing, independently each time that it occurs, a hydrogen atom or an alkyl, allenyl, allenylalkyl, alkenyl, alkynyl, cyanoalkyl, alkoxy or NR$^{42}$R$^{43}$ radical, R$^{42}$ and R$^{43}$ representing, independently each time that they occur, a hydrogen atom or an alkyl, allenyl, allenylalkyl, alkenyl, alkynyl or cyanoalkyl radical, and R$^2$ represents a hydrogen atom or an alkyl radical, or R$^1$ and R$^2$, taken together with the carbon atom which carries them, form a carbocycle with 3 to 7 members;

B represents a hydrogen atom or a —(CH$_2$)$_g$-Z$^3$R$^{44}$ radical,

Z$^3$ representing a bond, —O—, —NR$^{45}$— or —S—,

R$^{44}$ and R$^{45}$ representing, independently, a hydrogen atom or an alkyl, alkenyl, alkynyl, allenyl, allenylalkyl or cyanoalkyl radical;

Ω represents one of the NR$^{46}$R$^{47}$ or OR$^{48}$ radicals, in which:

R$^{46}$ and R$^{47}$ represent, independently, a hydrogen atom or an alkyl, cycloalkyl, alkenyl, alkynyl, allenyl, allenylalkyl, cyanoalkyl, —(CH$_2$)$_g$-Z$^4$R$^{50}$ or —(CH$_2$)$_k$—COR$^{51}$ radical, or also a radical chosen from the aryl, aralkyl, arylcarbonyl, aralkylcarbonyl, pyridinyl, pyridinylalkyl or pyridinylcarbonyl radicals, the aryl or heteroaryl group of said aryl, aralkyl, arylcarbonyl, aralkylcarbonyl, pyridinylalkyl or pyridinylcarbonyl radicals being optionally substituted by one or more of the substituents chosen independently from halogen, alkyl, alkoxy, nitro, cyano, cyanoalkyl, amino, alkylamino, dialkylamino, —(CH$_2$)$_k$-Z$^5$R$^{50}$, —(CH$_2$)$_k$—COR$^{51}$ and —(CH$_2$)$_k$—COOR$^{51}$, Z$^4$ and Z$^5$ representing a bond, —O—, —NR$^{52}$— or —S—, or R$^{46}$ and R$^{47}$ taken together form with the nitrogen atom a non aromatic heterocycle with 4 to 8 members, the elements of the chain being chosen from a group composed of —CH(R$^{53}$)—, —NR$^{54}$—, —O—, —S— and —CO—, said heterocycle being able to be for example an azetidine, a piperazine, a homopiperazine, a 3,5-dioxopiperazine, a piperidine, a pyrrolidine, a morpholine or a thiomorpholine, R$^{50}$ and R$^{52}$, representing, independently each time that they occur, a hydrogen atom or an alkyl, alkenyl, alkynyl, allenyl, allenylalkyl or cyanoalkyl radical, R$^{51}$ representing, independently each time that they occur; a hydrogen atom, a linear or branched alkyl radical containing 1 to 8 carbon atoms, an alkenyl, alkynyl, allenyl, allenylalkyl, cyanoalkyl or NR$^{58}$R$^{59}$ radical, R$^{58}$ and R$^{59}$ representing, independently, a hydrogen atom or an alkyl, alkenyl, alkynyl, alkoxy, allenyl, allenylalkyl or cyanoalkyl radical, R$^{53}$ and R$^{54}$ representing, independently, a hydrogen atom or a —(CH$_2$)$_k$-Z$^7$R$^{60}$ or —(CH$_2$)$_k$—COR$^{61}$ radical, Z$^7$ representing a bond, —O—, —NR$^{62}$— or —S—, R$^{60}$ and R$^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —(CH$_2$)$_k$-Z$^8$R$^{63}$ and —(CH$_2$)$_k$—COR$^{64}$ radicals, R$^{61}$ representing a hydrogen atom, an alkyl, allenyl, allenylalkyl, alkenyl, alkynyl, cyanoalkyl, alkoxy or NR$^{65}$R$^{66}$ radical, R$^{65}$ and R$^{66}$ representing, independently, a hydrogen atom or an alkyl, allenyl, allenylalkyl, alkenyl, alkynyl or cyanoalkyl radical, Z$^8$ representing a bond, —O—, —NR$^{67}$— or —S—, R$^{63}$ and R$^{67}$ representing, independently, a hydrogen atom, an alkyl, allenyl, allenylalkyl, alkenyl, alkynyl or cyanoalkyl radical, R$^{64}$ representing a hydrogen atom, an alkyl, allenylalkyl, alkenyl, alkenyl, alkynyl, cyanoalkyl, alkoxy or NR$^{68}$R$^{69}$ radical, R$^{68}$ and R$^{69}$ representing, independently, a hydrogen atom or an alkyl, allenyl, allenylalkyl, alkenyl, alkynyl or cyanoalkyl radical, and R$^{48}$ represents a hydrogen atom or an alkyl, alkynyl or cyanoalkyl radical;

g and p, each time that they occur, being independently integers from 1 to 6, and k and n, each time that they occur, being independently integers from 0 to 6.

More preferentially, the compounds of general formula (I) (or their salts), when they are intended to have an inhibitory activity on MAO's and/or ROS's, will be such that:

A represents either a

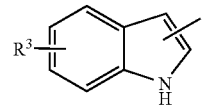

radical in which R$^3$ represents a hydrogen atom, the OH group or an alkoxy or alkyl radical, or a

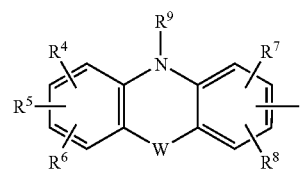

radical in which R$^4$, R$^5$, R$^6$, R$^7$ and R$^8$ represent, independently, a hydrogen atom, or an alkyl or alkoxy radical, R$^9$ represents a hydrogen atom, and W doesn't exist, or represents a bond, or —O—, —S— or —NR$^{18}$—, in which R$^{18}$ represents a hydrogen atom or an alkyl radical;

or a

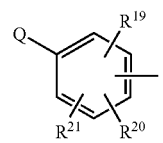

radical in which Q represents —OR$^{22}$, —SR$^{22}$ or a phenyl radical substituted by an OH radical and optionally one or more of the additional substituents chosen independently from a halogen atom and an OH, alkyl or alkoxy radical, R$^{22}$ representing a hydrogen atom or an alkyl radical, and R$^{19}$, R$^{20}$ and R$^{21}$ represent, independently, a hydrogen, a halogen, the OH or SR$^{26}$ group, or an alkyl or alkoxy radical, R$^{26}$ representing a hydrogen atom or an alkyl radical, or a

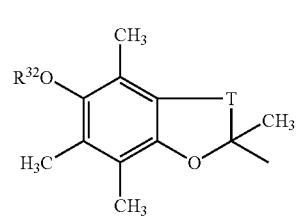

radical in which R$^{32}$ represents a hydrogen atom or an alkyl radical, and T represents a —$(CH_2)_m$— radical with m=1 or 2, or finally a

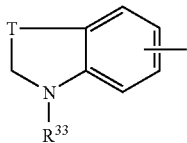

radical in which $R^{33}$ represents a hydrogen atom or an alkyl, -Σ-$NR^{34}R^{35}$ or -Σ-$CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro or alkoxy radicals, and T represents a —$(CH_2)_m$— radical with m=1 or 2, X represents S or $NR^{38}$, $R^{38}$ representing a hydrogen atom or an alkyl or cyanoalkyl radical, Y represents O or S;

$R^1$ represents a hydrogen atom, an alkyl, cycloalkyl, alkenyl, allenyl, allenylalkyl, alkynyl, cyanoalkyl, —$(CH_2)_g$-$Z^1R^{39}$, —$(CH_2)_g$—$COR^{40}$, aryl, aralkyl, arylcarbonyl, or aralkylcarbonyl radical, the aryl group of the aryl, aralkyl, arylcarbonyl, or aralkylcarbonyl radicals being itself optionally substituted by one or more substituents chosen from the group constituted by the alkyl, halogen, alkoxy, nitro, cyano, cyanoalkyl, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom or an alkyl radical, or $R^1$ and $R^2$, taken together with the carbon atom which carries them, form a carbocycle with 3 to 7 members;

B represents a hydrogen atom or a —$(CH_2)_g$-$Z^3R^{44}$ radical, $Z^3$ representing a bond, —O—, —$NR^{45}$— or —S—, $R^{44}$ and $R^{45}$ representing, independently, a hydrogen atom or an alkyl, alkenyl, alkynyl, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, alkenyl, alkynyl, allenyl, allenylalkyl, cyanoalkyl, —$(CH_2)_g$-$Z^4R^{50}$ or —$(CH_2)_k$—$COR^{51}$ radical, or also a radical chosen from the aryl, aralkyl, arylcarbonyl, aralkylcarbonyl, pyridinyl, pyridinylalkyl or pyridinylcarbonyl radicals, the aryl or heteroaryl group of said aryl, aralkyl, arylcarbonyl, aralkylcarbonyl, pyridinylalkyl or pyridinylcarbonyl radicals being optionally substituted by one or more of the substituents chosen independently from halogen, alkyl, alkoxy, nitro, cyano, cyanoalkyl, amino, alkylamino, dialkylamino, —$(CH_2)_k$-$Z^5R^{50}$, —$(CH_2)_k$—$COR^{51}$ and —$(CH_2)_k$—$COOR^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group comprising —$CH(R^{53})$—, —$NR^{54}$—, —O—, —S— and —CO—, said heterocycle being able to be for example an azetidine, a piperazine, a homopiperazine, a 3,5-dioxopiperazine, a piperidine, a pyrrolidine, a morpholine or a thiomorpholine, $R^{50}$ and $R^{52}$, representing, independently each time that they occur, a hydrogen atom or an alkyl, alkenyl, alkynyl, allenyl, allenylalkyl or cyanoalkyl radical, $R^{51}$ representing, independently each time that they occur, a hydrogen atom, a linear or branched alkyl radical containing 1 to 8 carbon atoms, an alkenyl, alkynyl, allenyl, allenylalkyl, cyanoalkyl or $NR^{58}R^{59}$ radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—$COR^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —$(CH_2)_k$-$Z^8R^{63}$ and —$(CH_2)_k$—$COR^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, —O—, —$NR^{67}$— or —S—, $R^{63}$ and $R^{67}$ representing, independently, a hydrogen atom, an alkyl, allenyl, allenylalkyl, alkenyl, alkynyl or cyanoalkyl radical, $R^{64}$ representing a hydrogen atom, an alkyl, allenylalkyl, alkenyl, alkenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, and $R^{48}$ represents a hydrogen atom or an alkyl, alkynyl or cyanoalkyl radical;

g and p, each time that they occur, being independently integers from 1 to 6, and k and n, each time that they occur, being independently integers from 0 to 6.

As regards the compounds of general formula (I) (or their salts) more especially intended to have an inhibitory activity on MAO's and the ROS's, the said compounds compounds having at least one of the following characteristics will generally be preferred:

the compound corresponds to general sub-formula $(I)_1$ or $(I)_2$ in which X represents S, the compounds corresponds to general formula $(I)_3$ in which Y represents O or the compound corresponds to general sub-formula $(I)_4$;

A represents the radical
either the

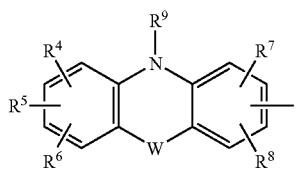

radical in which $R^4$, $R^5$, $R^6$, $R^7$ and $R^8$ represent, independently, a hydrogen atom, or an alkyl or alkoxy radical, $R^9$ represents a hydrogen atom, and W doesn't exist, or represents a bond, —O— or —S—, or the

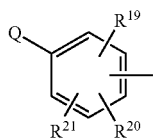

radical in which Q represents OH, two of the $R^{19}$, $R^{20}$ and $R^{21}$ radicals represent the radicals chosen independently from the alkyl, alkoxy, alkylthio, amino, alkylamino or dialkylamino radicals and the third represents a radical chosen from a hydrogen atom and the alkyl, alkoxy, alkylthio, amino, alkylamino or dialkylamino radicals, or in which Q represents a phenyl radical substituted by an OH radical and a radical or radicals chosen independently from a halogen atom and an OH, alkyl, alkoxy or —$NR^{10}R^{11}$ radical in which $R^{10}$ and $R^{11}$ represent independently a hydrogen atom or an alkyl radical, or also the

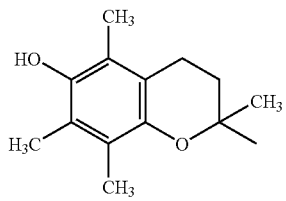

radical
or finally the

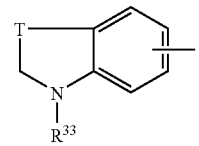

radical in which T represents —$CH_2$— and $R^{33}$ represents a hydrogen atom, an aminoalkyl, alkylaminoalkyl or dialkylaminoalkyl radical;

B represents H;

n represents 0 or 1;

$R^1$ and $R^2$ both represent H;

Ω represents preferably: an $NR^{46}R^{47}$ radical such that $NR^{46}R^{47}$ represents the N-piperazinyl radical or the N-piperazinyl radical optionally N-substituted by an alkyl radical or in which one of $R^{46}$ and $R^{47}$ represents H or a hydroxyalkyl, alkynyl or cyanoalkyl radical and the other represents H or an alkyl radical.

or the $OR^{48}$ radical in which $R^{48}$ represents a hydrogen atom or an alkyl, alkynyl or cyanoalkyl radical.

As regards the compounds of general formula (I) (or their salts) more especially intended to have an inhibitory activity on MAO's and the ROS's, the said compounds having at least one of the following characteristics will be quite particularly preferred:

the compound corresponds to general sub-formula $(I)_1$ or $(I)_2$ in which X represents S or the compound corresponds to general formula $(I)_3$ in which Y represents O;

A represents the

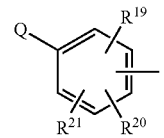

radical in which Q represents OH, two of the $R^{19}$, $R^{20}$ and $R^{21}$ radicals represent an alkyl radical and the third represents H, or in which Q represents a phenyl radical substituted by an OH radical and one or more radicals chosen independently from the alkyl radicals;

B represents H;

n represents 0 or 1;

$R^1$ and $R^2$ both represent H;

Ω represents:

preferably: an $NR^{46}R^{47}$ radical such that $NR^{46}R^{47}$ represents an N-piperazinyl radical or in which one of $R^{46}$ and $R^{47}$ represents H or a hydroxyalkyl, alkynyl or cyanoalkyl radical and the other represents H or an alkyl radical, or the OH radical.

In particular, the compounds of Examples 1 to 30, 210, 291, 316, 319 to 323, 329 to 336 and 346 to 349 (sometimes described in the form of salts) or their pharmaceutically acceptable salts are preferred when an inhibitory activity on MAO's and/or the ROS's is sought in the first place. Even more preferentially, the compounds of Examples 1, 3, 6, 22, 24, 26 to 29, 323 and 332 (sometimes described in the form of salts), or their pharmaceutically acceptable salts, are preferred when an inhibitory activity on MAO's and/or the ROS's is sought in the first place.

According to another variant of the invention, the compounds of general formula (I)$_G$ or their pharmaceutically acceptable salts are more especially intended to have an modulating activity on the sodium channels and they are then preferably such that they correspond to general subformulae (I)$_{G1}$ and (I)$_{G2}$ and that:

A represents either a

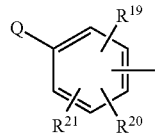

radical in which Q represents H, —OR$^{22}$, SR$^{22}$ or a phenyl radical optionally substituted by one or more of the substituents chosen independently from a halogen atom, an alkyl haloalkyl, alkoxy or alkylthio radical, and a group of two substituents together representing a methylenedioxy or ethylenedioxy radical, or Q represents a —COPh, —OPh, —SPh, —SO$_2$Ph or —CH$_2$Ph radical, said —COPh, —OPh, —SPh, —SO$_2$Ph or —CH$_2$Ph radical being optionally substituted on its aromatic part by one or more of the substituents chosen independently from an alkyl or alkoxy radical and a halogen atom, R$^{22}$ representing a hydrogen atom or an alkyl radical, and R$^{19}$, R$^{20}$ and R$^{21}$ represent, independently, a hydrogen, a halogen, the OH group or an alkyl, alkoxy, cyano, nitro, cycloalkyl, —SO$_2$NHR$^{49}$, —CONHR$^{55}$, —S(O)$_q$R$^{56}$, —NH(CO)R$^{57}$, —CF$_3$, —OCF$_3$ or NR$^{27}$R$^{28}$ radical, R$^{27}$ and R$^{28}$ representing, independently, a hydrogen atom or an alkyl radical or R$^{27}$ and R$^{28}$ forming together with the nitrogen atom which carries them a heterocycle with 5 to 6 members chosen from —CH$_2$—, —NH— and —O—, R$^{49}$ and R$^{55}$ representing, independently each time that they occur, a hydrogen atom or an alkyl or alkylcarbonyl radical, q representing an integer from 0 to 2, R$^{56}$ and R$^{57}$ representing, independently each time that they occur, a hydrogen atom or an alkyl or alkoxy radical, or a

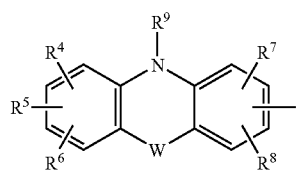

radical in which R$^4$, R$^5$, R$^6$, R$^7$ and R$^8$ represent, independently, a hydrogen atom, a halogen, the OH group or an alkyl, alkoxy or NR$^{10}$R$^{11}$ radical, R$^{10}$ and R$^{11}$ representing, independently, a hydrogen atom or an alkyl radical, or R$^{10}$ and R$^{11}$ forming together with the nitrogen atom an optionally substituted heterocycle comprising 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, R$^9$ represents a hydrogen atom or an alkyl radical, and W does not exist, or represents a bond, or —O—, —S— or —NR$^{18}$—, in which R$^{18}$ represents a hydrogen atom or an alkyl radical;

or a

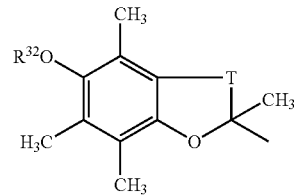

radical in which R$^{32}$ represents a hydrogen atom or an alkyl radical, and T represents a —(CH$_2$)$_m$— radical with m=1 or 2, or also A represents an alkyl, cycloalkyl or cycloalkylalkyl radical;

B represents a hydrogen atom, a linear or branched alkyl radical containing 1 to 6 carbon atoms or a carbocyclic aryl radical optionally substituted 1 to 3 times by the radicals chosen from the group composed of a halogen atom, an alkyl or alkoxy radical, a hydroxy, cyano or nitro radical, an amino, alkylamino or dialkylamino radical and a carbocyclic aryl radical;

X represents NR$^{38}$ or S,

R$^{38}$ representing a hydrogen atom or an alkyl, aralkyl, alkylcarbonyl or aralkylcarbonyl radical, R$^1$ and R$^2$ represent, independently, a hydrogen atom, an alkyl, cycloalkyl, cycloalkylalkyl, alkoxyalkyl, aminoalkyl, —(CH$_2$)$_g$—NH—CO—R radical or an aralkyl or heteroarylalkyl radical optionally substituted on the aryl or heteroaryl group by one or more groups chosen from the group composed of a halogen atom, an alkyl or alkoxy radical, a hydroxy, cyano or nitro radical and an amino, alkylamino or dialkylamino radical, R$^{70}$ representing, independently each time that it occurs, an alkyl or alkoxy radical;

R$^1$ and R$^2$ taken together can optionally form with the carbon atom which carries them a carbocycle with 3 to 7 members;

Ω represents OH or an NR$^{46}$R$^{47}$ radical, in which:

R$^{46}$ and R$^{47}$ represent, independently, a hydrogen atom or an alkyl, cycloalkyl or cycloalkylalkyl, —CO—NH—R$^{51}$, —CO—O—R$^{51}$ or —SO$_2$—R72 radical or one of the heteroaryl, aralkyl, aryloxyalkyl or arylimino radicals optionally substituted on the heteroaryl or aryl group by one or more groups chosen from the group composed of a halogen atom, a linear or branched alkyl or alkoxy radical containing 1 to 6 carbon atoms, a hydroxy, cyano or nitro radical, an amino, alkylamino or dialkylamino radical, R$^{51}$ representing a hydrogen atom, one of the cycloalkyl or cycloalkylalkyl radicals in which the cycloalkyl radical contains 3 to 7 carbon atoms, a linear or branched alkyl radical containing 1 to 8 carbon atoms, a haloalkyl radical, an alkoxyalkyl radical or also an aryl or aralkyl radical, said aryl or aralkyl radical being able to be substituted by one or more of the substituents chosen independently from a halogen atom and an alkyl or alkoxy radical, and $R^{72}$ representing an alkyl radical, or one of the phenyl or aralkyl radicals optionally substituted on the aromatic ring by one or more of the radicals chosen from a halogen atom, an alkyl or alkoxy radical;

g represents an integer from 1 to 6; and finally n represents an integer from 0 to 6.

According to said variant of the invention, the compounds of general formula $(I)_G$ or their pharmaceutically acceptable salts that are more especially intended to have an modulating activity on the sodium channels will preferably be compounds of general formula (I) that correspond to general sub-formulae $(I)_1$ and $(I)_2$ and that:

A represents either a

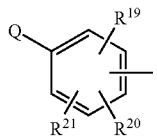

radical in which Q represents H, —$OR^{22}$, $SR^{22}$ or a phenyl radical optionally substituted by one or more of the substituents chosen independently from a halogen atom, an alkyl or alkoxy radical, and a group of two substituents together representing a methylenedioxy or ethylenedioxy radical, or Q represents a —COPh, —OPh, —SPh, —$SO_2$Ph or —$CH_2$Ph radical, said —COPh, —OPh, —SPh, —$SO_2$Ph or —$CH_2$Ph radical being optionally substituted on its aromatic part by one or more of the substituents chosen independently from an alkyl or alkoxy radical and a halogen atom, $R^{22}$ representing a hydrogen atom or an alkyl radical, and $R^{19}$, $R^{20}$ and $R^{21}$ represent, independently, a hydrogen, a halogen, the OH group or an alkyl, alkoxy, cyano, nitro, cycloalkyl, —$SO_2NHR^{49}$, —$CONHR^{55}$, —$S(O)_q R^{56}$, —NH(CO)$R^{57}$, —$CF_3$, —$OCF_3$ or $NR^{27}R^{28}$ radical, $R^{27}$ and $R^{28}$ representing, independently, a hydrogen atom or an alkyl radical or $R^{27}$ and $R^{28}$ forming together with the nitrogen atom which carries them a heterocycle with 5 to 6 members chosen from —$CH_2$—, —NH— and —O—, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy-radical, or a

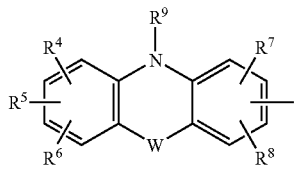

radical in which $R^4$, $R^5$, $R^6$, $R^7$ and $R^8$ represent, independently, a hydrogen atom, a halogen, the OH group or an alkyl, alkoxy or $NR^{10}R^{11}$ radical, $R^{10}$ and $R^{11}$ representing, independently, a hydrogen atom or an alkyl radical, or $R^{10}$ and $R^{11}$ forming together with the nitrogen atom an optionally substituted heterocycle comprising 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^9$ represents a hydrogen atom or an alkyl radical, and W does not exist, or represents a bond, or —O—, —S— or —$NR^{18}$—, in which $R^{18}$ represents a hydrogen atom or an alkyl radical;

or a

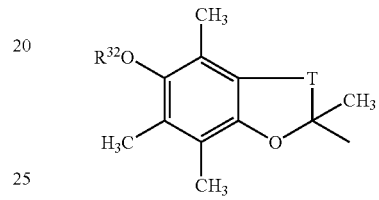

radical in which $R^{32}$ represents a hydrogen atom or an alkyl radical, and T represents a —$(CH_2)_m$— radical with m=1 or 2, or also A represents an alkyl, cycloalkyl or cycloalkylalkyl radical;

B represents a hydrogen atom, a linear or branched alkyl radical containing 1 to 6 carbon atoms or a carbocyclic aryl radical optionally substituted 1 to 3 times by the radicals chosen from the group composed of a halogen atom, an alkyl or alkoxy radical, a hydroxy, cyano or nitro radical, an amino, alkylamino or dialkylamino radical and a carbocyclic aryl radical;

X represents $NR^{38}$ or S, $R^{38}$ representing a hydrogen atom or an alkyl, aralkyl, alkylcarbonyl or aralkylcarbonyl radical, $R^1$ and $R^2$ represent, independently, a hydrogen atom, an alkyl, cycloalkyl, cycloalkylalkyl, alkoxyalkyl, aminoalkyl, —$(CH_2)_g$—NH—CO—$R^{70}$ radical or an aralkyl or heteroarylalkyl radical optionally substituted on the aryl or heteroaryl group by one or more groups chosen from the group composed of a halogen atom, an alkyl or alkoxy radical, a hydroxy, cyano or nitro radical and an amino, alkylamino or dialkylamino radical, $R^{70}$ representing, independently each time that it occurs, an alkyl or alkoxy radical;

$R^1$ and $R^2$ taken together can optionally form with the carbon atom which carries them a carbocycle with 3 to 7 members;

Ω represents OH or an $NR^{46}R^{47}$ radical, in which:

$R^{46}$ and $R^{47}$ represent, independently, a hydrogen atom or an alkyl, cycloalkyl or cycloalkylalkyl, —CO—NH—$R^{51}$, —CO—O—$R^{51}$ or —$SO_2$—$R^{72}$ radical or one of the heteroaryl, aralkyl, aryloxyalkyl or arylimino radicals optionally substituted on the heteroaryl or aryl group by one or more groups chosen from the group composed of a halogen atom, a linear or branched alkyl or alkoxy radical containing 1 to 6 carbon atoms, a hydroxy, cyano or nitro radical, an amino, alkylamino or dialkylamino radical, $R^{51}$ representing a hydrogen atom, one of the cycloalkyl or cycloalkylalkyl radicals in which the cycloalkyl radical contains 3 to 7 carbon atoms, a linear or branched alkyl radical containing 1 to 8 carbon atoms, an alkoxyalkyl radical or also an aryl or aralkyl radical, said aryl or aralkyl radical being able to be substituted by one or more of the substituents chosen independently from a halogen atom and an alkyl or alkoxy radical, and $R^{72}$ representing an alkyl radical, or one of the phenyl or aralkyl radicals optionally substituted on the aromatic ring by one or more of the radicals chosen from a halogen atom, an alkyl or alkoxy radical;

g represents an integer from 1 to 6; and finally n represents an integer from 0 to 6.

More preferentially, the compounds of general formula (I) (or their pharmaceutically acceptable salts) intended to have a modulating activity on the sodium channels corresponding to general sub-formulae (I), and (I)$_2$ and will be such that:

A represents the

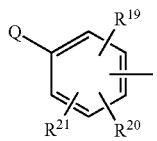

radical in which Q represents H, $-OR^{22}$, $-SR^{22}$ or a phenyl radical optionally substituted by one or more of the substituents chosen independently from a halogen atom and an alkyl or alkoxy radical, or also Q represents a $-COPh$, $-OPh$, $-SPh$, $-SO_2Ph$ or $-CH_2Ph$ radical, said $-COPh$, $-OPh$, $-SPh$, $-SO_2Ph$ or $-CH_2Ph$ radical being optionally substituted on its aromatic part by one or more of the substituents chosen from an alkyl or alkoxy radical and a halogen atom, $R^{22}$ representing a hydrogen atom or an alkyl radical, and $R^{19}$, $R^{20}$ and $R^{21}$ represent, independently, a hydrogen, a halogen, the OH group or an alkyl, alkoxy, cyano, nitro, cycloalkyl, $-SO_2NHR^{49}$, $-CONHR^{55}$, $-S(O)_qR^{56}$, $-NH(CO)R^{57}$, $-OCF_3$ or $NR^{27}R^{28}$ radical, $R^{27}$ and $R^{28}$ representing, independently, a hydrogen atom or an alkyl radical or $R^{27}$ and $R^{28}$ forming together with the nitrogen atom which carries them a heterocycle with 5 to 6 members chosen from $-CH_2-$, $-NH-$ and $-O-$, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, or also A represents an alkyl, cycloalkyl or cycloalkylalkyl radical, B represents a hydrogen atom, a linear or branched alkyl radical containing 1 to 6 carbon atoms or a carbocyclic aryl radical optionally substituted 1 to 3 times by the radicals chosen from the group composed of a halogen atom, an alkyl or alkoxy radical, a hydroxy, cyano or nitro radical, an amino, alkylamino or dialkylamino radical and a carbocyclic aryl radical;

X represents $NR^{38}$ or S, $R^{38}$ representing a hydrogen atom or an alkyl, aralkyl, alkylcarbonyl or aralkylcarbonyl radical, $R^1$ and $R^2$ represent, independently, a hydrogen atom, an alkyl, cycloalkyl, cycloalkylalkyl, alkoxyalkyl, aminoalkyl, $-(CH_2)_g-NH-CO-R^{70}$ radical or an aralkyl or heteroarylalkyl radical optionally substituted on the aryl or heteroaryl group by one or more groups chosen from the group composed of a halogen atom, an alkyl or alkoxy radical, a hydroxy, cyano or nitro radical and an amino, alkylamino or dialkylamino radical, $R^{70}$ representing, independently each time that it occurs, an alkyl or alkoxy radical;

$R^1$ and $R^2$ taken together can optionally form with the carbon atom which carries them a carbocycle with 3 to 7 members;

Ω represents the $NR^{46}R^{47}$ radical, in which:

$R^{46}$ and $R^{47}$ represent, independently, a hydrogen atom or an alkyl, cycloalkyl or cycloalkylalkyl, $-CO-NH-R^{51}$, $-CO-O-R^{51}$ or $-SO_2-R^{72}$ radical or one of the heteroaryl, aralkyl, aryloxyalkyl or arylimino radicals optionally substituted on the heteroaryl or aryl group by one or more groups chosen from the group composed of a halogen atom, a linear or branched alkyl or alkoxy radical containing 1 to 6 carbon atoms, a hydroxy, cyano or nitro radical, an amino, alkylamino or dialkylamino radical, $R^{51}$ representing a hydrogen atom, one of the cycloalkyl or cycloalkylalkyl radicals in which the cycloalkyl radical contains 3 to 7 carbon atoms, a linear or branched alkyl radical containing 1 to 8 carbon atoms, an alkoxyalkyl radical or also an aryl or aralkyl radical, said aryl or aralkyl radical being able to be substituted by one or more of the substituents chosen independently from a halogen atom and an alkyl or alkoxy radical, and $R^{72}$ representing an alkyl radical, or one of the phenyl or aralkyl radicals optionally substituted on the aromatic ring by one or more of the radicals chosen from a halogen atom, an alkyl or alkoxy radical and finally;

n represents an integer from 0 to 6.

As regards the compounds of general formula (I) (or their salts) more especially intended to have a modulating activity on the sodium channels, said compounds of general sub-formula (I), or (I)$_2$ will generally be preferred having at least one of the following characteristics:

A represents:
the

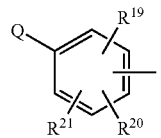

radical in which Q represents a hydrogen atom, a halogen atom, the OH group, an alkoxy, alkylthio or phenyl radical optionally substituted by one or more radicals chosen from a halogen atom and an alkoxy radical, and $R^{19}$, $R^{20}$ and $R^{21}$ represent, independently, a hydrogen atom, a halogen atom, the OH group or an alkyl, alkoxy, cyano, nitro, cycloalkyl, $-SO_2NHR^{49}$, $-CONHR^{55}$, $-S(O)_qR^{56}$, $-NH(CO)R^{57}$, $-CF_3$, $-OCF_3$ or $NR^{27}R^{28}$ radical, $R^{27}$ and $R^{28}$ representing, independently, a hydrogen atom or an alkyl radical or $R^{27}$ and $R^{28}$ forming together with the nitrogen atom which carries them a heterocycle with 5 to 6 members chosen from $-CH_2-$, $-NH-$ and $-O-$, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical;

or an alkyl, cycloalkyl or cycloalkylalkyl radical;

B represents H, alkyl, or phenyl;

n represents 0 or 1;

$R^1$ and $R^2$ are such that:

$R^1$ and $R^2$ represent independently H, an alkyl, cycloalkyl radical and in particular cyclohexyl, cycloalkylalkyl, or also an aralkyl or heteroarylalkyl radical optionally substituted on the aryl or heteroaryl group by one or more groups chosen from the group comprising a halogen atom, an alkyl or alkoxy radical; in particular, $R^1$ represents a linear or branched alkyl radical containing 2 to 6 carbon atoms, and preferably 4 to 6 carbon atoms, the cyclohexyl radical or the indolylmethyl radical optionally substituted and R2 represents H;

or $R^1$ and $R^2$ taken together with the carbon atom which carries them a carbocycle with 3 to 7 members;

Ω represents an OH radical or preferably an $NR^{46}R^{47}$ radical in which $R^{46}$ represents H, an alkyl radical and in particular isopropyl, n-pentyl or n-hexyl, a cycloalkylalkyl radical, a cycloalkyl radical and in particular cyclobutyl, cyclopentyl or cyclohexyl, an alkylcarbonyl radical, an alkoxycarbonyl radical, a (cycloalkyl)oxycarbonyl radical, a cycloalkylalkoxycarbonyl radical, an alkylaminocarbonyl radical or also a benzyl radical optionally substituted by an alkoxy radical, and $R^{47}$ represents H;

X represents S or preferably the $NR^{38}$ radical in which $R^{38}$ represents a hydrogen atom or an alkyl, aralkyl, alkylcarbonyl or aralkylcarbonyl radical.

As regards the compounds of general formula (I) (or their salts) more particularly intended to have a modulatory activity on the sodium channels, said compounds of general sub-formula (I)₁ or (I)₂ comprising at least one of the following characteristics will be even more particularly preferred:

A represents:

the

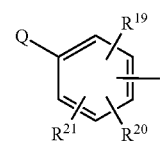

radical in which Q represents a hydrogen atom, a halogen atom or an alkoxy, alkylthio or phenyl radical optionally substituted by one or more radicals chosen from a halogen atom and an alkoxy radical, and $R^{19}$, $R^{20}$ and $R^{21}$ represent, independently, a hydrogen atom, a halogen atom or an alkyl, alkoxy, cyano, cycloalkyl, $-CF_3$ or $NR^{27}R^{28}$ radical, $R^{27}$ and $R^{28}$ representing, independently, a hydrogen atom or an alkyl radical or $R^{27}$ and $R^{28}$ forming together with the nitrogen atom which carries them a heterocycle with 5 to 6 members chosen from $-CH_2-$ and $-NH-$;

or a cycloalkyl radical;

B represents H;

n represents 0 or 1;

$R^1$ represents H, an alkyl, cycloalkyl and in particular a cyclohexyl radical, and $R^2$ represents H;

Ω represents an $NR^{46}R^{47}$ radical in which $R^{46}$ represents a cycloalkylalkyl radical, a cycloalkyl radical and in particular cyclobutyl or cyclohexyl, an alkoxycarbonyl radical, a (cycloalkyl)oxycarbonyl radical, a cycloalkylalkoxycarbonyl radical or also a benzyl radical optionally substituted by an alkoxy radical, and $R^{47}$ represents H;

X represents the NH radical.

Furthermore, still for the compounds more particularly intended to have a modulatory activity on sodium channels, when n represents 1, $R^1$ and $R^2$ will preferably represent hydrogen atoms.

In particular, the compounds of Examples 1, 3, 6, 7, 9 to 11, 13, 15 to 17, 20, 24, 26, 28 to 318, 321, 324 to 330, 337 to 345, 378 to 398, 437, 443 to 461 and 469 (sometimes described in the form of salts), or their pharmaceutically acceptable salts, and notably the compounds of Examples 1, 3, 6, 7, 9 to 11, 13, 15 to 17, 20, 24, 26, 28 to 318, 321, 324 to 330 and 337 to 345 (sometimes described in the form of salts), or their pharmaceutically acceptable salts, are preferred when a modulating activity on the sodium channels is sought in the first place.

More preferentially, the compounds of Examples 1, 6, 7, 11, 13, 15, 17, 20, 24, 31 to 38, 42, 43, 46 to 48, 53, 56, 57, 59 to 61, 64 to 80, 82 to 88, 92 to 95, 97, 105, 106, 108, 110, 113, 117, 118, 121 to 123, 125, 128, 130 to 139, 142 to 145, 149, 151, 152, 154, 162 to 166, 168 to 178, 181, 183 to 186, 188, 190 to 196, 198 to 206, 208 to 210, 212 to 218, 220 to 231, 233 to 250, 252 to 259, 261 to 281, 283 to 288, 293 to 313, 324 and 338 to 340 (sometimes described in the form of salts), or their pharmaceutically acceptable salts, are preferred when a modulating activity on the sodium channels is sought in the first place.

According to a more particular variant of the invention, the compounds of the invention of general formula (I) as defined previously in which:

Het is such that the compounds of general formula (I) correspond to one of the general sub-formulae (I)₁ and (I)₂ in which X represents NH or S or general sub-formula (I)₃ in which Y represents O;

A represents a

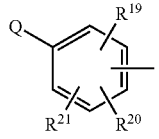

radical in which Q represents OH, two of the $R^{19}$, $R^{20}$ and $R^{21}$ radicals represent an alkyl radical and the third represents a hydrogen atom, or in which Q represents a phenyl radical substituted by an OH radical and one or more radicals chosen independently from alkyl radicals;

B represents a hydrogen atom;

n represents 0 or 1;

$R^1$ and $R^2$ both represent a hydrogen atom;

and Ω represents an $NR^{46}R^{47}$ radical in which $R^{46}$ represents a hydrogen atom or an alkyl, alkynyl, hydroxyalkyl or cyanoalkyl radical and $R^{47}$ represents a hydrogen atom or an alkyl radical or also $R^{46}$ and $R^{47}$ form together with the nitrogen atom which carries them a non-aromatic heterocycle with 5 to 7 members, the additional members being chosen from —CH$_2$— and —NH—;

can be used to prepare a medicament intended both to inhibit MAO's and lipidic peroxidation and to modulate the sodium channels.

More preferentially, the compounds of general formula (I) which can be used to prepare a medicament intended both to inhibit MAO's and lipidic peroxidation and to modulate the sodium channels will be such that:

Het is such that the compounds of general formula (I) correspond to general sub-formula (I)$_1$ in which X represents S or to general sub-formula (I)$_3$ in which Y represents O;

A represents a

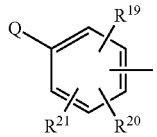

radical in which Q represents OH, two of the radicals $R^{19}$, $R^{20}$ and $R^{21}$ represent an alkyl radical and the third represents a hydrogen atom;

B represents a hydrogen atom;

n represents 0 or 1;

R1 and $R^2$ both represent a hydrogen atom;

and Ω represents an $NR^{46}R^{47}$ radical in which $R^{46}$ represents a hydrogen atom or an alkyl, hydroxyalkyl or cyanoalkyl radical and $R^{47}$ represents a hydrogen atom or an alkyl radical or also $R^{46}$ and $R^{47}$ form together with the nitrogen atom which carries them an N-piperazinyl radical.

Still for the compounds of general formula (I) which can be used to prepare a medicament intended both to inhibit the MAO's and lipidic peroxidation and to modulate the sodium channels, n will preferably represent 0 when Het is such that the compounds of general formula (I) correspond to general sub-formula (I)$_1$ in which X represents S and preferably 1 when Het is such that the compounds of general formula (I) correspond to general sub-formula (I)$_3$ in which Y represents O.

In particular, the compounds of Examples 1, 3, 6, 24, 26, 28 and 29 (sometimes described in the form of salts) or their pharmaceutically acceptable salts will be preferred if one wishes to prepare a medicament intended both to inhibit MAO's and lipidic peroxidation and to modulate the sodium channels.

The invention also offers, as medicaments, the compounds of general formula (II)

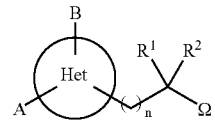

(II)

in racemic, enantiomeric form or any combinations of these forms, in which Het is a heterocycle with 5 members comprising 2 heteroatoms and such that general formula (II) correspond exclusively to one of the following sub-formulae:

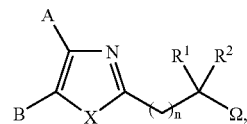

(II)$_1$

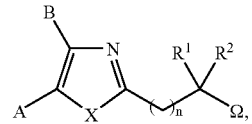

(II)$_2$

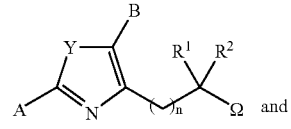

(II)$_3$ and

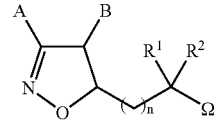

(II)$_4$ in which

A represents either a

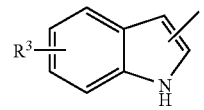

radical in which $R^3$ represents a hydrogen atom, the OH group or an alkoxy or alkyl radical, or a

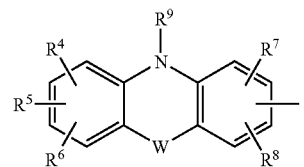

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, $R^9$ represents a hydrogen atom, an alkyl radical or a —$COR^{15}$ group, $R^{15}$ representing a hydrogen atom or an alkyl, alkoxy or $NR^{16}R^{17}$ radical, $R^{16}$ and $R^{17}$ representing, independently, a hydrogen atom or an alkyl radical, or $R^{16}$ and $R^{17}$ forming together with the nitrogen atom an optionally substituted heteroatom with 4 to 7 members and 1 to 3 heteroatoms including the nitrogen atom already present, the additional heteroatoms being chosen independently from the group constituted by the O, N and S atoms, and W doesn't exist, or represents a bond, or —O—, —S— or —$NR^{18}$—, in which $R^{18}$ represents a hydrogen atom or an alkyl radical;

or a

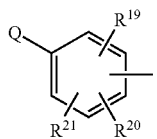

radical in which Q represents H, —$OR^{22}$, —$SR^{22}$, —$NR^{23}R^{24}$, a phenyl radical optionally substituted by one or more of the substituents chosen independently from a halogen atom, an OH, cyano, nitro, alkyl, alkoxy or —$NR^{10}R^{11}$ radical and a group with two substituents together representing a methylenedioxy or ethylenedioxy radical, or also Q represents a —COPh, —$SO_2$Ph or —$CH_2$Ph radical, said —COPh, —$SO_2$Ph or —$CH_2$Ph radical being optionally substituted on its aromatic part by one or more of the substituents chosen independently from an alkyl or alkoxy radical and a halogen atom, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{12}$ representing a hydrogen atom, an alkyl or alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, $R^{22}$ representing a hydrogen atom, an alkyl radical or an aryl radical optionally substituted by one or more substituents chosen from the alkyl, OH, halogen, nitro and alkoxy radicals, $R^{23}$ and $R^{24}$ representing, independently, a hydrogen atom, an alkyl radical or a —CO—$R^{25}$ radical, $R^{25}$ representing an alkyl radical, and $R^{19}$, $R^{20}$ and $R^{21}$ represent, independently, a hydrogen, a halogen, the OH or $SR^{26}$ group, or an alkyl, cycloalkyl, alkenyl, alkoxy, cyano, nitro, —$SO_2NHR^{49}$, —$CONHR^{55}$, —$S(O)_qR^{56}$, —$NH(CO)R^{57}$, —$CF_3$, —$OCF_3$ or $NR^{27}R^{28}$ radical, $R^{26}$ representing a hydrogen atom or an alkyl radical, $R^{27}$ and $R^{28}$ representing, independently, a hydrogen atom, an alkyl radical or a —$COR^{29}$ group, or $R^{27}$ and $R^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, $R^{29}$ representing a hydrogen atom, an alkyl, alkoxy or —$NR^{30}R^{31}$ radical, $R^{30}$ and $R^{31}$ representing, independently, a hydrogen atom or an alkyl radical, or $R^{30}$ and $R^{31}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, or a

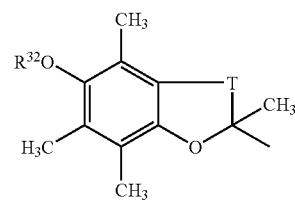

radical in which $R^{32}$ represents a hydrogen atom or an alkyl radical, and T represents a —$(CH_2)_m$— radical with m=1 or 2, or finally a

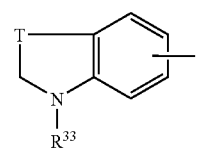

radical in which $R^{33}$ represents a hydrogen atom or an alkyl, —Σ—$NR^{34}R^{35}$ or —Σ—$CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or $NR^{10}R^{11}$ radicals, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, and T represents a —$(CH_2)_m$— radical with m=1 or 2, or also A represents an alkyl, cycloalkyl or cycloalkylalkyl radical;

X represents S or $NR^{38}$, $R^{38}$ representing a hydrogen atom or an alkyl, cyanoalkyl, aralkyl, alkylcarbonyl or aralkylcarbonyl radical, Y represents O or S;

$R^1$ represents a hydrogen atom, an alkyl, aminoalkyl, alkoxyalkyl, cycloalkyl, cycloalkylalkyl, trifluoromethylalkyl, alkenyl, allenyl, allenylalkyl, alkynyl, cyanoalkyl, —$(CH_2)_g$-$Z^1R^{39}$, —$(CH_2)_g$—$COR^{40}$, —$(CH_2)_g$—$NHCOR^{70}$, aryl, aralkyl, arylcarbonyl, heteroarylalkyl or aralkylcarbonyl radical, the aryl group of the aryl, aralkyl, arylcarbonyl, heteroarylalkyl or aralkylcarbonyl radicals being itself optionally substituted by one or more substituents chosen from the group constituted by the alkyl, halogen, alkoxy, nitro, cyano, cyanoalkyl, amino, alkylamino, dialkylamino, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom, an alkyl, aminoalkyl, alkoxyalkyl, cycloalkyl, cycloalkylalkyl, trifluoromethylalkyl or —$(CH_2)_g$—$NHCOR^{71}$ radical, or also one of the aralkyl or heteroarylalkyl radicals optionally substituted on the aryl or heteroaryl group by one or more of the groups chosen independently from the group composed of a halogen atom and an alkyl, alkoxy, hydroxy, cyano, nitro, amino, alkylamino or dialkylamino radical, $R^{70}$ and $R^{71}$ representing independently an alkyl or alkoxy radical;

or $R^1$ and $R^2$, taken together with the carbon atom which carries them, form a carbocycle with 3 to 7 members;

B represents a hydrogen atom, an alkyl radical, a —$(CH_2)_g$-$Z^3R^{44}$ radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, $Z^3$ representing a bond, —O—, —$NR^{45}$— or —S—, $R^{44}$ and $R^{45}$ representing, independently, a hydrogen atom or an alkyl, alkenyl, alkynyl, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —$(CH_2)_g$-$Z^4R^{50}$, —$(CH_2)_k$—$COR^{51}$, —$(CH_2)_k$—$COOR^{51}$, —$(CH_2)_k$—$CONHR^{51}$ or —$SO_2R^{51}$ radical, or also a radical chosen from the aryl, aralkyl, aryloxyalkyl, arylcarbonyl, arylimino, aralkylcarbonyl, heteroaryl and in particular pyridinyl, pyridinylalkyl or pyridinylcarbonyl radicals, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by one or more of the substituents chosen independently from halogen, alkyl, alkoxy, hydroxy, nitro, cyano, cyanoalkyl, amino, alkylamino, dialkylamino, —$(CH_2)_k$-$Z^5R^{50}$, —$(CH_2)_k$—$COR^{51}$ and —$(CH_2)_k$—$COOR^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group composed of —$CH(R^{53})$—, —$NR^{54}$—, —O—, —S— and —CO—, $R^{50}$ and $R^{52}$, representing, independently each time that they occur, a hydrogen atom or an alkyl, alkenyl, alkynyl, allenyl, allenylalkyl or cyanoalkyl radical, $R^{51}$ representing, independently each time that they occur, a hydrogen atom, one of the cycloalkyl or cycloalkylalkyl radicals in which the cycloalkyl radical contains 3 to 7 carbon atoms, a linear or branched alkyl radical containing 1 to 8 carbon atoms, an alkenyl, alkynyl, allenyl, allenylalkyl, cyanoalkyl, alkoxyalkyl or $NR^{58}R^{59}$ radical, or also an aryl or aralkyl radical, said aryl or aralkyl radical being able to be substituted by one or more of the substituents chosen independently from a halogen atom and an alkyl or alkoxy radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—$COR^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, $-(CH_2)_k-Z^8R^{63}$ and $-(CH_2)_k-COR^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, $-O-$, $-NR^{67}-$ or $-S-$, $R^{63}$ and $R^{67}$ representing, independently, a hydrogen atom, an alkyl, allenyl, allenylalkyl, alkenyl, alkynyl or cyanoalkyl radical $R^{64}$ representing a hydrogen atom, an alkyl, allenylalkyl, alkenyl, alkenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, and $R^{48}$ represents a hydrogen atom or an alkyl, alkynyl or cyanoalkyl radical;

g and p, each time that they occur, being independently integers from 1 to 6, and k and n, each time that they occur, being independently integers from 0 to 6;

it being understood that when Het is such that the compound of general formula (II) corresponds to general sub-formula $(II)_4$, then:

A represents the 4-hydroxy-2,3-di-tertiobutyl-phenyl radical;

B, $R^1$ and $R^2$ all represent H; and finally

Ω represents OH;

it also being understood that at least one of the following characteristics must be present:
Het is a thiazole, oxazole or isoxazoline ring, and
A represents a

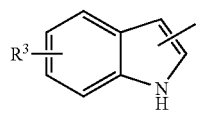

radical in which $R^3$ represents a hydrogen atom, the OH group or an alkoxy or alkyl radical,
or A represents a

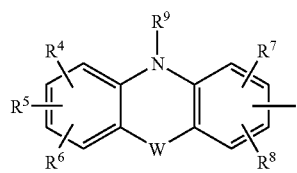

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom or an alkyl radical $R^9$ represents a hydrogen atom or an alkyl radical, and W doesn't exist, or represents a bond, or $-O-$, $-S-$ or $-NR^{18}-$, in which $R^{18}$ represents a hydrogen atom or an alkyl radical,
or A represents a

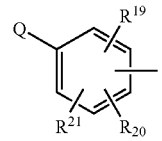

radical in which Q represents OH or Q represents a phenyl radical substituted by an OH radical and one or more of the radicals chosen independently from a halogen atom and an OH, alkyl, alkoxy or $-NR^{10}OR^{11}$ radical in which $R^{10}$ and $R^{11}$ represent independently a hydrogen atom or an alkyl radical,
or also A represents a

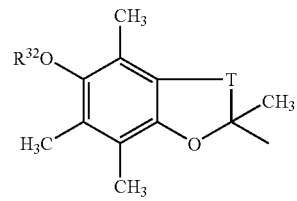

radical in which $R^{32}$ represents a hydrogen atom or an alkyl radical and T represents a $-(CH_2)_m-$ radical with m=1 or 2,
or finally A represents a

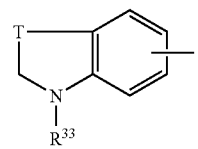

radical in which the $R^{33}$ radical represents a hydrogen atom or an alkyl, $-\Sigma-NR^{34}R^{35}$ or $-\Sigma-CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or $NR^{10}R^{11}$ radicals, $R^{10}$ and $R^{11}$ representing, independently, a hydrogen atom, an alkyl radical, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and T represents a —(CH$_2$)$_m$— radical with m=1 or 2;

Het is an imidazole ring,

A represents a

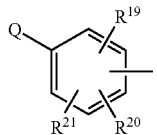

radical in which Q represents OH, and Ω represents NR$^{46}$R$^{47}$ in which R$^{46}$ or R$^{47}$ represents an aminophenyl, nitrophenyl, aminophenylcarbonyl, nitrophenylcarbonyl, aminophenylalkyl or nitrophenylalkyl radical;

A represents a

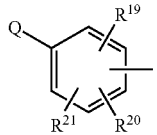

radical B represents a carbocyclic aryl radical optionally substituted 1 to 3 times by radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, and one of R$^1$ and R$^2$ represents one of the optionally substituted arylalkyl or heteroarylalkyl radicals;

A represents a cycloalkyl or cycloalkylalkyl radical;

Ω represents NR$^{46}$R$^{47}$ and one of R$^{46}$ and R$^{47}$ represents an alkenyl, allenyl, allenylalkyl, alkynyl, cyanoalkyl or hydroxyalkyl radical;

one of R$^1$ and R$^2$ represents a cycloalkyl or cycloalkylalkyl radical;

none of R$^1$ and R$^2$ represents H;

n=1 and A represents a biphenyl, phenoxyphenyl, phenylthiophenyl, phenylcarbonylphenyl or phenylsulphonylphenyl radical;

when Het is a thiazole ring and Ω represents the OR$^{48}$ radical in which R$^{48}$ is a cyanoalkyl radical, then the cyano group is not attached to the carbon atom immediately adjacent to the oxygen atom;

or the pharmaceutically acceptable salts of the compounds of general formula (II).

Generally, the medicaments of general formula (II) having one of the following additional characteristics are preferred:

i. n=0,

Het is an oxazole, thiazole or isoxazoline ring

A represents a

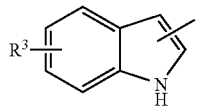

radical in which R$^3$ represents a hydrogen atom, the OH group or an alkoxy or alkyl radical, or A represents a

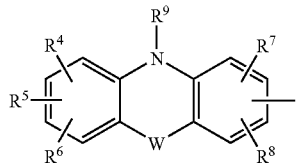

radical in which R$^4$, R$^5$, R$^6$, R$^7$, R$^8$ and R$^9$ represent hydrogen atoms and W doesn't exist, or represents a bond, or —O—, —S— or —NR$^{18}$— in which R$^{18}$ represents a hydrogen atom or an alkyl radical, or A represents a

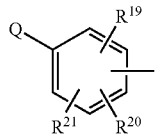

radical in which Q represents OH and two of the R$^{19}$, R$^{20}$ and R$^{21}$ radicals represent alkyl radicals, or in which Q represents a phenyl radical substituted by an OH radical and a radical or radicals chosen independently from a halogen atom and an OH, alkyl, alkoxy or —NR$^{10}$R$^{11}$ radical in which R$^{10}$ and R$^{11}$ represent independently a hydrogen atom or an alkyl radical, or also A represents a

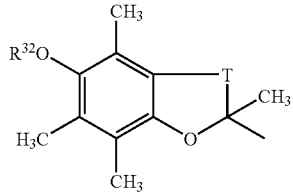

radical in which R$^{32}$ represents a hydrogen atom or an alkyl radical and T represents —(CH$_2$)$_2$—, or finally A represents a

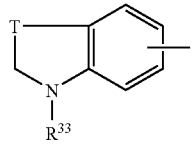

radical in which T represents the —CH$_2$— radical and the R$^{33}$ radical represents a hydrogen atom or a —Σ—NR$^{34}$R$^{35}$ radical, Σ representing a linear or branched alkylene radical containing 1 to 6 carbon atoms, and R$^{34}$ and R$^{35}$ representing, independently, a hydrogen atom or an alkyl radical, B represents H, R$^1$ and R$^2$ represent, independently, a hydrogen atom or an alkyl radical, and Ω represents an NR$^{46}$R$^{47}$ radical in which one of R$^{46}$ and R$^{47}$ represents an alkyl, alkenyl, allenyl, allenylalkyl, alkynyl, cyanoalkyl or hydroxyalkyl radical and the other represents a hydrogen atom or an alkyl radical; or ii. n=0, A represents a

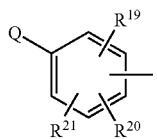

radical in which Q represents a hydrogen atom or an —OR$^{22}$ or —SR$^{22}$ radical in which R$^{22}$ represents an alkyl radical or an aryl radical optionally substituted by one or more substituents chosen from the alkyl, OH, halogen, nitro and alkoxy radicals, R$^{19}$, R$^{20}$ and R$^{21}$ represent, independently, a hydrogen, a halogen, an SR$^{26}$ radical, or an alkyl, cycloalkyl, alkenyl, alkoxy, cyano, nitro, —SO$_2$NHR$^{49}$, —CONHR$^{55}$, —S(O)$_q$R$^{56}$, —NH(CO)R$^{57}$, —CF$_3$, —OCF$_3$ or NR$^{27}$R$^{28}$ radical, R$^{26}$ representing an alkyl radical, R$^{27}$ and R$^{28}$ representing, independently, a hydrogen atom or an alkyl radical or R$^{27}$ and R$^{28}$ forming together with the nitrogen atom which carries them a heterocycle with 5 to 6 members chosen from —CH$_2$—, —NH— and —O—, R$^{49}$ and R$^{55}$ representing, independently each time that they occur, a hydrogen atom or an alkyl or alkylcarbonyl radical, q representing an integer from 0 to 2, R$^{56}$ and R$^{57}$ representing, independently each time that they occur, a hydrogen atom or an alkyl or alkoxy radical, and one of R$^1$ and R$^2$ represents a cycloalkyl or cycloalkylalkyl radical or none of R$^1$ and R$^2$ represent a hydrogen atom; or finally iii. n=1, A represents an optionally substituted biphenyl radical or the cyclohexylphenyl radical, B represents a hydrogen atom, R$^1$ and R$^2$ each represent a hydrogen atom, and Ω represents an NR$^{46}$R$^{47}$ radical in which R$^{46}$ represents a —COOR$^{51}$ radical, R$^{51}$ representing an alkyl, haloalkyl, cycloalkyl, cycloalkylalkyl or alkoxyalkyl radical (and in particular an alkyl, cycloalkyl, cycloalkylalkyl or alkoxyalkyl radical) and R$^{47}$ representing a hydrogen atom.

In case i., it is preferred moreover that A represents a

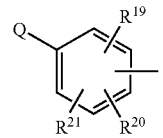

radical in which Q represents OH and two of the R$^{19}$, R$^{20}$ and R$^{21}$ radicals represent alkyl radicals.

In cases ii. and iii., it is preferred moreover that Het represents an imidazole ring.

Preferably, the medicaments of general formula (II) will be chosen from the compounds described (sometimes in the form of salts) in Examples 1 to 35, 52, 57, 61, 80, 82, 83, 85 to 87, 90, 94, 113, 115, 123, 127, 130, 132, 134, 138, 139, 147, 152, 154, 161, 164, 169, 171 to 173, 176 to 180, 203, 237 to 239, 243 to 247, 249, 251, 255, 258 to 262, 264 to 271, 273 to 275 and 277 to 349, or the pharmaceutically acceptable salts of these compounds.

More preferentially, the medicaments of general formula (II) will be chosen from the compounds described (sometimes in the form of salts) in Examples 1, 3, 6, 7, 11, 17, 24, 26 to 35, 57, 61, 82, 83, 85 to 87, 94, 113, 123, 130, 132, 134, 138, 139, 152, 154, 164, 169, 171 to 173, 176 to 178, 203, 237 to 239, 243 to 247, 249, 255, 258, 259, 261, 262, 264 to 271, 273 to 275, 277 to 281, 283 to 288, 293 to 313, 321, 323, 324, 332 and 338 to 340, or the pharmaceutically acceptable salts of these compounds.

Moreover, the same preferences as those indicated for the compounds of general formula (I) are moreover applicable by analogy to the compounds of general formula (II).

The invention also relates, as new industrial products, to the compounds of general formula (III)$_G$ (III)$_G$

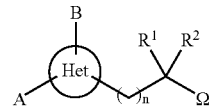

in racemic, enantiomeric form or any combination of these forms, in which Het is a heterocycle with 5 members comprising 2 heteroatoms and such that general formula (III)$_G$ corresponds exclusively to one of the following sub-formulae:

(III)$_{G1}$

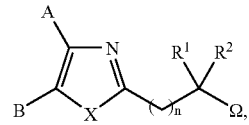

(III)$_{G2}$

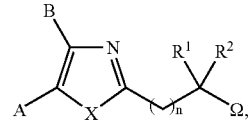

(III)$_{G3}$

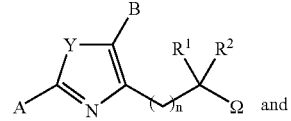

and

-continued

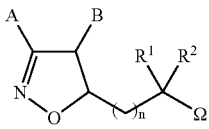
(III)$_{G4}$ in which

A represents either a

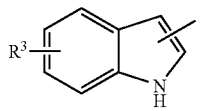

radical in which $R^3$ represents a hydrogen atom, the OH group or an alkoxy or alkyl radical, or a

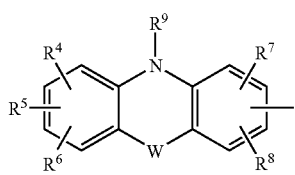

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^9$ represents a hydrogen atom, an alkyl radical or a —$COR^{15}$ group, $R^{15}$ representing a hydrogen atom or an alkyl, alkoxy or $NR^{16}R^{17}$ radical, $R^{16}$ and $R^{17}$ representing, independently, a hydrogen atom or an alkyl radical, or $R^{16}$ and $R^{17}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and W doesn't exist, or represents a bond, or —O—, —S— or —$NR^{18}$—, in which $R^{18}$ represents a hydrogen atom or an alkyl radical;

either a

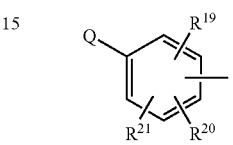

radical in which Q represents H, —$OR^{22}$, —$SR^{22}$, —$NR^{23}R^{24}$, a phenyl radical optionally substituted by one or more substituents chosen independently from a halogen atom, an OH, cyano, nitro, alkyl, haloalkyl, alkoxy, alkylthio or —$NR^{10}R^{11}$ radical and a group with two substituents representing together a methylenedioxy or ethylenedioxy radical, or also Q represents a —COPh, —$SO_2$Ph or —$CH_2$Ph radical, said —COPh, —$SO_2$Ph or —$CH_2$Ph radical being optionally substituted on its aromatic part by one or more of the substituents chosen independently from an alkyl or alkoxy radical and a halogen atom, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom, an alkyl or alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{22}$ representing a hydrogen atom, an alkyl radical or an aryl radical optionally substituted by one or more substituents chosen from the alkyl, OH, halogen, nitro and alkoxy radicals, $R^{23}$ and $R^{24}$ representing, independently, a hydrogen atom, an alkyl radical or a —CO—$R^{25}$ radical, $R^{25}$ representing an alkyl radical, and $R^{19}$, $R^{20}$ and $R^{21}$ represent, independently, a hydrogen, a halogen, the OH or $SR^{26}$ group, or an alkyl, cycloalkyl, alkenyl, alkoxy, cyano, nitro, —$SO_2NHR^{49}$, —$CONHR^{55}$, —$S(O)_qR^{56}$, —$NH(CO)R^{57}$, —$CF_3$, —$OCF_3$ or $NR^{27}R^{28}$ radical, $R^{26}$ representing a hydrogen atom or an alkyl radical, $R^{27}$ and $R^{28}$ representing, independently, a hydrogen atom, an alkyl radical or a —$COR^{29}$ group, or $R^{27}$ and $R^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, $R^{29}$ representing a hydrogen atom, an alkyl, alkoxy or —$NR^{30}R^{31}$ radical, $R^{30}$ and $R^{31}$ representing, independently, a hydrogen atom or an alkyl radical, or $R^{30}$ and $R^{31}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, or a

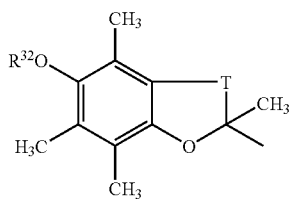

radical in which $R^{32}$ represents a hydrogen atom or an alkyl radical, and T represents a —$(CH_2)_m$— radical with m=1 or 2, or finally a

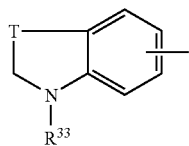

radical in which $R^{33}$ represents a hydrogen atom or an alkyl, —Σ—$NR^{34}R^{35}$ or —Σ—$CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or $NR^{10}R^{11}$ radicals, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and T represents a —$(CH_2)_m$— radical with m=1 or 2, or also A represents an alkyl, cycloalkyl or cycloalkylalkyl radical;

X represents S or $NR^{38}$, $R^{38}$ representing a hydrogen atom or an alkyl, cyanoalkyl, aralkyl, alkylcarbonyl or aralkylcarbonyl radical, Y represents O or S;

$R^1$ represents a hydrogen atom, an alkyl, aminoalkyl, alkoxyalkyl, cycloalkyl, cycloalkylalkyl, trifluoromethylalkyl, alkenyl, allenyl, allenylalkyl, alkynyl, cyanoalkyl, —$(CH_2)_g$-$Z^1R^{39}$, —$(CH_2)_g$—$COR^{40}$, —$(CH_2)_g$—NH-$COR^{70}$, aryl, aralkyl, arylcarbonyl, heteroarylalkyl or aralkylcarbonyl radical, the aryl group of the aryl, aralkyl, arylcarbonyl, heteroarylalkyl or aralkylcarbonyl radicals itself being optionally substituted by one or more substituents chosen from the group constituted by the alkyl, halogen, alkoxy, nitro, cyano, cyanoalkyl, amino, alkylamino, dialkylamino, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom, an alkyl, aminoalkyl, alkoxyalkyl, cycloalkyl, cycloalkylalkyl, trifluoromethylalkyl or —$(CH_2)_g$—$NHCOR^{71}$ radical, or also one of the aralkyl or heteroarylalkyl radicals optionally substituted on the aryl or heteroaryl group by one or more of the groups chosen independently from the group composed of a halogen atom and an alkyl, alkoxy, hydroxy, cyano, nitro, amino, alkylamino or dialkylamino radical, $R^{70}$ and $R^{71}$ representing independently an alkyl or alkoxy radical;

or $R^1$ and $R^2$, taken together with the carbon atom which carries them, form a carbocycle with 3 to 7 members;

B represents a hydrogen atom, an alkyl radical, a —$(CH_2)_g$-$Z^3R^{44}$ radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, $Z^3$ representing a bond, —O—, —$NR^{45}$— or —S—, $R^{44}$ and $R^{45}$ representing, independently, a hydrogen atom or an alkyl, alkenyl, alkynyl, alkoxy, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —$(CH_2)_g$-$Z^4R^{50}$, —$(CH_2)_k$—$COR^{51}$, —$(CH_2)_k$—$COOR^{51}$, —$(CH_2)_k$—$CONHR^{51}$, —$CSNHR^{51}$ or —$SO_2R^{51}$ radical, or also a radical chosen from the aryl, aralkyl, aryloxyalkyl, arylcarbonyl, arylimino, aralkylcarbonyl, heteroaryl and in particular pyridinyl, pyridinylalkyl or pyridinylcarbonyl radicals, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by one or more substituents chosen independently from halogen, alkyl, alkoxy, hydroxy, nitro, cyano, cyanoalkyl, amino, alkylamino, dialkylamino, —$(CH_2)_k$-$Z^5R^{50}$, —$(CH_2)_k$—$COR^{51}$ and —$(CH_2)_k$—$COOR^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group composed of —$CH(R^{53})$—, —$NR^{54}$—, —O—, —S— and —CO—, said heterocycle being able to be for example an azetidine, a piperazine, a homopiperazine, a 3,5-dioxopiperazine, a piperidine, a pyrrolidine, a morpholine or a thiomorpholine, $R^{50}$ and $R^{52}$, representing, independently each time that they occur, a hydrogen atom or an alkyl, alkenyl, alkynyl, allenyl, allenylalkyl or cyanoalkyl radical, $R^{51}$ representing, independently each time that it occurs, a hydrogen atom, one of the cycloalkyl or cycloalkylalkyl radicals in which the cycloalkyl radical has 3 to 7 carbon atoms, a linear or branched alkyl radical containing 1 to 8 carbon atoms, an alkenyl, alkynyl, allenyl, allenylalkyl, haloalkyl, cyanoalkyl, alkoxyalkyl or $NR^{58}R^{59}$ radical, or also an aryl or aralkyl radical, said aryl or aralkyl radical being able to be substituted by one or more of the substituents chosen independently from a halogen atom and an alkyl or alkoxy radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—$COR^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —$(CH_2)_k$-$Z^8R^{63}$ and —$(CH_2)_k$—$COR^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, —O—, —$NR^{67}$— or —S—, $R^{63}$ and $R^{67}$ representing, independently, a hydrogen atom, an alkyl, allenyl, allenylalkyl, alkenyl, alkynyl or cyanoalkyl radical, $R^{64}$ representing a hydrogen atom, an alkyl, allenylalkyl, alkenyl, allenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, and $R^{48}$ represents a hydrogen atom or an alkyl, alkynyl or cyanoalkyl radical;

g and p, each time that they occur, being independently integers from 1 to 6, and k and n, each time that they occur, being independently integers from 0 to 6;

it being understood that when Het is such that the compound of general formula $(III)_G$ corresponds to general sub-formula $(III)_{G4}$, then:

A represents the 4-hydroxy-2,3-di-tertiobutyl-phenyl radical;

B, $R^1$ and $R^2$ all represent H; and finally

Ω represents OH;

it being also understood that at least one of the following characteristics must be present:

when A represents a

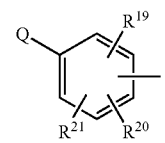

radical in which Q represents OH,

Ω does not represent an $NR^{46}R^{47}$ radical in which $R^{46}$ or $R^{47}$ are chosen from a hydrogen atom and an alkyl radical or an $NR^{46}R^{47}$ radical in which $R^{46}$ or $R^{47}$ represents an aminophenyl, nitrophenyl, aminophenylcarbonyl, nitrophenylcarbonyl, aminophenylalkyl or nitrophenylalkyl radical;

A represents a

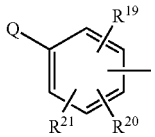

radical B represents a carbocyclic aryl radical optionally substituted 1 to 3 times by radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, and one of $R^1$ and $R^2$ represents one of the optionally substituted arylalkyl or heteroarylalkyl radicals;

A represents a cycloalkyl or cycloalkylalkyl radical;

$\Omega$ represents $NR^{46}R^{47}$ and one of $R^{46}$ and $R^{47}$ represents an alkenyl, allenyl, allenylalkyl, alkynyl, cyanoalkyl or hydroxyalkyl radical;

one of $R^1$ and $R^2$ represents a cycloalkyl or cycloalkylalkyl radical;

none of $R^1$ and $R^2$ represent H;

n=1 and A represents an optionally substituted biphenyl, phenoxyphenyl, phenylthiophenyl, phenylcarbonylphenyl or phenylsulphonylphenyl radical;

when Het is a thiazole ring and $\Omega$ represents the $OR^{48}$ radical in which $R^{48}$ is a cyanoalkyl radical, then the cyano group is not attached to the carbon atom immediately adjacent to the oxygen atom;

or the salts of compounds of general formula $(III)_G$.

The invention in particular relates, as new industrial products, to the compounds of general formula (III)

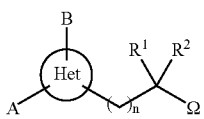

(III)

in racemic, enantiomeric form or any combinations of these forms, in which Het is a heterocycle with 5 members comprising 2 heteroatoms and such that general formula (III) corresponds exclusively to one of the following sub-formulae:

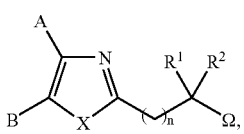

(III)$_1$

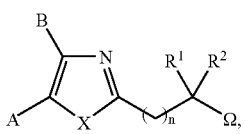

(III)$_2$

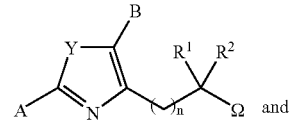

and (III)$_3$

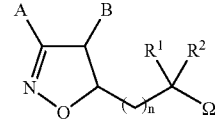

(III)$_4$ in which

A represents either a

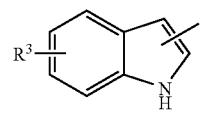

radical in which $R^3$ represents a hydrogen atom, the OH group or an alkoxy or alkyl radical, or a

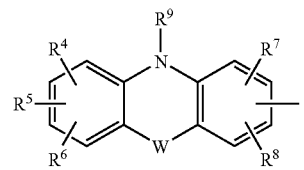

radical in which $R^4$, $R^5$, $R^6$, $R^7$ and $R^8$ represent, independently, a hydrogen atom, a halogen, the OH group or an alkyl, alkoxy, cyano, nitro or $NR^{10}R^{11}$ radical, $R^{10}$ and $R^{11}$ representing, independently, a hydrogen atom, an alkyl radical or a —$COR^{12}$ group, or $R^{10}$ and $R^{11}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, $R^{12}$ representing a hydrogen atom or an alkyl, alkoxy or $NR^{13}R^{14}$ radical, $R^{13}$ and $R^{14}$ represent, independently, a hydrogen atom or an alkyl radical, or $R^{13}$ and $R^{14}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, $R^9$ represents a hydrogen atom, an alkyl radical or a —$COR^{15}$ group, $R^{15}$ representing a hydrogen atom or an alkyl, alkoxy or $NR^{16}R^{17}$ radical, $R^{16}$ and $R^{17}$ representing, independently, a hydrogen atom or an alkyl radical, or $R^{16}$ and $R^{17}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, and W doesn't exist, or represents a bond, or —O—, —S— or —$NR^{18}$—, in which $R^{18}$ represents a hydrogen atom or an alkyl radical;

or a

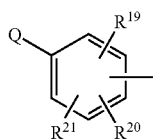

radical in which Q represents H, —$OR^{22}$, —$SR^{22}$, —$NR^{23}R^{24}$, a phenyl radical optionally substituted by one or more of the substituents chosen independently from a halogen atom, an OH, cyano, nitro, alkyl, alkoxy or —$NR^{10}R^{11}$ radical and a group of two substituents together representing a methylenedioxy or ethylenedioxy radical, or also Q represents a —COPh, —$SO_2$Ph or —$CH_2$Ph radical, said —COPh, —$SO_2$Ph or —$CH_2$Ph radical being optionally substituted on its aromatic part by one or more of the substituents chosen independently from an alkyl or alkoxy radical and a halogen atom, $R^{10}$ and $R^{11}$ representing, independently, a hydrogen atom, an alkyl radical or a $COR^{12}$ group, or $R^{10}$ and $R^{11}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{12}$ representing a hydrogen atom, an alkyl or alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle with 4 to 7 members and 1 to 3 heteroatoms including the nitrogen atom already present, the additional heteroatoms being chosen independently from the group constituted by the O, N and S atoms, $R^{22}$ representing a hydrogen atom, an alkyl radical or an aryl radical optionally substituted by one or more substituents chosen from the alkyl, OH, halogen, nitro and alkoxy radicals, $R^{23}$ and $R^{24}$ representing, independently, a hydrogen atom, an alkyl radical or a —CO—$R^{25}$ radical, $R^{25}$ representing an alkyl radical, and $R^{19}$, $R^{20}$ and $R^{21}$ represent, independently, a hydrogen, a halogen, the OH or $SR^{26}$ group, or an alkyl, cycloalkyl, alkenyl, alkoxy, cyano, nitro, —$SO_2NHR^{49}$, —$CONHR^{55}$, —$S(O)_qR^{56}$—NH(CO)$R^{57}$, —$CF_3$, —$OCF_3$ or $NR^{27}R^{28}$ radical, $R^{26}$ representing a hydrogen atom or an alkyl radical, $R^{27}$ and $R^{28}$ representing, independently, a hydrogen atom, an alkyl radical or a —$COR^{29}$ group, or $R^{27}$ and $R^{28}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, $R^{29}$ representing a hydrogen atom, an alkyl, alkoxy or —$NR^{30}R^{31}$ radical, $R^{30}$ and $R^{31}$ representing, independently, a hydrogen atom or an alkyl radical, or $R^{30}$ and $R^{31}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, or a

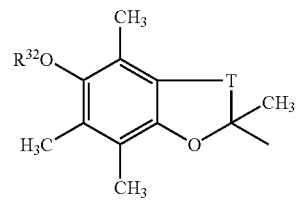

radical in which $R^{32}$ represents a hydrogen atom or an alkyl radical, and T represents a —$(CH_2)_m$— radical with m=1 or 2, or finally a

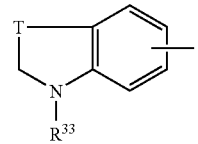

radical in which $R^{33}$ represents a hydrogen atom or an alkyl, —Σ—$NR^{34}R^{35}$ or —Σ—$CHR^{36}R^{37}$ radical, Σ representing a linear or branched alkylene radical containing 1 to 6 carbon atoms, $R^{34}$ and $R^{35}$ representing, independently, a hydrogen atom or an alkyl radical, $R^{36}$ and $R^{37}$ representing, independently, a hydrogen atom or a carbocyclic or heterocyclic aryl radical optionally substituted by one or more substituents chosen from the alkyl, OH, halogen, nitro, alkoxy or $NR^{10}R^{11}$ radicals, $R^{10}$ and R1 representing, independently, a hydrogen atom, an alkyl radical or a —$COR^{12}$ group, or $R^{10}$ and R1 forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, $R^{12}$ representing a hydrogen atom or an alkyl, alkoxy or $NR^{13}R^{14}$ radical, $R^{13}$ and $R^{14}$ representing, independently, a hydrogen atom or an alkyl radical, or $R^{13}$ and $R^{14}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, and T represents a —$(CH_2)_m$— radical with m=1 or 2, or also A represents an alkyl, cycloalkyl or cycloalkylalkyl radical;

X represents S or $NR^{38}$, $R^{38}$ representing a hydrogen atom or an alkyl, cyanoalkyl, aralkyl, alkylcarbonyl or aralkylcarbonyl radical, Y represents O or S;

$R^1$ represents a hydrogen atom, an alkyl, aminoalkyl, alkoxyalkyl, cycloalkyl, cycloalkylalkyl, trifluoromethylalkyl, alkenyl, allenyl, allenylalkyl, alkynyl, cyanoalkyl, —$(CH_2)_g$-$Z^1R^{39}$, —$(CH_2)_g$—$COR^{40}$, —$(CH_2)_g$—NHCOR$^{70}$, aryl, aralkyl, arylcarbonyl, heteroarylalkyl or aralkylcarbonyl radical, the aryl group of the aryl, aralkyl, arylcarbonyl, heteroarylalkyl or aralkylcarbonyl radicals being itself optionally substituted by one or more substituents chosen from the group constituted by the alkyl, halogen, alkoxy, nitro, cyano, cyanoalkyl, amino, alkylamino, dialkylamino, —$(CH_2)_k$-$Z^2R^{39}$ or —$(CH_2)_k$—$COR^{40}$ radicals, $Z^1$ and $Z^2$ representing a bond, —O—, —$NR^{41}$— or —S—, $R^{39}$ and $R^{41}$ representing, independently each time that they occur, a hydrogen atom or an alkyl, alkenyl, alkynyl or cyanoalkyl radical, $R^{40}$ representing, independently each time that it occurs, a hydrogen atom or an alkyl, allenyl, allenylalkyl, alkenyl, alkynyl, cyanoalkyl, alkoxy or $NR^{42}R^{43}$ radical, $R^{42}$ and $R^{43}$ representing, independently each time that they occur, a hydrogen atom or an alkyl, allenyl, allenylalkyl, alkenyl, alkynyl or cyanoalkyl radical, and $R^2$ represents a hydrogen atom, an alkyl, aminoalkyl, alkoxyalkyl, cycloalkyl, cycloalkylalkyl, trifluoromethylalkyl or —$(CH_2)_g$—NHCOR$^{71}$ radical, or also one of the aralkyl or heteroarylalkyl radicals optionally substituted on the aryl or heteroaryl group by one or more of the groups chosen independently from the group composed of a halogen atom and an alkyl, alkoxy, hydroxy, cyano, nitro, amino, alkylamino or dialkylamino radical, $R^{70}$ and $R^{71}$ representing independently an alkyl or alkoxy radical;

or $R^1$ and $R^2$, taken together with the carbon atom which carries them, form a carbocycle with 3 to 7 members;

B represents a hydrogen atom, an alkyl radical, a —$(CH_2)_g$-$Z^3R^{44}$ radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical, $Z^3$ representing a bond, —O—, —$NR^{45}$— or —S—, $R^{44}$ and $R^{45}$ representing, independently, a hydrogen atom or an alkyl, alkenyl, alkynyl, allenyl, allenylalkyl or cyanoalkyl radical;

Ω represents one of the $NR^{46}R^{47}$ or $OR^{48}$ radicals, in which:

$R^{46}$ and $R^{47}$ represent, independently, a hydrogen atom or an alkyl, cycloalkyl, cycloalkylalkyl, alkenyl, alkynyl, allenyl, allenylalkyl, cyanoalkyl, —$(CH_2)_g$-$Z^4R^{50}$, —$(CH_2)_k$—$COR^{51}$, —$(CH_2)_k$—$COOR^{51}$, —$(CH_2)_k$—$CONHR^{51}$ or —$SO_2R^{51}$ radical, or also a radical chosen from the aryl, aralkyl, aryloxyalkyl, arylcarbonyl, arylimino, aralkylcarbonyl, heteroaryl and in particular pyridinyl, pyridinylalkyl or pyridinylcarbonyl radicals, the aryl or heteroaryl group of said aryl, aralkyl, aryloxyalkyl, arylcarbonyl, arylimino, aralkylcarbonyl, heteroaryl, pyridinylalkyl or pyridinylcarbonyl radicals being optionally substituted by one or more of the substituents chosen independently from halogen, alkyl, alkoxy, hydroxy, nitro, cyano, cyanoalkyl, amino, alkylamino, dialkylamino, —$(CH_2)_k$-$Z^5R^{50}$, —$(CH_2)_k$—$COR^{51}$ and —$(CH_2)_k$—$COOR^{51}$, $Z^4$ and $Z^5$ representing a bond, —O—, —$NR^{52}$— or —S—, or $R^{46}$ and $R^{47}$ taken together form with the nitrogen atom a non aromatic heterocycle with 4 to 8 members, the elements of the chain being chosen from a group composed of —CH($R^{53}$)—, —$NR^{54}$—, —O—, —S— and —CO—, $R^{50}$ and $R^{52}$, representing, independently each time that they occur, a hydrogen atom or an alkyl, alkenyl, alkynyl, allenyl, allenylalkyl or cyanoalkyl radical, $R^{51}$ representing, independently each time that they occur, a hydrogen atom, one of the cycloalkyl or cycloalkylalkyl radicals in which the cycloalkyl radical contains 3 to 7 carbon atoms, a linear or branched alkyl radical containing 1 to 8 carbon atoms, an alkenyl, alkynyl, allenyl, allenylalkyl, cyanoalkyl, alkoxyalkyl or $NR^{58}R^{59}$ radical, or also an aryl or aralkyl radical, said aryl or aralkyl radical being able to be substituted by one or more the substituents chosen independently from a halogen atom and an alkyl or alkoxy radical, $R^{58}$ and $R^{59}$ representing, independently, a hydrogen atom or an alkyl, alkenyl, alkynyl, allenyl, allenylalkyl or cyanoalkyl radical, $R^{53}$ and $R^{54}$ representing, independently, a hydrogen atom or a —$(CH_2)_k$-$Z^7R^{60}$ or —$(CH_2)_k$—$COR^{61}$ radical, $Z^7$ representing a bond, —O—, —$NR^{62}$— or —S—, $R^{60}$ and $R^{62}$ representing, independently, a hydrogen atom or an alkyl, alkenyl, allenyl, allenylalkyl, alkynyl, cyanoalkyl, aryl, aralkyl, arylcarbonyl, aralkylcarbonyl, pyridinyl, pyridinylalkyl or pyridinylcarbonyl radical, the aryl or pyridinyl group of the aryl, aralkyl, arylcarbonyl, aralkylcarbonyl, pyridinyl, pyridinylalkyl or pyridinylcarbonyl radicals being optionally substituted by one or more substituents chosen from the group constituted by the alkyl, halogen, nitro, alkoxy, cyano, cyanoalkyl, —$(CH_2)_k$-$Z^8R^{63}$ and —$(CH_2)_k$—$COR^{64}$ radicals, $R^{61}$ representing a hydrogen atom, an alkyl, allenyl, allenylalkyl, alkenyl, alkynyl, cyanoalkyl, alkoxy or $NR^{65}R^{66}$ radical, $R^{65}$ and $R^{66}$ representing, independently, a hydrogen atom or an alkyl, allenyl, allenylalkyl, alkenyl, alkynyl or cyanoalkyl radical, $Z^8$ representing a bond, —O—, —$NR^{67}$— or —S—, $R^{63}$ and $R^{67}$ representing, independently, a hydrogen atom, an alkyl, allenyl, allenylalkyl, alkenyl, alkynyl or cyanoalkyl radical, $R^{64}$ representing a hydrogen atom, an alkyl, allenylalkyl, alkenyl, alkenyl, alkynyl, cyanoalkyl, alkoxy or $NR^{68}R^{69}$ radical, $R^{68}$ and $R^{69}$ representing, independently, a hydrogen atom or an alkyl, allenyl, allenylalkyl, alkenyl, alkynyl or cyanoalkyl radical, and $R^{48}$ represents a hydrogen atom or an alkyl, alkynyl or cyanoalkyl radical;

g and p, each time that they occur, being independently integers from 1 to 6, and k and n, each time that they occur, being independently integers from 0 to 6;

it being understood that when Het is such that the compound of general formula (III) corresponds to general sub-formula (III)$_4$, then:

A represents the 4-hydroxy-2,3-di-tertiobutyl-phenyl radical;

B, $R^1$ and $R^2$ all represent H; and finally

Ω represents OH;

it being also understood that at least one of the following characteristics must be present:
when A represents a

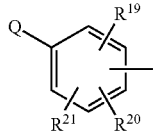

radical in which Q represents OH,
Ω does not represent an $NR^6R^{47}$ radical in which $R^{46}$ or $R^{47}$ are chosen from a hydrogen atom and an alkyl radical or an $NR^{46}R^{47}$ radical in which $R^{46}$ or $R^{47}$ represents an aminophenyl, nitrophenyl, aminophenylcarbonyl, nitrophenylcarbonyl, aminophenylalkyl or nitrophenylalkyl radical;
A represents a

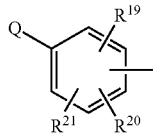

radical B represents a carbocyclic aryl radical optionally substituted 1 to 3 times by radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical,
and one of $R^1$ and $R^2$ represents one of the optionally substituted arylalkyl or heteroarylalkyl radicals;
A represents a cycloalkyl or cycloalkylalkyl radical;
Ω represents $NR^{46}R^{47}$ and one of $R^{46}$ and $R^{47}$ represents an alkenyl, allenyl, allenylalkyl, alkynyl, cyanoalkyl or hydroxyalkyl radical;

one of $R^1$ and $R^2$ represents a cycloalkyl or cycloalkylalkyl radical;
none of $R^1$ and $R^2$ represent H;
n=1 and A represents a biphenyl, phenoxyphenyl, phenylthiophenyl, phenylcarbonylphenyl or phenylsulphonylphenyl radical;
when Het is a thiazole ring and Ω represents the $OR^{48}$ radical in which $R^{48}$ is a cyanoalkyl radical, then the cyano group is not attached to the carbon atom immediately adjacent to the oxygen atom;

or the salts of the compounds of general formula (III).

According to one of the preferred variants of the invention, the compounds of general formula (III) will be both ROS and MAO inhibitors and have at least one of the following characteristics:

A representing the:

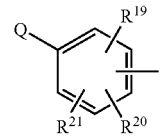

radical in which Q represents OH, two of the $R^{19}$, $R^{20}$ and $R^{21}$ radicals represent radicals chosen independently from the alkyl, alkoxy, alkylthio, amino, alkylamino or dialkylamino radicals and the third represents a radical chosen from a hydrogen atom and the alkyl, alkoxy, alkylthio, amino, alkylamino or dialkylamino radicals;

n representing 0 or 1;

$R^1$ and $R^2$ both representing H;

Ω representing OH or the $NR^{46}R^{47}$ radical in which one of $R^{46}$ and $R^{47}$ represents a cyanoalkyl radical and the other represents H or alkyl or also in which $R^{46}$ and $R^{47}$ taken together form with the nitrogen atom a non aromatic heterocycle with 4 to 8 members, the elements of the chain being chosen from a group composed of —CH($R^{53}$)—, —$NR^{54}$—, —O—, —S—, —CO—, $R^{53}$ and $R^{54}$ being as defined in general formula (III).

According to another preferred variant of the invention, the compounds of general formula (III) will be modulators of the sodium channels and preferably have one of the following two characteristics:

n=0,

A represents a

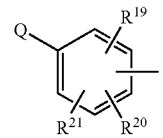

radical in which Q represents a hydrogen atom or an —$OR^{22}$ or —$SR^{22}$ radical in which $R^{22}$ represents an alkyl radical or an aryl radical optionally substituted by one or more substituents chosen from the alkyl, OH, halogen, nitro and alkoxy radicals, $R^{19}$, $R^{20}$ and $R^{21}$ represent, independently, a hydrogen, a halogen, an $SR^{26}$ radical, or an alkyl, cycloalkyl, alkenyl, alkoxy, cyano, nitro, —$SO_2NHR^{49}$, —$CONHR^{55}$, $S(O)_qR^{56}$, —NH(CO)$R^{57}$, —$CF_3$, —$OCF_3$ or $NR^{27}R^{28}$ radical, $R^{26}$ representing an alkyl radical, $R^{27}$ and $R^{28}$ representing, independently, a hydrogen atom or an alkyl radical or $R^{27}$ and $R^{28}$ forming together with the nitrogen atom which carries them a heterocycle with 5 to 6 members chosen from —$CH_2$—, —NH— and —O—, $R^{49}$ and $R^{55}$ representing, independently each time that they occur, a hydrogen atom or an alkyl or alkylcarbonyl radical, q representing an integer from 0 to 2, $R^{56}$ and $R^{57}$ representing, independently each time that they occur, a hydrogen atom or an alkyl or alkoxy radical, and one of $R^1$ and $R^2$ represents a cycloalkyl or cycloalkylalkyl radical or none of $R^1$ and $R^2$ represents a hydrogen atom; or finally n=1, A represents a biphenyl (optionally substituted) or cyclohexylphenyl radical, B represents a hydrogen atom, $R^1$ and $R^2$ each represent a hydrogen atom, and Ω represents an $NR^{46}R^{47}$ radical in which $R^{46}$ represents a —$COOR^{51}$ radical, $R^{51}$ representing an alkyl, cycloalkyl, cycloalkylalkyl or alkoxyalkyl radical and $R^{47}$ representing a hydrogen atom.

More preferentially, the compounds of general formula (III) which are modulators of the sodium channels are such that Het represents an imidazole ring (i.e. that they correspond to one of general formulae (III)$_1$ or (III)$_2$ in which X represents an $NR^{38}$ radical in which $R^{38}$ is as defined previously).

According to a further variant, the invention will relate to certain compounds of general formula (I)$_G$

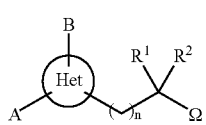

(I)$_G$ in racemic, enantiomeric form or any combination of these forms, in which Het is a heterocycle with 5 members comprising 2 heteroatoms and such that general formula (I)$_G$ corresponds exclusively to one of the following sub-formulae:

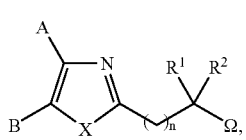

(I)$_{G1}$

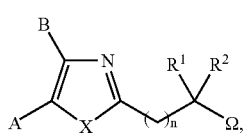

(I)$_{G2}$ in which

A represents a

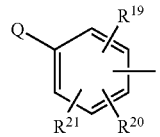

radical in which Q represents a phenyl radical optionally substituted by one or more substituents chosen independently from a halogen atom, an OH, cyano, nitro, alkyl, haloalkyl, alkoxy or alkylthio radical, and $R^{19}$, $R^{20}$ and $R^{21}$ represent, independently, a hydrogen, a halogen, or an alkyl or alkoxy radical, or Q is hydrogen and one of $R^{19}$, $R^{20}$ and $R^{21}$ is cycloalkyl of 3 to 7 carbon atoms while the two others are each hydrogen, X represents $NR^{38}$, $R^{38}$ representing a hydrogen atom or an alkyl, aralkyl, alkylcarbonyl or aralkylcarbonyl radical, $R^1$ represents a hydrogen atom or an alkyl radical, $R^2$ represents a hydrogen atom or an alkyl radical, or $R^1$ and $R^2$, taken together with the carbon atom which carries them, form a carbocycle with 3 to 7 members;

B represents a hydrogen atom, an alkyl radical or a carbocyclic aryl radical optionally substituted 1 to 3 times by the radicals chosen from the group composed of a halogen atom, a linear or branched alkyl or alkoxy radical containing 1 to 6 carbon atoms, a hydroxy, cyano or nitro radical, an amino, alkylamino or dialkylamino radical and a carbocyclic aryl radical;

Ω is the $NR^{46}R^{47}$ radical in which:

$R^{46}$ represents a —$COOR^{51'}$, —$CONHR^{51}$, —$CSNHR^{51}$ or —$SO_2R^{72}$ radical, $R^{47}$ represents a hydrogen atom, $R^{51}$ representing a hydrogen atom, one of the cycloalkyl or cycloalkylalkyl radicals, a linear or branched alkyl radical containing 1 to 8 carbon atoms, a haloalkyl, alkoxyalkyl radical, or also an aryl or aralkyl radical, said aryl or aralkyl radical being able to be substituted by one or more substituents chosen independently from a halogen atom and an alkyl or alkoxy radical, $R^{51'}$ representing a hydrogen atom, one of the cycloalkyl or cycloalkylalkyl radicals, a linear or branched alkyl radical containing 1 to 8 carbon atoms, a haloalkyl radical, an alkoxyalkyl radical, or also an aryl or aralkyl radical, said aryl or aralkyl radical being able to be substituted by one or more substituents chosen independently from a halogen atom and an alkyl or alkoxy radical, $R^{72}$ representing alkyl or one of the phenyl or aralkyl radicals optionally substituted on the aromatic ring by one or more radicals independently selected from the group consisting of a halogen atom and an alkyl or alkoxy radical;

n being an integer from 0 to 6;

and the salts of these compounds. These compounds (and more particularly those wherein $R^{46}$ is —COOR$^{51'}$), will be particularly preferred due to their sodium channel modulating activity. Preferably, these compounds will be such that n is an integer from 0 to 2, in particular such that n is 0 or 1 (and more preferably 1).

Generally, the compounds of general formula (III) will be preferably chosen from the compounds described (sometimes in the form of salts) in Examples 1 to 7, 9, 10, 24, 26 to 35, 52, 57, 61, 80, 82, 83, 85 to 87, 90, 94, 113, 115, 123, 127, 130, 132, 134, 138, 139, 147, 152, 154, 161, 164, 169, 171 to 173, 176 to 180, 203, 237 to 239, 243 to 247, 249, 251, 255, 258 to 262, 264 to 271, 273 to 275, 277 to 333 and 335 to 349, or the salts of these compounds.

More preferentially, the compounds of general formula (III) will be chosen from the compounds described (sometimes in the form of salts) in Examples 1, 3, 6, 7, 24, 26 to 35, 57, 61, 82, 83, 85 to 87, 94, 113, 123, 130, 132, 134, 138, 139, 152, 154, 164, 169, 171 to 173, 176 to 178, 203, 237 to 239, 243 to 247, 249, 255, 258, 259, 261, 262, 264 to 271, 273 to 275, 277 to 281, 283 to 288, 293 to 313, 321, 323, 324, 332 and 338 to 340, or the salts of these compounds.

According to a particular aspect of this invention, the latter further relates to a selection of compounds of general formula (I) described above, namely the following compounds (described in the corresponding Examples, sometimes in the form of salts):

2,6-ditert-butyl-4-{2-[2-(methylamino)ethyl]-1,3-thiazol-4-yl}phenol (hereafter compound 350);

2,6-ditert-butyl-4-[4-(hydroxymethyl)-1,3-oxazol-2-yl]phenol (hereafter compound 351);

2,6-ditert-butyl-4-{2-[1-(methylamino)ethyl]-1,3-thiazol-4-yl}phenol (hereafter compound 352);

2,6-ditert-butyl-4-[2-(methoxymethyl)-1,3-thiazol-4-yl]phenol (hereafter compound 353);

2,6-ditert-butyl-4-{4-[(methylamino)methyl]-1,3-oxazol-2-yl}phenol (hereafter compound 354);

N-{[4-(3,5-ditert-butyl-4-hydroxyphenyl)-1,3-thiazol-2-yl]methyl}acetamide (hereafter compound 355);

ethyl [4-(3,5-ditert-butyl-4-hydroxyphenyl)-1,3-thiazol-2-yl]methylcarbamate (hereafter compound 356);

2,6-ditert-butyl-4-[2-(morpholin-4-ylmethyl)-1,3-thiazol-4-yl]phenol (hereafter compound 357);

2,6-ditert-butyl-4-[2-(thiomorpholin-4-ylmethyl)-1,3-thiazol-4-yl]phenol (hereafter compound 358);

4-[2-(anilinomethyl)-1,3-thiazol-4-yl]-2,6-ditert-butylphenol (hereafter compound 359);

2,6-ditert-butyl-4-(2-{[[2-(dimethylamino)ethyl](methyl)amino]methyl}-1,3-thiazol-4-yl)phenol (hereafter compound 360);

2,6-ditert-butyl-4-{5-methyl-2-[(methylamino)methyl]-1,3-thiazol-4-yl}phenol (hereafter compound 361);

1-[4-(10H-phenothiazin-2-yl)-1,3-thiazol-2-yl]methanamine (hereafter compound 362);

N-{[4-(3,5-ditert-butyl-4-hydroxyphenyl)-1,3-thiazol-2-yl]methyl}-N-methylacetamide (hereafter compound 363);

1-[4-(3,5-ditert-butyl-4-methoxyphenyl)-1,3-thiazol-2-yl]-N-methylmethanamine (hereafter compound 364);

2,6-ditert-butyl-4-{2-[(ethylamino)methyl]-1,3-thiazol-4-yl}phenol (hereafter compound 365);

2,6-ditert-butyl-4-{2-[(4-phenylpiperazin-1-yl)methyl]-1,3-thiazol-4-yl}phenol (hereafter compound 366);

2,6-ditert-butyl-4-{2-[(4-methyl-1,4-diazepan-1-yl)methyl]-1,3-thiazol-4-yl}pheno (hereafter compound 367);

N-{1-[4-(4-anilinophenyl)-1,3-thiazol-2-yl]ethyl}-N-methylamine (hereafter compound 368);

2,6-ditert-butyl-4-{2-[(isopropylamino)methyl]-1,3-thiazol-4-yl}phenol (hereafter compound 369);

2,6-ditert-butyl-4-{2-[(cyclohexylamino)methyl]-1,3-thiazol-4-yl}phenol (hereafter compound 370);

2,6-ditert-butyl-4. {2-[(4-isopropylpiperazin-1-yl)methyl]-1,3-thiazol-4-yl}phenol (hereafter compound 371);

N-methyl-1-[4-(10H-phenothiazin-2-yl)-1,3-thiazol-2-yl]ethanamine (hereafter compound 372);

2,6-ditert-butyl-4-{2-[(4-ethylpiperazin-1-yl)methyl]-1,3-thiazol-4-yl}phenol (hereafter compound 373);

N-{[4-(4-anilinophenyl)-1,3-thiazol-2-yl]methyl}-N-ethylamine (hereafter compound 374);

N-{[4-(10H-phenothiazin-2-yl)-1,3-thiazol-2-yl]methyl}ethanamine (hereafter compound 375);

2,6-ditert-butyl-4-(2-{[4-(dimethylamino)piperidin-1-yl]methyl}-1,3-thiazol-4-yl)phenol (hereafter compound 376);

1-{[4-(3,5-ditert-butyl-4-hydroxyphenyl)-1,3-thiazol-2-yl]methyl}piperidin-4-ol (hereafter compound 377);

4-methylpentyl 2-[4-(1,1'-biphenyl-4-yl)-1H-imidazol-2-yl]ethylcarbamate (hereafter compound 378);

3,3-dimethylbutyl 2-[4-(4-pyrrolidin-1-ylphenyl)-1H-imidazol-2-yl]ethylcarbamate (hereafter compound 379);

isopentyl 2-[4-(1,1'-biphenyl-4-yl)-1H-imidazol-2-yl]ethylcarbamate (hereafter compound 380);

hexyl 2-[4-(4'-bromo-1,1'-biphenyl-4-yl)-1H-imidazol-2-yl]ethylcarbamate (hereafter compound 381);

benzyl 2-[4-(4-tert-butylphenyl)-1H-imidazol-2-yl]ethylcarbamate (hereafter compound 382);

3,3-dimethylbutyl 2-[4-(1,1'-biphenyl-4-yl)-1H-imidazol-2-yl]ethylcarbamate (hereafter compound 383);

hexyl 2-[4-(4-pyrrolidin-1-ylphenyl)-1H-imidazol-2-yl]ethylcarbamate (hereafter compound 384);

hexyl 2-[4-(3,5-ditert-butyl-4-hydroxyphenyl)-1H-imidazol-2-yl]ethylcarbamate (hereafter compound 386);

3,3-dimethylbutyl 2-[4-(3,5-ditert-butyl-4-hydroxyphenyl)-1H-imidazol-2-yl]ethylcarbamate (hereafter compound 387);

3,3-dimethylbutyl 2-[4-(4-methoxyphenyl)-1H-imidazol-2-yl]ethylcarbamate (hereafter compound 388);

benzyl 2-[4-(3,5-ditert-butyl-4-hydroxyphenyl)-1H-imidazol-2-yl]ethylcarbamate (hereafter compound 389);

benzyl 2-[4-(4-pyrrolidin-1-ylphenyl)-1H-imidazol-2-yl]ethylcarbamate (hereafter compound 390);

phenylethyl 2-[4-(1,1'-biphenyl-4-yl)-1H-imidazol-2-yl]ethylcarbamate (hereafter compound 391);

butyl 2-[4-(4'-fluoro-1,1'-biphenyl-4-yl)-1H-imidazol-2-yl]ethylcarbamate (hereafter compound 392);

butyl 2-[4-(1,1'-biphenyl-4-yl)-5-methyl-1H-imidazol-2-yl]ethylcarbamate (hereafter compound 393);

butyl 2-[4-(4'-methyl-1,1'-biphenyl-4-yl)-1H-imidazol-2-yl]ethylcarbamate (hereafter compound 394);

butyl 2-[4-(4'-chloro-1,1'-biphenyl-4-yl)-1H-imidazol-2-yl]ethylcarbamate (hereafter compound 395);

butyl 2-[4-(2'-fluoro-1,1'-biphenyl-4-yl)-1H-imidazol-2-yl]ethylcarbamate (hereafter compound 396);

butyl 2-[4-(2',4'-difluoro-1,1'-biphenyl-4-yl)-1H-imidazol-2-yl]ethylcarbamate (hereafter compound 398);

2,6-di-tert-butyl-4-{2-[(propylamino)methyl]-1,3-thiazol-4-yl}phenol (hereafter compound 399);

N-{[4-(10H-phenothiazin-2-yl)-1,3-thiazol-2-yl]methyl}-N-propylamine (hereafter compound 400);

N-{[4-(10H-phenothiazin-2-yl)-1,3-thiazol-2-yl]methyl}butan-1-amine (hereafter compound 401);
N-{[4-(10H-phenothiazin-2-yl)-1,3-thiazol-2-yl]methyl}pentan-1-amine (hereafter compound 402);
1-{[4-(3,5-di-tert-butyl-4-hydroxyphenyl)-1,3-thiazol-2-yl]methyl}piperidin-3-ol (hereafter compound 403);
1-{[4-(3,5-di-tert-butyl-4-hydroxyphenyl)-1,3-thiazol-2-yl]methyl}pyrrolidin-3-ol (hereafter compound 404);
[4-(10H-phenothiazin-2-yl)-1,3-thiazol-2-yl]methanol (hereafter compound 405);
N,N-dimethyl-N-{[4-(10H-phenothiazin-2-yl)-1,3-thiazol-2-yl]methyl}amine (hereafter compound 406);
2-{2-[(4-methylpiperazin-1-yl)methyl]-1,3-thiazol-4-yl}-10H-phenothiazine (hereafter compound 407);
2-[2-(piperidin-1-ylmethyl)-1,3-thiazol-4-yl]-10H-phenothiazine (hereafter compound 408);
2-[2-(piperazin-1-ylmethyl)-1,3-thiazol-4-yl]-10H-phenothiazine (hereafter compound 409);
1-{[4-(3,5-di-tert-butyl-4-hydroxyphenyl)-1,3-thiazol-2-yl]methyl}azetidin-3-ol (hereafter compound 410);
2-[2-(morpholin-4-ylmethyl)-1,3-thiazol-4-yl]-10H-phenothiazine (hereafter compound 411);
2-[2-(thiomorpholin-4-ylmethyl)-1,3-thiazol-4-yl]-10H-phenothiazine (hereafter compound 412);
2-{2-[(4-methyl-1,4-diazepan-1-yl)methyl]-1,3-thiazol-4-yl}-10H-phenothiazine (hereafter compound 413);
(3R)-1-{[4-(3,5-di-tert-butyl-4-hydroxyphenyl)-1,3-thiazol-2-yl]methyl}pyrrolidin-3-ol (hereafter compound 414);
(3S)-1-{[4-(3,5-di-tert-butyl-4-hydroxyphenyl)-1,3-thiazol-2-yl]methyl}pyrrolidin-3-ol (hereafter compound 415);
2,6-di-tert-butyl-4-[2-(pyrrolidin-1-ylmethyl)-1,3-thiazol-4-yl]phenol (hereafter compound 416);
2,6-di-tert-butyl-4-{2-[(butylamino)methyl]-1,3-thiazol-4-yl}phenol (hereafter compound 417);
2-{2-[(4-ethylpiperazin-1-yl)methyl]-1,3-thiazol-4-yl}-10H-phenothiazine (hereafter compound 418);
N-methyl-N-{[4-(10H-phenothiazin-2-yl)-1H-imidazol-2-yl]methyl}amine (hereafter compound 419);
methyl [4-(10H-phenothiazin-2-yl)-1,3-thiazol-2-yl]methylcarbamate (hereafter compound 420);
butyl [4-(10H-phenothiazin-2-yl)-1,3-thiazol-2-yl]methylcarbamate (hereafter compound 421);
N-neopentyl-N-{[4-(10H-phenothiazin-2-yl)-1,3-thiazol-2-yl]methyl}amine (hereafter compound 422);
1-{[4-(10H-phenothiazin-2-yl)-1,3-thiazol-2-yl]methyl}piperidin-4-ol (hereafter compound 423);
N-{[4-(10H-phenothiazin-2-yl)-1,3-thiazol-2-yl]methyl}acetamide (hereafter compound 424);
N-{[4-(10H-phenothiazin-2-yl)-1,3-thiazol-2-yl]methyl}butanamide (hereafter compound 425);
2,6-di-tert-butyl-4-{2-[(4-propylpiperazin-1-yl)methyl]-1,3-thiazol-4-yl}phenol (hereafter compound 426);
2,6-di-tert-butyl-4-{2-[2-methyl-1-(methylamino)propyl]-1,3-thiazol-4-yl}phenol (hereafter compound 427);
N,2-dimethyl-1-[4-(10H-phenothiazin-2-yl)-1,3-thiazol-2-yl]propan-1-amine (hereafter compound 428);
N-{[4-(10H-phenothiazin-2-yl)-1,3-thiazol-2-yl]methyl}hexanamide (hereafter compound 429);
(3R)-1-{[4-(10H-phenothiazin-2-yl)-1,3-thiazol-2-yl]methyl}pyrrolidin-3-ol (hereafter compound 430);
(3S)-1-{[4-(10H-phenothiazin-2-yl)-1,3-thiazol-2-yl]methyl}pyrrolidin-3-ol (hereafter compound 431);
1-{[4-(10H-phenothiazin-2-yl)-1,3-thiazol-2-yl]methyl}azetidin-3-ol (hereafter compound 432);
2-{2-[(4-propylpiperazin-1-yl)methyl]-1,3-thiazol-4-yl}-10H-phenothiazine (hereafter compound 433);
2-{2-[(4-acetylpiperazin-1-yl)methyl]-1,3-thiazol-4-yl}-10H-phenothiazine (hereafter compound 434);
2-{2-[(4-butylpiperazin-1-yl)methyl]-1,3-thiazol-4-yl}-10H-phenothiazine (hereafter compound 435);
methyl 4-{[4-(10H-phenothiazin-2-yl)-1,3-thiazol-2-yl]methyl}piperazine-1-carboxylate (hereafter compound 436);
4-[2-(aminomethyl)-1H-imidazol-4-yl]-2,6-di-tert-butylphenol (hereafter compound 437);
4-{2-[(benzylamino)methyl]-1,3-thiazol-4-yl}-2,6-di-tert-butylphenol (hereafter compound 438);
4-{2-[(4-acetylpiperazin-1-yl)methyl]-1,3-thiazol-4-yl}-2,6-di-tert-butylphenol (hereafter compound 439);
N-methyl-N-{[4-(10H-phenoxazin-2-yl)-1,3-thiazol-2-yl]methyl}amine (hereafter compound 440);
4-[2-(azetidin-1-ylmethyl)-1,3-thiazol-4-yl]-2,6-di-tert-butylphenol (hereafter compound 441);
2,6-di-tert-butyl-4-{2-[(4-butylpiperazin-1-yl)methyl]-1,3-thiazol-4-yl}phenol (hereafter compound 442);
butyl 2-[4-(3'-chloro-1,1'-biphenyl-4-yl)-1H-imidazol-2-yl]ethylcarbamate (hereafter compound 443);
butyl 2-[4-(3'-fluoro-1,1'-biphenyl-4-yl)-1H-imidazol-2-yl]ethylcarbamate (hereafter compound 444);
butyl 2-[4-(4-isobutylphenyl)-1H-imidazol-2-yl]ethylcarbamate (hereafter compound 445);
benzyl 2-[4-(4-isobutylphenyl)-1H-imidazol-2-yl]ethylcarbamate (hereafter compound 446);
butyl 2-[4-(3'-chloro-4'-fluoro-1,1'-biphenyl-4-yl)-1H-imidazol-2-yl]ethylcarbamate (hereafter compound 447);
butyl 2-[4-(3',4'-dichloro-1,1'-biphenyl-4-yl)-1H-imidazol-2-yl]ethylcarbamate (hereafter compound 448);
butyl 2-[4-(4-propylphenyl)-1H-imidazol-2-yl]ethylcarbamate (hereafter compound 449);
butyl 2-[4-(4-ethylphenyl)-1H-imidazol-2-yl]ethylcarbamate (hereafter compound 450);
butyl 2-[4-(4'-cyano-1,1'-biphenyl-4-yl)-1H-imidazol-2-yl]ethylcarbamate (hereafter compound 451);
butyl 2-[4-(1,1'-biphenyl-4-yl)-5-ethyl-1H-imidazol-2-yl]ethylcarbamate (hereafter compound 453);
butyl 2-[4-(2'-chloro-1,1'-biphenyl-4-yl)-1H-imidazol-2-yl]ethylcarbamate (hereafter compound 454);
butyl 2-[4-(2',3'-difluoro-1,1'-biphenyl-4-yl)-1H-imidazol-2-yl]ethylcarbamate (hereafter compound 455);
butyl 2-[4-(2'-bromo-1,1'-biphenyl-4-yl)-1H-imidazol-2-yl]ethylcarbamate (hereafter compound 456);
butyl 2-[4-(3',5'-difluoro-1,1'-biphenyl-4-yl)-1H-imidazol-2-yl]ethylcarbamate (hereafter compound 457);
butyl 2-[4-(2'-methoxy-1,1'-biphenyl-4-yl)-1H-imidazol-2-yl]ethylcarbamate (hereafter compound 458);
butyl 2-[4-(3'-nitro-1,1'-biphenyl-4-yl)-1H-imidazol-2-yl]ethylcarbamate (hereafter compound 459);
butyl 2-[4-(2',5'-difluoro-1,1'-biphenyl-4-yl)-1H-imidazol-2-yl]ethylcarbamate (hereafter compound 460);
butyl 2-[4-(3'-methoxy-1,1'-biphenyl-4-yl)-1H-imidazol-2-yl]ethylcarbamate (hereafter compound 461);
methyl 4-{[4-(3,5-di-tert-butyl-4-hydroxyphenyl)-1,3-thiazol-2-yl]methyl}piperazine-1-carboxylate (hereafter compound 462);
methyl [4-(3,5-di-tert-butyl-4-hydroxyphenyl)-1,3-thiazol-2-yl]methylcarbamate (hereafter compound 463);
N-{[4-(3,5-di-tert-butyl-4-hydroxyphenyl)-1,3-thiazol-2-yl]methyl}benzamide (hereafter compound 464);

N-{[4-(3,5-di-tert-butyl-4-hydroxyphenyl)-1,3-thiazol-2-yl]methyl}-2-phenylacetamide (hereafter compound 465);

N-{[4-(3,5-di-tert-butyl-4-hydroxyphenyl)-1,3-thiazol-2-yl]methyl}propanamide (hereafter compound 466);

1-{[4-(3,5-di-tert-butyl-4-hydroxyphenyl)-1,3-thiazol-2-yl]methyl}piperidin-4-yl acetate (hereafter compound 467);

1-{[4-(3,5-di-tert-butyl-4-hydroxyphenyl)-1,3-thiazol-2-yl]methyl}pyrrolidine-3,4-diol (hereafter compound 468);

and the salts of the latter.

In particular, the invention will relate to compounds 350 to 398 as well as the salts of the latter.

According to a particular variant of the particular aspect of the invention indicated above, the compounds of the invention are more specially intended to have an inhibitory activity on MAO's and/or ROS's and they are then preferably chosen from compounds 350 to 377, 399 to 442 and 462 to 468 and salts of these compounds (and in particular from compounds 1 to 28 and salts of these compounds). More preferentially, the compounds of the invention, when they are intended to have an inhibitory activity on MAO's and/or ROS's, are chosen from compounds 350, 352, 355 to 357, 361, 362, 364, 365, 367 to 369, 371 to 377, 399 to 411, 413 to 420, 422 to 435, 438, 440 to 442 and 468 and salts of these compounds (and in particular from compounds 350, 352, 355 to 357, 361, 362, 364, 365, 367 to 369, 371 to 377 and salts of these compounds). Still more preferentially, the compounds of the invention, when they are intended to have an inhibitory activity on MAO's and/or ROS's, are chosen from compounds 350, 352, 355 to 357, 361, 362, 364, 365, 367 to 369, 371 to 373, 375, 377, 399 to 401, 403, 404, 406, 407, 410, 411, 414 to 418, 422, 424, 426 to 431, 435, 438, 440, 441 and 468 and salts of these compounds (and in particular from compounds 350, 352, 355 to 357, 361, 362, 364, 365, 367 to 369, 371 to 373, 375 and 377 and salts of these compounds). In particular, the compounds of the invention, when they are intended to have an inhibitory activity on MAO's and/or ROS's, are chosen from compounds 350, 352, 355, 364, 365, 367, 369, 372, 373, 375, 377, 399, 401, 404, 410, 414 to 418, 426 to 428, 430, 435, 438, 440, 441 and 468 and salts of these compounds (and in particular from compounds 350, 352, 355, 364, 365, 367, 369, 372, 373, 375 and 377 and salts of these compounds). More particularly, the compounds of the invention, when they are intended to have an inhibitory activity on MAO's and/or ROS's, are chosen from compounds 352, 364, 365, 369, 372, 375, 377, 399, 404, 410, 414 to 417, 427, 428, 440 and 441 and salts of these compounds (and in particular from compounds 352, 364, 365, 369, 372, 375 and 377 and salts of these compounds). Even more particularly, the compounds of the invention, when they are intended to have an inhibitory activity on MAO's and/or ROS's, are chosen from compounds 352, 364, 365, 377, 404, 410, 414, 415 and 428 and salts of these compounds (and in particular from compounds 352, 364, 365 and 377 and salts of these compounds).

According to another variant of the particular aspect of the invention indicated above, the compounds of the invention are more specially intended to have a modulatory activity on sodium channels and they are then preferably chosen from compounds 350, 352, 354, 361, 364, 365, 378 to 384, 386 to 396, 398, 443 to 451, 453 to 461 and salts of these compounds (and in particular from compounds 350, 352, 354, 361, 364, 365, 378 to 384, 386 to 396 and 398 and salts of these compounds): More preferentially, the compounds of the invention intended to have a modulatory activity on the sodium channels are chosen from compounds 352, 364, 365, 378 to 384, 386 to 396, 398, 443 to 451 and 453 to 461 and salts of these compounds (and in particular from compounds 352, 364, 365, 378 to 384, 386 to 396 and 398 and salts of these compounds). Also more preferentially, the compounds of general formula (I) intended to have a modulatory activity on the sodium channels are chosen from compounds 379, 386, 391, 393 to 395, 397, 398, 455, 457, 458 and 461 and salts of these compounds (and in particular from compounds 379, 386, 391, 393 to 395, 397 and 398 and salts of these compounds).

Moreover, according to a further variant of the particular aspect of the invention indicated above the compounds more especially intended to have an inhibitory activity on lipidic peroxidation are chosen from compounds 350 to 377, 386, 387, 389, 399 to 442 and 462 to 468 and salts of these compounds (and in particular from compounds 350 to 377, 386, 387 and 389 and salts of these compounds). Preferably, the compounds more especially intended to have an inhibitory activity on lipidic peroxidation are chosen from compounds 350 to 377, 399 to 411, 413 to 442 and 462 to 468 and salts of these compounds (and in particular from compounds 350 to 377 and salts of these compounds). More preferably, the compounds more especially intended to have an inhibitory activity on lipidic peroxidation are chosen from compounds 362, 367, 368, 371 to 376, 400 to 402, 404 to 409, 411, 413, 418, 422 to 425, 428, 430 to 435 and 440 and salts of these compounds (and in particular from compounds 362, 367, 368 and 371 to 376 and salts of these compounds). More particularly, the compounds more especially intended to have an inhibitory activity on lipidic peroxidation are chosen from compounds 362, 372, 407, 413, 430, 431 and 440 and salts of these compounds (and in particular from compounds 362 and 372 and salts of these compounds).

A further aspect of this invention will relate to a further selection of compounds of general formula (I) described above, namely the compounds of Examples 469 to 496, as well as the salts of the latter.

According to a particular variant of the above mentioned further aspect, the compounds of the invention will more specially be intended to have an inhibitory activity on MAO's and/or ROS's and they will then preferably chosen from the compounds of Examples 470 to 496 and salts of these compounds.

According to another particular variant of the above mentioned further aspect, the compounds of the invention will more specially be intended to have a modulatory activity on sodium channels and they will then preferably chosen from the compounds of Examples 469 and 476 to 478 and salts of these compounds.

The same preferences as those indicated for the compounds of general formula (I) and (II) are moreover applicable by analogy to the compounds of general formula (III) or (III)$_G$.

In certain cases, the compounds according to the present invention (i.e. the compounds of general formula (I)$_G$, (I), (II), (III)$_G$ or (III)) can contain asymmetrical carbon atoms. As a result, the compounds according to the present invention have two possible enantiomeric forms, i.e. the "R" and "S" configurations. The present invention includes the two enantiomeric forms and all combinations of these forms, including the racemic "RS" mixtures. For the sake of simplicity, when no specific configuration is indicated in the structural formulae, it should be understood that the two enantiomeric forms and their mixtures are represented.

The invention also relates to the pharmaceutical compositions containing, as active ingredient, a compound of general formula (II) or a pharmaceutically acceptable salt of a compound general formula (II), as well as the use of the compounds of general formula (II) for preparing a medicament intended to inhibit the monoamine oxydases, in particular monoamine oxydase B, to inhibit lipidic peroxidation, to have a modulatory activity on the sodium channels or to have two of the three or all three aforementioned activities.

The invention relates moreover, as medicaments, to the compounds of general formula $(III)_G$ or (III) or their pharmaceutically acceptable salts. Similarly it relates to the pharmaceutical compositions containing, as active ingredient, a compound of general formula $(III)_G$ or (III) or a pharmaceutically acceptable salt of a compound of general formula $(III)_G$ or (III), as well as to the use of the compounds of general formula $(III)_G$ or (III) for preparing a medicament intended to inhibit monoamine oxydases, in particular monoamine oxydase B, to inhibit lipidic peroxidation, to have a modulatory activity on the sodium channels or to have two of the three or all three of the aforementioned activities.

In particular, the compounds of general formula $(I)_G$, (I), (II), $(III)_G$ or (III) can be used for preparing a medicament intended to treat one of the following disorders or one of the following diseases: Parkinson's disease, senile dementia, Alzheimer's disease, Huntington's chorea, amyotrophic lateral sclerosis, schizophrenia, depressions, psychoses, migraine or pains and in particular neuropathic pains.

The invention moreover relates to compounds of general formula (I'), a general formula identical to general formula (I) except that:

(a) either A is replaced by an A' radical

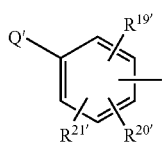

(A')

in which Q' represents a phenyl radical optionally substituted by one or more of the substituents chosen independently from a halogen atom, an OH, cyano, nitro, alkyl, haloalkyl, alkoxy, alkylthio or $-NR^{10'}R^{11'}$ radical and a group of two substituents together representing a methylenedioxy or ethylenedioxy radical, $R^{10'}$ and $R^{11'}$ representing, independently, a hydrogen atom, an alkyl radical or a $-COR^{12'}$ group, or $R^{10'}$ and $R^{11'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12'}$ representing a hydrogen atom, an alkyl or alkoxy or $NR^{13'}R^{14'}$ radical, $R^{13'}$ and $R^{14'}$ representing, independently, a hydrogen atom or an alkyl radical, or $R^{13'}$ and $R^{14'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and $R^{19'}$, $R^{20'}$ and $R^{21'}$ represent, independently, a hydrogen, a halogen, the OH or $SR^{26'}$ group, or an alkyl, cycloalkyl, alkenyl, alkoxy, alkylthio, cyano, nitro, $-SO_2NHR^{49'}$, $-CONHR^{55'}$, $-S(O)_qR^{56'}$, $-NH(CO)R^{57'}$, $-CF_3$, $-OCF_3$ or $NR^{27'}R^{28'}$ radical, $R^{26'}$ representing a hydrogen atom or an alkyl radical, $R^{27'}$ and $R^{28'}$ representing, independently, a hydrogen atom, an alkyl radical or a $-COR^{29'}$ group, or $R^{27'}$ and $R^{28'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{49'}$ and $R^{55'}$ representing, independently each time they occur, a hydrogen atom or an alkyl or alkylcarbonyl radical, q representing an integer from 0 to 2, $R^{56'}$ and $R^{57'}$ representing, independently each time they occur, a hydrogen atom or an alkyl or alkoxy radical, $R^{29'}$ representing a hydrogen atom, an alkyl, alkoxy or $-NR^{30'}R^{31'}$ radical, $R^{30'}$ and $R^{31'}$ representing, independently, a hydrogen atom or an alkyl radical, or $R^{30'}$ and $R^{31'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{51}$ being moreover replaced by an $R^{51'}$ radical, said $R^{51'}$ radical representing one of the radicals of the definition of $R^{51}$ in general formula (I) or a haloalkyl radical, it being understood that either Q' represents a phenyl radical substituted by at least one haloalkyl radical, or that at least one of Q', $R^{19'}$, $R^{20'}$ and $R^{21'}$ represents an alkylthio radical;

(b) or Ω is replaced by an Ω' radical, said Ω' radical representing an $NR^{46}R^{47}$ radical in which one of $R^{46'}$ and $R^{47'}$ represents a $-COOR^{51'}$ radical and the other represents a hydrogen atom, $R^{51'}$ representing a haloalkyl radical;

and the salts of said compounds.

In particular, this aspect of the invention relates to compounds of general formula (I'), a general formula identical to general formula (I) except that:

(a) either A is replaced by an A' radical

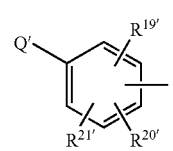

(A')

in which Q' represents a phenyl radical optionally substituted by one or more substituents chosen independently from a halogen atom, an OH, cyano, nitro, alkyl, alkoxy, alkylthio or $-NR^{10'}R^{11'}$ radical and a group of two substituents together representing a methylenedioxy or ethylenedioxy radical, $R^{10'}$ and $R^{11'}$ representing, independently, a hydrogen atom, an alkyl radical or a —$COR^{12'}$ group, or $R^{10'}$ and $R^{11'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{12'}$ representing a hydrogen atom, an alkyl or alkoxy or $NR^{13'}R^{14'}$ radical, $R^{13'}$ and $R^{14'}$ representing, independently, a hydrogen atom or an alkyl radical, or $R^{13'}$ and $R^{14'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, and $R^{19'}$, $R^{20'}$ and $R^{21'}$ represent, independently, a hydrogen, a halogen, the OH or $SR^{26'}$ group, or an alkyl, cycloalkyl, alkenyl, alkoxy, alkylthio, cyano, nitro, —$SO_2NHR^{49'}$, —$CONHR^{55'}$, —$S(O)_qR^{56}$, —$NH(CO)R^{57'}$, —$CF_3$, —$OCF_3$ or $NR^{27'}R^{28'}$ radical, $R^{26'}$ representing a hydrogen atom or an alkyl radical, $R^{27'}$ and $R^{28'}$ representing, independently, a hydrogen atom, an alkyl radical or a —$COR^{29'}$ group, or $R^{27'}$ and $R^{28'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{49'}$ and $R^{55'}$ representing, independently each time they occur, a hydrogen atom or an alkyl or alkylcarbonyl radical, q representing an integer from 0 to 2, $R^{56'}$ and $R^{57'}$ representing, independently each time they occur, a hydrogen atom or an alkyl or alkoxy radical, $R^{29'}$ representing a hydrogen atom, an alkyl, alkoxy or —$NR^{30'}R^{31'}$ radical, $R^{30'}$ and $R^{31'}$ representing, independently, a hydrogen atom or an alkyl radical, or $R^{30'}$ and $R^{31'}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being able to be for example azetidine, pyrrolidine, piperidine, piperazine, morpholine or thiomorpholine, $R^{51}$ being moreover replaced by an $R^{51'}$ radical, said $R^{51'}$ radical representing one of the radicals of the definition of $R^{51}$ in general formula (I) or a haloalkyl radical, it being understood that at least one of Q', $R^{19'}$, $R^{20'}$ and $R^{21'}$ represents an alkylthio radical;

(b) or Ω is replaced by an Ω' radical, said Ω' radical representing an $NR^{46'}R^{47'}$ radical in which one of $R^{46'}$ and $R^{47'}$ represents a —$COOR^{51'}$ radical and the other represents a hydrogen atom, $R^{51'}$ representing a haloalkyl radical;

and the salts of said compounds.

In case (a), the compounds of general formula (I') are preferably such that n represents 0 or 1 and Ω represents an $NR^{46}R^{47}$ radical (one of $R^{46}$ and $R^{47}$ preferably representing a $COOR^{51}$ radical when n=1). Similarly, $R^1$ and $R^2$ are preferably chosen independently from the group constituted by a hydrogen atom and an alkyl or cycloalkyl radical (and preferably a methyl radical). Still preferably for case (a), the compounds of general formula (I') will correspond to one of the general sub-formulae $(I)_1$ or $(I)_2$, X preferably representing S or NH, and more preferentially NH. Moreover, the alkylthio radical is preferably an ethylthio or methylthio radical, more preferentially a methylthio radical.

In case (b), the compounds of general formula (I') are preferably such that n represents 0 or 1 (and preferably 1). Similarly, $R^1$ and $R^2$ are preferably hydrogen atoms.

Moreover, still in case (b), the haloalkyl radical is preferably a radical substituted exclusively by one or more fluorine atoms (for example the 4,4,4-trifluorobutyl radical).

Still preferably for case (b), the compounds of general formula (I') will correspond to one of general sub-formulae $(I)_1$ or $(I)_2$, X preferably representing S or NH, and more preferentially NH.

The invention therefore also relates in particular to the following compounds of general formula (I'):

butyl 2-{4-[4'-(methylthio)-1,1'-biphenyl-4-yl]-1H-imidazol-2-yl}ethylcarbamate;

4,4,4-trifluorobutyl 2-[4-(4-pyrrolidin-1-ylphenyl)-1H-imidazol-2-yl]ethylcarbamate;

butyl-{4-[4'-(trifluoromethyl)-1,1'-biphenyl-4-yl]-1H-imidazol-2-yl}ethylcarbamate;

and the salts of said compounds;

and in particular:

butyl 2-{4-[4'-(methylthio)-1,1'-biphenyl-4-yl]-1H-imidazol-2-yl}ethylcarbamate;

4,4,4-trifluorobutyl 2-[4-(4-pyrrolidin-1-ylphenyl)-1H-imidazol-2-yl]ethylcarbamate;

and the salts of said compounds;

The invention moreover relates, as medicaments, to the compounds of general formula (I') defined previously and their pharmaceutically acceptable salts. The invention also relates to compositions containing, as active ingredient, at least one of the compounds of general formula (I') defined previously or a pharmaceutically acceptable salt of one of these compounds.

A subject of the invention is also the use of one of the compounds of general formula (I') defined previously or of a pharmaceutically acceptable salt of one of these compounds for preparing a medicament intended to have at least one of the following three activities:

to inhibit monoamine oxidases, in particular monoamine oxidase B, to inhibit lipidic peroxidation, to have a modulatory activity vis-à-vis the sodium channels.

In particular, the invention relates to the use of one of the compounds of general formula (I') defined previously or of a pharmaceutically acceptable salt of one of these compounds for preparing a medicament intended to treat one of the following disorders or diseases: Parkinson's disease, senile dementia, Alzheimer's disease, Huntington's chorea, amyotrophic lateral sclerosis, schizophrenia, depressions, psychoses, migraine or pains and in particular neuropathic pains.

By salt is notably meant in the instant application addition salts with organic or inorganic acids as well as salts formed using bases.

By pharmaceutically acceptable salt, is meant in particular the addition salts with inorganic acids such as hydrochloride, hydrobromide, hydroiodide, sulphate, phosphate, diphosphate and nitrate or with organic acids such as acetate, maleate, fumarate, tartrate, succinate, citrate, lactate, methanesulphonate, p-toluenesulphonate, pamoate and stearate. Also included in the field of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, similarly their mixtures, in varying proportions, in water.

The administration of a medicament according to the invention can be done by topical, oral, parenteral route, by intramuscular injection, etc.

The administration dose envisaged for a medicament according to the invention is comprised between 0.1 mg to 10 g according to the type of active compound used.

In accordance with the invention, the compounds of general formula (I) can be prepared by the processes described below.

PREPARATION OF THE COMPOUNDS OF THE INVENTION

Generalities

The preparations of the compounds of the invention which correspond to general formulae (I), (II) or (III) in which Ω represents OH are carried out in a similar fashion to those described in the PCT Patent Application WO 99/09829 and the European Patent Application EP 432 740.

As regards the compounds of the invention which correspond to general formulae (I), (II) and (III) and in which Het is an imidazole ring, a person skilled in the art can also usefully consult the PCT Patent Application WO 99/64401.

The preparations of the other compounds of the invention which correspond to general formulae (I), (II) and (III) are carried out in a similar fashion to those described in the PCT Patent Application WO 98/58934 (cf. in particular on pages 39 to 45 of this document the syntheses of intermediates of general formulae (XXV) and (XXVIII)) or according to the procedures described hereafter.

Furthermore, the compounds of general formula $(I)_G$ or (I') are prepared in a similar manner to the compounds of general formula (I); in other words, the teachings of the following disclosure for the compounds of general formula (I) can generally be extended to the synthesis of the compounds of general formula $(I)_G$ or (I'). The same applies mutatis mutandis to the compounds of general formula $(III)_G$ and (III).

Preparation of the Compounds of General Formula (I)

The compounds of general formula (I) can be prepared by the 8 synthesis routes illustrated below (Diagram 1) starting from the intermediates of general formula (IV), (V), (VI), (VII), (VIII), (IX), (X) and (I)a in which A, B, Ω, $R^1$, $R^2$, Het and n are as defined above, L is a parting group such as for example a halogen, Alk is an alkyl radical, Gp is a protective group for an amine function, for example a 2-(trimethylsilyl)ethoxymethyl (SEM) group, and Gp' a protective group for an alcohol function, for example a group of benzyl, acetate or also silyl type such as tert-butyldimethylsilyl, and finally Λ represents a bond or a —$(CH_2)_x$—, —CO—$(CH_2)_x$—, —$(CH_2)_y$—O— or —C(=NH)— radical. Of course, a person skilled in the art can choose to use protective groups other than Gp and Gp' from those which are known, and in particular those mentioned in: *Protective groups in organic synthesis*, 2nd ed., (John Wiley & Sons Inc., 1991).

Diagram 1

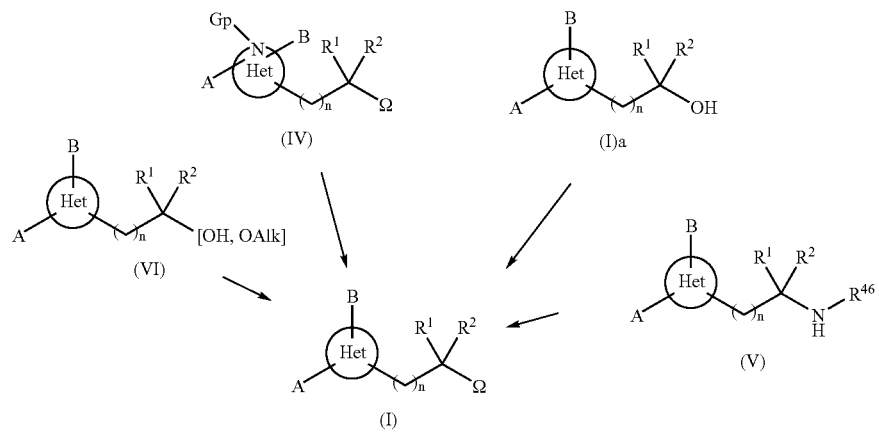

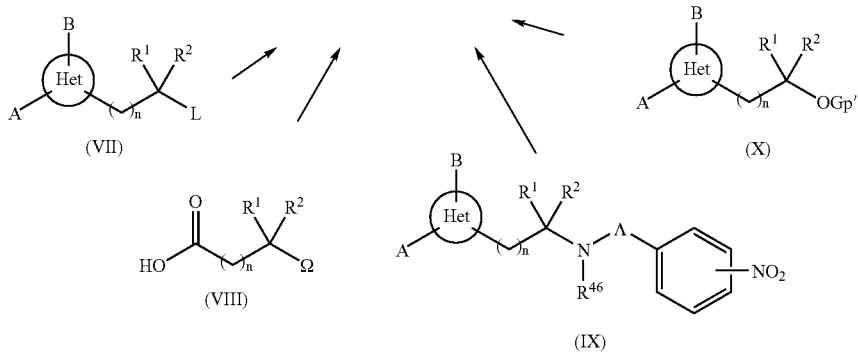

(VII)    (VIII)    (IX)    (X)

Route 1: Het is Imidazole and Ω is $NR^{46}R^{47}$ but not a Radical of Carbamate Type The amines and carboxamides of general formula (I), Diagram 2, in which A, B, $R^1$, $R^2$, $R^{46}$, $R^{47}$, Het and n are as defined above, are prepared by deprotection for example, in the case where Gp represents SEM, with tert-butylammonium fluoride (TBAF) in THF, of the amine of general formula (IV) in order to release the amine of the heterocycle of the compound of general formula (I). The protected amines of general formula (IV) are accessible by a general synthesis route described in *Biorg. and Med. Chem. Lett.*, 1993, 3, 915 and *Tetrahedron Lett.*, 1993. 34, 1901 and more particularly in the PCT Patent Application WO 98/58934.

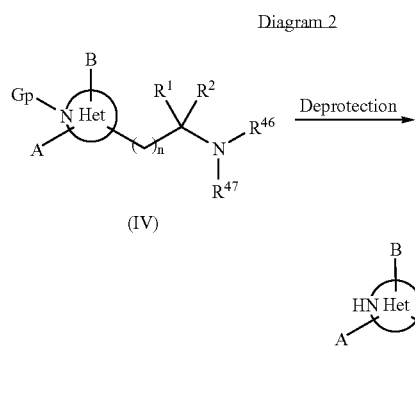

Diagram 2

(IV)  →  Deprotection  →  (I)

Route 2: Het is Imidazole, Oxazole or Thiazole and Ω is $NR^{46}R^{47}$

The amines and carboxamides of general formula (I), Diagram 3, in which A, B, $R^1$, $R^2$, $R^{46}$, Het, g, k and n are as defined above, Δ represents an alkyl, cycloalkylalkyl, arylalkyl, aryl, allenyl, allenylalkyl, alkenyl, alkynyl, cyanoalkyl or hydroxyalkyl radical and Δ' represents an alkyl, cycloalkylalkyl, arylalkyl or aryl radical when g or k do not represent 0, or Δ' represents an alkyl, cycloalkylalkyl, arylalkyl radical or an aryl radical preferably deactivated (i.e. an aryl radical substituted by an electron attractor group such as for example a nitro or cyano group) when g or k represents 0, are prepared by condensation of the amines of general formula (V) with carboxylic acids (or the corresponding acid chlorides) of general formula (XIII) under standard conditions of peptide synthesis, with the aldehydes of general formula (XII) in the presence of a reducing agent such as sodium triacetoxyborohydride or sodium borohydride, in a lower aliphatic alcohol such as methanol and optionally in the presence of molecular sieves, or with halogenated derivatives (Hal=halogen atom) of general formula (XI). In particular, when A represents an allenyl, allenylalkyl, alkenyl, alkynyl, cyanoalkyl or hydroxyalkyl radical, the compounds of general formula (V) are converted to the corresponding compounds of general formula (I) by reaction with the halogenated derivatives of general formula (XI) in a solvent such as acetonitrile, dichloromethane or acetone and in the presence of a base such as for example triethylamine or potassium carbonate at a temperature comprised between ambient temperature and the reflux temperature of the solvent.

The derivatives of general formula (V) are in particular accessible by a general synthesis route described in *Biorg. and Med. Chem. Lett.*, 1993, 3, 915 and *Tetrahedron Lett.*, 1993. 34, 1901, and more particularly in the Patent Application WO 98/58934. When $R^{46}$=H, the compounds of general formula (V) can be prepared, for example, according to a protocol described in the Patent Application WO 98/58934 (using the appropriate amino acid in place of N-Boc-sarcosinamide).

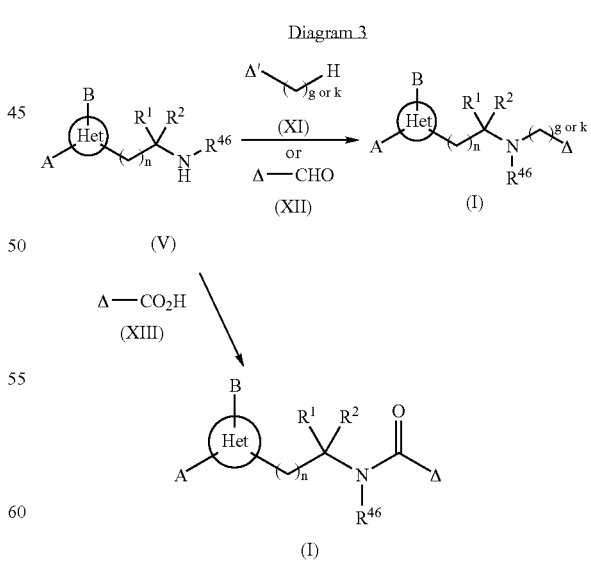

Diagram 3

In the particular case where $R^{47}$ represents a cycloalkyl radical, the amines of general formula (I), Diagram 3a, in which A, B, $R^1$, $R^2$, $R^{46}$, Het and n are as defined above and i represents an integer from 0 to 4 are prepared by condensation of the amines of general formula (V) with the cycloalkylketones of general formula (XIV) in the presence of a reducing agent such as sodium triacetoxyborohydride or sodium borohydride in a lower aliphatic alcohol such as methanol and optionally in the presence of molecular sieves at ambient temperature.

Diagram 3a

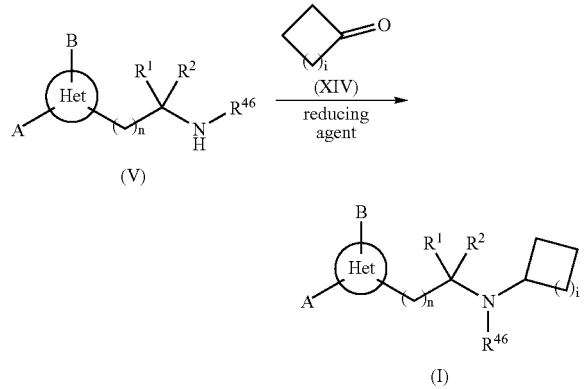

The sulphonamides of general formula (I), Diagram 3b, in which A, B, $R^1$, $R^2$, $R^{46}$, Het and n are as defined above, $R^{47}$ represents an —$SO_2$-Δ radical and Δ represents an alkyl, cycloalkyl, cycloalkylalkyl or arylalkyl radical, are prepared by condensation of the amines of general formula (V) with the sulphochlorides of general formula (XV) under standard conditions, for example in a solvent such as dimethylformamide at ambient temperature.

Diagram 3b

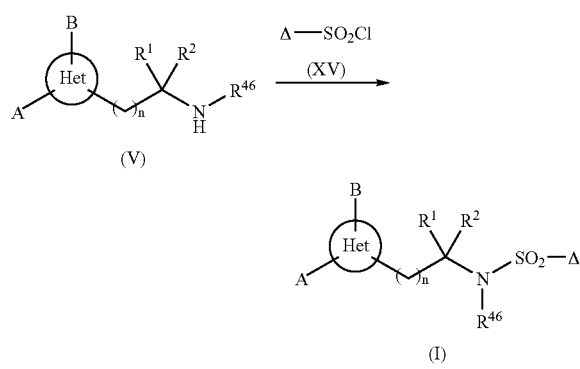

The ureas of general formula (I), Diagram 3c, in which A, B, $R^1$, $R^2$, $R^{46}$, Het and n are as defined above, $R^{47}$ represents a —CO—NH-Δ radical and Δ represents an alkyl, cycloalkyl, cycloalkylalkyl or arylalkyl radical, are prepared by reaction of the amines of general formula (V) with the isocyanates of general formula (XVI) in an inert solvent such as dichloromethane or 1,2-dichloroethane.

Diagram 3c

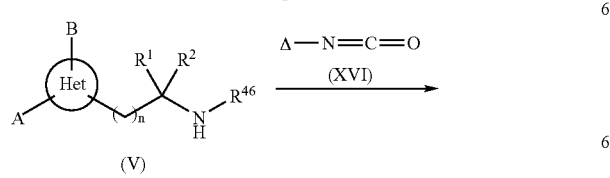

-continued

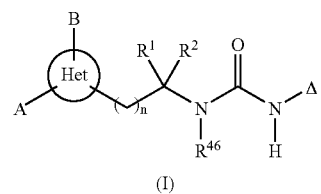

Route 3: Het is Oxazole or Thiazole, $R^1$ and $R^2$ are Both H and Ω is OH.

The alcoholic derivatives of general formula (I), Diagram 4, in which A, B, Het and n are as defined above and $R^1$ and $R^2$ are hydrogen atoms are obtained by reduction of the acids or esters of general formula (VI) (accessible by a general synthesis route described in *J. Med Chem.*, 1996, 39, 237-245 and the PCT Patent Application WO 99/09829).

This reduction can, for example, be carried out by the action of boron hydride or lithium aluminium hydride or also diisobutylaluminium hydride in an aprotic polar solvent such as tetrahydrofuran.

Diagram 4

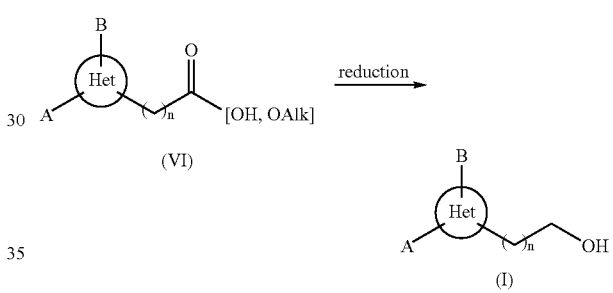

Route 4: Het is Oxazole or Thiazole and Ω is $NR^{46}R^{47}$.

The amines of general formula (I), Diagram 5, in which A, B, $R^1$, $R^2$, $R^{46}$, $R^{47}$, Het, and n are as defined above, are prepared by condensation of the primary or secondary amines of general formula $R^{46}$—$NHR^{47}$ with the compounds of general formula (VII) (in which L preferably represents a halogen atom Hal, but can also represent a mesylate or tosylate group) according to a general synthesis route described in *J. Med. Chem.*, 1996, 39, 237-245 and the PCT Patent Application WO 99/09829 or the U.S. Pat. No. 4,123,529. This synthesis route can in particular be used when $R^{46}$ and $R^{47}$ taken together form with the nitrogen atom which carries them a non-aromatic heterocycle with 4 to 8 members. The reaction typically takes place in an anhydrous solvent (for example dimethylformamide, dichloromethane, tetrahydrofuran or acetone) in the presence of a base (for example $Na_2CO_3$ or $K_2CO_3$ in the presence of triethylamine), and preferably while heating.

Diagram 5

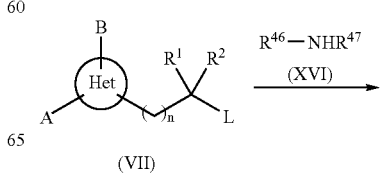

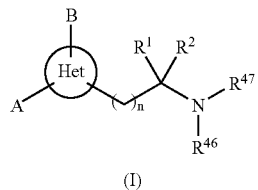

Route 5: Het is Imidazole and Ω is a Radical of Carbamate Type

When Ω is a radical of carbamate type, the acids of general formula (VIII) can be cyclized in the form of derivatives of imidazoles of general formula (I), Diagram 6, by the addition of caesium carbonate followed by a condensation with an α-halogenoketone of formula A—CO—CH(B)—[Br, Cl] followed by the addition of a large excess of ammonium acetate (for example 15 or 20 equivalents per equivalent of acid of general formula (VIII)). This reaction is preferably carried out in a mixture of xylenes and while heating (one can also, if appropriate, simultaneously eliminate the water formed during the reaction).

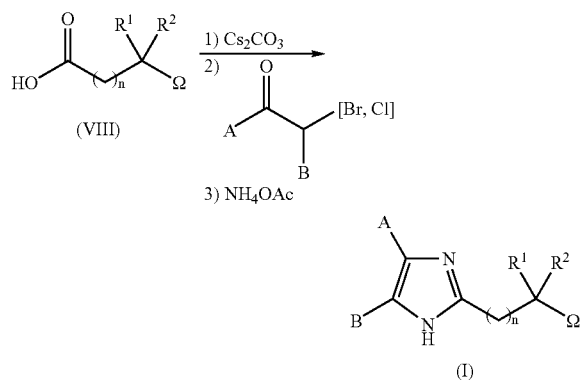

Route 6: Het is Imidazole, Oxazole or Thiazole and Ω is $NR^{46}R^{47}$

When Ω is an $NR^{46}R^{47}$ radical in which $R^{47}$ is a radical comprising a termination of aminophenylene, alkylaminophenylene or dialkylaminophenylene type, the compounds of general formula (I), in which A, B, Het, n, $R^1$, $R^2$ and $R^{46}$ are as defined above and A represents a bond or a —$(CH_2)_x$—, —CO—$(CH_2)_x$—, —$(CH_2)_y$—O— or —C(=NH)— radical, x and y being integers from 0 to 6, can be obtained, Diagram 7, by reduction of the compound of general formula (IX), for example by the action of hydrogen in the presence of a catalyst of palladium on carbon type in a solvent such as for example methanol, ethanol, dichloromethane or tetrahydrofuran. Reduction of the nitro function can also be carried out, for example, by heating the product in an appropriate solvent such as ethyl acetate with a little ethanol in the presence of $SnCl_2$ (*J. Heterocyclic Chem.* (1987), 24, 927-930; *Tetrahedron Letters* (1984), 25 (8), 839-842) or in the presence of $SnCl_2/Zn$ (*Synthesis.* (1996),9,1076-1078), using $NaBH_4$—$BiCl_3$ (*Synth. Com.* (1995) 25 (23), 3799-3803) in a solvent such as ethanol, or then by using Raney Ni with hydrazine hydrate added to it (*Monatshefte für Chemie*, (1995), 126, 725-732), or also using indium in a mixture of ethanol and ammonium chloride under reflux (*Synlett* (1998) 9, 1028).

When $R^{47}$ is a radical of aminophenylene, alkylaminophenylene or dialkylaminophenylene type (Alk and Alk' are identical or different alkyl radicals), the compound of general formula (IX) is reduced in order to produce the aniline derivative of general formula (I) and optionally mono- or di-alkylated according to standard reactions known to a person skilled in the art. The mono-alkylation is carried out by reducing amination with an aldehyde or by a nucleophilic substitution by reaction with an equivalent of halogenoalkyl Alk-Hal. A second alkylation can then be carried out if appropriate using a halogenoalkyl Alk'-Hal.

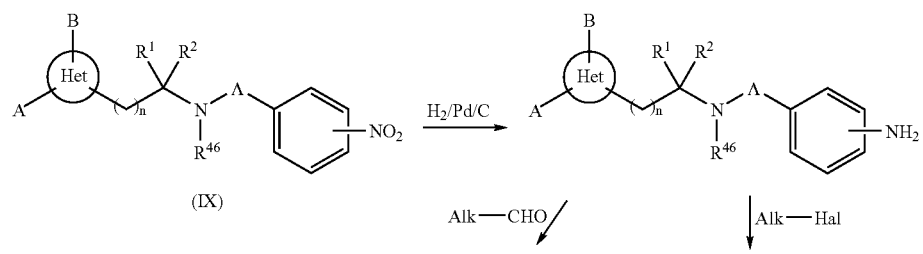

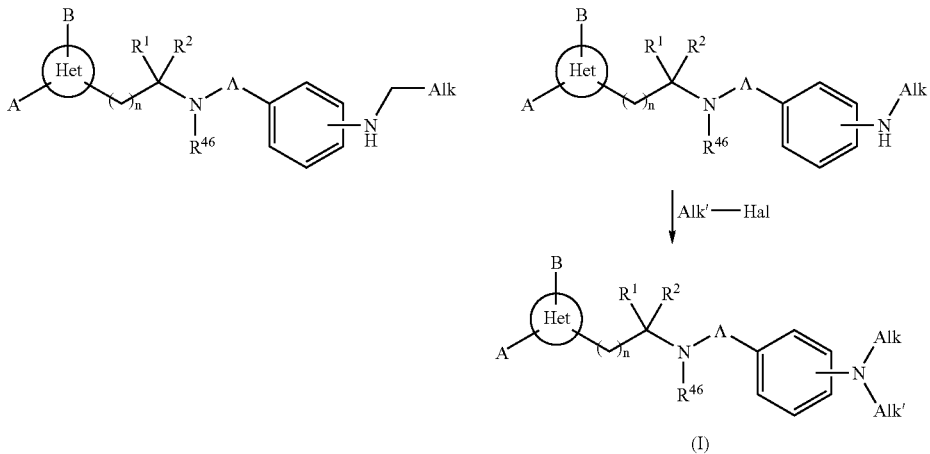

(I)

In the particular case where Alk=Alk'=—CH₃ and where A does not represents —CH₂—, the nitro derivative of general formula (IX) will be treated with suitable quantities of paraformaldehyde under a flow of hydrogen in a solvent such as ethanol and in the presence of a catalyst of palladium on carbon type (Diagram 7a).

Diagram 7a

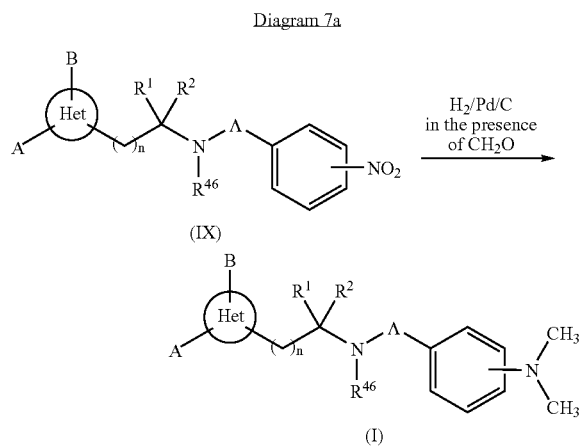

Route 7: Het is Imidazole, Oxazole or Thiazole and Ω is OH

This route can be used when Ω is OH. Contrary to route 3, $R^1$ and $R^2$ cannot be hydrogen atoms. In this case, the compounds of general formula (I) can be obtained, Diagram 8, by deprotection of the protected alcohol of general formula (X).

In the case where Gp' is a protective group of silyl type, the deprotection can be carried out, for example, by adding tetra-tert-butylammonium fluoride in a solvent such as tetrahydrofuran. In the case where Gp' is a protective group of benzyl type, the deprotection will be carried out by hydrogenation in a solvent such as for example methanol, ethanol, dichloromethane or tetrahydrofuran. In the case where Gp' is a protective group of acetate type, the deprotection can be carried out, for example, using sodium or potassium carbonate in an alcoholic solvent such as methanol. For other cases, a person skilled in the art will usefully consult the following document: *Protective groups in organic synthesis*, 2nd ed., (John Wiley & Sons Inc., 1991).

Diagram 8

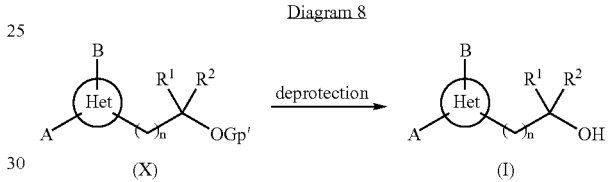

Route 8: Het is Imidazole, Oxazole or Thiazole and Ω is $OR^{48}$ with $R^{48}H$ The compounds of general formula (I) in which Ω is an $OR^{48}$ radical with $R^{48}H$ are obtained, for example, Diagram 9, from alcohols of general formula (I)a (which are compounds of general formula (I) as defined previously in which Ω represents OH) by reacting the latter with a halide of general formula $R^{48}$-Hal (Hal=Br, Cl or I) in a solvent such as dichloromethane, acetonitrile, anhydrous tetrahydrofuran or anhydrous ether and in the presence of a base such as potassium or sodium carbonate, sodium hydride or triethylamine.

In the case where the A, B, $R^1$ and $R^2$ radicals contain alcohol, phenol, amine or aniline functions, it may be necessary to add protection/deprotection stage for these functions according to standard methods known to a person skilled in the art (stages not represented in Diagram 9).

Diagram 9

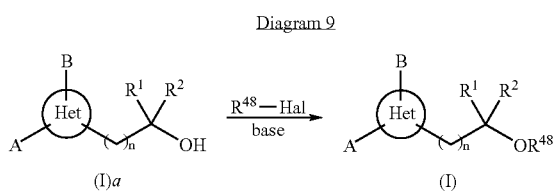

Preparation of the Synthesis Intermediates

Preparation of the Imidazoles and Thiazoles of General Formula (V)

General Outline

The non-commercial ketonic derivative of general formula (V.i) or (V.i)₂ in which A and B are as defined in general formula (I) is converted, Diagram 3.1, to the corresponding α-bromo-ketone of general formula (V.ii) ou (V.ii)₂ by reaction with a bromination agent such as CuBr₂ (*J. Org. Chem.* (1964), 29, 3459), bromine (*J. Het. Chem.* (1988), 25, 337), N-bromosuccinimide (*J. Amer. Chem. Soc.* (1980), 102, 2838) in the presence of acetic acid in a solvent such as ethyl acetate or dichloromethane, HBr or Br₂ in ether, ethanol or acetic acid (*Biorg. Med. Chem. Lett.* (1996), 6(3), 253-258; *J. Med. Chem.* (1988), 31(10), 1910-1918) *J. Am. Chem. Soc.* (1999), 121, 24) or also using a bromination resin (*J. Macromol. Sci. Chem.* (1977), A11, (3) 507-514). In the particular case where A is a p-dimethylaminophenyl radical, it is possible to use the operating method appearing in the publication *Tetrahedron Lett.*, 1998, 39 (28), 4987. The amine of general formula (V) is then obtained according to the procedures shown in Diagrams 3.2 (imidazoles) and 3.3 (thiazoles) hereafter.

Diagram 3.2

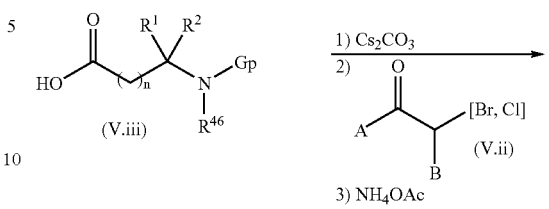

Diagram 3.1

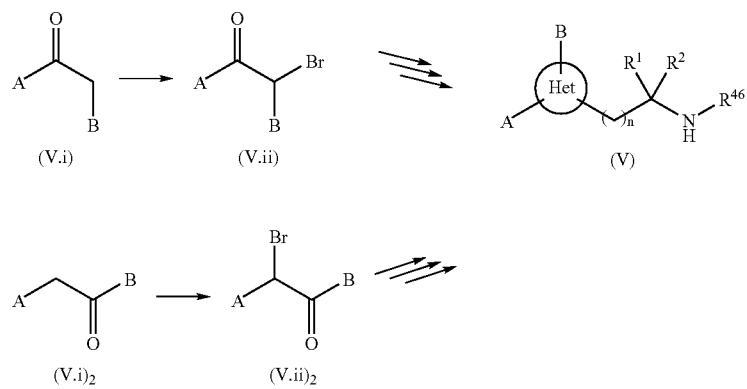

Alternatively to the synthesis shown in Diagram 3.1, a person skilled in the art can, if appropriate, use an α-chloro-ketone in place of an α-bromo-ketone.

Obtaining the Imidazoles of General Formula (V)

The acid of general formula (V.iii), in which Gp represents a protective group for an amine function, for example a protective group of carbamate type, is treated, Diagram 3.2, with Cs₂CO₃ in a solvent such as methanol or ethanol. The α-halogeno-ketone of general formula (V.ii) in an inert solvent such as dimethylformamide is added to the caesium salt recovered. The intermediate ketoester is cyclized by heating to reflux in xylene (mixture of isomers) in the presence of a large excess of ammonium acetate (15 or 20 equivalents for example) in order to produce the imidazole derivative of general formula (V.iv) (the water formed being optionally eliminated during the reaction).

In the case where R³⁸ is not H, the amine function of the imidazole ring of the compound of general formula (V.iv) is substituted by reaction with the halogenated derivative R³⁸-Hal (Hal=halogen atom); the protected amine function is then deprotected under standard conditions (for example: trifluoroacetic acid or HCl in an organic solvent when it is a protective group of carbamate type, or also hydrogenation in the presence of palladium on carbon when the protective group is a benzyl carbamate).

-continued

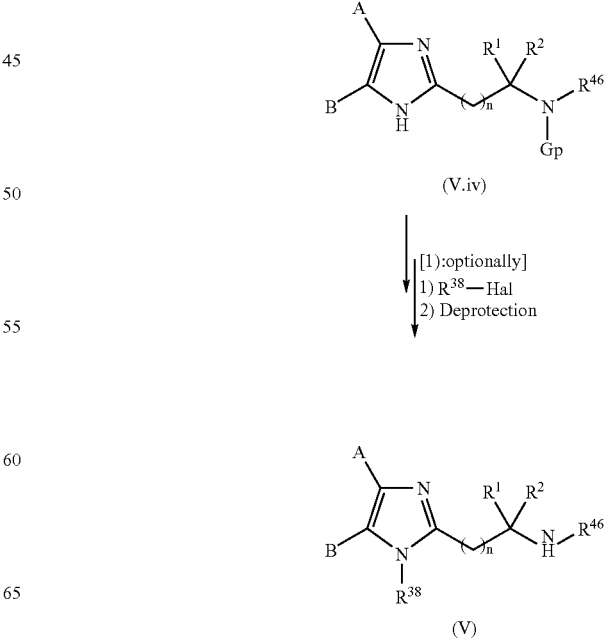

Obtaining the Thiazoles of General Formula (V) Intended for the Preparation of Compounds of General Formulae (I)$_1$ or (I)$_2$:

The thiocarboxamide of general formula (V.v), in which Gp represents a protective group for an amine function, for example a protective group of carbamate type, obtained for example by reaction of the corresponding carboxamide with Lawesson reagent or with (P$_2$S$_5$)$_2$, is reacted, Diagram 3.3, with the α-bromo-ketone of general formula (V.ii) or (V.ii)$_2$ according to an experimental protocol described in the literature (*J. Org. Chem.*, (1995), 60, 5638-5642). The protected amine function is then deprotected under standard conditions in a strong acid medium (for example: trifluoroacetic acid or HCl in an organic solvent when it is a protective group of carbamate type), releasing the amine of general formula (V).

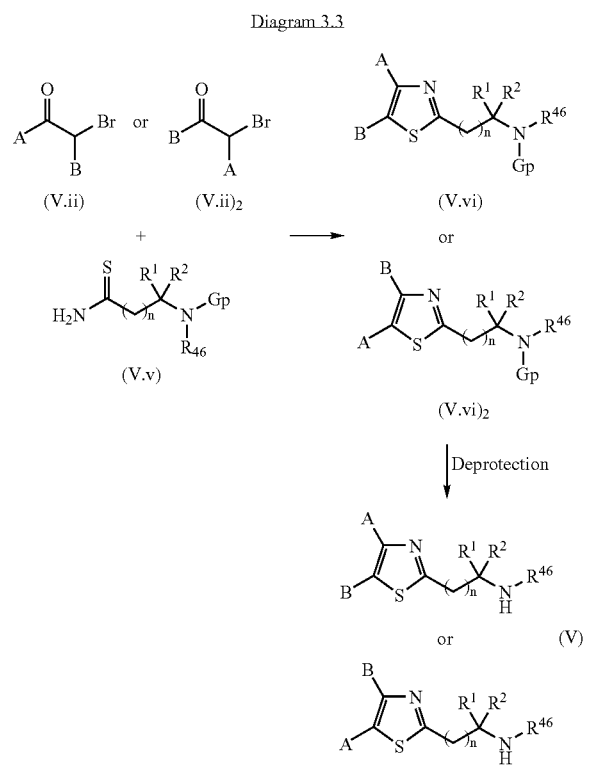

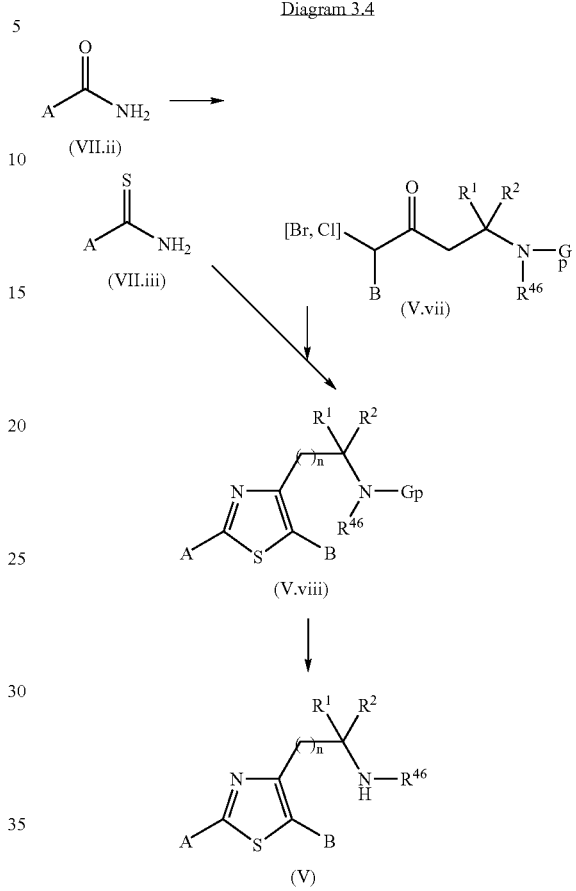

Obtaining the Thiazoles of General Formula (V) Intended for the Preparation of Compounds of General Formula (I)$_3$:

These compounds are obtained according to a method summarized in Diagram 3.4 below. The carboxamide of general formula (VII.ii) is firstly treated, for example, with Lawesson reagent or with (P$_2$S$_5$)$_2$ then the thiocarboxamide of general formula (VII.iii) obtained is reacted with the halogenated derivative of general formula (V.vii) (cf. *Biorg. Med. Chem. Lett.* (1996), 6(3), 253-258; *J. Med. Chem.* (1988), 31(10), 1910-1918; *Tetrahedron Lett.*, (1993), 34 (28), 4481-4484; or *J. Med. Chem.* (1974), 17, 369-371; or also *Bull. Acd. Sci. USSR Div. Chem. Sci.* (Engl Transl) (1980) 29, 1830-1833). The protected amine of general formula (V.viii) thus obtained is then deprotected under standard conditions for a person skilled in the art (for example: trifluoroacetic acid or HCl in an organic solvent when Gp is a protective group of carbamate type).

Obtaining the Oxazoles of General Formula (V) Intended for the Preparation of Compounds of General Formula (I)$_3$:

These compounds are obtained according to a method summarized in Diagram 3.5 below. The carboxamide of general formula (VII.ii) is reacted with the halogenated derivative of general formula (V.vii). The protected amine of general formula (V.ix) thus obtained is then deprotected under standard conditions for a person skilled in the art in order to produce the compound of general formula (V) (for example: trifluoroacetic acid or HCl in an organic solvent when Gp is a protective group of carbamate type).

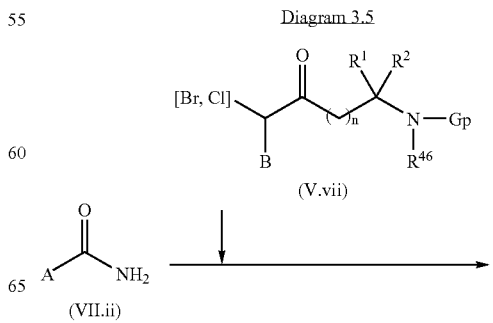

-continued

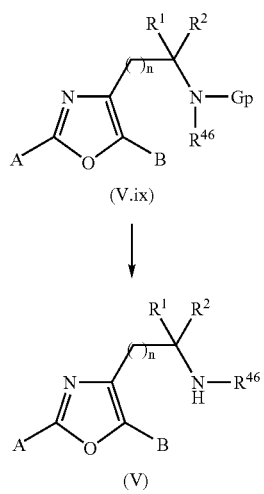

(V.ix)

↓

(V)

Preparation of the Ketonic Derivatives of General Formula (V.i) and of Certain α-Bromoketonic Derivatives of General Formula (V.ii), (V.ii)₂, or (V.vii)

The non-commercial ketonic derivatives of general formula (V.i) or their α-bromoketonic homologues are accessible from methods in the literature or similar methods adapted by a person skilled in the art. In particular:

when A represents an indolinyl or tetrahydroquinolyl radical, the compounds of general formula (V.i) are accessible from methods in the literature such as for example *J. Med. Chem.* (1986), 29, (6), 1009-1015 or *J. Chem. Soc., Perkin Trans.* 1 (1992), 24, 3401-3406;

Alternatively, the compounds of general formula (V.ii) in which A represents an indolinyl or tetrahydroquinolyl radical in which $R^{33}$ represents H can be synthesized according to a protocol which is slightly modified compared to that described in *J. Chem. Soc., Perkin Trans* 1 (1992), 24, 3401-3406. This protocol is summarized in Diagram 3.6 below.

Diagram 3.6

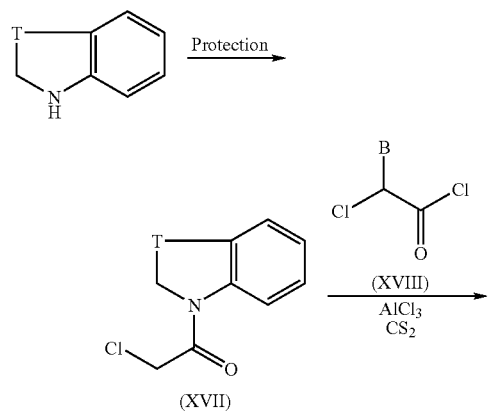

-continued

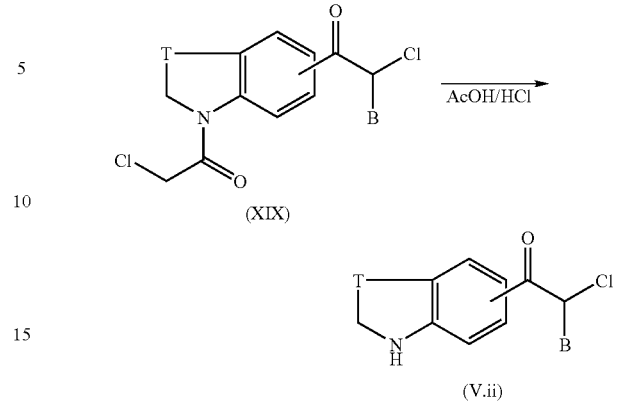

(XIX)

(V.ii)

The indoline or tetrahydroquinoline (T represents —CH₂— or —(CH₂)₂—) is protected using chloroacetyl chloride in order to produce the compound of general formula (XVII) which is subjected to a Friedel-Crafts reaction (substituted chloroacetyl chloride of general formula (XVIII), in which B has the meaning indicated previously, in a solvent such as carbon disulphide and in the presence of aluminium chloride) in order to produce the compound of general formula (XIX). Then the compound of general formula (XIX) is hydrolyzed in the presence of acid, for example an acetic acid/HCl mixture, in order to produce the compounds of general formula (V.ii) in the form of a mixture of meta and para isomers. These isomers can be separated by fractioned crystallization from a solvent such as glacial acetic acid.

A person skilled in the art will know how to adapt the syntheses described previously to the case where A represents an indolinyl or tetrahydroquinolyl radical in which $R^{33}$ does not represent H. For example, when $R^{33}$ represents an alkyl or aralkyl radical, the protection and deprotection stages will be unnecessary.

when A represents a radical of 4-(4-hydroxyphenyl)-phenyl type, the compounds of general formula (V.i) are accessible from methods in the literature such as for example *J. Org. Chem.*, (1994), 59(16), 4482-4489.

Alternatively, the compounds of general formula (V.i) and (V.ii) in which A represents a radical of 4-(4-hydroxyphenyl)-phenyl type are accessible for example by the method illustrated in Diagram 3.7 below.

Diagram 3.7

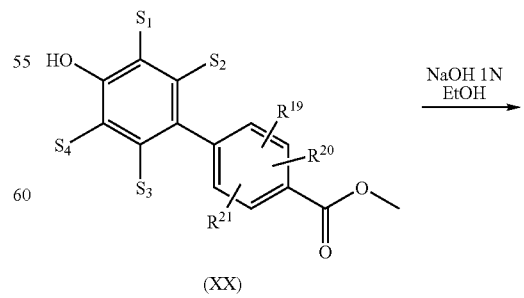

(XX)

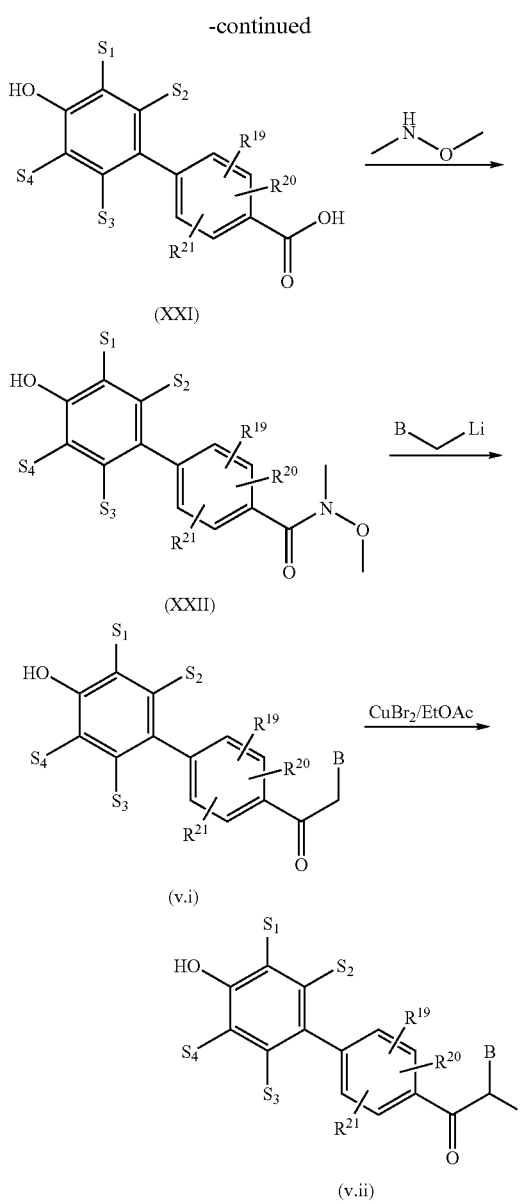

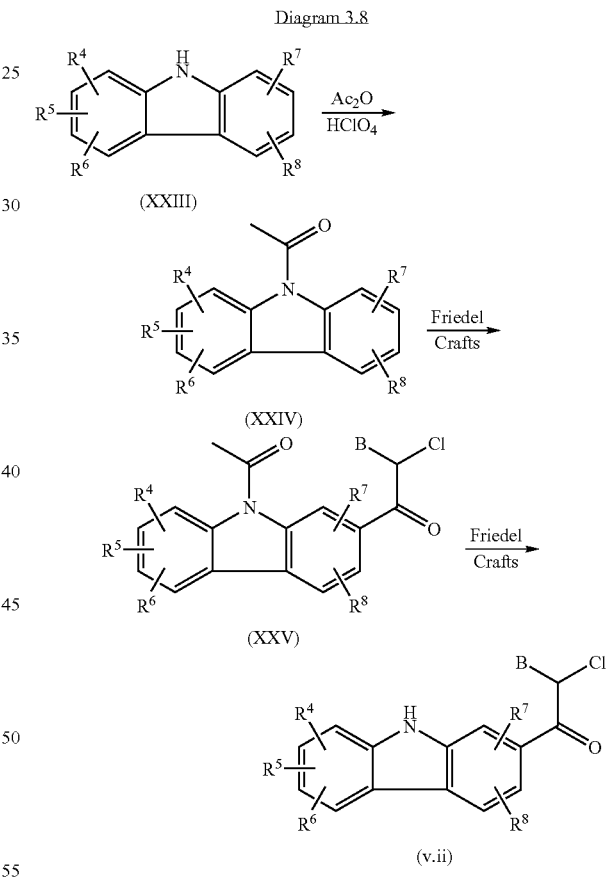

presence of a base such as triethylamine with dicyclohexylcarbodiimide or 1-(3-dimethylaminopropyl)-3-ethylcarbodiimide hydrochloride and hydroxybenzotriazole, in order to produce the intermediates of general formula (XXII). The compounds of general formula (V.i) are prepared from the compounds of general formula (XXII) by a substitution reaction with MeLi (J. Med. Chem. (1992), 35(13), 2392). The bromoacetophenones of general formula (V.ii) are now accessible from the acetophenone of general formula (V.i) under the conditions described previously.

when A represents a carbazolyl radical, the compounds of general formula (V.i) are accessible from methods in the literature such as for example J. Org. Chem., (1951), 16, 1198 or Tetrahedron (1980), 36, 3017.

Alternatively, the compounds of general formula (V.ii) in which A represents a carbazolyl radical in which R9 represents H can be synthesized according to a protocol which is slightly modified with respect to that described for A=carbazolyl in Tetrahedron (1980), 36, 3017. This method is summarized in Diagram 3.8 hereafter:

The carbazole of general formula (XXIII) is protected using acetic anhydride in order to produce the compound of general formula (XXIV), which is subjected to a Friedel-Crafts reaction (substituted chloroacetyl chloride of general formula (XVIII) as defined previously in a solvent such as carbon disulphide and in the presence of aluminium chloride) in order to produce the compound of general formula (XXV).

Then the acyl group protecting the amine function is hydrolyzed in the presence of acid, for example an AcOH/HCl mixture, in order to produce the compound of general The compounds of general formula (V.i) or (V.ii), in which $S_1$, $S_2$, $S_3$ and $S_4$ are chosen independently from a hydrogen atom and OH, cyano, nitro, alkyl, alkoxy or —$NR^{10}R^{11}$ as defined in general formula (I), are prepared, Diagram 3.7, from the esters of general formula (XX) (cf. in particular Chem. Lett. (1998), 9, 931-932 and Synthesis (1993), 8, 788-790). Of course, the phenol or aniline functions resulting from the nature of the $R^{19}$, $R^{20}$, $R^{21}$, $S_1$, $S_2$, $S_3$ and $S_4$ substituents can lead a person skilled in the art to add to the stages represented in Diagram 3.7 protection stages (and, subsequently in the synthesis of the compounds of general formula (I), deprotection stages) of these functions so that they do not interfere with the remainder of the chemical synthesis. The esters of general formula (XX) are hydrolyzed in order to produce the acids of general formula (XXI). The latter are then subjected to coupling with N,O-dimethylhydroxylamine (Syn. Commun. (1995), 25(8), 1255; Tetrahedron Lett. (1999), 40(3), 411-414) in a solvent such as dimethylformamide or dichloromethane, in the formula (V.ii). When A represents a carbazolyl radical in which R⁹ represents alkyl or a —COR¹⁵ group (case not shown in Diagram 3.8), the initial acylation stage is unnecessary and the last two stages of Diagram 3.8 allow the compounds of general formula (V.ii) to be obtained. Of course, the phenol or aniline functions resulting from the nature of the R⁴, R⁵, R⁶, R⁷ and R⁸ substituents can lead a person skilled in the art to add to the stages represented in Diagram 3.8 protection stages (and, subsequently in the synthesis of the compounds of general formula (I), deprotection stages) of these functions so that they do not interfere with the remainder of the chemical synthesis.

- when A represents a phenothiazinyl radical, the intermediates of general formula (V.i) and (V.ii) are accessible from methods in the literature: *J. Heterocyclic. Chem.* (1978), 15, 175-176 and *Arzneimittel Forschung* (1962), 12, 48.

Alternatively, the intermediates of general formula (V.ii) in which A represents a phenothiazinyl radical can be prepared according to a protocol which is slightly modified with respect to that described for the phenothiazinyl radical in *Arzneimittel Forschung* (1962), 12, 48, which is summarized in Diagram 3.9 hereafter (see also the examples). The phenothiazine of general formula (XXVI) is protected using chloroacetyl chloride in order to produce the compound of general formula (XXVII), which is then subjected to a Friedel-Crafts reaction (compound of general formula (XVIII) in a solvent such as carbon disulphide in the presence of aluminium chloride) in order to produce the compound of general formula (XXVIII). During the last stage of the process, hydrolysis with HCl/acetic acid is accompanied by a halogen exchange and allows the chloroketone of general formula (V.ii) to be obtained. Of course, the phenol or aniline functions resulting from the nature of the R⁴, R⁵, R⁶, R⁷ and R⁸ substituents can lead a person skilled in the art to add to the stages shown in Diagram 3.9 protection stages (and, subsequently in the synthesis of the compounds of general formula (I), deprotection stages) of these functions so that they do not interfere with the remainder of the chemical synthesis.

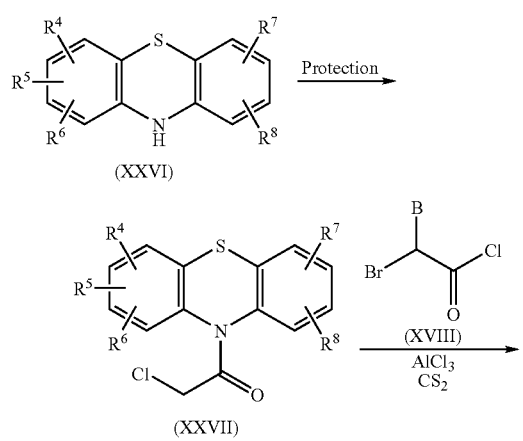

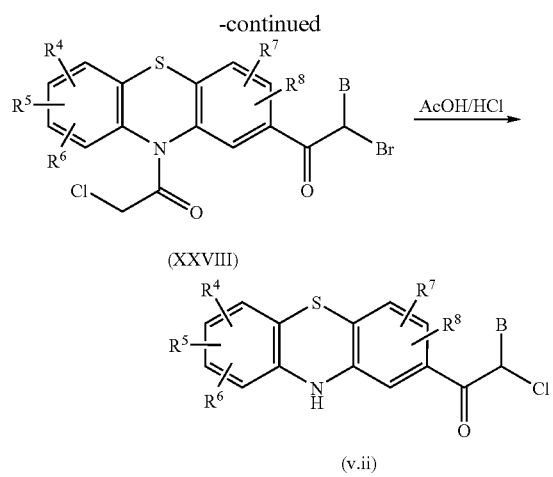

- when A represents a phenylaminophenyl radical, the compounds of general formula (V.i) are accessible from methods in the literature such as for example *Chem. Commun.*, (1998), 15, (6) 1509-1510 or *Chem Ber.*, (1986), 119, 3165-3197, or similar methods which a person skilled in the art will have adapted.

For example, the intermediates of general formula (V.i)a and (V.ii)a in which A represents a phenylaminophenyl radical (which correspond to the corresponding compounds of general formula (V.i) and (V.ii) the aniline function of which has been acetylated), can be prepared according to a protocol which is slightly modified with respect to that described for the phenylaminophenyl radical in *Chem Ber.* (1986), 119, 3165-3197. This protocol is summarized in Diagram 3.10 hereafter.

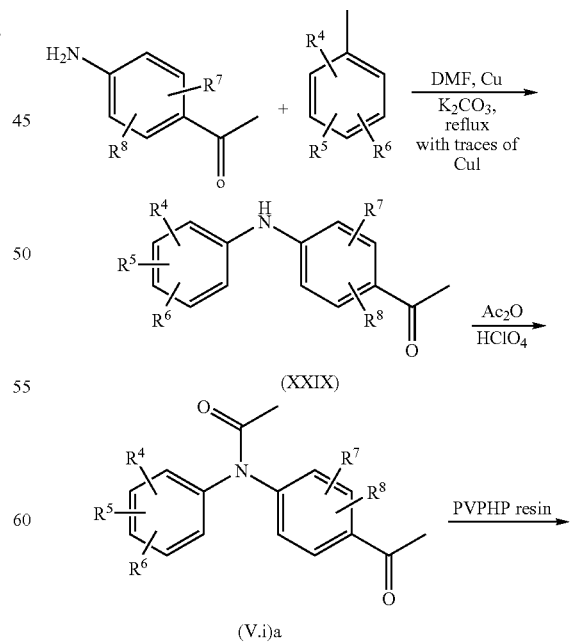

-continued

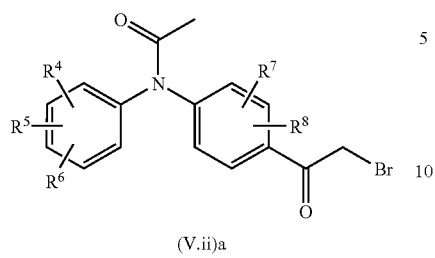

(V.ii)a

In the case (shown in Diagram 3.10) where the $R^9$ radical of the compound of general formula (I) to be synthesized is a hydrogen atom or an acetyl group, the diphenylamine of general formula (XXIX) formed after the coupling reaction in the presence of CuI is protected by acetylation using, for example, acetic anhydride in order to produce the compound of general formula (V.i)a. In the case (not shown in Diagram 3.10) where the $R^9$ radical of the compound of general formula (I) to be synthesized is not a hydrogen atom or an acetyl radical, the acetylation stage is replaced by a substitution stage of the aniline according to standard methods known to a person skilled in the art in order to produce the corresponding compound of general formula (V.i). The compound of general formula (V.i)a (or (V.i), in the case not shown in Diagram 3.10) is then subjected to a bromination reaction using a bromination resin, PVPHP resin (Poly (VinylPyridinium Hydrobromide Perbromide), described in *J. Macromol. Sci. Chem.* (1977), A11, (3), 507-514, in order to produce the compound of general formula (V.ii)a (or (V.ii), in the case not shown in Diagram 3.10). Of course, the phenol or aniline functions resulting from the nature of the $R^4$, $R^5$, $R^6$, $R^7$ and $R^8$ substituents can lead a person skilled in the art to add to the stages shown in Diagram 3.10 protection stages (and, subsequently in the synthesis of the compounds of general formula (I), deprotection stages) of these functions so that they do not interfere with the remainder of the chemical synthesis. The deprotection of the acetylated aniline function will be carried out in principle during the last stage of the synthesis of the compounds of general formula (I).

when A represents a benzopyran or benzofuran radical as defined in general formula (I) with $R^{32}$ representing a hydrogen atom, the intermediates of general formula (V.i) and (V.ii) are accessible by the methods illustrated in Diagram 3.11 below.

Diagram 3.11

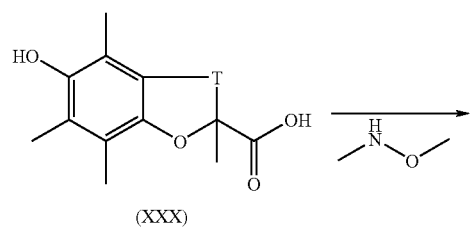

(XXX)

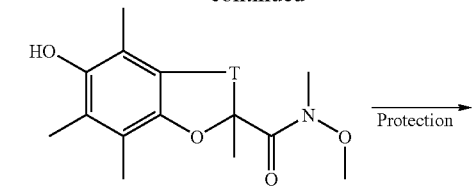

(XXXI)

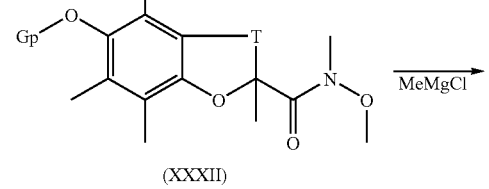

(XXXII)

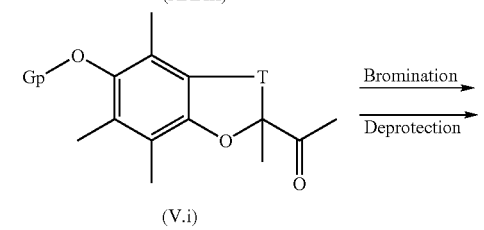

(V.i)

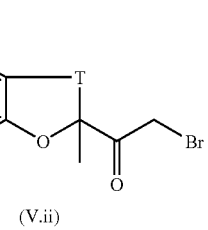

(V.ii)

The compounds of general formulae (V.i) and (V.ii), according to Diagram 3.11, in which T is as defined above and Gp=protective group, are prepared from the acids of general formula (XXX). The acids of general formula (XXX) are subjected to coupling with N,O-dimethylhydroxylamine (*Syn. Commun.* (1995), 25, (8), 1255; *Tetrahedron Lett.* (1999), 40, (3), 411-414) in a solvent such as dimethylformamide or dichloromethane, in the presence of a base such as triethylamine with dicyclohexylcarbodiimide or 1-(3-dimethylaminopropyl)-3-ethylcarbodiimide hydrochloride and hydroxybenzotriazol, in order to produce the intermediates of general formula (XXXI). The protection of the phenol function in the form of a benzylated or tert-butyldimethylsilylated derivative or by other protective groups (Gp) known to a person skilled in the art is then carried out in order to produce the compounds of general formula (XXXII). The compounds of general formula (V.i) are prepared from the compounds of general formula (XXXII) by a substitution reaction with a Grignard reagent, MeMgCl (*J. Het. Chem.* (1990), 27, 1709-1712) or with MeLi (*J. Med. Chem.* (1992), 35, 13). The bromoacetophenones of general formula (V.ii) are now accessible from the acetophenone of general formula (V.i) under previously described conditions.

Alternatively, the compound of general formula (V.ii) in which $R^{32}$ represents a hydrogen atom or an alkyl radical can be prepared according to a process in only 3 stages (cf. Diagram 3.12—see also the examples). In this process, the bromination in the last stage of the compound of general formula (V.i) in order to produce the compound of general formula (V.ii) will preferably be carried out according to *J. Am. Chem. Soc.* (1999), 121, 24.

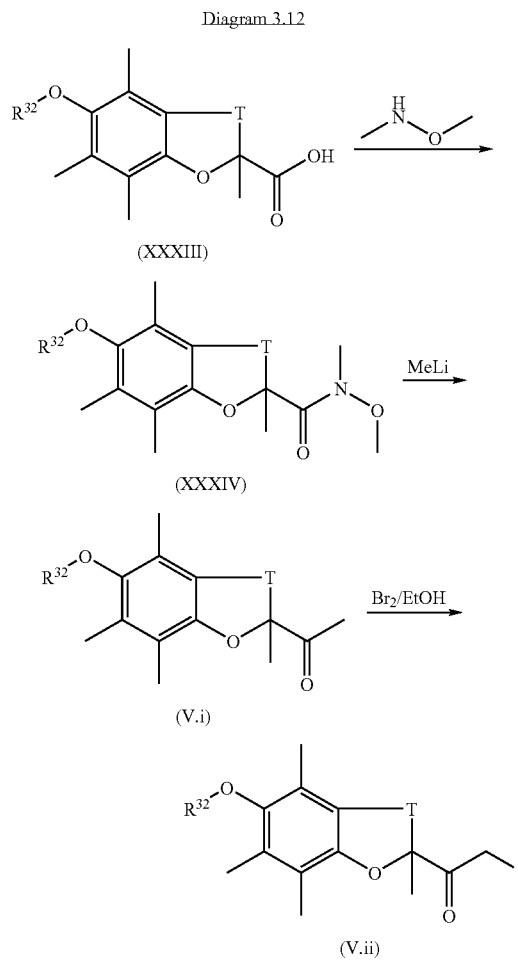

Diagram 3.12

(XXXIII)

(XXXIV)

(V.i)

(V.ii)

When A represents a substituted phenol radical, it can be necessary to use intermediates of general formula (V.ii) as defined previously the phenol function of which has been acetylated (hereafter designated as compounds of general formula (V.ii)b). In particular:

when A represents a 4-hydroxy-3,5-diisopropylphenyl radical, the homologous α-bromoketonic derivatives of the compound of formula (V.ii) the phenol function of which is protected by an acetyl radical can be prepared as summarized in Diagram 3.13 hereafter.

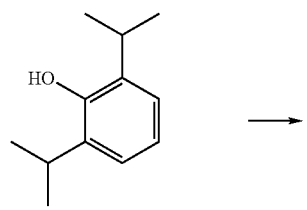

Diagram 3.13

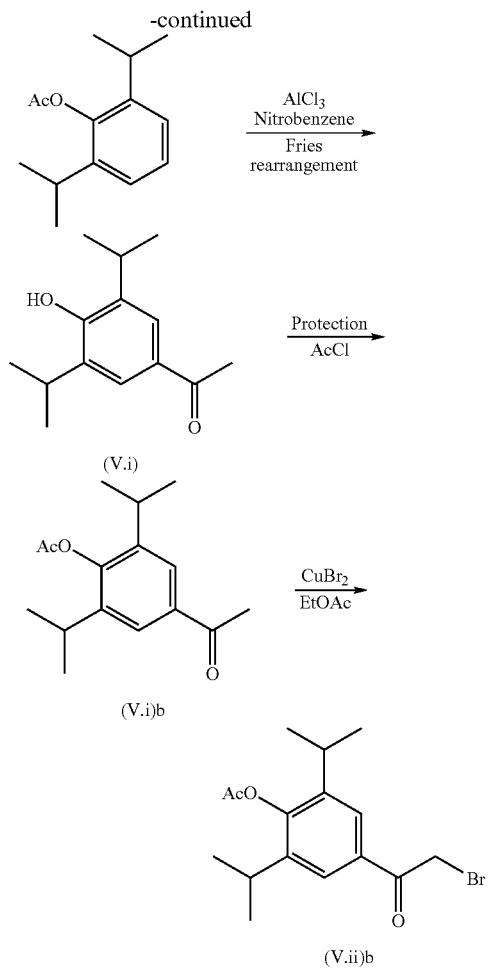

(V.i)

(V.i)b (V.ii)b 2,6-diisopropylphenol is acetylated according to methods known to a person skilled in the art, for example by reacting it with acetic acid in the presence of trifluoroacetic acid anhydride or with acetyl chloride in the presence of a base such as for example $K_2CO_3$. The acetylated homologue of 2,6-diisopropylphenol is then subjected to a Fries rearrangement in the presence of aluminium chloride in a solvent such as nitrobenzene in order to produce the compound of formula (V.i). Then the compound of formula (V.i) is acetylated in order to produce the compound of formula (V.i)b. Bromination is then carried out with $CuBr_2$ as previously described in order to produce the compound of formula (V.ii)b. The deprotection stage to release the phenol function will occur subsequently in the synthesis of the compounds of general formula (I) (at the time considered most appropriate by a person skilled in the art).

when A represents a radical of dimethoxyphenol type, the compounds of general formula (V.ii)b can be prepared in a similar fashion to the synthesis described for the compound of formula (V.ii)b derived from 2,6-diisopropylphenol, optionally with a few minor modifications within the scope of a person skilled in the art. For example, when A represents the 3,5-dimethoxy-4-hydroxyphenyl radical, the corresponding α-bromoketonic derivative of formula (V.ii)b can be prepared, for example, as indicated in Diagram 3.13 from the commercial compound of formula (XXXV):

Diagram 3.14

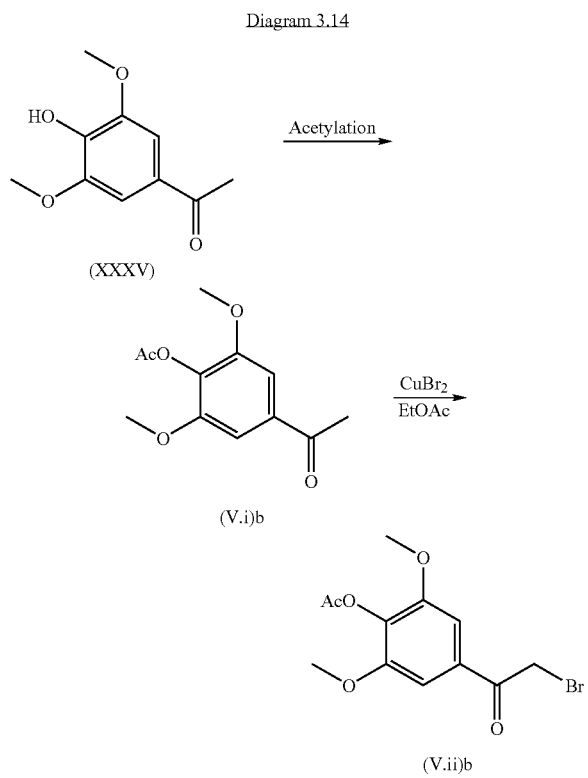

(XXXV)

(V.i)b (V.ii)b

The compounds of general formula (V.ii)$_2$ in which A and B are as defined previously can be prepared according to the method summarized in Diagram 3.15 hereafter.

Diagram 3.15

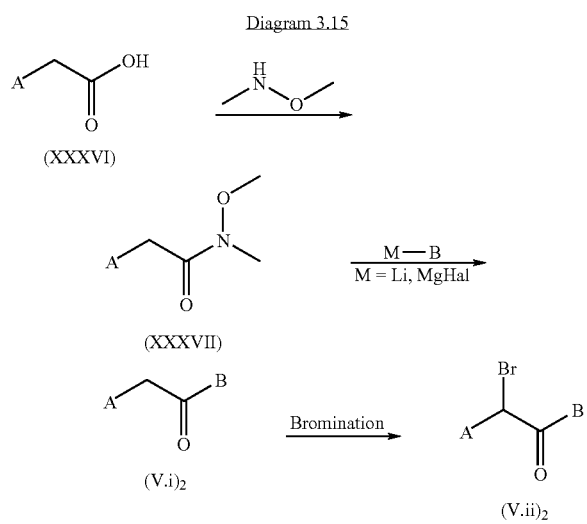

(XXXVI)

(XXXVII)

(V.i)$_2$ (V.ii)$_2$

The acids of general formula (XXXVI) are subjected to coupling with N,O-dimethylhydroxylamine (*Syn. Commun.* (1995), 25, (8), 1255; *Tetrahedron Lett.* (1999), 40, (3), 411-414) in a solvent such as dimethylformamide or dichloromethane, in the presence of a base such as triethylamine with dicyclohexylcarbodiimide or 1-(3-dimethylaminopropyl)-3-ethylcarbodiimide hydrochloride and hydroxybenzotriazol, in order to produce the intermediates of general formula (XXXVII). The compounds of general formula (V.i)$_2$ are prepared from the compounds of general formula (XXXVII) by a substitution reaction with lithium compound or magnesium compound derivatives of general formula B-M in which M represents Li or MgHal (Hal=I, Br or Cl) in solvents such as ether or anhydrous tetrahydrofuran. The α-bromo- or α-chloroketones of general formula (V.ii)$_2$ can now be accessed from the ketones of general formula (V.i)$_2$ under the conditions previously described.

Moreover, the non commercial α-halogenoketonic derivatives of general formula (V.vii) are accessible from methods in the literature. In particular, they can be obtained according to a procedure summarized in Diagram 3.16.

Diagram 3.16

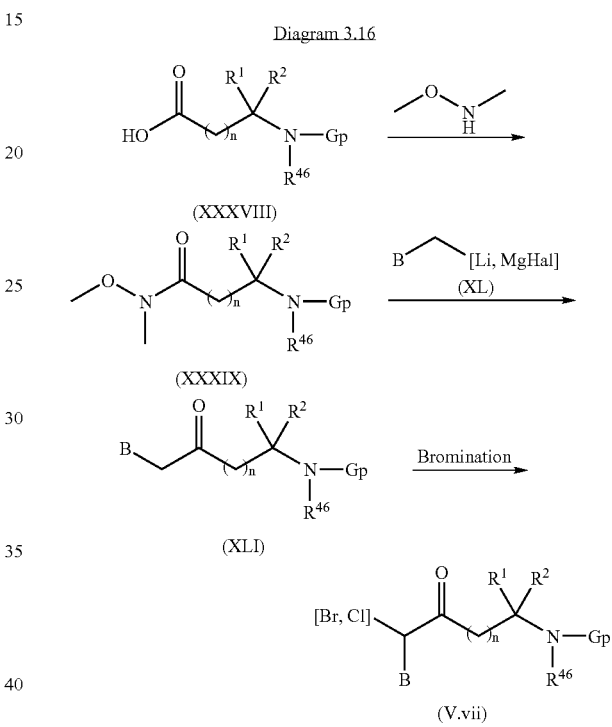

(XXXVIII)

(XXXIX)

(XLI)

(V.vii)

The protected amino acids of general formula (XXXVIII) are obtained by protection of the corresponding amino acids by a group of carbamate type according to methods known to a person skilled in the art. The acids of general formula (XXXVIII) are then subjected to coupling with N,O-dimethylhydroxylamine (*Syn. Commun.* (1995), 25, (8), 1255; *Tetrahedron Lett.* (1999), 40, (3), 411-414) in a solvent such as dimethylformamide or dichloromethane, in the presence of a base such as triethylamine with dicyclohexylcarbodiimide or 1-(3-dimethylaminopropyl)-3-ethylcarbodiimide hydrochloride and hydroxybenzotriazole, in order to produce the intermediates of general formula (XXXIX). The compounds of general formula (XLI) are prepared from the compounds of general formula (XXXIX) by a substitution reaction with lithium compound or magnesium compound derivatives of general formula (XL) (in which Hal=I, Br or Cl) in solvents such as ether or anhydrous tetrahydrofuran. The bromo or chloroacetophenones of general formula (V.vii) are now accessible from the acetophenone of general formula (XLI) under the conditions previously described.

Alternatively, a person skilled in the art can also use or adapt the syntheses described in *Angew. Chem. Int.* (1998), 37 (10), 411-414, *Liebigs Ann. Chem.* (1995), 1217 or *Chem. Pharm. Bull.* (1981), 29(11), 3249-3255.

Preparation of the Acid Derivatives of General Formula (V.iii)

The acid derivatives of general formula (V.iii) can be obtained, Diagram 3.17, directly by reaction of the commercial amino acid of general formula (V.vi) with the compounds of (ar)alkylchloroformate or di(ar)alkylcarbonate type (Δ represents an alkyl or benzyl radical) under standard conditions known to a person skilled in the art.

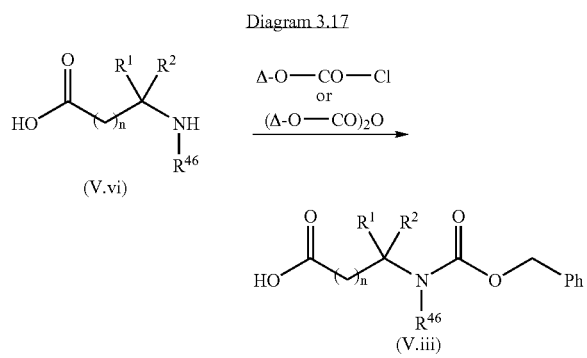

Preparation of the Compounds of General Formula (V.v)

The thiocarboxamides of general formula (V.v) can be obtained in three stages starting from the compounds of general formula (V.vi) as indicated in the Diagram 3.18 below. The amine function of the amino acid of general formula (V.vi) is firstly protected under standard conditions with tBu—O—CO—Cl or (tBu—O—CO)$_2$O (or other protective groups known to a person skilled in the art), then the intermediate obtained is converted to its corresponding amide by methods described in the literature (cf. for example, *J. Chem. Soc., Perkin Trans.* 1, (1998), 20, 3479-3484 or the PCT Patent Application WO 99/09829). Finally, the carboxamide is converted to the thiocarboxamide of general formula (V.v), for example by reaction with Lawesson reagent in a solvent such as dioxane or tetrahydrofuran at a temperature preferably comprised between ambient temperature and the reflux temperature of the mixture, or also using (P$_2$S$_5$)$_2$ under standard conditions for a person skilled in the art.

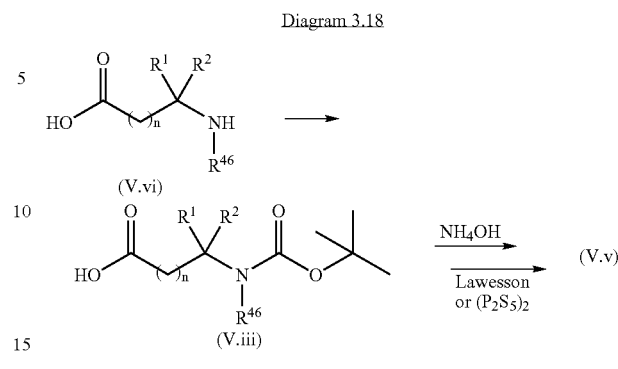

Alternatively, the thiocarboxamides of general formula (V.v) can also be obtained, Diagram 3.19, by the addition of H$_2$S on the corresponding cyano derivatives of general formula (V.x) under standard conditions known to a person skilled in the art.

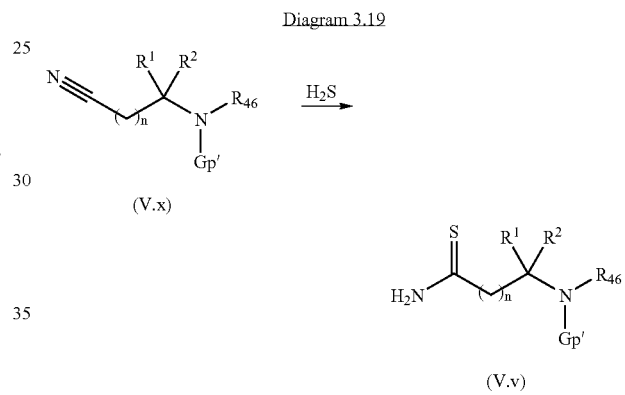

Preparation of the Acids of General Formula (VI)

Preparation of the Acid Derivatives of Thiazoles of General Formula (VI)

The acids of general formula (VI) derived from thiazoles can be prepared according to the procedures represented in Diagram 4.1 below.

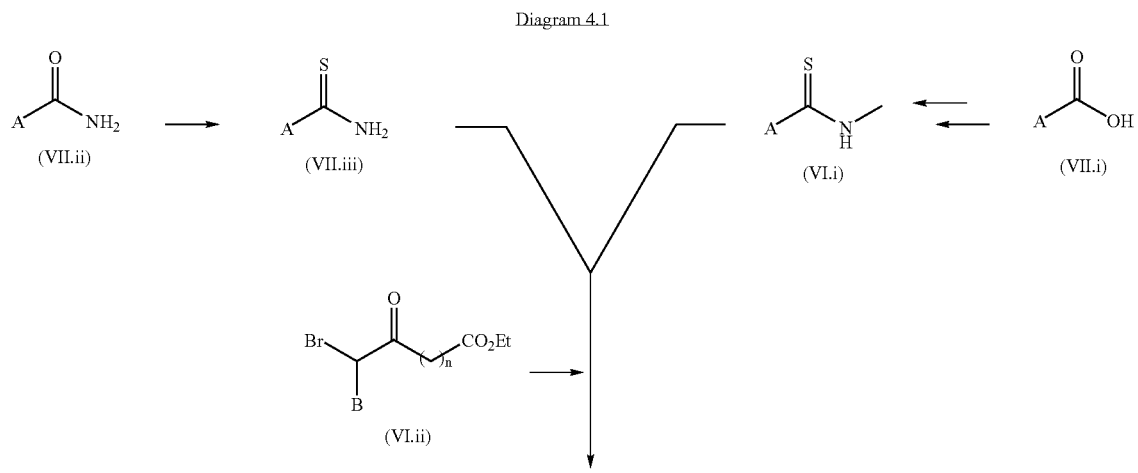

-continued

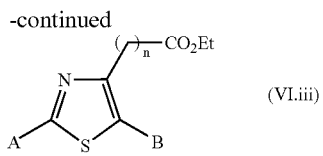

(VI.iii)

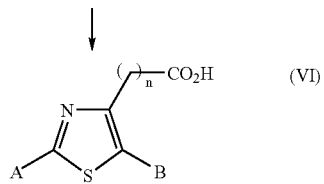

(VI)

The carboxamides of general formula (VII.ii) are treated under standard conditions in order to produce the thiocarboxamide of general formula (VII.iii), for example by Lawesson reagent or also using $(P_2S_5)_2$ under standard conditions for a person skilled in the art. Alternatively the acid of general formula (VII.i) is activated by the action of 1.1'-carbonyldiimidazole then treated with methylamine in an aprotic polar solvent such as for example tetrahydrofuran. The carboxamide intermediate obtained is converted to the thiocarboxamide of general formula (VI.i) under standard conditions, for example using Lawesson reagent or also using $(P_2S_5)_2$ under standard conditions for a person skilled in the art. The thiocarboxamide of general formula (VII.iii) or (VI.i) is then reacted with the compound of general formula (VI.ii), for example while heating at reflux in a solvent such as benzene, dioxane or dimethylformamide. The ester of general formula (VI.iii) obtained can then be saponified by the action of a base such as for example potash in alcoholic medium or LiOH in tetrahydrofuran in order to produce the acid of general formula (VI).

Preparation of the Acid Derivatives of Oxazoles of General Formula (VI)

The acids of general formula (VI) derived from oxazoles can be prepared according to a procedure represented in Diagram 4.2 below.

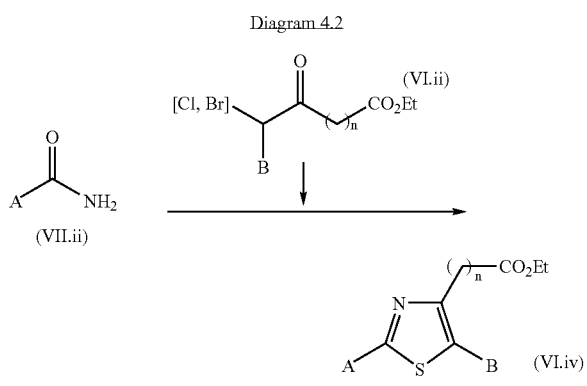

-continued

The carboxamides of general formula (VII.ii) are reacted with the compound of general formula (VI.ii) while heating, for example at reflux, in the absence or in the presence of a solvent such as dimethylformamide. The ester of general formula (VI.iv) obtained can then be saponified by the action of a base such as for example potash in alcoholic medium or LiOH in tetrahydrofuran in order to produce the acid of general formula (VI).

Preparation of the Acid Derivatives of Isoxazolines of General Formula (VI)

The acid derivatives of isoxazolines of general formula (VI), used in the preparation of compounds of general formula $(I)_4$, can be prepared according to a procedure represented in Diagram 4.3 below.

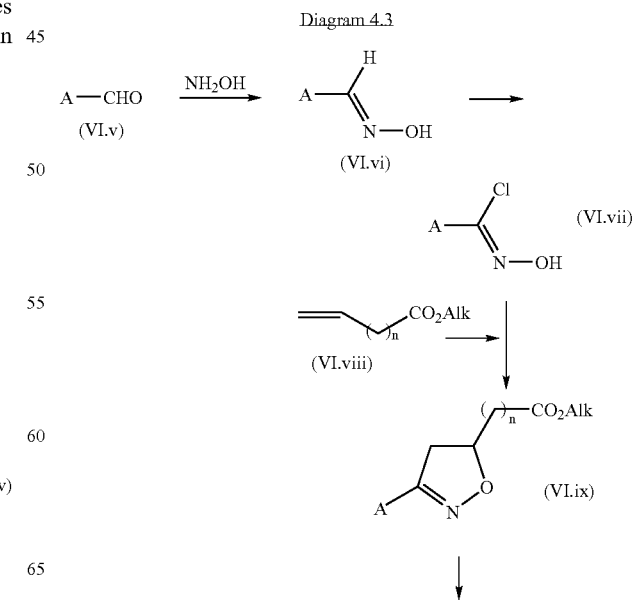

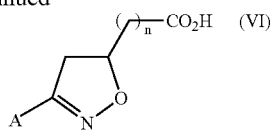

The acids of general formula (VI) derived from isoxazolines can be prepared as follows: the commercial aldehydes of general formula (VI.v) are reacted with hydroxylamine hydrochloride. The oxime of general formula (VI.vi) thus obtained is activated in the form of oxime chloride, of general formula (VI.vii), by reaction with N-chlorosuccinimide in DMF before reacting with the esters of general formula (VI.viii) (in which Alk represents an alkyl radical) in order to produce the isoxazoline derivatives according to an experimental protocol described in the literature (*Tetrahedron Lett.*, 1996, 37 (26), 4455; *J. Med. Chem.*, 1997, 40, 50-60 and 2064-2084). Saponification of the isoxazolines of general formula (VI.ix) is then carried out in a standard fashion (for example by the action of KOH in an alcoholic solvent or LiOH in a solvent such as tetrahydrofuran) in order to produce the acid derivative of general formula (VI).

The non-commercial unsaturated esters of general formula (VI.x) can be prepared according to the methods described in the literature (*J. Med. Chem.*, 1987, 30, 193; *J. Org. Chem.*, 1980, 45, 5017).

Preparation of the Thiazoles and Oxazoles of General Formula (VII)

General Outline

The acids of general formula (VII.i), Diagram 5.1, are converted to the corresponding carboxamides of general formula (VII.ii) by methods described in the literature (cf. for example, *J. Chem. Soc., Perkin Trans.* 1, (1998), 20, 3479-3484 or the PCT Patent Application WO 99/09829). The compounds of general formula (VII) can then be obtained in a standard fashion according to the procedures represented in Diagrams 5.2 and 5.3 (thiazoles) and Diagram 5.4 (oxazoles) hereafter.

This synthesis route is useful for then preparing the compounds corresponding to general sub-formulae $(I)_1$ and $(I)_3$.

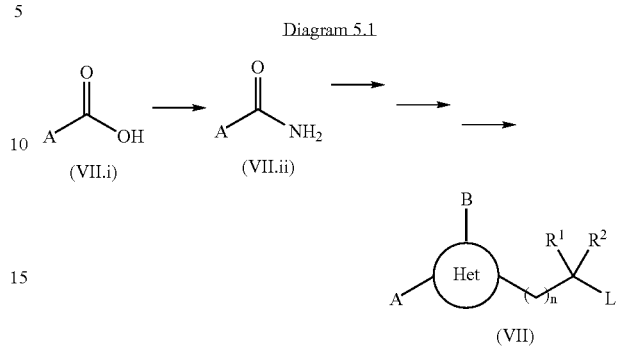

Obtaining the Thiazoles of General Formula (VII)

When $R^1$ and $R^2$ both represent H, the thiazoles of general formula (VII) intended for the preparation of compounds of general formula $(I)_3$ can be prepared according to the method summarized in Diagram 5.2. The carboxamide of general formula (VII.ii) is converted to the corresponding thiocarboxamide of general formula (VII.iii) in the presence of Lawesson reagent in a solvent such as dioxane or benzene at a temperature preferably comprised between ambient temperature and that of reflux of the mixture. The thiocarboxamide of general formula (VII.iii) is then treated with the α-halogenoketoester of general formula (VII.iv) in which Alk represents an alkyl radical (for example methyl, ethyl or tert-butyl), in order to produce the ester of general formula (VII.v), which is reduced to the corresponding alcohol of general formula (VII.vi), for example by the action of lithium aluminium hydride or diisobutylaluminium hydride in a solvent such as tetrahydrofuran. This latter can then be converted to a halogenated derivative of general formula (VII) according to the methods known to a person skilled in the art, for example, in the case of a brominated derivative (L=Br), by reaction with $CBr_4$ in the presence of triphenylphosphine in dichloromethane at ambient temperature.

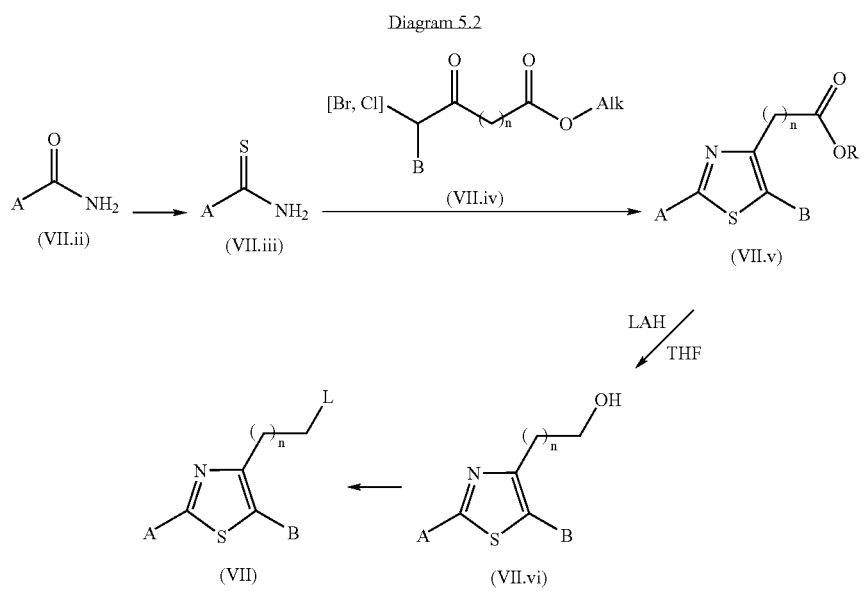

The thiazoles of general formula (VII) intended for the preparation of compounds of general formula (I)$_1$ can be prepared according to the method summarized in Diagram 5.3. The cyano derivative of general formula (VII.vii) in which Gp' is a protective group for an alcohol function (for example a benzyl or —CO—ρ group in which ρ represents alkyl, for example methyl or tert-butyl) is converted to the corresponding thiocarboxamide of general formula (VII.viii) by the action of H$_2$S in a solvent such as ethanol in the presence of triethanolamine at a temperature preferably comprised between ambient temperature and that of reflux of the mixture. The thiocarboxamide of general formula (VII.viii) is then treated with the α-halogenoketone of general formula (VII.ix) in order to produce the compound of general formula (VII.x), which is deprotected in order to produce the corresponding alcohol of general formula (VII.xi) according to methods known to a person skilled in the art (for example when Gp' is a protective group of acetate type, this is removed in situ by the action of an aqueous solution of sodium carbonate). This latter can then be converted to a halogenated derivative of general formula (VII) according to the methods known to a person skilled in the art, for example, in the case of a brominated derivative (L=Br), by reaction with CBr$_4$ in the presence of triphenylphosphine in dichloromethane at ambient temperature.

one starts from the acid. This latter can then be converted to a halogenated derivative of general formula (VII) according to methods known to a person skilled in the art, for example, in the case of a brominated derivative (L=Br), by reaction with CBr$_4$ in the presence of triphenylphosphine in dichloromethane at ambient temperature.

Diagram 5.4

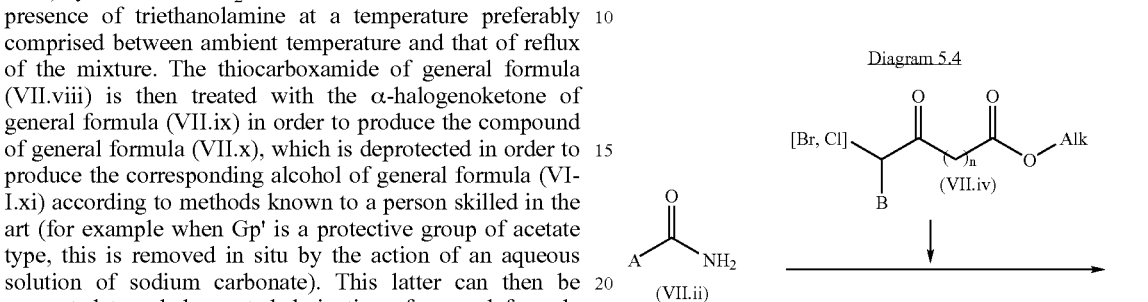

Diagram 5.3

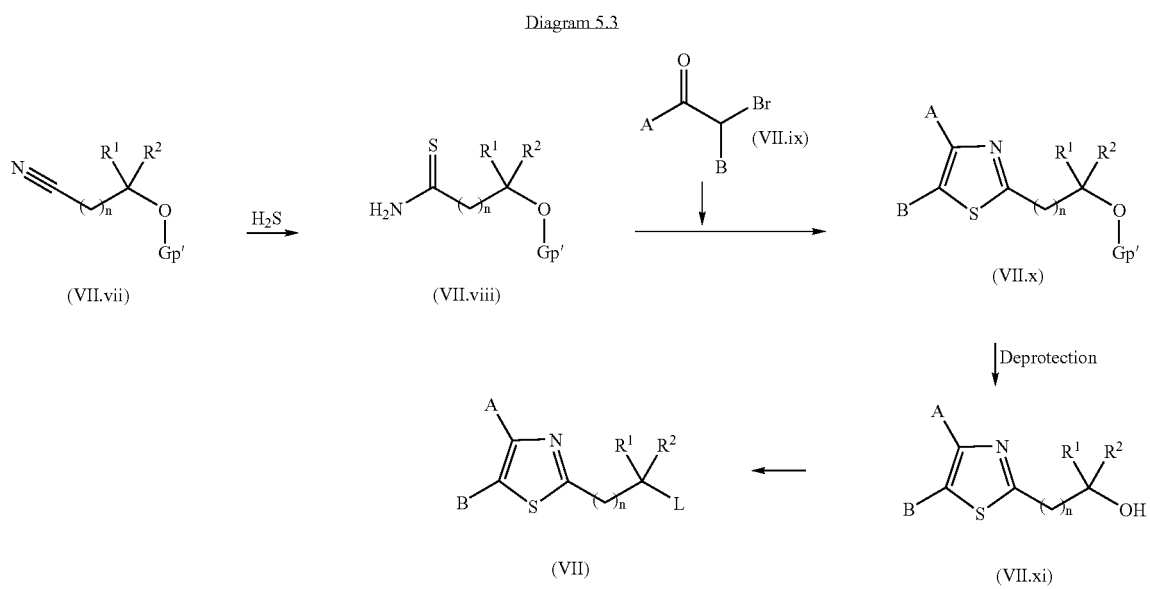

Obtaining the Oxazoles of General Formula (VII)

When R$^1$ and R$^2$ both represent H, the oxazoles of general formula (VII) intended for the preparation of compounds of general formula (1)$_3$ can be prepared according to the method summarized in Diagram 5.4. The carboxamide of general formula (VII.ii) is treated with the α-halogenoketoester of general formula (VII.iv) in which Alk represents an alkyl radical (for example methyl, ethyl or tert-butyl), in order to produce the ester/acid of general formula (VII.xii). This latter is reduced to the corresponding alcohol of general formula (VII.xiii), for example by the action of lithium and aluminium hydride or diisobutylaluminium hydride in a solvent such as tetrahydrofuran when one starts from the ester or by the action of diborane in tetrahydrofuran when -continued

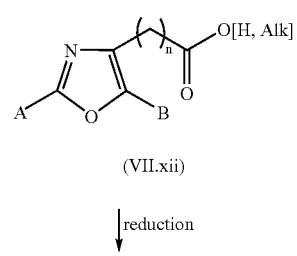

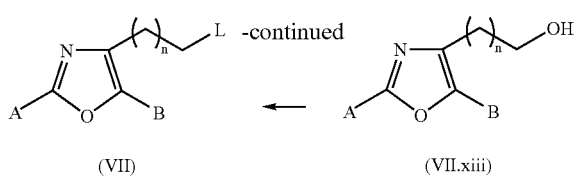

(VII)   (VII.xiii)

Preparation of the Acids of General Formula (VII.i)

The non-commercial acids of general formula (VII.i) are accessible from methods in the literature. In particular:

when A represents a phenothiazinyl radical, the acids of general formula (VII.i) are accessible from methods in the literature such as for example *J. Med. Chem.* (1992), 35, 716-724, *J. Med. Chem.* (1998), 41, 148-156; *Synthesis* (1988) 215-217; or *J. Chem. Soc. Perkin. Trans.* 1 (1998), 351-354;

when A represents an indolinyl radical, the acids of general formula (VII.i) are accessible from methods in the literature such as for example *J. Het. Chem.* (1993), 30, 1133-1136 or *Tetrahedron* (1967), 23, 3823;

when A represents a phenylaminophenyl radical, the acids of general formula (VII.i) are accessible from methods in the literature such as for example *J. Amer. Chem Soc.* (1940), 62, 3208; *Zh. Obshch. Khim.* (1953), 23, 121-122 or *J. Org. Chem.* (1974), 1239-1243;

when A represents a carbazolyl radical, the acids of general formula (VII.i) are accessible from methods in the literature such as for example *J. Amer. Chem Soc.*, (1941), 63, 1553-1555; *J. Chem. Soc.* (1934), 1142-1144; *J. Chem. Soc.* (1945), 945-956; or *Can. J. Chem. Soc.* (1982), 945-956; and when A represents a radical of 4-(4-hydroxyphenyl)-phenyl type, reference will be made for example to the following publication: *Synthesis* (1993) 788-790.

Preparation of the Compounds of General Formula (VIII)

When $R^1$ and $R^2$ both represent H, the protected amino acids of general formula (VIII) are either commercial, or obtained by protection of commercial amino acids by a group of carbamate type according to the methods known to a person skilled in the art.

When at least one of $R^1$ and $R^2$ is not H, and n=0, the protected amino acids of general formula (VIII) are obtained in one stage, Diagram 6.1, by alkylation, in a solvent such as tetrahydrofuran and at low temperature, of commercial compound of general formula (VIII.i) using 3 equivalents of butyllithium and approximately one equivalent of the halogenated derivative of general formula (VIII.ii) in which $R^1$ represents a radical of alkyl, cycloalkyl, cycloalkylalkyl or arylalkyl type and Hal a halogen atom. Depending on the case, a second alkylation (not represented in Diagram 6.1) can be carried out in a similar fashion, thus allowing the compounds of general formula (VIII) to be obtained in which neither $R^1$ nor $R^2$ represents H.

Diagram 6.1

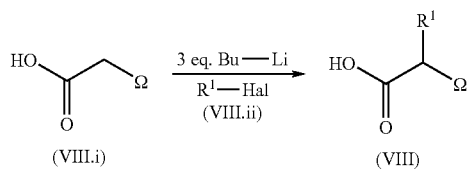

(VIII.i)   (VIII)

Preparation of the imidazoles, thiazoles and oxazoles of general formula (IX)

The preparation of the intermediates of general formula (IX) is described in the Patent Application WO 98/58934 (cf. in particular pages 10 to 50 and the examples of this document) or carried out by analogy from commercial starting products Preparation of the Protected Alcohols of General Formula (X)

Preparation of the Compounds of the General Formula (X) Derived from Imidazoles

The acid of general formula (X.i) is successively treated, Diagram 8.1, with $Cs_2CO_3$, the compound of general formula (V.ii) and with $NH_4OAc$, in order to produce the compound of general formula (X). The reaction conditions are similar to those described above for this type of synthesis.

Diagram 8.1

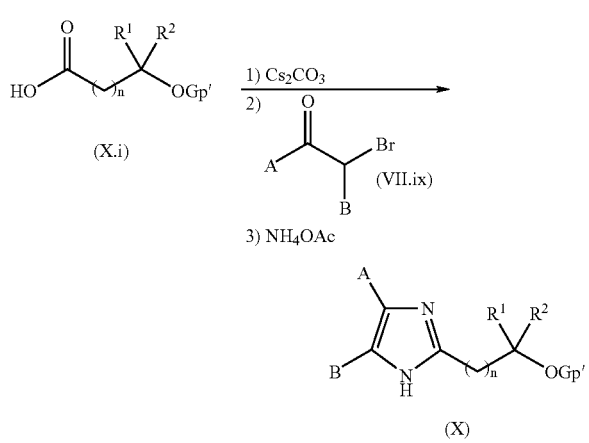

Preparation of the Compounds of General Formula (X) Derived from Thiazoles

The cyano derivative of general formula (X.ii) is treated, Diagram 8.2, with $H_2S$ in order to produce the thiocarboxamide of general formula (X.iii), which, condensed with the compound of general formula (V.ii), allows the compound of general formula (X) to be obtained. The reaction conditions are similar to those described above (Diagram 5.3) for this type of synthesis.

Diagram 8.2

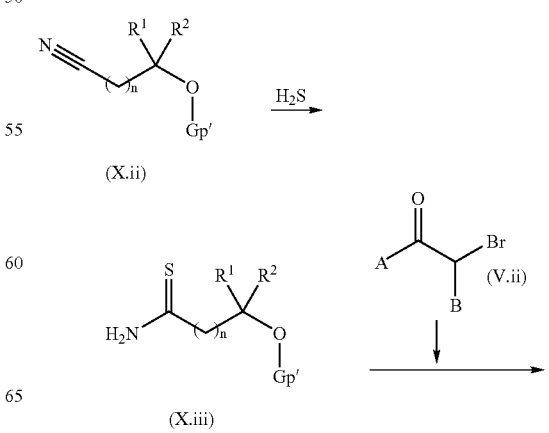

-continued

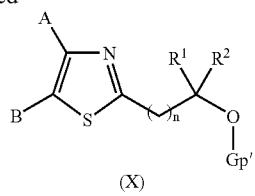

(X)

Preparation of the Acids of General Formula (XXXVI)

The non commercial acids of general formula (XXXVI) are accessible from methods in the literature or similar methods adapted by a person skilled in the art. In particular:

when A represents a phenothiazinyl radical, the acids of general formula (XXXVI) are accessible from methods in the literature: *J. Org. Chem.*, (1956), 21, 1006; *Chem. Abstr.*, 89, 180029 and *Arzneimittel Forschung* (1969), 19, 1193.

when A represents a diphenylamine radical, the acids of general formula (XXXVI) can be accessed from methods in the literature: *Chem Ber.*, (1986), 119, 3165-3197; *J. Heterocyclic. Chem.* (1982), 15, 1557-1559; *Chem. Abstr.*, (1968), 68, 68730x; or by adaptation of these methods by a person skilled in the art;

when A represents a radical of 4-(4-hydroxyphenyl)-phenyl type, the acids of general formula (XXXVI) can be accessed from methods in the literature such as for example *Tetrahedron Lett.* (1968), 4739 or *J. Chem. Soc.* (1961), 2898.

when A represents a carbazolyl radical, the acids of general formula (XXXVI) can be accessed from methods in the literature such as for example *J. Amer. Chem.*, (1946), 68, 2104 or *J. Het. Chem* (1975), 12, 547-549.

when A represents a radical of benzopyrane or benzofurane type, the acids of general formula (XXXVI) can be accessed by the methods in the literature such as for example *Syn. Commun.* (1982), 12(8), 57-66; *J. Med. Chem.* (1995), 38(15), 2880-2886; or *Helv. Chim. Acta.* (1978), 61, 837-843.

when A represents an indolinyl or tetrahydroquinolyl radical, the acids of general formula (XXXVI) can be accessed from methods in the literature such as for example *J. Med. Chem.* (1997), 40, (7), 1049-1062; *Bioorg. Med. Chem. Lett.* (1997), 1519-1524; *Chem. Abstr.* (1968), 69, 43814k; or *Chem. Abstr.* (1966), 66, 17538c.

Of course, the phenol, amine or aniline functions resulting from the nature of the substituents on the A radical of the compounds of general formula (XXXVI) can lead a person skilled in the art to add protection/deprotection stages of these functions to the stages described so that they do not interfere with the rest of the chemical synthesis.

Unless defined otherwise, all the technical and scientific terms used here have the same meaning as that usually understood by an ordinary specialist in the field to which this invention belongs. Likewise, all publications, patent applications, all patents and all other references mentioned here are incorporated by way of reference.

The following examples are presented to illustrate the above procedures and must in no case be considered as limiting the scope of the invention.

EXAMPLES

Example 1

4-[3,5-bis(1,1-dimethylethyl)-4-hydroxyphenyl]-N-methyl-2-thiazolemethanamine

This product is obtained according to the procedure described in the PCT Patent Application WO 98/58934. Alternatively, it can also be prepared according to the method described below.

1.1) N-Boc-sarcosinamide:

15.0 g (0.120 mol) of sarcosinamide hydrochloride (N-Me-Gly-NH$_2$.HCl) is dissolved in dichloromethane containing 46.2 ml (0.265 mol) of diisopropylethylamine. The mixture is cooled down to 0° C. then Boc-O-Boc (28.8 g; 0.132 mol) is added in fractions and the mixture is stirred overnight at ambient temperature. The reaction medium is then poured into ice-cooled water followed by extraction with dichloromethane. The organic phase is washed successively with a 10% aqueous solution of sodium bicarbonate and with water, then finally with a saturated solution of sodium chloride. The organic phase is then dried over magnesium sulphate, filtered and concentrated under vacuum. The product obtained is purified by crystallization from diisopropyl ether in order to produce a white solid with a yield of 72%. Melting point: 103° C.

1.2) 2-([[(1,1-dimethylethoxy)carbonyl]methyl/amino-ethanethioamide:

16.0 g (0.085 mol) of intermediate 1.1 is dissolved in dimethoxyethane (500 ml) and the solution obtained is cooled down to 5° C. Sodium bicarbonate (28.5 g; 0.34 mol) then, in small portions, (P$_2$S$_5$)$_2$ (38.76 g; 0.17 mol) are added. The reaction medium is allowed to return to ambient temperature under stirring over 24 hours. After evaporation of the solvents under vacuum, a 10% aqueous solution of sodium bicarbonate is added to the residue and the solution is extracted using ethyl acetate. The organic phase is washed successively with a 10% aqueous solution of sodium bicarbonate and with water, then finally with a saturated solution of sodium chloride. The organic phase is then dried over magnesium sulphate, filtered and concentrated under vacuum. The product obtained is purified by crystallization from ether in order to produce a white solid with a yield of 65%. Melting point: 150-151° C.

1.3) 4-[3,5-bis(1,1-dimethylethyl)-4-hydroxyphenyl]-N-[(1,1-dimethylethoxy)-carbonyl]-N-methyl-2-thiazolemethanamine:

Intermediate 1.2 (4.3 g; 2.11 mmol) and bromo-1-(3,5-ditert-butyl-4-hydroxyphenyl)ethanone (6,9 g; 2,11 mmol) are dissolved in benzene (75 ml) under an argon atmosphere, then the mixture is stirred at ambient temperature for 12 hours. The reaction medium is heated under reflux for 4 hours. After evaporation of the solvents, the residue is diluted with dichloromethane and washed with a saturated solution of NaCl. The organic phase is separated, dried over magnesium sulphate, filtered and concentrated under vacuum. The expected product is obtained after chromatography on a silica column (eluent: 20% ethyl acetate in heptane) in the form of an oil which crystallizes very slowly in a refrigerator with a yield of 28%. Melting point: 126.5-127.3° C.

1.4) 4-[3,5-bis(1,1-dimethylethyl)-4-hydroxyphenyl]-N-methyl-2-thiazolemethanamine:

2.3 ml (29 mmol) of trifluoroacetic acid is added dropwise, at 0° C. to a solution of 2.5 g (5.8 mmol) of intermediate 1.3 and 2 ml (1.6 mmol) of triethylsilane in 50 ml of dichloromethane. After stirring for one hour, the reaction mixture is concentrated under vacuum and the residue is diluted in 100 ml of ethyl acetate and 50 ml of a saturated solution of NaHCO$_3$. After stirring and decantation, the organic phase is dried over magnesium sulphate, filtered and concentrated under vacuum. The residue is taken up in heptane in order to produce, after drying, a white solid with a yield of 73%. Melting point: 136° C.

1.5) 4-[3,5-bis(1,1-dimethylethyl)-4-hydroxyphenyl]-N-methyl-2-thiazolemethanamine hydrochloride:

2.0 g (0.602 mmol) of intermediate 1.4 is dissolved in anhydrous ether. The solution is cooled down to 0° C. then 18 ml (1.81 mmol) of a 1N solution of HCl in ether is added dropwise. The mixture is allowed to return to ambient temperature under stirring. After filtering and drying under vacuum, a white solid is obtained with a yield of 92%.

Melting point: 185.3-186.0° C.

Example 2

2,6-di(tert-butyl)-4-(2-{[methyl(2-propynyl)amino]methyl}-1,3-thiazol-4-yl)phenol 0.52 ml (3.7 mmol) of triethylamine and an excess of 0.56 g (7.5 mmol) of chloropropargyl are added dropwise at 0° C. to a solution of 0.5 g (1.5 mmol) of the compound of Example 1 in 15 ml of acetonitrile. After stirring overnight, the reaction mixture is concentrated under vacuum and the residue is diluted with dichloromethane and 50 ml of a saturated solution of NaCl. After stirring and decantation, the organic phase is separated and dried over magnesium sulphate, filtered and concentrated under vacuum. The expected product is obtained after chromatography on a silica column (eluent: 20% ethyl acetate in heptane). After evaporation, the pure fractions produce a white solid with a yield of 20%. Melting point: 210-215° C.

MH+=371.20.

Example 3

2-[({4-[3,5-di(tert-butyl)-4-hydroxyphenyl]-1,3-thiazol-2-yl}methyl)(methyl)amino]acetonitrile The experimental protocol used is identical to that described for Example 2, chloroacetonitrile being used as starting product in place of the chloropropargyl. A beige solid is obtained with a yield of 54%. Melting point: 150-156° C.

MH+=372.30

Example 4

5-[({4-[3,5-di(tert-butyl)-4-hydroxyphenyl]-1,3-thiazol-2-yl}methyl)(methyl)amino]pentanenitrile The experimental protocol used is identical to that described for Example 2, bromovaleronitrile being used as starting product in place of the chloropropargyl. A yellow oil is obtained with a yield of 24%.

MH+=414.30

Example 5

6-[({4-[3,5-di(tert-butyl)-4-hydroxyphenyl]-1,3-thiazol-2-yl}methyl)(methyl)amino]hexanenitrile The experimental protocol used is identical to that described for Example 2, bromohexanenitrile being used as starting product in place of the chloropropargyl. A red oil is obtained with a yield of 35%.

MH+=428.40.

Example 6

2,6-di(tert-butyl)-4-(2-{[(2-hydroxyethyl)(methyl)amino]methyl}-1,3-thiazol-4-yl)phenol The experimental protocol used is identical to that described for Example 2, 2-bromoethanol is used as starting product in place of the chloropropargyl. A yellow oil is obtained with a yield of 57%.

MH+=377.30

Example 7

4-(2-{[benzyl(methyl)amino]methyl}-1,3-thiazol-4-yl)-2,6-di(tert-butyl)phenol

The experimental protocol used is identical to that described for Example 2, benzyl chloride being used as starting product in place of the chloropropargyl. A white solid is obtained with a yield of 52%. Melting point: 165-170° C.

MH+=423.30

Example 8

2,6-di(tert-butyl)-4-{2-[(methyl-4-nitroanilino)methyl]-1,3-thiazol-4-yl}phenol

This product is obtained according to the procedure described in the PCT Patent Application WO 98/58934.

Example 9

2,6-di(tert-butyl)-4-(2-{[4-(dimethylamino)(methyl)anilino]methyl}-1,3-thiazol-4-yl)phenol 0.8 ml of paraformaldehyde and 0.10 g of 10% palladium on carbon is added to a solution of 0.5 g (1.1 mmol) of Example 8 in 20 ml of ethanol. The medium is placed under hydrogen for 4 hours. The catalyst is filtered out and the solvent evaporated to dryness. The expected product is obtained after chromatography on a silica column (eluent: 3% ethanol in dichloromethane). The expected compound is obtained in the form of a brown oil with a yield of 54%.

MH+=452.30

Example 10 benzyl {4-[3,5-di(tert-butyl)-4-hydroxyphenyl]-1,3-thiazol-2-yl}methylcarbamate

The compound is produced according to an experimental protocol described in the Patent Application WO 98/58934 (see preparation of intermediates 26.1 and 26.2), using Z-Gly-NH$_2$ in place of the N-Boc sarcosinamide. The expected compound is obtained in the form of a pale yellow oil with a yield of 99%.

MH+=453.20

Example 11

4-[2-(aminomethyl)-1,3-thiazol-4-yl]-2,6-di(tert-butyl)phenol 0.1 ml of a 40% solution of potassium hydroxide is added dropwise to a solution of 0.106 g (1.1 mmol) of the compound of Example 10 in 10 ml of methanol. After overnight stirring under reflux, the reaction mixture is concentrated under vacuum and the residue is diluted with dichloromethane and washed with a 1N solution of HCl then with 50 ml of a saturated solution of NaCl. The organic phase is separated and dried over magnesium sulphate, filtered and concentrated under vacuum. The expected product is obtained after chromatography on a silica column (eluent: 5% ethanol in dichloromethane) in the form of a brown foam with a yield of 76%.

MH+=319.29.

Example 12

2,6-di(tert-butyl)-4-(2-{[methyl(4-nitrobenzyl)amino]methyl}-1,3-thiazol-4-yl)phenol The experimental protocol used is identical to that described for Example 2, 4-nitro-benzyl bromide being used as starting product in place of the chloropropargyl. A yellow solid is obtained with a yield of 63%. Melting point: 114.4-111.7° C.

MH+=468.3

Example 13

4-(2-{[(4-aminobenzyl)(methyl)amino]methyl}-1,3-thiazol-4-yl)-2,6-di(tert-butyl)phenol 0.059 g (0.26 mmol) of SnCl$_2$, 2H$_2$O and 0.017 g (0.26 mmol) of Zn are added successively to a solution of 0.05 g (0.107 mmol) of the compound of Example 12 in a mixture of 0.55 ml of glacial acetic acid and 0.07 ml of a 12N solution of HCl. The mixture is stirred for 18 hours at 20° C. The reaction mixture is then made basic by adding a 30% aqueous solution of NaOH. The product is then extracted using two times 50 ml of CH$_2$Cl$_2$. The organic solution is washed with 50 ml of salt water, dried over MgSO$_4$, filtered and concentrated under vacuum. The residue is purified on a silica column (eluent: 5% ethanol in dichloromethane). A yellow gum is obtained with a yield of 52%.

MH+=438.29.

Example 14

2,6-di(tert-butyl)-4-(2-{[(4-nitrobenzyl)amino]methyl}-1,3-thiazol-4-yl)phenol 0.5 g (1.57 mmol) of the compound of Example 9, 0.237 g (1.57 mmol) of 4-nitrobenzaldehyde and 1 g of previously activated pulverulent 4 Å molecular sieve are added successively to a flask containing 30 ml of anhydrous MeOH, under an inert atmosphere. The reaction mixture is vigorously stirred for 18 hours before the addition, by portions, of 0.06 g (1.57 mmol) of NaBH$_4$. Stirring is maintained for another 4 hours before the addition of 5 ml of water. After a quarter of hour, the sieve is filtered out and the reaction mixture is extracted with two times 100 ml of CH$_2$Cl$_2$. The organic phase is washed successively with 50 ml of water then with 50 ml of salt water, dried over sodium sulphate, filtered and concentrated under vacuum. The residue is purified on a silica column (eluent: 50% ethyl acetate in heptane). A yellow oil is obtained with a yield of 55%.

MH+=454.20.

Example 15

4-(2-{[(4-aminobenzyl)amino]methyl}-1,3-thiazol-4-yl)-2,6-di(tert-butyl)phenol

The experimental protocol used is identical to that described for Example 13, the compound of Example 14 being used as starting product in place of the compound of Example 12. A yellow gum is obtained with a yield of 83%.

MH+=424.20.

The Compounds of the Examples 16 to 22 can be Obtained According to the Procedures Described in the PCT Patent Application WO 98/58934.

Example 16

4-[3,5-bis(1,1-dimethylethyl)-4-hydroxyphenyl]-N-methyl-N-(4-aminophenyl)-2-thiazolemethanamine

[is intermediate 26.5 of the PCT Application WO 98/58934]

Example 17

4-[3,5-bis(1,1-dimethylethyl)-4-hydroxyphenyl]-N-methyl-1H-imidazole-2-methanamine Intermediate 26.2 of the PCT Application WO 98/58934 is subjected to a hydrogenation as described in Stage 1.2 of the same document using ethanol as reaction solvent in place of methanol. The expected product is isolated in the form of a red foam.

MH+=316.33.

Example 18

4-[3,5-bis(1,1-dimethylethyl)-4-hydroxyphenyl]-N-methyl-N-(4-nitrophenyl)-1H-imidazole-2-methanamine

[is intermediate 27.2 of the PCT Application WO 98/58934]

Example 19

4-[3,5-bis(1,1-dimethylethyl)-4-hydroxyphenyl]-N-methyl-N-(4-aminophenyl)-1H-imidazole-2-methanamine

[is intermediate 27.3 of the PCT Application WO 98/58934]

Example 20

4-[3,5-bis-(1,1-dimethylethyl)-4-hydroxyphenyl]-N-methyl-N-(4-nitrobenzoyl)-1H-imidazole-2-methanamine

[is intermediate 22.6 of the PCT Application WO 98/58934]

Example 21

4-[3,5-bis-(1,1-dimethylethyl)-4-hydroxyphenyl]-N-methyl-N-(4-aminobenzoyl)-1H-imidazole-2-methanamine

[is intermediate 22.7 of the PCT Application WO 98/58934]

Example 22

3-[3,5-bis(1,1-dimethylethyl)-4-hydroxyphenyl]-4,5-dihydro-5-isoxazoleethanol

[is intermediate 28.1 of the PCT Application WO 98/58934]

The Compound of Example 23 can be Obtained According to the Procedures Described in the PCT Patent Application WO 99/09829.

Example 23

2-[3,5-bis(1,1-dimethylethyl)-4-hydroxyphenyl]-4-oxazoleethanol

[is intermediate 1.C of the PCT Application WO 99/09829; alternatively, this compound can also be obtained according to the procedure described in *J. Med. Chem.* (1996), 39, 237-245.]

Example 24

4-[{[4-(3,5-ditert-butyl-4-hydroxyphenyl)-1,3-thiazol-2-yl]methyl}(methyl)amino]butanenitrile The experimental protocol used is identical to that described for Example 2, bromobutyronitrile being used as starting product in place of the chloropropargyl. A yellow oil is obtained with a yield of 18%.
MH+=400.30.

Example 25

2,6-ditert-butyl-4-(2-{[(3-nitrobenzyl)amino]methyl}-1,3-thiazol-4-yl)phenol

The experimental protocol used is identical to that described for Example 14, 3-nitrobenzaldehyde being used as starting product in place of the 4-nitrobenzaldehyde.
A yellow oil is obtained with a yield of 28%.
MH+=454.20.

Example 26

2,6-ditert-butyl-4-(4-{2-[methyl(2-propynyl)amino]ethyl}-1,3-oxazol-2-yl)phenol

The compound of Example 23 is converted to brominated derivative, intermediate 3, according to the procedure indicated in Diagram 1(c) of the PCT Application WO 99/09829. Then the brominated derivative (0.5 g;1.31 mmol) is added to a solution of N-methylpropargylamine 0.34 ml (3.94 mmol) and potassium carbonate (1.11 g) in dimethylformamide (20 ml). After overnight stirring at 80° C., the reaction mixture is concentrated under vacuum and the residue is diluted with dichloromethane and 50 ml of a saturated solution of NaCl. After stirring and decantation, the organic phase is separated and dried over magnesium sulphate, filtered and concentrated under vacuum. The expected product is obtained after chromatography on a silica column (eluent: 50% ethyl acetate in heptane). After evaporation, the pure fractions produce a yellow oil with a yield of 24%.
MH+=369.30.

Example 27

[{2-[2-(3,5-ditert-butyl-4-hydroxyphenyl)-1,3-oxazol-4-yl]ethyl}(methyl)amino]acetonitrile The experimental protocol used is identical to that described for the compound of Example 26, methylaminoacetonitrile being used as starting product in place of the N-methylpropargylamine. A white solid is obtained with a yield of 36%. Melting point: 165-167.8° C.

Example 28

3-[{2-[2-(3,5-ditert-butyl-4-hydroxyphenyl)-1,3-oxazol-4-yl]ethyl}(methyl)amino]propanenitrile The experimental protocol used is identical to that described for Example 26, N-methyl-β-alaninenitrile being used as starting product in place of the N-methylpropargylamine. A white solid is obtained with a yield of 56%. Melting point: 104-104.8° C.

Example 29

2,6-ditert-butyl-4-{4-[2-(1-piperazinyl)ethyl]-1,3-oxazol-2-yl}phenol hydrochloride 29.1) tert-butyl 4-{2-[2-(3,5-ditert-butyl-4-hydroxyphenyl)-1,3-oxazol-4-yl]ethyl}-1-piperazinecarboxylate The experimental protocol used is identical to that described for Example 26, tert-butyl piperazinecarboxylate being used as starting product in place of the N-methylpropargylamine. A brown oil is obtained with a yield of 72%.
MH+=486.20.

29.2) 2,6-ditert-butyl-4-{4-[2-(1-piperazinyl)ethyl]-1,3-oxazol-2-yl}phenol hydrochloride A stream of HCl gas is passed bubblewise into a solution at 0° C. of intermediate 29.1 (0.450 g; 9.27 mmol) in ethyl acetate (30 ml). The mixture is left to return to ambient temperature overnight. A stream of argon is passed through the reaction mass, then the powder obtained is filtered and washed with ethyl acetate then with ether in order to produce a white solid with a yield of 70%. Melting point: >200° C.

Example 30

N-methyl[4-(10H-phenothiazin-2-yl)-1,3-thiazol-2-yl]methanamine hydrochloride

The experimental protocol used is identical to that described for Example 1,2-bromo-1-(10H-phenothiazin-2-yl)ethanone (*J. Heterocyclic. Chem.*, (1978), 15, 175-176 and *Arzneimittel Forschung*, (1962), 12, 48), being used as starting product in place of the 2-bromo-1-(3,5-ditert-butyl-4-hydroxyphenyl)ethanone. The product obtained is purified by recrystallization from glacial acetic acid in order to produce a greenish solid.
Melting point: >275° C.

Alternatively, this compound can be obtained according to a similar method, but using 2-chloro-1-(10H-phenothiazin-2-yl)ethanone instead of 2-bromo-1-(10H-phenothiazin-2-yl)ethanone 30.1) 2-chloro-1-(10H-phenothiazin-2-yl)ethanone 2-bromo-1-[10-(chloroacetyl)-10H-phenothiazin-2-yl]ethanone (2.2 g; 5.55 mmol; prepared according to a protocol described in *J. Heterocyclic. Chem.* (1978), 15, 175, followed by a Friedel-Crafts reaction) is dissolved hot in a mixture of acetic acid (20 ml) and 20% HCl (5.5 ml) and the mixture obtained is heated under reflux for 30 minutes. The reaction mixture is allowed to cool down, the precipitate is filtered, the mixture rinsed with acetic acid (5 ml) and dried under vacuum, the solid obtained is purified by crystallization from toluene in order to produce a brown product with a yield of 82%. Melting point: 190-191° C. (value in the literature: 197-198° C.).

30.2) N-methyl[4-(10H-phenothiazin-2-yl)-1,3-thiazol-2-yl]methanamine hydrochloride Intermediate 30.1 (0.280 g; 1.0 mmol) and tert-butyl 2-amino-2-thioxoethyl(methyl)carbamate (0.204 g; 1.0 mmol; described for example in PCT Patent Application WO 98/58934) are dissolved in toluene and the mixture is heated under reflux for 18 hours. After the toluene is evaporated off and the reaction mixture cooled down to 0° C., the latter is taken up in a 4N solution of HCl in dioxane (10 ml) and the mixture stirred for one hour at 0° C. before allowing the temperature to return to ambient temperature. The solid formed is filtered and rinsed with ether. The expected product is obtained after purification by crystallization from hot acetic acid in order to obtain a greenish solid. Melting point: >275° C.

Example 31 butyl 2-(4-[1,1'-biphenyl]-4-yl-1H-imidazol-2-yl)ethylcarbamate 31.1) N-(butoxycarbonyl)-β-alanine A solution containing β-alanine (8.9 g; 0.1 mol) and 100 ml of a 1N solution of sodium hydroxide is cooled down to 10° C. n-butyl chloroformate (13.66 g; 0.1 mol) and 50 ml of a 2N solution of sodium hydroxide are added simultaneously. After stirring for 16 hours at 23° C., approximately 10 ml of a solution of concentrated hydrochloric acid (approximately 11 N) is added in order to adjust the pH to 4-5. The oil obtained is extracted with ethyl acetate (2×50 ml), washed with water then dried over magnesium sulphate. The product crystallizes from isopentane in the form of a white powder (yield of 68%). Melting point: 50.5° C.

31.2) butyl 2-(4-[1,1'-biphenyl]-4-yl-]H-imidazol-2-yl)ethylcarbamate

A mixture of N-(butoxycarbonyl)-β-alanine (prepared in Stage 31.1; 5.67 g; 0.03 mol) and caesium carbonate (4.89 g; 0.015 mol) in 100 ml of ethanol is stirred at 23° C. for 1 hour. The ethanol is eliminated by evaporation under reduced pressure in a rotary evaporator. The mixture obtained is dissolved in 100 ml of dimethylformamide then 4-phenyl-bromoacetophenone (8.26 g; 0.03 mol) is added. After stirring for 16 hours, the solvent is evaporated off under reduced pressure. The mixture obtained is taken up in ethyl acetate then the caesium bromide is filtered. The ethyl acetate of the filtrate is evaporated and the reaction oil is taken up in a mixture of xylene (100 ml) and ammonium acetate (46.2 g; 0.6 mol). The reaction medium is heated at reflux for approximately one hour and 30 minutes then, after cooling down, a mixture of ice-cooled water and ethyl acetate is poured into the reaction medium. After decantation, the organic phase is washed with a saturated solution of sodium bicarbonate, dried over magnesium sulphate then evaporated under vacuum. The solid obtained is filtered then washed with ether in order to produce a light beige-coloured powder (yield of 50%).

Melting point: 136.7° C.

MH+=364.3.

Example 32

N-[2-(4-[1,1'-biphenyl]-4-yl-1H-imidazol-2-yl)ethyl]pentanamide 32.1) tert-butyl 2-(4-[1,1'-biphenyl]-4-yl-1H-imidazol-2-yl)ethylcarbamate This compound is obtained according to an operating method similar to that of Stage 31.2 of Example 31, N-(tert-butoxycarbonyl)-β-alanine acid replacing the β-alanine. A yellow-coloured powder is obtained with a yield of 37%.

MH+=364.2.

32.2) 2-(4-[1,1'-biphenyl]-4-yl-H-imidazol-2-yl)ethylamine tert-butyl 2-(4-[1,1'-biphenyl]-4-yl-1H-imidazol-2-yl)ethylcarbamate (4.8 g; 0.013 mol) is stirred in 120 ml of a solution of ethyl acetate saturated in hydrochloric acid for 2 hours 30 minutes at a temperature of 55° C. The solid obtained is filtered and washed with ether. A light beige-coloured powder is obtained with a yield of 89%.

MH+=264.2.

32.3) N-[2-(4-[1,1'-biphenyl]-4-yl-1H-imidazol-2-yl)ethyl]pentanamide

A mixture containing valeric acid (0.24 ml; 0.002 mol), dicyclohexylcarbodiimide (2.2 ml; 1M solution in methylene chloride) and 1-hydroxybenzotriazole hydrate (336 mg; 0.0022 mol) in 15 ml of dimethylformamide (DMF) is stirred at 23° C. for thirty minutes. The 2-(4-[1,1'-biphenyl]-4-yl-1H-imidazol-2-yl)ethylamine prepared previously is added then the mixture is stirred for 48 hours at 23° C. The dicyclohexylurea formed is filtered then the DMF is evaporated off under reduced pressure. The residue obtained is taken up in ethyl acetate then the residual dicyclohexylurea is filtered again. The filtrate is washed with water and extracted using ethyl acetate. The solvent is evaporated-off then purification is carried out on a silica column (eluent: $CH_2Cl_2$-MeOH/95-05). A white-coloured powder is obtained with a yield of 13%. Melting point: 166-167° C.

MH+=348.2.

Example 33

N-[2-(4-[1,1'-biphenyl]-4-yl-1H-imidazol-2-yl)ethyl]-1-butanesulphonamide

A mixture containing 2-(4-[1,1'-biphenyl]-4-yl-1H-imidazol-2-yl)ethylamine (obtained in Stage 32.2 of Example 32; 660 mg; 0.0025 mol) and n-butane sulphochloride (390 mg; 0.0025 mol) in 20 ml of DMF is stirred for two hours at 23° C. Potassium carbonate (345 mg; 0.0025 mol.) is then added, then stirring is continued for two hours. The solvent is evaporated off and the reaction mixture is taken up in water and dichloromethane. The organic phase is washed with a saturated solution of sodium chloride then dried. The solvent is evaporated off and the residue obtained is purified on a silica column (eluent: $CH_2Cl_2$-MeOH/93-07). A light beige-coloured powder is obtained with a yield of 19%. Melting point: 168.5° C.

MH+=384.2.

Example 34

4-[2-(2-{[butylamino)carbonyl]amino}ethyl)-1H-imidazol-4-yl]-1,1'-biphenyl

A mixture containing 2-(4-[1,1'-biphenyl]-4-yl-1H-imidazol-2-yl)ethylamine (obtained in Stage 32.2 of Example 32; 660 mg; 0.0025 mol) and n-butyl isocyanate (341 mg; 0.0025 mol) in 20 ml of 1,2-dichloroethane is stirred for fifteen minutes at 60° C. The suspension is stirred for sixteen hours at 23° C. and filtered. The solid obtained is washed with 1,2-dichloroethane and with ether. A white-coloured powder is obtained with a yield of 66%. Melting point: 178° C.

MH+=363.3.

Example 35

N-{(S)-cyclohexyl[4-(4-fluorophenyl)-1H-imidazol-2-yl]methyl}cyclobutanamine 35.1 tert-butyl) (S)-cyclohexyl[4-(4-fluorophenyl)-1H-imidazol-2-yl]methylcarbamate This compound is obtained according to an operating method similar to the preparation of the compound of Stage 31.2 of Example 31 using Boc-aminocyclohexylglycine (9.4 g; 0.036 mol) in place of the N-(butoxycarbonyl)-β-alanine and parafluorobromoacetophenone (7.9 g; 0.036 mol) in place of the 4-phenyl-bromoacetophenone. A white-coloured powder is obtained with a yield of 53%.

MH+=374.2.

35.2) (S)-cyclohexyl[4-(4-fluorophenyl)-1H-imidazol-2-yl]methanamine

This compound is prepared according to an operating method similar to that of Stage 32.2 of Example 32 using tert-butyl (S)-cyclohexyl[4-(4-fluorophenyl)-1H-imidazol-2-yl]methylcarbamate (7.5 g; 0.02 mol) as starting compound. A white-coloured powder is obtained with a yield of 92%.

MH+=274.2.

35.3) N-{(S)-cyclohexyl[4-(4-fluorophenyl)-1H-imidazol-2-yl]methyl}cyclobutanamine A mixture containing (S)-cyclohexyl[4-(4-fluorophenyl)-1H-imidazol-2-yl]methanamine (prepared in Stage 5.2; 519 mg; 0.0015 mol), triethylamine (0.4 ml; 0.003 mol) and butanone (140 mg; 0.002 mol) in 10 ml of methanol is stirred for thirty minutes at 23° C. Sodium triacetoxyborohydride (630 mg; 0.003 mol) is then added. The reaction mixture is stirred for sixteen hours then poured into water. After extraction with ethyl acetate, the organic phase is washed with a saturated solution of sodium chloride then dried over magnesium sulphate. The solvent is evaporated off and the residue is purified on a silica column (eluent: $CH_2Cl_2$-MeOH mixture/95-05). A white-coloured powder is obtained with a yield of 12%. Melting point: 170-172° C.

MH+=328.2.

Example 36

N-[1-(4-cyclohexyl-1H-imidazol-2-yl)heptyl]cyclohexanamine 36.1) 2-bromo-1-cyclohexylethanone Cyclohexylacetone (5.4 ml, 0.039 mol) and bromine (2 ml, 0.039 mol) are stirred at 23° C. in 100 ml of methanol. After decolourization, 100 ml of water are gently added. The mixture obtained is neutralized with 5 g of sodium bicarbonate. Extraction is carried out with ether followed by washing the organic phase with 100 ml of water. After drying over magnesium sulphate, the mixture is concentrated with a rotary evaporator. An oil is obtained with a yield of 97%.

NMR $^1$H (δ ppm, DMSO): 1.21-1.27 (m, 5H); 1.59-1.83 (m, 5H); 2.59-2.64 (m, 1H); 4.42 (s, 2H).

36.2) 2-[(tert-butoxycarbonyl)amino]octanoic acid

A mixture of 2-amino-octanoic acid (25.25 g; 0.156 mol) and di-tert-butyl dicarbonate (37.8 g; 0.173 mol) in 425 ml of dioxane is stirred at reflux for three hours. After returning to 23° C., the mixture is again stirred for twenty four hours then the insoluble part is filtered out. The filtrate is evaporated. An oil is obtained with a yield of 99%.

NMR $H^1$ (δ ppm, DMSO): 0.85 (t, 3H); 1.11-1.27 (m, 8H); 1.37 (s, 9H); 1.51-1.65 (m, 2H); 3.81-3.87 (m, 1H); 6.96-6.97 (m, 1H); 12.3 (s, 1H).

IR (cm$^{-1}$): 3500; 2860; 1721 ($v_{C=O}$ (acid)); 1680 ($v_{C=O}$ (carbamate)); 1513 ($v_{C-NH}$ (carbamate)).

36.3) tert-butyl 1-(4-cyclohexyl-1H-imidazol-2-yl)heptylcarbamate

This compound is obtained according to an operating method similar to that of Stage 31.2 of Example 31, using 2-[(tert-butoxycarbonyl)amino]octanoic acid (8.1 g; 0.0314 mol) in place of the N-(butoxycarbonyl)-β-alanine and 2-bromo-1-cyclohexylethanone (6.4 g; 0.0314 mol) in place of the 4-phenyl-bromoacetophenone. An oil is obtained which is sufficiently pure to be used in the following reaction (yield of 88%).

36.4) 1-(4-cyclohexyl-1H-imidazol-2-yl)-1-heptanamine

This compound is obtained according to an operating method similar to that of Stage 32.2 of Example 32 using as starting compound tert-butyl 1-(4-cyclohexyl-1H-imidazol-2-yl)heptylcarbamate (prepared in Stage 6.3; 10 g; 0.0275 mol). A yellow solid is obtained in the form of a paste (yield of 37%).

MH+=264.2.

36.5) N-[1-(4-cyclohexyl-1H-imidazol-2-yl)heptyl]cyclohexanamine

This compound is obtained according to an operating method similar to that of Stage 35.3 of Example 35 using as starting amine 1-(4-cyclohexyl-1H-imidazol-2-yl)-1-heptanamine (obtained in Stage 6.4; 2.5 g; 0.074 mol) and as ketone, cyclohexanone (1 ml; 0.0097 mol). After purification on a silica column (eluent: ethyl acetate-heptane/7-3 with $CH_2Cl_2$-MeOH/95-05), a white-coloured powder is obtained with a yield of 12%. Melting point: 172-174° C.

MH+=346.3.

Example 37

N-{1-[4-(3-bromophenyl)-1H-imidazol-2-yl]-5-methylhexyl}-N-cyclohexylamine 37.1) 2-[(tert-butoxycarbonyl)amino]-6-methylheptanoic acid A solution of diisopropylamine (13.2 ml; 0.094 mol) in 130 ml of tetrahydrofuran (THF) is cooled down to −40° C. n-butyllithium (37 ml of a 2.5 M solution in hexane; 0.094 mol) is added dropwise. The temperature is allowed to rise to 0° C. At this temperature, Boc-glycine (5 g; 0.028 mol) in solution in 30 ml of THF is introduced into the mixture. The reaction medium is left for ten minutes at this temperature then 1-bromo-4-methylpentane (7.9 ml; 0.056 mol) in solution in 20 ml of THF is added rapidly. The temperature is allowed to return to 23° C. and the mixture is stirred at this temperature for one hour. After hydrolysis with 100 ml of water then acidification with 150 ml of a saturated solution of potassium hydrogen sulphate, the mixture obtained is extracted twice with 50 ml of ethyl acetate. The organic phase is washed with 100 ml of water then with 100 ml of a saturated solution of sodium chloride. After drying over magnesium sulphate and evaporating the solvent, the residue obtained is purified on a silica column (eluent: ethyl acetate-heptane/6-4) in order to produce a white-coloured powder with a yield of 50%.

MH+=260.3.

37.2) tert-butyl 1-[4-(3-bromophenyl)-1H-imidazol-2-yl]-5-methylhexylcarbamate

This compound is obtained according to an operating method similar to that of Stage 31.2 of Example 31 using 2-[(tert-butoxycarbonyl)amino]-6-methylheptanoic acid (3.5 g; 0.0135 mol) in place of the N-(butoxycarbonyl)-β-alanine and 3-bromophenacyl bromide (3.75 g; 0.0135 mol) in place of the 4-phenyl-bromoacetophenone. A white powder is obtained with a yield of 63%. Melting point: 134-136° C.

MH+=436.2.

37.3) 1-[4-(3-bromophenyl)-1H-imidazol-2-yl]-5-methyl-1-hexanamine

This compound is obtained according to an operating method similar to that of Stage 32.2 of Example 32 using as starting compound tert-butyl 1-[4-(3-bromophenyl)-1H-imidazol-2-yl]-5-methylhexylcarbamate (obtained in Stage 37.2; 3.5 g; 0.008 mol). A white-coloured powder is obtained with a yield of 97%. Melting point: 200-202° C.

MH+=336.2.

37.4) N-{1-[4-(3-bromophenyl)-1H-imidazol-2-yl]-5-methylhexyl}-N-cyclohexylamine This compound is obtained according to an operating method similar to that of Stage 35.3 of Example 35 using as starting amine, 1-[4-(3-bromophenyl)-1H-imidazol-2-yl]-5-methyl-1-hexanamine (obtained in Stage 7.3; 0.8 g; 0.0019 mol) and as ketone, cyclohexanone (0.32 ml; 0.0023 mol). A white-coloured powder is obtained with a yield of 38%. Melting point: 236-238° C.

MH+=418.2.

Example 38

N-{1-[4-(4-fluorophenyl)-1H-imidazol-2-yl]heptyl}cyclohexanamine 38.1) tert-butyl 1-[4-(4-fluorophenyl)-1H-imidazol-2-yl]heptylcarbamate This compound is obtained according to an operating method similar to that of Stage 31.2 of Example 31 using 2-[(tert-butoxycarbonyl)amino]octanoic acid (6.2 g; 0.024 mol) in place of the N-(butoxycarbonyl)-β-alanine and 2-bromo-4-fluoroacetophenone (5.2 g; 0.024 mol) in place of the 4-phenyl-bromoacetophenone. A white powder is obtained (yield: 58%) which is sufficiently pure to be used as it is for the following stage.

38.2) 1-[4-(4-fluorophenyl)-1H-imidazol-2-yl]-1-heptanamine

This compound is obtained according to an operating method similar to that of Stage 32.2 of Example 32 using as starting compound tert-butyl 1-[4-(4-fluorophenyl)-1H-imidazol-2-yl]heptylcarbamate (5.2 g; 0.014 mol). After purification on a silica column (eluent: $CH_2Cl_2$-MeOH—$NH_4OH$/89-10-1), a grey-coloured powder is obtained (yield of 72%). Melting point: 148-150° C.

MH+=276.2.

38.3) N-{1-[4-(4-fluorophenyl)-1H-imidazol-2-yl]heptyl}cyclohexanamine

This compound is obtained according to an operating method similar to that of Stage 35.3 of Example 35 using as starting amine, 1-[4-(4-fluorophenyl)-1H-imidazol-2-yl]-1-heptanamine (0.5 g; 0.0014 mol) and as ketone, cyclohexanone (0.17 ml; 0.0014 mol). A white-coloured powder is obtained with a yield of 15%.

Melting point: 190-192° C.

MH+=358.2.

Example 39

(1R)-N-benzyl-1-(1-benzyl-4-tert-butyl-1H-imidazol-2-yl)-2-(1H-indol-3-yl)ethanamine Triethylamine (0.83 ml; 0.006 mol) is added at 23° C. to a solution containing (1R)-1-(1-benzyl-4-tert-butyl-1H-imidazol-2-yl)-2-(1H-indol-3-yl)ethanamine (0.7 g; 0.002 mol; prepared under experimental conditions similar to those previously and using suitable starting reagents and reaction products) in 15 ml of acetonitrile. The mixture is stirred for one hour at 23° C. then benzyl chloride (0.23 ml; 0.002 mol) is added. Stirring is maintained for 16 hours. The reaction mixture is concentrated using a rotary evaporator and the oil obtained is taken up in ethyl acetate and water. The aqueous phase is extracted with ethyl acetate and washed with water then with a saturated solution of sodium chloride. The solvents are evaporated off under vacuum. After purification on a silica column (eluent: AE-heptane/7-3), a deep beige-coloured solid is obtained in the form of a paste (yield of 5%). Free base. Melting point: 60-62° C.

MH+=463.3.

Example 40

(R,S)-N-benzyl-1-(1-benzyl-4-phenyl-1H-imidazol-2-yl)-1-heptanamine (R,S)-1-(4-phenyl-1H-imidazol-2-yl)heptylamine (1 g; 0.003 mol; prepared under experimental conditions similar to those previously and using suitable starting reagents and reaction products) is diluted in 20 ml of dimethylformamide. Potassium carbonate (2.2 g; 0.016 mol) is added at 23° C. then benzyl bromide (1.2 ml; 0.010 mol) is added fairly slowly. The mixture is stirred for 72 hours at 23° C. before being poured into ice-cooled water. The mixture is extracted with ethyl acetate. The organic phase is washed with water then with a saturated solution of sodium chloride. After drying over magnesium sulphate, the solvents are concentrated using a rotary evaporator. After purification on a silica column (eluent: ethyl acetate-heptane/10-90), a white-coloured powder is obtained (yield of 31%). Free base. Melting point: 94-96° C.

MH+=438.3.

Example 41

N-benzyl-N-[(4-[1,1'-biphenyl]-4-yl-1H-imidazol-2-yl)methyl]-1-hexanamine

N-benzyl(4-[1,1'-biphenyl]-4-yl-1H-imidazol-2-yl)methanamine (1 g; 0.0024 mol; prepared under experimental conditions similar to those previously and using suitable starting reagents and reaction products) is diluted in 15 ml of dimethylformamide. Potassium carbonate (1 g; 0.0073 mol) is added at 23° C. then hexane bromide (0.34 ml; 0.0024 mol) is added fairly slowly. The reaction mixture is brought to about 70° C. for 3 hours before being poured into ice-cooled water. The mixture is extracted with ethyl acetate and the organic phase is washed with water. After drying over magnesium sulphate, the solvents are concentrated using a rotary evaporator. After purification on a silica column (eluent: ethyl acetate-heptane/7-3), a light yellow-coloured solid is obtained in the form of a paste (yield of 13%). Free base. Melting point: 120-122° C.

MH+=424.3.

Example 42

N-benzyl(4-[1,1'-biphenyl]-4-yl-1H-imidazol-2-yl)-N-methylmethanamine (4-[1,1'-biphenyl]-4-yl-1H-imidazol-2-yl)-N-methylmethanamine (1 g; 0.003 mol; prepared under experimental conditions similar to those previously and using suitable starting reagents and reaction products) is diluted in 20 ml of dimethylformamide. Potassium carbonate (1.23 g; 0.009 mol) is added at 23° C. then benzyl bromide (0.34 ml; 0.003 mol) is added fairly slowly. The reaction mixture is stirred at this temperature for 48 hours then poured in ice-cooled water. The mixture is extracted with ethyl acetate and the organic phase washed with water. After drying over magnesium sulphate, the solvents are concentrated using a rotary evaporator. After purification on a silica column (eluent: ethyl acetate-heptane/8-2), a white-coloured solid is obtained in the form of a paste (yield of 16%). Free base. Melting point: 106-108° C.

MH+=354.2.

Example 43

(R,S)-N,N-dihexyl-1-(4-phenyl-1H-imidazol-2-yl)-1-heptanamine (R,S)-1-(4-phenyl-1H-imidazol-2-yl)-1-heptanamine (1 g; 0.003 mol; prepared under experimental conditions similar to those previously and using suitable starting reagents and reaction products) is diluted in 10 ml of methanol. Triethylamine (0.9 ml; 0.006 mol) is added dropwise then the mixture is stirred for 30 minutes at 23° C. Hexanal (0.45 ml; 0.0036 mol) is then added then the mixture is stirred for one hour at 23° C. Sodium triacetoxyborohydride (1.3 g; 0.006 mol) is finally added. After stirring for two hours at 23° C., water is added and the reaction mixture is extracted with ethyl acetate. The organic phase is washed with water and dried over magnesium sulphate before evaporation of the solvents. After purification on a silica column (eluent: ethyl acetate-heptane/6-4), a brown-coloured solid is obtained in the form of a paste (yield of 3%). Free base. The melting point could not be measured (paste).

MH+=426.4.

Example 44

N-[(1R)-2-(1H-indol-3-yl)-1-(4-phenyl-1H-imidazol-2-yl)ethyl]-2-pyrimidinamine (1R)-2-(1H-indol-3-yl)-1-(4-phenyl-1H-imidazol-2-yl)ethanamine (2 g; 0.0066 mol; prepared under experimental conditions similar to those previously and using suitable starting reagents and reaction products) is diluted in 10 ml of n-butanol. 2-bromopyrimidine (1 g; 0.0066 mol) then diisoethylamine (1.15 ml, 0.0066 mol) are added dropwise. The mixture is then heated to about 80° C. for 16 hours. The n-butanol is evaporated off then the residue is taken up in water and ethyl acetate. The organic phase is washed with water then with a saturated solution of sodium chloride before being dried over magnesium sulphate and concentrated using a rotary evaporator. After purification on a silica column (eluent: ethyl acetate-heptane/7-3 then $CH_2Cl_2$-MeOH—$NH_4OH$/95-4.5-0.5 then ethyl acetate), a white-coloured powder is obtained (the yield is 20%). Free base. Melting point: 138-140° C.

MH+=381.2.

Example 45

(1-benzyl-4-phenyl-1H-imidazol-2-yl)-N,N-dimethylmethanamine (1-benzyl-4-phenyl-1H-imidazol-2-yl)methanamine (0.6 g; 0.0018 mol; prepared under experimental conditions similar to those previously and using suitable starting reagents and reaction products) is diluted in 15 ml of tetrahydrofuran. Triethylamine (1.12 ml; 0.008 mol) then methyl 4-toluenesulphonate (0.75 g; 0.004 mol) are added dropwise. The mixture is stirred for 48 hours at 23° C. then poured into ice-cooled water. After extraction with ether then decantation, the organic phase is washed with water then with a saturated solution of sodium chloride. The organic phase is then dried over magnesium sulphate and concentrated using a rotary evaporator. After purification on a silica column (eluent: ethyl acetate-heptane/7-3 then $CH_2Cl_2$-MeOH/95-5), a white-coloured powder is obtained (yield of 44%). Free base. Melting point: 78-80° C.

MH+=292.2.

Example 46

(1R)-N-benzyl-2-(1H-indol-3-yl)-N-methyl-1-(4-phenyl-1H-imidazol-2-yl)ethanamine (1R)-N-benzyl-2-(1H-indol-3-yl)-1-(4-phenyl-1H-imidazol-2-yl)ethanamine (0.5 g; 0.00127 mol; prepared under experimental conditions similar to that of Example 38 and using suitable starting reagents and reaction products) is diluted in 25 ml of tetrahydrofuran. Methyl tosylate (0.24 g; 0.00127 mol) is added to the previous solution at 23° C. then potassium tert-butylate (0.15 g; 0.00127 mol) is added fairly slowly. Stirring is maintained for two hours at 23° C. then the mixture is heated to about 60° C. for eight hours. The solvent is evaporated off and the residue obtained taken up in ethyl acetate and a 10% solution of sodium bicarbonate. After decantation, the organic phase is washed with water and dried over magnesium sulphate. The solvent is then evaporated off. After purification on a silica column (eluent: ethyl acetate-heptane/7-3), a light beige-coloured solid is obtained in the form of a paste (yield of 4%). Free base. Melting point: 110-112° C.

MH+=407.3.

The Compounds of Examples 47 to 318 are Obtained, According to Procedures Similar to Those Described for Examples 31 to 46 or Above in the Part Entitled "Preparation of the Compounds of General Formula (I)".

Example 47

(1R)-2-(1H-indol-3-yl)-N-(2-phenylethyl)-1-(4-phenyl-1H-imidazol-2-yl)ethanamine Free base. The melting point could not be measured (paste).

Example 48

(1R)-N-benzyl-2-phenyl-1-(4-phenyl-1H-imidazol-2-yl)ethanamine

Free base. Melting point: 228-230° C.

Example 49

N-benzyl(4-phenyl-1H-imidazol-2-yl)methanamine

Free base. The melting point could not be measured (paste).

Example 50 tert-butyl (1R)-1-(4-tert-butyl-1H-imidazol-2-yl)-2-(1H-indol-3-yl)-ethylcarbamate Free base. Melting point: 104-106° C.:

Example 51

(4-phenyl-1H-imidazol-2-yl)methanamine

Hydrochloride. Melting point: 228-230° C.

Example 52

1-methyl-1-(4-phenyl-1H-imidazol-2-yl)ethylamine

Hydrochloride. Melting point: 200-204° C.

Example 53

N-[(1S)-2-(1H-indol-3-yl)-1-(4-phenyl-1H-imidazol-2-yl)ethyl]-1-hexanamine

Hydrochloride. Melting point: 132-134° C.

Example 54 tert-butyl (R,S)-1-(4-phenyl-1H-imidazol-2-yl)heptylcarbamate

Free base. Melting point: 102-104° C.

Example 55

(4-[1,1'-biphenyl]-4-yl-1-methyl-1H-imidazol-2-yl)methanamine

Hydrochloride. Melting point: 279-280° C.

Example 56

(1S)-3-methyl-1-(4-phenyl-1H-imidazol-2-yl)-1-butanamine

Hydrochloride. Melting point: 150-152° C.

Example 57 butyl 2-[4-(4-phenoxyphenyl)-1H-imidazol-2-yl]ethylcarbamate

Free base. The melting point could not be measured (paste).

Example 58

(R,S)-N-[2-(1-methyl-1H-indol-3-yl)-1-(4-phenyl-1H-imidazol-2-yl)ethyl]-1-butanamine Free base. The melting point could not be measured (paste).

Example 59

(R,S)-4-(2-{1-[(tert-butoxycarbonyl)amino]pentyl}-1H-imidazol-4-yl)-1,1'-biphenyl Free base. Melting point: 172-176° C.

Example 60

(R,S)—N-benzyl-1-(4-[1,1'-biphenyl]4-yl-1H-imidazol-2-yl)-1-pentanamine

Free base. Melting point: 201-203° C.

Example 61

N-[2-(4-[1,1'-biphenyl]-4-yl-1H-imidazol-2-yl)ethyl]-3,3-dimethyl-butanamide

Free base. Melting point: 186-188° C.

Example 62

(1R)-N-benzyl-1-(4,5-dimethyl-1,3-oxazol-2-yl)-2-(1H-indol-3-yl)ethanamine

Free base. The melting point could not be measured (paste).

Example 63 tert-butyl (R,S)-1-(4-phenyl-1H-imidazol-2-yl)hexylcarbamate

Free base. The melting point could not be measured (paste).

Example 64

(R,S)-N-hexyl-1-(4-phenyl-1H-imidazol-2-yl)-1-heptanamine

Free base. Melting point: 140-142° C.

Example 65

(R,S)-1-(4-phenyl-1H-imidazol-2-yl)hexylamine

Hydrochloride. Melting point: 146-148° C.

Example 66

(R,S)-N-benzyl-1-[4-(4-methoxyphenyl)-1H-imidazol-2-yl]-1-heptanamine

Hydrochloride. Melting point: from 115° C.

Example 67

(R,S)-N-(2,6-dichlorobenzyl)-1-(4-phenyl-1H-imidazol-2-yl)-1-heptanamine

Free base. The melting point could not be measured (paste).

Example 68

(R,S)-N-(4-chlorobenzyl)-1-(4-phenyl-1H-imidazol-2-yl)-1-heptanamine

Free base. The melting point could not be measured (paste).

Example 69

(R,S)-1-[4-(3-methoxyphenyl)-1H-imidazol-2-yl]heptylamine

Hydrochloride. Melting point: 110-112° C.

Example 70

(R,S)-N-(2-chlorobenzyl)-1-(4-phenyl-1H-imidazol-2-yl)-1-heptanamine

Free base. The melting point could not be measured (paste).

Example 71

(R,S)-N-(2-fluorobenzyl)-1-(4-phenyl-1H-imidazol-2-yl)-1-heptanamine

Free base. The melting point could not be measured (paste).

Example 72

(R,S)-N-butyl-1-(4-phenyl-1H-imidazol-2-yl)-1-heptanamine

Free base. The melting point could not be measured (paste).

Example 73

(R,S)-N-isopentyl-N-[1-(4-phenyl-1H-imidazol-2-yl)heptyl]amine

Free base. The melting point could not be measured (paste).

Example 74

(R,S)-1-[4-(3-bromophenyl)-1H-imidazol-2-yl]-N-hexyl-1-heptanamine

Free base. The melting point could not be measured (paste).

Example 75

(R,S)-N-pentyl-1-(4-phenyl-1H-imidazol-2-yl)-1-heptanamine

Free base. Melting point: 118-120° C.

Example 76

(R,S)-N-[1-(4-phenyl-1H-imidazol-2-yl)heptyl]cyclohexanamine

Free base. Melting point: 68-70° C.

Example 77

(R,S)-N-benzyl-1-[4-(3,4-dichlorophenyl)-1H-imidazol-2-yl]-1-heptanamine

Free base. Melting point: 192-194° C.

Example 78 butyl (4-[1,1'-biphenyl]-4-yl-1H-imidazol-2-yl)methylcarbamate

Free base. Melting point: 130-132° C.

Example 79

(R,S)-N-[1-(4-phenyl-1H-imidazol-2-yl)heptyl]cyclopentanamine

Free base. The melting point could not be measured (paste).

Example 80

(S)-cyclohexyl(4-phenyl-1H-imidazol-2-yl)methylamine

Hydrochloride. Melting point: 208-210° C.

Example 81

(R,S)-N-{1-[4-(2-chlorophenyl)-1H-imidazol-2-yl]heptyl}-cyclohexanamine

Hydrochloride. Melting point: 155-157° C.

Example 82

N-[(S)-cyclohexyl(4-cyclohexyl-1H-imidazol-2-yl)methyl]-cyclohexanamine

Hydrochloride. Melting point: 180-182° C.

Example 83

N-[(S)-cyclohexyl(4-phenyl-1H-imidazol-2-yl)methyl]-cyclobutanamine

Hydrochloride. Melting point: 210-212° C.

Example 84

(R,S)-N-{1-[4-(4-fluorophenyl)-1H-imidazol-2-yl]heptyl}-cyclobutanamine

Hydrochloride. Melting point: 144-146° C.

Example 85

N-{(S)-cyclohexyl[4-(3-fluoro-4-methoxyphenyl)-1H-imidazol-2-yl]methyl}cyclobutanamine Free base. Melting point: from 95° C.

Example 86

N-((S)-cyclohexyl{4-[4-(trifluoromethyl)phenyl]-1H-imidazol-2-yl}methyl)cyclobutanamine Free base. Foam.

Example 87

N-{(S)-cyclohexyl[4-(3-fluorophenyl)-1H-imidazol-2-yl]methyl}-cyclobutanamine

Free base. Melting point: 172-176° C.

Example 88

(1R)-N-benzyl-2-(1H-indol-3-yl)-1-(4-phenyl-1H-imidazol-2-yl)ethanamine

Free base. Melting point: 100-102° C.

Example 89

(R,S)-2-(1H-indol-3-yl)-1-(5-methyl-4-phenyl-1H-imidazol-2-yl)ethanamine

Hydrochloride. Melting point: 208-210° C.

Example 90

(1R)-1-(4,5-diphenyl-1H-imidazol-2-yl)-2-(1H-indol-3-yl)ethanamine

Hydrochloride. Melting point: >260° C.

Example 91

(R,S)-2-phenyl-1-(4-phenyl-1H-imidazol-2-yl)ethanamine

Hydrochloride. Melting point: 180-182° C.

Example 92

(R,S)-2-(1-methyl-1H-indol-3-yl)-1-(4-phenyl-1H-imidazol-2-yl)ethylamine

Hydrochloride. Melting point: 110-114° C.

Example 93

(1S)-N-benzyl-2-(1H-indol-3-yl)-1-(4-phenyl-1H-imidazol-2-yl)ethanamine

Free base. Melting point: 118-120° C.

Example 94

(1R)-N-benzyl-1-(4,5-diphenyl-1H-imidazol-2-yl)-2-(1H-indol-3-yl)ethanamine

Free base. Melting point: 146-148° C.

Example 95

(1R)-N-benzyl-2-(1H-indol-3-yl)-1-(5-methyl-4-phenyl-1H-imidazol-2-yl)ethanamine Free base. Melting point: 120-122° C.

Example 96 tert-butyl (1R)-2-(1H-indol-3-yl)-1-(4-phenyl-1H-imidazol-2-yl)-ethylcarbamate

Free base. Melting point: 208-210° C.

Example 97

(1R)-2-(1H-indol-3-yl)-1-(4-phenyl-1H-imidazol-2-yl)ethanamine

Hydrochloride. The melting point could not be measured (paste).

Example 98

N-[(1R)-2-(1H-indol-3-yl)-1-(4-phenyl-1H-imidazol-2-yl)ethyl]benzamide

Free base. Melting point: 218-220° C.

Example 99 benzyl (1R)-2-(1H-indol-3-yl)-1-(4-phenyl-1H-imidazol-2-yl)ethylcarbamate

Free base. Melting point: 105-108° C.

Example 100

(1R)-N-benzyl-2-(1H-indol-3-yl)-1-(4-phenyl-1,3-thiazol-2-yl)ethanamine

Free base. Melting point: 134-136° C.

Example 101

N-[(1R)-2-(1H-indol-3-yl)-1-(4-phenyl-1,3-thiazol-2-yl)-ethyl]benzamide

Free base. Melting point: 108-110° C.

Example 102 tert-butyl (1R)-2-(1H-indol-3-yl)-1-[4-(4-nitrophenyl)-1H-imidazol-2-yl]-ethylcarbamate Free base. Melting point: 220-222° C.

Example 103 tert-butyl (4-phenyl-1H-imidazol-2-yl)methylcarbamate

Free base. Melting point: 170-172° C.

Example 104 tert-butyl (1-benzyl-4-phenyl-1H-imidazol-2-yl)methylcarbamate

Free base. Melting point: 140-142° C.

Example 105

(R,S)-N-benzyl-2-(6-fluoro-1H-indol-3-yl)-1-(4-phenyl-1H-imidazol-2-yl)ethanamine Free base. Melting point: 98-100° C.

Example 106

(1R)-2-(1H-indol-3-yl)-1-[4-(4-nitrophenyl)-1H-imidazol-2-yl]ethanamine

Hydrochloride. Melting point: becomes pasty at about 220° C.

Example 107

(1-benzyl-4-phenyl-1H-imidazol-2-yl)methanamine

Hydrochloride. Melting point: 248-250° C.

Example 108

(1R)-2-(1H-indol-3-yl)-N-(2-phenoxyethyl)-1-(4-phenyl-1H-imidazol-2-yl)ethanamine Free base. Melting point: 94-96° C.

Example 109

(1R)-1-(4-tert-butyl-1H-imidazol-2-yl)-2-(1H-indol-3-yl)ethylamine

Hydrochloride. Melting point: 230-232° C.

Example 110

N-benzyl(1-benzyl-4-phenyl-1H-imidazol-2-yl)methanamine

Free base. Melting point: 60-62° C.

Example 111

(1R)-2-(1-benzothien-3-yl)-N-benzyl-1-(4-phenyl-1H-imidazol-2-yl)ethanamine

Free base. Melting point: 152-154° C.

Example 112

(1R)-2-(1H-indol-3-yl)-N-(2-phenoxyethyl)-1-(4-phenyl-1,3-thiazol-2-yl)ethanamine Free base. Melting point: 124-126° C.

Example 113 tert-butyl 1-(4-phenyl-1H-imidazol-2-yl)cyclohexylcarbamate

Free base. Melting point: 170-172° C.

Example 114 tert-butyl (R,S)-2-(6-chloro-1H-indol-3-yl)-1-(4-phenyl-1H-imidazol-2-yl)ethylcarbamate Free base. Melting point: 208-210° C.

Example 115

1-(4-phenyl-1H-imidazol-2-yl)cyclohexanamine

Hydrochloride. Melting point: 202-204° C.

Example 116

N-[(1R)-2-(1H-indol-3-yl)-1-(4-phenyl-1H-imidazol-2-yl)ethyl]-N'-phenylurea

Free base. Compound described in the PCT Application WO 99/64401.

Example 117

N-[(1R)-2-(1H-indol-3-yl)-1-(4-phenyl-1H-imidazol-2-yl)ethyl]benzenecarboximidamide Free base. Compound described in the PCT Application WO 99/64401.

Example 118

(1R)-N-(cyclohexylmethyl)-2-(1H-indol-3-yl)-1-(4-phenyl-1H-imidazol-2-yl)ethanamine Free base. Compound described in the PCT Application WO 99/64401.

Example 119

(R,S)-N$^1$-benzyl-1-(4-phenyl-1H-imidazol-2-yl)-1,5-pentanediamine

Free base. Compound described in the PCT Application WO 99/64401.

Example 120 tert-butyl (R,S)-5-(benzylamino)-5-(4-phenyl-1H-imidazol-2-yl)pentylcarbamate

Free base. Compound described in the PCT Application WO 99/64401.

Example 121

N-[(1R)-2-(1H-indol-3-yl)-1-(4-phenyl-1H-imidazol-2-yl)ethyl]-4-methoxybenzenecarboximidamide Free base. Compound described in the PCT Application WO 99/64401.

Example 122

(R,S)-2-(6-chloro-1H-indol-3-yl)-1-(4-phenyl-1H-imidazol-2-yl)ethylamine

Hydrochloride. Melting point: 210-212° C.

Example 123

N-benzyl-1-(4-phenyl-1H-imidazol-2-yl)cyclohexanamine

Free base. Melting point: 114-116° C.

Example 124 tert-butyl (1R)-3-methyl-1-(4-phenyl-1H-imidazol-2-yl)butylcarbamate

Free base. Melting point: 88-90° C.

Example 125

(1R)-N-benzyl-3-methyl-1-(4-phenyl-1H-imidazol-2-yl)-1-butanamine

Free base. Melting point: 134-135° C.

Example 126 tert-butyl (R,S)-phenyl(4-phenyl-1H-imidazol-2-yl)methylcarbamate

Free base. Melting point: 134-136° C.

Example 127 tert-butyl 1-methyl-1-(4-phenyl-1H-imidazol-2-yl)ethylcarbamate

Free base. Melting point: 130-132° C.

Example 128

(R,S)-phenyl(4-phenyl-1H-imidazol-2-yl)methylamine

Hydrochloride. The melting point could not be measured (paste).

Example 129 tert-butyl (1R)-3-phenyl-1-(4-phenyl-1H-imidazol-2-yl)propylcarbamate

Free base. Melting point: 72-74° C.

Example 130 tert-butyl (1R)-2-cyclohexyl-1-(4-phenyl-1H-imidazol-2-yl)ethylcarbamate

Free base. Melting point: 184-185° C.

Example 131

(1R)-3-phenyl-1-(4-phenyl-1H-imidazol-2-yl)-1-propanamine

Hydrochloride. Melting point: 174-176° C.

Example 132

(1R)-2-cyclohexyl-1-(4-phenyl-1H-imidazol-2-yl)ethanamine

Hydrochloride. Melting point: 196-198° C.

Example 133

(R,S)-N-benzyl(phenyl)(4-phenyl-1H-imidazol-2-yl)methanamine

Free base. Melting point: 144-146° C.

Example 134

(1R)-N-benzyl-2-cyclohexyl-1-(4-phenyl-1H-imidazol-2-yl)ethanamine

Free base. Melting point: 52-54° C.

Example 135

(1R)-N-benzyl-3-phenyl-1-(4-phenyl-1H-imidazol-2-yl)-1-propanamine

Free base. Melting point: 142-144° C.

Example 136

(R,S)-N-{5,5,5-trifluoro-1-[4-(4-fluorophenyl)-1H-imidazol-2-yl]pentyl}cyclohexanamine Free base. Melting point: 220° C.

Example 137

4-(2-{[(tert-butoxycarbonyl)amino]methyl}-1H-imidazol-4-yl)-1,1'-biphenyl

Free base. Melting point: 100-102° C.

Example 138

N-{(S)-cyclohexyl[4-(4-methylsulphonylphenyl)-1H-imidazol-2-yl]methyl}cyclohexanamine Free base. Melting point: 152-154° C.

Example 139

N-benzyl-2-(4-phenyl-1H-imidazol-2-yl)-2-propanamine

Free base. Melting point: 136-138° C.

Example 140

4-(1-benzyl-2-{[(tert-butoxycarbonyl)amino]methyl}-1H-imidazol-4-yl)-1,1'-biphenyl Free base. Melting point: 167-169° C.

Example 141

(4-[1,1'-biphenyl]4-yl-1H-imidazol-2-yl)methanamine

Hydrochloride. Melting point: 240-242° C.

Example 142

(R,S)-1-(4-phenyl-1H-imidazol-2-yl)heptylamine

Hydrochloride. Melting point: 131-134° C.

Example 143

(1-benzyl-4-[1,1'-biphenyl]-4-yl-1H-imidazol-2-yl)methanamine

Hydrochloride. Melting point: 170-174° C.

Example 144

N,N-dibenzyl(4-[1,1'-biphenyl]4-yl-1H-imidazol-2-yl)methanamine

Free base. Melting point: 70-74° C.

Example 145

(R,S)-N-benzyl-1-(4-phenyl-1H-imidazol-2-yl)-1-heptanamine

Free base. Melting point: 160-162° C.

Example 146

4-(2-{[(tert-butoxycarbonyl)amino]methyl}-1-methyl-1H-imidazol-4-yl)-1,1'-biphenyl Free base. Melting point: 208-210° C.

Example 147 tert-butyl (1S)-1-(4,5-diphenyl-1H-imidazol-2-yl)-2-(1H-indol-3-yl)ethylcarbamate Free base. Melting point: 142-143° C.

Example 148 tert-butyl (1R)-2-(1H-indol-3-yl)-1-(1-methyl-4-phenyl-1H-imidazol-2-yl)ethylcarbamate Free base. Melting point: 96-100° C.

Example 149

4-(2-{[(tert-butoxycarbonyl)(methyl)amino]methyl}-1H-imidazol-4-yl)-1,1'-biphenyl Free base. Melting point: 72-74° C.

Example 150

4-(2-{(1R)-1-[(tert-butoxycarbonyl)amino]-2-cyclohexylethyl}-1H-imidazol-4-yl)-1,1'-biphenyl Free base. Melting point: 112-114° C.

Example 151

(1R)-2-(1H-indol-3-yl)-1-(1-methyl-4-phenyl-1H-imidazol-2-yl)ethanamine

Hydrochloride. Melting point: 206-210° C.

Example 152

4-(2-{2-[(tert-butoxycarbonyl)amino]ethyl}-1H-imidazol-4-yl)-1,1'-biphenyl

Free base. Melting point: 140-142° C.

Example 153 tert-butyl methyl[(5-methyl-4-phenyl-1H-imidazol-2-yl)methyl]carbamate

Free base. Melting point: 70-72° C.

Example 154

(1R)-1-(4-[1,1'-biphenyl]-4-yl-1H-imidazol-2-yl)-2-cyclohexylethanamine

Hydrochloride. Melting point: 178-180° C.

Example 155

(4-[1,1'-biphenyl]-4-yl-1H-imidazol-2-yl)-N-methyl-methanamine

Hydrochloride. Melting point: 218-220° C.

Example 156 tert-butyl (4,5-diphenyl-1H-imidazol-2-yl)methyl(methyl)carbamate

Free base. Melting point: 170-172° C.

Example 157 tert-butyl (4,5-diphenyl-1H-imidazol-2-yl)methylcarbamate

Free base. Melting point: 144-146° C.

Example 158

N-methyl-(5-methyl-4-phenyl-1H-imidazol-2-yl)methanamine

Hydrochloride. Melting point: 218-220° C.

Example 159

(R,S)-N,N-dibenzyl-1-(1-benzyl-4-phenyl-1H-imidazol-2-yl)-1-heptanamine

Hydrochloride. Melting point: 130-132° C.

Example 160

(4,5-diphenyl-1H-imidazol-2-yl)methanamine

Hydrochloride. Melting point: 210-212° C.

Example 161

2-(4-[1,1'-biphenyl]4-yl-1H-imidazol-2-yl)ethanamine

Hydrochloride. Melting point: 228-230° C.

Example 162

(4,5-diphenyl-1H-imidazol-2-yl)-N-methylmethanamine

Hydrochloride. Melting point: 198-200° C.

Example 163

N-benzyl(4,5-diphenyl-1H-imidazol-2-yl)methanamine

Free base. Melting point: 160-162° C.

Example 164

N-benzyl-2-(4-[1,1'-biphenyl]-4-yl-1H-imidazol-2-yl)ethanamine

Free base. Melting point: 174-176° C.

Example 165

4-(2-{[benzyl(tert-butoxycarbonyl)amino]methyl}-1H-imidazol-4-yl)-1,1'-biphenyl

Free base. Melting point: 130-132° C.

Example 166

(1R)-1-(4-[1,1'-biphenyl]-4-yl-1H-imidazol-2-yl)-3-phenyl-1-propanamine

Hydrochloride. Melting point: 215-218° C.

Example 167

4-(2-{(1R)-1-[(tert-butoxycarbonyl)amino]-3-phenylpropyl}-1H-imidazol-4-yl)-1,1'-biphenyl Free base. Melting point: 154-156° C.

Example 168

N-benzyl(4-[1,1'-biphenyl]4-yl-1H-imidazol-2-yl)methanamine

Hydrochloride. Melting point: >250° C.

Example 169

(1R)-N-benzyl-1-(4-[1,1'-biphenyl]-4-yl-1H-imidazol-2-yl)-2-cyclohexylethanamine Free base. Melting point: 233-238° C.

Example 170

(1R)-N-benzyl-1-(4-[1,1'-biphenyl]-4-yl-1H-imidazol-2-yl)-3-phenyl-1-propanamine Free base. Melting point: 210-213° C.

Example 171

4-(2-{3-[(tert-butoxycarbonyl)amino]propyl}-1H-imidazol-4-yl)-1,1'-biphenyl

Free base. Melting point: 145-146° C.

Example 172

4-[2-(2-{[(tert-butylamino)carbothioyl]amino}ethyl)-1H-imidazol-4-yl]-1,1'-biphenyl Free base. Melting point: 98-99° C.

Example 173 tert-butyl 6-(4-phenyl-1H-imidazol-2-yl)hexylcarbamate

Free base. The melting point could not be measured (paste).

Example 174 tert-butyl (R,S)-1-(4-phenyl-1H-imidazol-2-yl)pentylcarbamate

Free base. Melting point: 126° C.

Example 175

(R,S)-1-(4-[1,1'-biphenyl]-4-yl-1H-imidazol-2-yl)-1-pentanamine

Hydrochloride. Melting point: 197-200° C.

Example 176

N-[2-(4-[1,1'-biphenyl]-4-yl-1H-imidazol-2-yl)ethyl]-1-hexanamine

Free base. Melting point: 152-154° C.

Example 177

4-[2-(2-{[(tert-butylamino)carbonyl]amino}ethyl)-1H-imidazol-4-yl]-1,1'-biphenyl Free base. Melting point: 195-196° C.

Example 178

N-benzyl-3-(4-[1,1'-biphenyl]-4-yl-1H-imidazol-2-yl)-1-propanamine

Free base. Melting point: 254-256° C.

Example 179

3-(4-[1,1'-biphenyl]-4-yl-1H-imidazol-2-yl)-1-propanamine

Hydrochloride. Melting point: >260° C.

Example 180

6-(4-phenyl-1H-imidazol-2-yl)hexylamine

Hydrochloride. Melting point: 244-246° C.

Example 181

(R,S)-1-(4-phenyl-1H-imidazol-2-yl)pentylamine

Hydrochloride. Melting point: 178-180° C.

Example 182 tert-butyl (R,S)-1-[4-(4-methylphenyl)-1H-imidazol-2-yl]heptylcarbamate

Free base. Melting point: 77-80° C.

Example 183 tert-butyl (R,S)-1-[4-(2-methoxyphenyl)-1H-imidazol-2-yl]heptylcarbamate

Free base. Melting point: 64-65° C.

Example 184

(R,S)-1-[4-(4-methylphenyl)-1H-imidazol-2-yl]-1-heptanamine

Hydrochloride. Melting point: 157-160° C.

Example 185

(R,S)-1-[4-(2-methoxyphenyl)-1H-imidazol-2-yl]heptylamine

Hydrochloride. Melting point: 238-240° C.

Example 186

(R,S)-N-benzyl-1-(4-phenyl-1H-imidazol-2-yl)-1-pentanamine

Free base. Melting point: 200-202° C.

Example 187 tert-butyl (R,S)-1-[4-(4-methoxyphenyl)-1H-imidazol-2-yl]heptylcarbamate

Free base. Melting point: 125-127° C.

Example 188

(R,S)-1-(4-[1,1'-biphenyl]-4-yl-1H-imidazol-2-yl)-heptanamine

Hydrochloride. Melting point: 182-184° C.

Example 189 tert-butyl (R,S)-1-[4-(3-bromophenyl)-1H-imidazol-2-yl]heptylcarbamate

Free base. Melting point: 141-143° C.

Example 190

(R,S)-1-[4-(4-methoxyphenyl)-1H-imidazol-2-yl]heptylamine

Hydrochloride. Melting point: 231-232° C.

Example 191

(R,S)-1-[4-(3-bromophenyl)-1H-imidazol-2-yl]-1-heptanamine

Hydrochloride. Melting point: 230-231° C.

Example 192

(R,S)-4-(2-{1-[(tert-butoxycarbonyl)amino]heptyl}-1H-imidazol-4-yl)-1,1'-biphenyl Free base. Melting point: 142-144° C.

Example 193

(R,S)-N-benzyl-1-[4-(3-bromophenyl)-1H-imidazol-2-yl]-1-heptanamine

Acetate. Melting point: 115-116° C.

Example 194

4-(2-{(1S)-1-[(tert-butoxycarbonyl)amino]propyl}-1H-imidazol-4-yl)-1,1'-biphenyl Free base. Melting point: 138-140° C.

Example 195

(R,S)-N-benzyl-1-(4-[1,1'-biphenyl]-4-yl-1H-imidazol-2-yl)-1-heptanamine

Free base. Melting point: 100-102° C.

Example 196

(1S)-1-(4-[1,1'-biphenyl]-4-yl-1H-imidazol-2-yl)-1-propanamine

Hydrochloride. Melting point: >250° C.

Example 197 tert-butyl (1S)-1-(4,5-diphenyl-1H-imidazol-2-yl) propylcarbamate

Free base. Melting point: 136-138° C.

Example 198

(1S)-N-benzyl-1-(4-[1,1'-biphenyl]4-yl-1H-imidazol-2-yl)-1-propanamine

Free base. Melting point: 220-222° C.

Example 199

(1S)-1-(4,5-diphenyl-1H-imidazol-2-yl)-1-propanamine

Hydrochloride. Melting point: 224-226° C.

Example 200

(R,S)-N-benzyl-1-[4-(4-methylphenyl)-1H-imidazol-2-yl]-1-heptanamine

Hydrochloride. Melting point: 185-188° C.

Example 201

(R,S)-N-benzyl-1-[4-(2-methoxyphenyl)-1H-imidazol-2-yl]-1-heptanamine

Free base. Melting point: 155-157° C.

Example 202

(R,S)-N-benzyl-1-(4-phenyl-1H-imidazol-2-yl)-1-hexanamine

Free base. Melting point: 192-194° C.

Example 203

4-[2-(2-{[(neopentyloxy)carbonyl]amino}ethyl)-1H-imidazol-4-yl]-1,1'-biphenyl

Free base. Melting point: 162-164° C.

Example 204

(1S)-N-benzyl-1-(4,5-diphenyl-1H-imidazol-2-yl)-1-propanamine

Free base. Melting point: 182-184° C.

Example 205

(R,S)-4-[2-(1-aminoheptyl)-1H-imidazol-4-yl]benzonitrile

Hydrochloride. Melting point: 218-220° C.

Example 206

(R,S)-1-[4-(4-bromophenyl)-1H-imidazol-2-yl]-1-heptanamine

Free base. Melting point: from 126° C.

Example 207 tert-butyl (1R)-1-(4-phenyl-1H-imidazol-2-yl)butylcarbamate

Free base. Melting point: 156-158° C.

Example 208

4-(2-{(1R)-1-[(tert-butoxycarbonyl)amino]butyl}-1H-imidazol-4-yl)-1,1'-biphenyl

Free base. Melting point: 145.6° C.

Example 209

(1R)-1-(4-[1,1'-biphenyl]-4-yl-1H-imidazol-2-yl)-1-butanamine

Hydrochloride. Melting point: 155.4° C.

Example 210

(R,S)-4-[2-(1-aminoheptyl)-1H-imidazol-4-yl]-2,6-di(tert-butyl)-phenol

Hydrochloride. Melting point: 204-206° C.

Example 211

(1R)-1-(4-phenyl-1H-imidazol-2-yl)-1-butanamine

Hydrochloride. Melting point: 182-184° C.

Example 212

(R,S)-N-benzyl-1-[4-(4-bromophenyl)-1H-imidazol-2-yl]-1-heptanamine

Free base. Melting point: becomes pasty from 130° C.

Example 213

(1R)-N-benzyl-1-(4-[1,1'-biphenyl]-4-yl-1H-imidazol-2-yl)-1-butanamine

Free base. Melting point: 78.6° C.

Example 214

(1R)-N-benzyl-1-(4-phenyl-1H-imidazol-2-yl)-1-butanamine

Free base. Melting point: 218-220° C.

Example 215

(R,S)-N-(3-chlorobenzyl)-1-(4-phenyl-1H-imidazol-2-yl)-1-heptanamine

Free base. The melting point could not be measured (paste).

Example 216

(R,S)-N-benzyl-1-[4-(3-methoxyphenyl)-1H-imidazol-2-yl]-1-heptanamine

Free base. Melting point: 141-142° C.

Example 217

(R,S)-4-{2-[1-(benzylamino)heptyl]-1H-imidazol-4-yl}benzonitrile

Free base. Melting point: 188-189° C.

Example 218

(R,S)-4-[2-(1-aminoheptyl)-1H-imidazol-4-yl]-N,N-diethylaniline

Hydrochloride. Melting point: 192° C.

Example 219

(1R)-1-(4-phenyl-1H-imidazol-2-yl)ethanamine

Hydrochloride. Melting point: 178-181° C.

Example 220

(R,S)-1-[4-(4-fluorophenyl)-1H-imidazol-2-yl]-1-heptanamine

Hydrochloride. Melting point: 148-150° C.

Example 221

(R,S)-1-[4-(2-chlorophenyl)-1H-imidazol-2-yl]-1-heptanamine

Hydrochloride. Melting point: 138-140° C.

Example 222

N-[(1S)-1-(4-[1,1'-biphenyl]-4-yl-1H-imidazol-2-yl)propyl]-1-butanamine

Free base. The melting point could not be measured (paste).

Example 223

(1R)-N-benzyl-1-(4-phenyl-1H-imidazol-2-yl)ethanamine

Free base. The melting point could not be measured (paste).

Example 224

(R,S)-N-[1-(4-phenyl-1H-imidazol-2-yl)heptyl]-N-propylamine

Free base. Melting point: 94-98° C.

Example 225

(R,S)-N-benzyl-1-[4-(3-methoxyphenyl)-1H-imidazol-2-yl]-1-heptanamine

Hydrochloride. Melting point: from 120° C.

Example 226

(R,S)-4-{2-[1-(benzylamino)heptyl]-1H-imidazol-4-yl}benzonitrile

Hydrochloride. Melting point: from 185° C.

Example 227

(R,S)-N-(4-methoxybenzyl)-1-(4-phenyl-1H-imidazol-2-yl)-1-heptanamine

Free base. Melting point: 126-128° C.

Example 228

(R,S)-N-benzyl-1-[4-(4-fluorophenyl)-1H-imidazol-2-yl]-1-heptanamine

Hydrochloride. Melting point: from 110° C.

Example 229

(R,S)-N-benzyl-1-[4-(2-chlorophenyl)-1H-imidazol-2-yl]-1-heptanamine

Hydrochloride. Melting point: from 90° C.

Example 230

(R,S)-N-benzyl-N-(1-{4-[4-(diethylamino)phenyl]-1H-imidazol-2-yl}heptyl)amine

Hydrochloride. Melting point: 170° C.

Example 231

(R,S)-1-[4-(3,4-dichlorophenyl)-1H-imidazol-2-yl]-1-heptanamine

Hydrochloride. Melting point: 148-150° C.

Example 232 tert-butyl (R,S)-1-[4-(3-bromophenyl)-1H-imidazol-2-yl]-5-methylhexylcarbamate

Free base. Melting point: 134-136° C.

Example 233

(R,S)-1-[4-(3-bromophenyl)-1H-imidazol-2-yl]-5-methyl-1-hexanamine

Hydrochloride. Melting point: 200-202° C.

Example 234

(R,S)-N-isobutyl-1-(4-phenyl-1H-imidazol-2-yl)-1-heptanamine

Acetate. Melting point: 70-72° C.

Example 235

(R,S)-N-benzyl-1-[4-(3-bromophenyl)-1H-imidazol-2-yl]-5-methyl-1-hexanamine

Free base. Melting point: 92-94° C.

Example 236

(R,S)-N-benzyl-1-[4-(4-methoxyphenyl)-1H-imidazol-2-yl]-1-heptanamine

Free base. Oil.

Example 237

4-[2-(2-{[(benzyloxy)carbonyl]amino}ethyl)-1H-imidazol-4-yl]-1,1'-biphenyl

Free base. Melting point: 134-136° C.

Example 238

4-(2-{1-[(butoxycarbonyl)amino]-1-methylethyl}-1H-imidazol-4-yl)-1,1'-biphenyl

Free base. Melting point: 170-172° C.

Example 239

4-(2-{2-[(isobutoxycarbonyl)amino]ethyl}-1H-imidazol-4-yl)-1,1'-biphenyl

Free base. Melting point: 134-135° C.

Example 240

(R,S)-N-[1-(4-phenyl-1H-imidazol-2-yl)heptyl]cyclobutanamine

Free base. Melting point: 148-150° C.

Example 241

4-(2-{(1S)-1-[(butoxycarbonyl)amino]ethyl}-1H-imidazol-4-yl)-1,1'-biphenyl

Free base. Melting point: 118-122° C.

Example 242

4-(2-{(1R)-1-[(butoxycarbonyl)amino]ethyl}-1H-imidazol-4-yl)-1,1'-biphenyl

Free base. Melting point: 114-116° C.

Example 243

N-[(S)-cyclohexyl(4-phenyl-1H-imidazol-2-yl)methyl]-cyclohexanamine

Free base. Melting point: 240-242° C.

Example 244

4-(2-{2-[(methoxycarbonyl)amino]ethyl}-1H-imidazol-4-yl)-1,1'-biphenyl

Free base. Melting point: 177.2° C.

Example 245

4-(2-{2-[(propoxycarbonyl)amino]ethyl}-1H-imidazol-4-yl)-1,1'-biphenyl

Free base. Melting point: 141.2° C.

Example 246

4-(2-{2-[(ethoxycarbonyl)amino]ethyl}-1H-imidazol-4-yl)-1,1'-biphenyl

Free base. Melting point: 132.5° C.

Example 247

4-[2-(1-{[(benzyloxy)carbonyl]amino}-1-methylethyl)-1H-imidazol-4-yl]-1,1'-biphenyl Free base. Melting point: 148-152° C.

Example 248

(R,S)-N-isopropyl-N-[1-(4-phenyl-1H-imidazol-2-yl)heptyl]amine

Free base. Melting point: 114-116° C.

Example 249

N-[2-(4-[1,1'-biphenyl]4-yl-1H-imidazol-2-yl)ethyl]-cyclohexanamine

Free base. Melting point: 207-210° C.

Example 250

(R,S)-N-{1-[4-(3,4-dichlorophenyl)-1H-imidazol-2-yl]heptyl}-cyclohexanamine

Hydrochloride. Melting point: 194° C.

Example 251 butyl 2-[4-(4-fluorophenyl)-1H-imidazol-2-yl]ethyl-carbamate

Free base. Melting point: 87° C.

Example 252

(R,S)-N-[1-(4-[1,1'-biphenyl]-4-yl-1H-imidazol-2-yl)heptyl]-cyclohexanamine

Hydrochloride. Melting point: 168-170° C.

Example 253

(R,S)-2-(5-fluoro-1H-indol-3-yl)-1-[4-(4-fluorophenyl)-1H-imidazol-2-yl]ethylamine Hydrochloride. Melting point: 220-222° C.

Example 254

N-{[4-(3-bromophenyl)-1H-imidazol-2-yl]methyl}cyclohexanamine

Free base. Melting point: 202-204° C.

Example 255 hexyl 2-(4-[1,1'-biphenyl]-4-yl-1H-imidazol-2-yl)ethylcarbamate

Free base. Melting point: 116.5-116.8° C.

Example 256

(R,S)-N-{2-(5-fluoro-1H-indol-3-yl)-1-[4-(4-fluorophenyl)-1H-imidazol-2-yl]ethyl}cyclobutanamine Hydrochloride. Melting point: 180-190° C.

Example 257

(R,S)-N-{1-[4-(4-fluorophenyl)-1H-imidazol-2-yl]4-methylpentyl}-cyclohexanamine

Hydrochloride. Melting point: 230-232° C.

Example 258

(S)-cyclohexyl[4-(3,4-difluorophenyl)-1H-imidazol-2-yl]-methanamine

Hydrochloride. Melting point: 222-223° C.

Example 259

(S)-cyclohexyl[4-(3-fluoro-4-methoxyphenyl)-1H-imidazol-2-yl]-methanamine

Hydrochloride. Melting point: 225-227° C.

Example 260

(R,S)-cyclopropyl[4-(4-fluorophenyl)-1H-imidazol-2-yl]-methanamine

Hydrochloride. Melting point: 230-232° C.

Example 261

N-{(S)-cyclohexyl[4-(4-fluorophenyl)-1H-imidazol-2-yl]methyl}-2-propanamine

Free base. Melting point: 210-212° C.

Example 262

N-{(S)-cyclohexyl[4-(3,4-difluorophenyl)-1H-imidazol-2-yl]methyl}cyclobutanamine Free base. Melting point: 200-202° C.

Example 263

(R,S) N-(cyclohexylmethyl)-1-(4-phenyl-1H-imidazol-2-yl)-1-heptanamine

Hydrochloride. Melting point: 142-144° C.

Example 264

N-{(S)-cyclohexyl[4-(4-fluorophenyl)-1H-imidazol-2-yl]methyl}cyclohexanamine

Hydrochloride. Melting point: >250° C.

Example 265

(S)-cyclohexyl-N-(cyclohexylmethyl)(4-phenyl-1H-imidazol-2-yl)methanamine

Hydrochloride. Melting point: 180-182° C.

Example 266

(R,S)-N-{cyclopropyl[4-(4-fluorophenyl)-1H-imidazol-2-yl]methyl}cyclohexanamine

Hydrochloride. The melting point could not be measured (paste).

Example 267

(S)-cyclohexyl-N-(cyclopropylmethyl)(4-phenyl-1H-imidazol-2-yl)methanamine

Hydrochloride. Melting point: 151-152° C.

Example 268 butyl 2-[4-(4-cyclohexylphenyl)-1H-imidazol-2-yl]ethylcarbamate

Free base. Melting point: 138.4° C.

Example 269

4-[2-(2-{[(cyclohexyloxy)carbonyl]amino}ethyl)-1H-imidazol-4-yl]-1,1'-biphenyl

Free base. Melting point: 150° C.

Example 270

N-((S)-cyclohexyl{4-[4-(trifluoromethoxy)phenyl]-1H-imidazol-2-yl}methyl)-cyclobutanamine Free base. Melting point: 136-140° C.

Example 271

4-[2-(2-{[(cyclopentyloxy)carbonyl]amino}ethyl)-1H-imidazol-4-yl]-1,1'-biphenyl

Free base. Melting point: 140.5° C.

Example 272

(R,S)-N-{1-[4-(3-bromophenyl)-1H-imidazol-2-yl]-5-methylhexyl}-cyclohexanamine

Hydrochloride. Melting point: 216.7° C.

Example 273

(S)-cyclohexyl-N-(cyclopropylmethyl)[4-(4-fluorophenyl)-1H-imidazol-2-yl]-methanamine Hydrochloride. Melting point: 221.4° C.

Example 274

(R,S)-N-{cyclopentyl[4-(4-fluorophenyl)-1H-imidazol-2-yl]methyl}cyclobutanamine

Free base. Melting point: 146-148° C.

Example 275

N-{(S)-cyclohexyl[4-(4-cyclohexylphenyl)-1H-imidazol-2-yl]methyl}cyclobutanamine Hydrochloride. Melting point: 190-192° C.

Example 276

N-{(1R)-1-[4-(4-fluorophenyl)-1H-imidazol-2-yl]-2-methylpropyl}-cyclohexanamine

Free base. Melting point: 224-226° C.

Example 277

N-((S)-cyclohexyl{4-[4-(trifluoromethyl)phenyl]-1H-imidazol-2-yl}methyl)cyclobutanamine Acetate. Melting point: from 130° C.

Example 278 butyl 2-[4-(2,3-dihydro-1,4-benzodioxin-6-yl)-1H-imidazol-2-yl]ethylcarbamate

Free base. Gum.

Example 279

N-{(S)-cyclohexyl[4-(4-fluorophenyl)-1-methyl-1H-imidazol-2-yl]methyl}cyclohexanamine Hydrochloride. Melting point: 190-194° C.

Example 280 cyclohexylmethyl 2-(4-[1,1'-biphenyl]-4-yl-1H-imidazol-2-yl)ethylcarbamate

Free base. Melting point: 132-134° C.

Example 281

4-bromo-4'-(2-{2-[(butoxycarbonyl)amino]ethyl}-1H-imidazol-4-yl)-1,1'-biphenyl

Free base. Melting point: 166° C.

Example 282

N-((S)-cyclohexyl{4-methylthiophenyl]-1H-imidazol-2-yl}methyl)cyclohexanamine

Free base. Melting point: 96-98° C.

Example 283

N-{(S)-cyclohexyl[4-(4-fluorophenyl)-1H-imidazol-2-yl]methyl}-cyclohexanamine

Free base. Melting point: 260-262° C.

Example 284

N-[(S)-{4-[3,5-bis(trifluoromethyl)phenyl]-1H-imidazol-2-yl}(cyclohexyl)methyl]cyclohexanamine Free base. Melting point: 180-182° C.

Example 285 cyclobutylmethyl 2-(4-[1,1'-biphenyl]-4-yl-1H-imidazol-2-yl)ethylcarbamate

Free base. Melting point: 144-145° C.

Example 286 cyclobutylmethyl 2-[4-(4-fluorophenyl)-1H-imidazol-2-yl]ethylcarbamate

Free base. Melting point: 149-150° C.

Example 287

N-{(S)-cyclohexyl[4-(3,4-difluorophenyl)-1H-imidazol-2-yl]methyl}cyclohexanamine Free base. Melting point: 182.3° C.

Example 288

4-[2-(2-{[(2-methoxyethoxy)carbonyl]amino}ethyl)-1H-imidazol-4-yl]-1,1'-biphenyl Free base. Melting point: 123.3° C.

Example 289

(S)-1-[4-(3-bromophenyl)-1H-imidazol-2-yl]-1-cyclohexyl-N-(cyclohexylmethyl)methanamine Free base. Melting point: 134.3° C.

Example 290

4-(2-{(S)-cyclohexyl[(cyclohexylmethyl)amino]methyl}-1H-imidazol-4-yl)-N,N-diethylaniline Hydrochloride. Melting point: 204-206° C.

Example 291

2,6-ditert-butyl-4-(2-{(S)-cyclohexyl[(cyclohexylmethyl)amino]-methyl}-1H-imidazol-4-yl)phenol Hydrochloride. Melting point: 254.6° C.

Example 292

4-{2-[(S)-cyclohexyl(cyclohexylamino)methyl]-1H-imidazol-4-yl}-N,N-diethylaniline Hydrochloride. Melting point: 204-210° C.

Example 293

(S)-1-cyclohexyl-N-(cyclohexylmethyl)-1-[4-(4-fluorophenyl)-1H-imidazol-2-yl]methanamine Free base. Melting point: 184.8° C.:

Example 294 butyl 2-[4-(4-tert-butylphenyl)-1H-imidazol-2-yl]ethylcarbamate

Free base. Melting point: 106-108° C.

Example 295

(S)-1-cyclohexyl-N-(cyclohexylmethyl)-1-[4-(4-fluorophenyl)-1H-imidazol-2-yl]methanamine Hydrochloride. Melting point: 190-192° C.

Example 296

N-((S)-cyclohexyl{4-[4-(trifluoromethyl)phenyl]-1H-imidazol-2-yl}methyl)cyclohexanamine Hydrochloride. Melting point: 214.1° C.

Example 297

N-[(S)-[4-(3-bromophenyl)-1H-imidazol-2-yl](cyclohexyl)methyl]-cyclohexanamine

Hydrochloride. Melting point: 230.4° C.

Example 298

N-((S)-cyclohexyl{4-[4-(trifluoromethyl)phenyl]-1H-imidazol-2-yl}methyl)cyclohexanamine Free base.

Example 299 butyl 2-[4-(4-bromophenyl)-1H-imidazol-2-yl]ethylcarbamate

Free base. Melting point: 99-100° C.

Example 300 butyl 2-{4-[4-(trifluoromethyl)phenyl]-1H-imidazol-2-yl}ethylcarbamate

Free base. Melting point: 104-105° C.

Example 301

N-{(S)-cyclohexyl[4-(4-fluorophenyl)-1H-imidazol-2-yl]methyl}cycloheptanamine

Free base. Melting point: 140-142° C.

Example 302 cyclohexylmethyl 2-[4-(4-tert-butylphenyl)-1H-imidazol-2-yl]ethylcarbamate

Free base. Melting point: 104-106° C.

Example 303 cyclohexylmethyl 2-[4-(4'-bromo-1.1'-biphenyl-4-yl)-1H-imidazol-2-yl]ethylcarbamate Free base. Melting point: 130-132° C.

Example 304

N-((S)-cyclohexyl{4-[3-(trifluoromethyl)phenyl]-1H-imidazol-2-yl}methyl)cyclohexanamine Free base. Melting point: 186-188° C.

Example 305

(S)-1-cyclohexyl-N-(cyclohexylmethyl)-1-{4-[3-(trifluoromethyl)-phenyl]-1H-imidazol-2-yl}methanamine Free base. Melting point: 143.9° C.

Example 306

(S)-1-[4-(3-bromophenyl)-1H-imidazol-2-yl]-1-cyclohexyl-N-(cyclohexylmethyl)methanamine Hydrochloride. Melting point: 206.3° C.

Example 307

(S)-1-cyclohexyl-N-(cyclohexylmethyl)-1-{4-[3-(trifluoromethyl)-phenyl]-1H-imidazol-2-yl}methanamine Hydrochloride. Melting point: 198-200° C.

Example 308

(1R)-2-cyclohexyl-1-[4-(4-fluorophenyl)-1H-imidazol-2-yl]ethanamine

Hydrochloride. Melting point: 148-149° C.

Example 309

N-{(1R)-2-cyclohexyl-1-[4-(4-fluorophenyl)-1H-imidazol-2-yl]ethyl}cyclohexanamine Free base. Melting point: 217-218° C.

Example 310

4-{2-[(S)-amino(cyclohexyl)methyl]-1H-imidazol-4-yl}-N,N-diethylaniline

Hydrochloride. Melting point: 216-217° C.

Example 311

(S)-1-cyclohexyl-1-[4-(3-fluorophenyl)-1H-imidazol-2-yl]methanamine

Hydrochloride. Melting point: 238-241° C.

Example 312

(S)-1-cyclohexyl-N-(cyclohexylmethyl)-1-[4-(3-fluorophenyl)-1H-imidazol-2-yl]methanamine Hydrochloride. Melting point: 180-186° C.

Example 313 butyl 2-[4-(4-pyrrolidin-1-ylphenyl)-1H-imidazol-2-yl]ethylcarbamate

Free base. Melting point: 125° C.

Example 314

N-{(S)-cyclohexyl[4-(3-fluorophenyl)-1H-imidazol-2-yl]methyl}cyclohexanamine

Hydrochloride. Melting point: 213.9° C.

Example 315

N-{(1R)-2-cyclohexyl-1-[4-(4-fluorophenyl)-1H-imidazol-2-yl]ethyl}cyclohexanamine Hydrochloride. Melting point: decomposes from 250° C.

Example 316

4-{2-[(S)-amino(cyclohexyl)methyl]-1H-imidazol-4-yl}-2,6-ditert-butylphenol

Hydrochloride. Melting point: 222-228° C.

Example 317 butyl 2-[4-(4-pyrrolidin-1-ylphenyl)-1H-imidazol-2-yl]ethylcarbamate

Hydrochloride. Melting point: 165-166° C.

Example 318

(R)-1-cyclohexyl-N-(cyclohexylmethyl)-1-[4-(4-fluorophenyl)-1H-imidazol-2-yl]methanamine Hydrochloride. Melting point: 188.2° C.

Example 319

2,6-ditert-butyl-4-[4-(hydroxymethyl)-1,3-thiazol-2-yl]phenol

The compound of Example 319 can be obtained according to a protocol analogous to that described for the compound of Example 38, Stage E of PCT Patent Application WO 99/09829, except that ethyl bromopyruvate replaces the 3-chloroacetoacetate in Stage 38.C and that disobutylaluminium hydride replaces the lithium aluminium hydride in Stage 38.E.

Alternatively, this compound can also be obtained according to the procedure described in *J. Med. Chem.* (1996), 39, 237-245. White solid. Melting point: 123-124° C.

Example 320 meta-[4-(2,3-dihydro-1H-indol-6-yl)-1,3-thiazol-2-yl]-N-methylmethanamine hydrochloride 320.1) Mixture of meta-2-chloro-1-[1-(chloroacetyl)-2,3-dihydro-1H-indol-6-yl]ethanone and para-2-chloro-1-[1-(chloroacetyl)-2,3-dihydro-1H-indol-6-yl]ethanone 1-(chloroacetyl)-2,3-dihydro-1H-indole (3.9 g; 20 mmol) is dissolved in carbon disulphide (40 ml). $AlCl_3$ (6.15 g; 46 mmol) is added slowly then chloroacetyl chloride (1.835 ml; 22 mmol) is added dropwise to the mixture which is then heated under reflux for 18 hours. After the reaction medium is cooled down, the $CS_2$ is decanted and ice-cooled water containing concentrated HCl is added. After extraction with dichloromethane, the organic phase is separated and dried over magnesium sulphate before being filtered and concentrated under vacuum. The expected product (a 50/50 mixture of the meta and para isomers) is obtained by purification by crystallization from glacial acetic acid. White-coloured solid (1.6 g; yield of 30%).

MH+=271.

320.2) meta-2-chloro-1-(2,3-dihydro-1H-indol-6-yl)ethanone hydrochloride

Intermediate 320.1 (mixture of isomers; 1.6 g; 6.0 mmol) is dissolved hot in a mixture of acetic acid (10 ml) and 20% HCl (2 ml). The reaction medium is heated under reflux for 24 hours. After evaporation then purification by crystallization of the hydrochloride from glacial acetic acid in order to separate the mixture of isomers, the meta isomer crystallizes in the form of a brown solid (the para isomer remains in the mother liquors) with a yield of 47%. Melting point: decomposition from 158° C.

MH+=196.

The meta structure of the compound was established by NMR/NOESY.

320.3) meta-[4-(2,3-dihydro-1H-indol-6-yl)-1,3-thiazol-2-yl]-N-methylmethanamine hydrochloride The experimental protocol used is identical to that described for compound 30.2 of Example 30, intermediate 320.2 being used as the starting product instead of intermediate 30.1, tetrahydrofuran replacing the toluene in the presence of one equivalent of triethylamine in order to release the base of the salt. A brown-coloured solid is obtained with a yield of 9%. Melting point: decomposition from 235° C.

MH+=246.

Example 321

2,5,7,8-tetramethyl-2-{2-[(methylamino)methyl]-1,3-thiazol-4-yl}-6-chromanol hydrochloride 321.1) 6-hydroxy-N-methoxy-N, 2,5,7,8-pentamethyl-2-chromanecarboxamide 2.2 g (22.0 mmol) of O,N-dimethylhydroxylamine hydrochloride, triethylamine (6.2 ml), 3.0 g (22.0 mmol) of hydroxybenzotriazole and 4.2 g (22.0 mmol) of 1-(3-dimethylaminopropyl)-3-ethyl-carbodiimide hydrochloride are added successively to a solution of 5.0 g (20.0 mmol) of (R,S) 6-hydroxy-2,5,7,8-tetramethyl-2-chromanecarboxylic acid (Trolox®) in 175 ml of DMF. After the reaction mixture is stirred overnight at 25° C., the mixture is diluted with ice-cooled water and stirring is maintained for 30 more minutes. The product is extracted using 3 times 100 ml of ethyl acetate. The organic solution is washed successively with a 10% aqueous solution of sodium bicarbonate, with water, with a 10% aqueous solution of citric acid and finally with a saturated solution of sodium chloride. The organic phase is then dried over magnesium sulphate, filtered and concentrated under vacuum. The product obtained is purified by crystallization from ether in order to produce a white-coloured solid with a yield of 63%. Melting point: 139-140° C.

MH+=294.

321.2) 1-(6-hydroxy-2,5,7,8-tetramethyl-3,4-dihydro-2H-chromen-2-yl)ethanone

A solution of methyllithium (1.6 M; 31.25 ml; 50.0 mmol) is added dropwise at a temperature of −30° C. to a solution of 2.93 g (10.0 mmol) of intermediate 321.1 in 100 ml of THF and the mixture is left under stirring for 1 hour at −10° C. The reaction medium is hydrolyzed with $NH_4Cl$ in a saturated aqueous solution. The product is extracted using 3 times 150 ml of ethyl acetate. The organic phase is finally washed with sodium chloride in a saturated aqueous solution before being dried over magnesium sulphate, filtered and concentrated under vacuum. The product obtained is purified by crystallization from diisopropyl ether in order to produce a white solid with a yield of 80.7%. Melting point: 97-98° C.

MH+=248.

321.3) 2-bromo-1-(6-hydroxy-2,5,7,8-tetramethyl-3,4-dihydro-2H-chromen-2-yl)ethanone Intermediate 321.2 (0.777 g; 3.13 mmol) is dissolved in ethanol (25 ml) under a stream of argon. The solution is cooled down to 0° C. and bromine (0.18 ml; 4.20 mmol) is added in one go (see *J. Am. Chem. Soc.* (1999), 121, 24), then the mixture is stirred for 30 minutes allowing the temperature to rise to ambient temperature. The excess bromine is eliminated by bubbling through argon then the mixture is left under stirring for 2.5 hours. The ethanol is evaporated off and the product obtained is purified by crystallization from toluene. After filtering and washing with isopentane, a brown solid is obtained with a yield of 36%. Melting point: decomposition from 125° C.

MH+=326.

321.4) 2,5,7,8-tetramethyl-2-{2-[(methylamino)methyl-1,3-thiazol-4-yl}-6-chromanol hydrochloride The experimental protocol used is analogous to that described for compound 30.2 of Example 30, intermediate 321.3 being used as the starting product instead of intermediate 30.1, and benzene replacing the toluene as solvent. The product obtained is purified by crystallization from a minimum amount of dichloromethane in order to produce a white solid with a yield of 48%. Melting point: 153-155° C.

Example 322

N-{[4-(9H-carbazol-2-yl)-1,3-thiazol-2-yl]methyl}-N-methylamine hydrochloride 322.1) 9-acetyl-9H-carbazole This compound is obtained according to *Tetrahedron* (1980), 36, 3017-3019. The carbazole (10 g; 60 mmol) is suspended in 150 ml of acetic anhydride. 70% perchloric acid (0.5 ml) is added. After stirring for 30 minutes at ambient temperature, the mixture is poured into ice and the precipitate formed is filtered. After drying under vacuum, redissolving in dichloromethane and treatment with bone charcoal, the suspension is filtered on celite, the solvents are evaporated off and the product recrystallized from heptane. 12 g of brown crystals (yield of 90%) is obtained in this way. Melting point: 70-71° C. (literature: 72-74° C.).

322.2) 1-(9-acetyl-9H-carbazol-2-yl)-2-chloroethanone

This compound is obtained according to a protocol analogous to that of Stage 320.1 of Example 320, using 5 g (24 mmol) of intermediate 322.1. 5.4 g of the expected compound is obtained (yield of 79%). White solid. Melting point: 175-176° C.

322.3) 1-(9H-carbazol-2-yl)-2-chloroethanone

Intermediate 322.2 (2.85 g;1 mmol) is suspended in a mixture of acetic acid (50 ml) and concentrated HCl (5 ml). The reaction medium is heated under reflux for 2 hours before being left to return to ambient temperature. The new precipitate formed is filtered. After drying under vacuum, 1.9 g of a greenish solid is obtained (yield of 78%). Melting point: 203-204° C.

322.4) N-{[4-(9H-carbazol-2-yl) -1,3-thiazol-2-yl]methyl}-N-methylamine hydrochloride This compound is obtained according to a protocol analogous to that of Stage 30.2 from 487 mg (2 mmol) of intermediate 322.3 and 408 mg (2 mmol) of tert-butyl 2-amino-2-thioxoethyl(methyl)carbamate. 300 mg of the expected product is obtained (yield of 43%). White solid. Melting point: >250° C.

Example 323

3,5-ditert-butyl-4'-{2-[(methylamino)methyl]-1,3-thiazol-4-yl}-1,1'-biphenyl-4-ol hydrochloride 323.1) 3',5'-ditert-butyl-4'-hydroxy-1,1'-biphenyl-4-carboxylic acid 5.0 g (1.41 mmol) of ethyl 3',5'-ditert-butyl-4'-hydroxy-1,1'-biphenyl-4-carboxylate (Chem. Lett. (1998), 9, 931-932) is dissolved in ethanol (25 ml). The solution is cooled down to 0° C. then a 1N solution of soda is added dropwise. After stirring overnight at ambient temperature, the reaction medium is heated under reflux in order to complete the reaction. After evaporation of the solvents and dilution of the residue with water, the mixture obtained is acidified with a 1N solution of HCl and extraction is carried out with dichloromethane. The organic phase is washed with sodium chloride in a saturated aqueous solution before being dried over magnesium sulphate, filtered and concentrated under vacuum. The product obtained is purified by crystallization from diisopropyl ether in order to produce a yellow-white solid with a yield of 47%. Melting point: >240° C.

323.2) 31,5'-ditert-butyl-4'-hydroxy-N-methoxy-N-methyl-1,1'-biphenyl-4-carboxamide The experimental protocol used is identical to that described for intermediate 321.1, with acid 323.1 replacing the Trolox® as starting product. A yellowish solid is obtained with a yield of 93%. Melting point: 175.6-177° C.

323.3) 1-(3',5'-ditert-butyl-4'-hydroxy-1,1'-biphenyl-4-yl)ethanone

The experimental protocol used is identical to that described for intermediate 321.2, intermediate 323.2 replacing intermediate 321.1. A white solid is obtained with a yield of 74%. Melting point: 144-144.7° C.

323.4) 2-bromo-1-(3',5'-ditert-butyl-4'-hydroxy-1,1'-biphenyl-4-yl)ethanone

The experimental protocol used is identical to that described for intermediate 321.3, intermediate 323.3 replacing intermediate 321.2. A yellow-orange oil is obtained which is sufficiently pure to be used in the following stage (yield of 100%).

323.5) tert-butyl [4-(3',5'-ditert-butyl-4'-hydroxy-1,1'-biphenyl-4-yl)-1,3-thiazol-2-yl]methyl(methyl)carbamate This compound is prepared according to the experimental protocol described in Example 1, Stage 1.3, using intermediate 323.4 instead of bromo-1-(3,5-ditert-butyl-4-hydroxyphenyl)ethanone. The expected compound is obtained in the form of a colourless oil with a yield of 46%.

MH+=509.43.

323.6) 3,5-ditert-butyl-4'-{2-[(methylamino)methyl]-1,3-thiazol-4-yl}-1,1'-biphenyl-4-ol hydrochloride 0.230 g (0.452 mmol) of intermediate 323.5 is dissolved in ethyl acetate (20 ml). HCl gas is bubbled through the solution previously obtained cooled down to 0° C. The stirred mixture is then allowed to return to ambient temperature. The solid formed is filtered and washed with ethyl acetate then with ether before being dried under vacuum. A white solid is obtained with a yield of 85%. Melting point: 220-221° C.

The Compounds of Examples 324 to 330 are Obtained According to Procedures Analogous to Those Described for Examples 31 to 46 or Above in the Part Entitled "Preparation of Compounds of General Formula (I)".

Example 324

(1R)-1-[4-(4-fluorophenyl)-1H-imidazol-2-yl]-2-phenylethanamine

Hydrochloride. Melting point: 173-180° C.

Example 325 cyclohexylmethyl 2-{4-[4-(diethylamino)phenyl]-1H-imidazol-2-yl}ethylcarbamate

Hydrochloride. Melting point: decomposes from 168° C.

Example 326 cyclohexylmethyl 2-[4-(4-pyrrolidin-1-ylphenyl)-1H-imidazol-2-yl]ethylcarbamate

Free base. Melting point: 128.5° C.

Example 327

N-{(1R)-1-[4-(4-fluorophenyl)-1H-imidazol-2-yl]-2-phenylethyl}cyclohexanamine

Hydrochloride. Melting point: 210-213° C.

Example 328

(1R)-N-(cyclohexylmethyl)-1-[4-(4-fluorophenyl)-1H-imidazol-2-yl]-2-phenylethanamine Hydrochloride. Melting point: from 140° C.

Example 329 cyclohexylmethyl 2-[4-(3,5-ditert-butyl-4-hydroxyphenyl)-1H-imidazol-2-yl]ethylcarbamate Hydrochloride. Melting point: 111.5° C.

Example 330 butyl 2-[4-(3,5-ditert-butyl-4-hydroxyphenyl)-1H-imidazol-2-yl]ethylcarbamate

Free base. Melting point: 180.9° C.

Example 331

2,6-dimethoxy-4-{2-[(methylamino)methyl]-1,3-thiazol-4-yl}phenol hydrochloride 331.1) 4-acetyl-2,6-dimethoxyphenyl acetate 3.0 g (15.3 mmol) of 3,5-dimethoxy-4-hydroxyacetophenone is dissolved in dichloromethane (30 ml) and 2.53 g (18.3 mmol) of $K_2CO_3$ is added. Triethylamine (2.6 ml) is then added dropwise. The reaction medium is cooled down to 0° C. and acetyl chloride (1.31 ml; 18.3 mmol) is added. The mixture is stirred for 24 hours at ambient temperature then poured into ice-cooled water. After extraction with dichloromethane, the organic phase is washed with sodium chloride in a saturated aqueous solution before being dried over magnesium sulphate, filtered and concentrated under vacuum. The product obtained is purified by crystallization from ether in order to produce a white solid with a yield of 99%. Melting point: 145° C.

331.2) 4-(bromoacetyl)-2,6-dimethoxyphenyl acetate

Intermediate 331.1 (0.850 g; 3.57 mmol) is solubilized in ethyl acetate then 1.35 g (6.07 mmol) of previously dried $CuBr_2$ is added. The mixture is heated under reflux for 2.5 hours before being left to return to ambient temperature. Ground charcoal is added and the mixture is stirred for 10 minutes. After filtering and evaporating to dryness, the solid obtained is taken up in diisopropyl ether. After filtering, a grey solid is obtained with a yield of 75%. Melting point: 124.2-126.3° C.

331.3) 4-(2-{[(tert-butoxycarbonyl)(methyl)amino]methyl}-1,3-thiazol-4-yl)-2,6-dimethoxyphenyl acetate Intermediate 331.3 is prepared according to an experimental protocol described in Example 1, Stage 1.3, using intermediate 331.2 instead of bromo-1-(3,5-ditert-butyl-4-hydroxyphenyl)ethanone. The expected compound is obtained in the form of a white solid with a yield of 55%. Melting point: 135.2-137.4° C.

331.4) tert-butyl [4-(4-hydroxy-3,5-dimethoxyphenyl)-1,3-thiazol-2-yl]methyl(methyl)carbamate 0.530 g (1.25 mmol) of intermediate 331.3 is dissolved in methanol (20 ml). The solution is cooled down using an ice bath then a 1N solution of NaOH is added dropwise. The mixture is left to return to ambient temperature under stirring. After evaporation to dryness and dilution of the residue with water, the solution is neutralised using citric acid followed by extraction with dichloromethane. The organic phase is washed with sodium chloride in a saturated aqueous solution before being dried over magnesium sulphate, filtered and concentrated under vacuum. The product is obtained in the form of a yellow oil with a yield of 96%. MH+=381.20.

331.5) 2,6-dimethoxy-4-{2-[(methylamino)methyl]-1,3-thiazol-4-yl}phenol hydrochloride The experimental protocol used is identical to that described for intermediate 323.6, intermediate 331.4 replacing intermediate 323.5. A light beige solid is obtained with a yield of 97%. Melting point: 229.8-232.0° C.

Example 332

2,6-diisopropyl-4-{2-[(methylamino)methyl]-1,3-thiazol-4-yl}phenol hydrochloride 332.1) 2,6-diisopropylphenyl acetate 3.45 g (16.4 mmol) of trifluoroacetic anhydride is added to 0.83 ml (14.6 mmol) of acetic acid at 0° C. while leaving the mixture to return to ambient temperature over 2 hours. The mixture is then cooled down to 0° C. and 1.95 g (11.0 mmol) of 2,6-diisopropylphenol is added dropwise. The reaction medium is maintained under stirring for 12 hours before being poured into ice-cooled water. After extraction with dichloromethane, the organic phase is washed with sodium chloride in a saturated aqueous solution before being dried over magnesium sulphate, filtered and concentrated under vacuum. A colourless oil is obtained with a yield of 86%. This product is sufficiently pure to be used directly in the following stage.

332.2) 1-(4-hydroxy-3,5-diisopropylphenyl)ethanone acetate 1.94 g (14.53 mmol) of $AlCl_3$ is dissolved in nitrobenzene (5 ml). At the same time, 2.0 g (9.08 mmol) of intermediate 332.1 is dissolved in nitrobenzene (1 ml). The solution of intermediate 332.1 is added dropwise to the solution of $AlCl_3$ at ambient temperature. The mixture is taken to 50° C. for 48 hours before being left to return to ambient temperature. The reaction medium is then poured into ice-cooled water. A 1N solution of HCl (5 ml) and then a concentrated solution of HCl (2 ml) are added. The mixture is stirred at ambient temperature followed by extraction with dichloromethane. The organic phase is washed with sodium chloride in a saturated aqueous solution before being dried over magnesium sulphate, filtered and concentrated under vacuum. The expected product is obtained after chromatography on a silica column (eluent: 13% of ethyl acetate in heptane). After evaporation, the pure fractions produce a grey-white solid with a yield of 25%. Melting point: 88-93° C.

332.3) 4-acetyl-2,6-diisopropylphenyl acetate

The experimental protocol used is identical to that described for intermediate 331.1, intermediate 332.2 replacing the 3,5-dimethoxy-4-hydroxyacetophenone. A sand-coloured solid is obtained with a yield of 95%. Melting point: 102-103° C.

332.4) 4-(bromoacetyl)-2,6-diisopropylphenyl acetate

The experimental protocol used is identical to that described for intermediate 331.2, intermediate 332.3 replacing intermediate 331.1. A yellow oil is obtained which crystallizes slowly with a yield of 88%. This product is sufficiently pure to be used directly in the following stage.

332.5) 4-(2-{[(tert-butoxycarbonyl)(methyl)amino]methyl}-1,3-thiazol-4-yl)-2,6-diisopropylphenyl acetate Intermediate 332.5 is prepared according to a protocol identical to that described for Example 1, Stage 1.3, using intermediate 332.4 instead of the bromo-1-(3,5-ditert-butyl- 4-hydroxyphenyl)ethanone. The expected compound is obtained in the form of a pale yellow solid with a yield of 76%.

MH+=447.20.

332.6) tert-butyl [4-(4-hydroxy-3,5-diisopropylphenyl)-1,3-thiazol-2-yl]methyl(methyl)carbamate acetate The experimental protocol used is identical to that described for intermediate 331.4, intermediate 332.5 replacing intermediate 331.3. An ochre oil is obtained with a yield of 91%. This product is sufficiently pure to be used directly in the following stage.

MH+=405.20.

332.7) 2,6-diisopropyl-4-{2-[(methylamino)methyl]-1,3-thiazol-4-yl}phenol hydrochloride The experimental protocol used is identical to that described for intermediate 323.6, intermediate 332.6 replacing intermediate 323.5. A beige-pink solid is obtained with a yield of 69%. Melting point: loses its colour at 162° C. and melts at 173-177° C.

Example 333

4-{2-[(methylamino)methyl]-1,3-thiazol-4-yl}phenol hydrochloride 333.1) 2-bromo-1-(4-hydroxyphenyl)ethanone The experimental protocol used is identical to that described for intermediate 331.2, 4-hydroxy-acetophenone replacing intermediate 331.1. A brown-pink solid is obtained with a yield of 60%. Melting point: 118° C.

333.2) tert-butyl [4-(4-hydroxyphenyl)-1,3-thiazol-2-yl]methyl(methyl)carbamate

Intermediate 333.2 is prepared according to a protocol identical to that described for Example 1, Stage 1.3, using intermediate 333.1 instead of the bromo-1-(3,5-ditert-butyl-4-hydroxyphenyl)ethanone and toluene replacing the benzene. The expected compound is obtained in the form of a clear-yellow oil which very slowly crystallizes cold with a yield of 35%.

MH+=321.30.

333.3) 4-{2-[(methylamino)methyl]-1,3-thiazol-4-yl}phenol hydrochloride

The experimental protocol used is identical to that described for intermediate 323.6, intermediate 333.2 replacing intermediate 323.5. A pale yellow solid is obtained with a yield of 100%. Melting point: 258-260° C.

Example 334

2,6-ditert-butyl-4-[2-(hydroxymethyl)-1,3-thiazol-4-yl]phenol

[This is Intermediate 6.d$_1$) of Patent Application EP 432 740]

334.1) [4-(3,5-ditert-butyl-4-hydroxyphenyl)-1,3-thiazol-2-yl]methyl pivalate

Intermediate 334.1 is prepared according to a protocol identical to that described for Example 1, Stage 1.3, using 2-(tert-butylcarbonyloxy)thioacetamide instead of the 2-{[(1,1-dimethylethoxy)carbonyl]methyl}amino-ethanethioamide and toluene replacing the benzene. The expected compound is obtained in the form of a white solid with a yield of 100%. Melting point: 114.6-116.0° C.

334.2) 2,6-ditert-butyl-4-[2-(hydroxymethyl)-1,3-thiazol-4-yl]phenol

The experimental protocol used is identical to that described for intermediate 331.4, intermediate 334.1 replacing intermediate 331.3. A white solid is obtained with a yield of 88%. Melting point: 126.4-127.4° C.

Example 335

N-{[4-(4-anilinophenyl)-1,3-thiazol-2-yl]methyl}-N-methylamine hydrochloride 335.1) 1-(4-anilinophenyl)ethanone 4-amino-acetophenone (4.87 g; 36.0 mmol) is dissolved in dimethylformamide (75 ml). 15 g (0.108 mol) of potassium carbonate (previously dried at 170° C. under an argon atmosphere), 7.236 g (36.0 mmol) of iodobenzene, 0.4 g of copper powder and a catalytic quantity of copper iodide are added. The reaction mixture is taken to reflux for 12 hours. After leaving the reaction medium to return to ambient temperature, the latter is filtered on celite and poured into ice-cooled water. After extraction with ethyl acetate, the organic phase is washed with water before being dried over magnesium sulphate, filtered and concentrated under vacuum. The product obtained is purified by crystallization from heptane in order to produce a yellow solid with a yield of 53.4%.

Melting point: 105° C.

335.2) N-(4-acetylphenyl)-N-phenylacetamide

The experimental protocol used is identical to that described for intermediate 322.1, with intermediate 335.1 replacing the 9-acetyl-9H-carbazole and the reaction medium being however heated for 15 minutes at 70° C. After crystallization from heptane, a yellow solid is obtained with a yield of 54.2%. Melting point: 118-120° C. (value in the literature: 122-123° C.).

335.3) N-[4-(bromoacetyl)phenyl]-N-phenylacetamide

Intermediate 335.2 (0.633 g; 2.5 mmol) is dissolved in methanol (20 ml) and 1 g (2.0 mmol) of bromination resin PVPHP (*J. Macromol. Sci. Chem.* (1977), A11, (3), 507-514) is added. After stirring under an argon atmosphere for 4 hours, filtration is carried out and the resins are rinsed with methanol. After evaporation of the filtrate solvents and crystallization from methanol, a white solid is obtained with a yield of 59%. Melting point: 152-153° C.

335.4) tert-butyl (4-{4-[acetyl(phenyl)amino]phenyl}-1,3-thiazol-2-yl)methyl(methyl)carbamate Intermediate 335.4 is prepared according to a protocol identical to that described for Example 1, Stage 1.3, using intermediate 335.3 instead of the bromo-1-(3,5-ditert-butyl-4-hydroxyphenyl)ethanone and toluene replacing the benzene. The expected compound is obtained in the form of an oil with a yield of 73%.

MH+=438.30.

335.5) N-(4-{2-[(methylamino)methyl]-1,3-thiazol-4-yl}phenyl)-N-phenylacetamide hydrochloride The experimental protocol used is identical to that described for intermediate 322.3, intermediate 335.4 replacing intermediate 322.2. A white-cream solid is obtained with a yield of 53%. Melting point: >250° C.

335.6) N-{[4-(4-anilinophenyl)-1,3-thiazol-2-yl]methyl}-N-methylamine hydrochloride The experimental protocol used is identical to that described for intermediate 322.3, intermediate 335.5 replacing intermediate 322.2 and the reaction medium being heated under reflux for 12 hours instead of 2 hours. A grey solid is obtained with a yield of 68%. Melting point: >250° C.

Example 336

2,6-ditert-butyl-4-{2-[(dimethylamino)methyl]-1,3-thiazol-4-yl}phenol hydrochloride 336.1) 4-[2-(bromomethyl)-1, 3-thiazol-4-yl]-2,6-ditert-butylphenol 1.5 g (4.70 mmol) of intermediate 334.2, (2,6-ditert-butyl-4-[2-(hydroxymethyl)-1,3-thiazol-4-yl]phenol is dissolved in dichloromethane (30 ml). After adding $CBr_4$ (2.02 g; 6.10 mmol), the reaction medium is cooled down to 0° C. $PPh_3$ (1.48 g; 5.63 mmol) is added by fractions then the mixture is left to return to ambient temperature. The reaction medium is then poured into ice-cooled water before being extracted with dichloromethane. The organic phase is washed with salt water before being dried over magnesium sulphate, filtered and concentrated under vacuum. The expected product is obtained after chromatography on a silica column (eluent: 30% of ethyl acetate in heptane), in order to produce a brown oil with a yield of 92%. This product is sufficiently pure to be used directly in the following stage.

MH+=382.20.

336.2) 2,6-ditert-butyl-4-{2-[(dimethylamino)methyl]-1,3-thiazol-4-yl}phenol hydrochloride 0.8 ml (1.57 mmol) of dimethylamine and 0.4 ml (2.62 mmol) of triethylamine are dissolved in dimethylformamide (15 ml). 0.400 g (1.05 mmol) of intermediate 336.1 dissolved in dimethylformamide (5 ml) is added then the mixture is stirred at ambient temperature for 18 hours. The reaction medium is then poured into ice-cooled water followed by extraction with ethyl acetate. The organic phase is washed with salt water before being dried over magnesium sulphate, filtered and concentrated under vacuum. The expected product is obtained after chromatography on a silica column (eluent: 50% of ethyl acetate in heptane), in order to produce an orange oil with a yield of 92%. The hydrochloride is then obtained by solubilizing the base in ether and adding 1.2 ml of a 1N solution of HCl in ether. After filtering and washing of the solid formed with ether then with isopentane, a beige-pink solid is obtained with a yield of 15.2%.

Melting point 166.8-169.0° C.

The Compounds of Examples 337 to 345 are Obtained According to Procedures Analogous to Those Described for Examples 31 to 46 or Above in the Part Entitled "Preparation of Compounds of General Formula (I)".

Example 337 cyclobutylmethyl 2-[4-(4'-bromo-1,1'-biphenyl-4-yl)-1H-imidazol-2-yl]ethylcarbamate Hydrochloride. Melting point: 214-215° C.

Example 338 isobutyl 2-[4-(4'-bromo-1,1'-biphenyl-4-yl)-1H-imidazol-2-yl]ethylcarbamate

Free base. Melting point: 158.7° C.

Example 339 isobutyl 2-[4-(4-tert-butylphenyl)-1H-imidazol-2-yl]ethylcarbamate

Free base. Melting point: 110.6° C.

Example 340 cyclobutylmethyl 2-[4-(4-tert-butylphenyl)-1H-imidazol-2-yl]ethylcarbamate

Free base. Melting point: 103° C.

Example 341 cyclohexyl 2-[4-(4'-bromo-1.1'-biphenyl-4-yl)-1H-imidazol-2-yl]ethylcarbamate

Free base. Melting point: 180° C.

Example 342 cyclohexyl 2-[4-(4-tert-butylphenyl)-1H-imidazol-2-yl]ethylcarbamate

Free base. Melting point: 127-130° C.

Example 343

3-[4-(4-fluorophenyl)-1H-imidazol-2-yl]propan-1-amine

Hydrochloride. Melting point: 245-246° C.

Example 344

4,4,4-trifluorobutyl 2-[4-(4'-bromo-1,1'-biphenyl-4-yl)-1H-imidazol-2-yl]ethylcarbamate Free base. Melting point: 176.5° C.

Example 345

4,4,4-trifluorobutyl 2-[4-(1,1'-biphenyl-4-yl)-1H-imidazol-2-yl]ethylcarbamate

Free base. Melting point: 157.3° C.

Example 346

2,6-ditert-butyl-4-{4-[(methylamino)methyl]-1,3-thiazol-2-yl}phenol hydrochloride 346.1) 4-[4-(bromomethyl)-1,3-thiazol-2-yl]-2,6-ditert-butylphenol The experimental protocol used is identical to that described for intermediate 336.1, the compound of Example 319 replacing intermediate 334.2, 1,2-dichloroethane replacing the dimethylformamide and the reaction medium being heated under reflux for 12 hours. A reddish oil is obtained with a yield of 77%. This product is used as it is directly in the following stage.

346.2) 2,6-ditert-butyl-4-{4-[(methylamino)methyl]-1,3-thiazol-2-yl}phenol

The experimental protocol used is identical to that described for intermediate 336.2, intermediate 346.1 replacing intermediate 336.1, a 2N solution of methylamine in tetrahydrofuran replacing the dimethylamine and acetonitrile replacing the dimethylformamide. The hydrochloride is obtained by solubilizing the base in ether and adding a 1N solution of HCl in ether. The solid formed is filtered and purified by recrystallization from acetone in order to produce a white solid with a yield of 18%.

Melting point: 184.0-185.0° C.

Example 347

2,6-ditert-butyl-4-[2-(piperidin-1-ylmethyl)-1,3-thiazol-4-yl]phenol hydrochloride The experimental protocol used is identical to that described for intermediate 336.2, piperidine replacing the dimethylamine. A white solid is obtained with a yield of 56%.

Melting point: >195° C.

Example 348

2,6-ditert-butyl-4-{2-[(4-methylpiperazin-1-yl)methyl]-1,3-thiazol-4-yl}phenol hydrochloride The experimental protocol used is identical to that described for intermediate 336.2, N-methylpiperazine replacing the dimethylamine. A light brown solid is obtained with a yield of 62%. Melting point: 234.6-235.2° C.

Example 349

2,6-ditert-butyl-4-[2-(piperazin-1-ylmethyl)-1,3-thiazol-4-yl]phenol hydrochloride 349.1) tert-butyl 4-{[4-(3,5-ditert-butyl-4-hydroxyphenyl)-1,3-thiazol-2-yl]methyl}piperazine-1-carboxylate The experimental protocol used is identical to that described for intermediate 336.2, N-Boc-piperazine replacing the dimethylamine. A pale orange solid is obtained with a yield of 64%. Melting point: 108-109° C.

349.2) 2,6-ditert-butyl-4-[2-(piperazin-1-ylmethyl)-1,3-thiazol-4-yl]phenol hydrochloride The experimental protocol used is identical to that described for intermediate 323.6, intermediate 349.1 replacing intermediate 323.5. A white solid is obtained with a yield of 86%. Melting point: 255.4-257.7° C.

Example 350

2,6-ditert-butyl-4-{2-[2-(methylamino)ethyl]-1,3-thiazol-4-yl}phenol hydrochloride 350.1) tert-butyl 2-cyanoethyl(methyl)carbamate:

0.1 mol of N-methyl-β-alaninenitrile is dissolved in dichloromethane (100 ml) containing 20.9 ml (0.12 mol) of diisopropylethylamine. The mixture is then cooled down to 0° C. then Boc-O-Boc (26.2 g; 0.12 mol) is added by fractions, then the mixture is stirred overnight at ambient temperature. The reaction medium is then poured into ice-cold water and extracted with dichloromethane. The organic phase is washed successively with a 10% aqueous solution of sodium bicarbonate and with water, then finally with a saturated solution of sodium chloride. The organic phase is then dried over magnesium sulphate, filtered and concentrated under vacuum. The reddish brown oil obtained is used as it is in the following stage.

350.2) tert-butyl 3-amino-3-thioxopropyl(methyl)carbamate:

43.4 mmol of intermediate 350.1 is dissolved in ethanol (40 ml) containing triethylamine (6.1 ml). $H_2S$ is then bubbled through the mixture for 3 hours before evaporating the solvents to dryness. The expected product is obtained after chromatography on a silica column (eluent: 50% ethyl acetate in heptane) in the form of a light orange oil. Crystallization of this oil from diisopropyl ether gives a white solid with a yield of 15% Melting point: 104° C.

350.3) 4-[3,5-bis(1,1-dimethylethyl)-4-hydroxyphenyl]-N-[(1,1-dimethylethoxy)-carbonyl]-N-methyl-2-thiazoleethanamine:

Intermediate 350.2 (2.11 mmol) and bromo-1-(3,5-ditert-butyl-4-hydroxyphenyl)ethanone (6.9 g; 2.11 mmol) are dissolved in toluene (75 ml) under an argon atmosphere then the mixture is stirred at ambient temperature for 12 hours. The reaction medium is taken to reflux for 4 hours. After evaporation of the solvents, the residue is diluted with dichloromethane and washed with a saturated solution of NaCl.

The organic phase is separated, dried over magnesium sulphate, filtered and concentrated under vacuum. The expected product is crystallized in the form of a white solid. Melting point: 204° C.

350.4) 2,6-ditert-butyl-4-{2-[2-(methylamino)ethyl]-1,3-thiazol-4-yl}phenol hydrochloride:

1.95 mmol of intermediate 350.3 is dissolved in ethyl acetate (20 ml). The solution is cooled down to 0° C. then HCl gas is bubbled through for 10 minutes. The mixture is left to return to ambient temperature while stirring is maintained. After filtration and drying under vacuum, the expected product is recovered in the form of white crystals which are washed with ether. Quantitative yield. Melting point: 206-208° C.

Example 351

2,6-ditert-butyl-4-[4-(hydroxymethyl)-1,3-oxazol-2-yl]phenol

This compound can be obtained according to a procedure similar to that described for intermediate 1.C of the PCT Application WO 99/09829 in which ethyl bromopyruvate replaces 4-chloroacetoacetate and the intermediate ester isolated is then reduced using DIBAL in dichloromethane at 0° C. The reaction mixture is then treated with an aqueous solution of $NH_4Cl$ and filtered on celite. Extraction is carried out using a 50/50 mixture of dichloromethane and ethyl acetate. After decanting, drying over magnesium sulphate, filtration and evaporation of the filtrate, crystallisation from ethanol allows the expected product to be obtained in the form of a white powder. Melting point: 167-168° C.

Example 352

2,6-ditert-butyl-4-{2-[1-(methylamino)ethyl]-1,3-thiazol-4-yl}phenol hydrochloride 352.1) N'-(tert-butoxycarbonyl)-N'-methylalaninamide:

12 mmol of Boc-N-Me-DL-Ala-OH is dissolved in dimethoxyethane. N-methylmorpholine is added dropwise, then iso-butyl chloroformate. After stirring the mixture for 15 minutes at −15° C., ammonia (NH$_3$) is bubbled through then the mixture is kept under stirring at this temperature overnight. The precipitate obtained is filtered. The product, once dried, is used as it is in the following stage.

352.2) tert-butyl 2-amino-1-methyl-2-thioxoethyl(methyl) carbamate:

This compound is obtained by reaction with P$_2$S$_5$ under the conditions described in Example 361, Stage 361.2.

352.3) tert-butyl 1-[4-(3,5-ditert-butyl-4-hydroxyphenyl)-1,3-thiazol-2-yl]ethyl(methyl)carbamate:

Intermediate 352.2 and bromo-1-(3,5-ditert-butyl-4-hydroxyphenyl)ethanone are condensed according to a protocol similar to that described in Stage 350.3.

352.4) 2,6-ditert-butyl-4-{2-[1-(methylamino)ethyl]-1,3-thiazol-4-yl}phenol hydrochloride:

The experimental protocol used is the same as that described for Stage 350.4 of Example 350, with intermediate 352.3 replacing intermediate 350.3. The expected product is obtained in the form of a white powder. Melting point: 236-237° C.

Example 353

2,6-ditert-butyl-4-[2-(methoxymethyl)-1,3-thiazol-4-yl]phenol 353.1) [4-(3,5-ditert-butyl-4-hydroxyphenyl)-1,3-thiazol-2-yl]methyl pivalate:

Intermediate 353.1 is prepared according to a protocol identical to that described for Example 350, Stage 350.3, using 2-(tert-butylcarbonyloxy)thioacetamide instead of intermediate 350.2 and with toluene replacing the benzene. The expected compound is obtained in the form of a white solid with a yield of 100%. Melting point: 114.6-116.0° C.

353.2) 2,6-ditert-butyl-4-[2-(hydroxymethyl)-1,3-thiazol-4-yl]phenol:

Intermediate 353.1 (1.25 mmol) is dissolved in methanol (20 ml). The solution is cooled down using an ice bath then a 1N solution of NaOH is added dropwise. The mixture is left to return to ambient temperature while stirring. After evaporation to dryness and dilution of the residue with water, the solution is neutralized using citric acid and extraction is carried out with dichloromethane. The organic phase is washed with sodium chloride in a saturated aqueous solution before being dried over magnesium sulphate, filtered and concentrated under vacuum. A white solid is obtained with a yield of 88%. Melting point: 126.4-127.4° C.

353.3) 2,6-ditert-butyl-4-[2-(methoxymethyl)-1,3-thiazol-4-yl]phenol:

Intermediate 353.2 (1 equivalent) is methylated by reaction with 1.1 equivalent of iodomethyl in the presence of 2 equivalents of triethylamine, the reaction being carried out in tetrahydrofuran. A dark cream powder is obtained. Melting point: 115.8-117° C.

Example 354

2,6-ditert-butyl-4-{4-[(methylamino)methyl]-1,3-oxazol-2-yl}phenol hydrochloride 354.1) 2,6-ditert-butyl-4-[4-(bromomethyl)-1,3-oxazol-2-yl]phenol:

The compound of Example 351 (4.70 mmol) is dissolved in dichloromethane (30 ml). After adding CBr$_4$ (2.02 g; 6.10 mmol), the reaction medium is cooled down to 0° C. PPh$_3$ (1.48 g; 5.63 mmol) is added by fractions then the mixture is left to return to ambient temperature. The reaction medium is then poured into ice-cold water before being extracted with dichloromethane. The organic phase is washed with salt water before being dried over magnesium sulphate, filtered and concentrated under vacuum. The crude oil obtained is sufficiently pure to be used directly in the following stage.

354.2) 2,6-ditert-butyl-4-{4-[(methylamino)methyl]-1,3-oxazol-2-yl}phenol hydrochloride:

33 mmol of methylamine (2M solution in THF) is dissolved in acetonitrile (50 ml). 5.48 mmol of intermediate 354.1 dissolved in acetonitrile (50 ml) is added at 0° C. then the mixture is stirred at ambient temperature for 3 hours. The solvents are evaporated then the residue is shared between ethyl acetate and a 10% aqueous solution of NaHCO$_3$. The organic phase is washed with salt water before being dried over magnesium sulphate, filtered and concentrated under vacuum. The hydrochloride is then obtained by solubilizing the base in ether and adding 1.2 ml of a 1N solution of HCl in ether. After filtration and washing of the solid formed with ether, a dark orange powder is obtained. Melting point: decomposes at 150° C.

Example 355

N-{[4-(3,5-ditert-butyl-4-hydroxyphenyl)-1,3-thiazol-2-yl]methyl}acetamide 355.1) benzyl {4-[3,5-di(tert-butyl)-4-hydroxyphenyl]-1,3-thiazol-2-yl}methylcarbamate:

This compound is prepared according to an experimental protocol described in the Patent Application WO 98/58934 (see preparation of intermediates 26.1 and 26.2), using Z-Gly-NH$_2$ instead of N-Boc sarcosinamide. The expected compound is obtained in the form of a pale yellow oil with a yield of 99%. MH+=453.20

355.2) 4-[2-(aminomethyl)-1,3-thiazol-4-yl]-2,6-di(tert-butyl)phenol:

0.1 ml of a 40% solution of potassium hydroxide is added dropwise to a solution of 0.106 g (1.1 mmol) of intermediate 355.1 in 10 ml of methanol. After stirring overnight under reflux, the reaction mixture is concentrated under vacuum and the residue is diluted with dichloromethane and washed with a 1N HCl solution then with 50 ml of a saturated solution of NaCl. The organic phase is separated and dried over magnesium sulphate, filtered and concentrated under vacuum. The expected product is obtained after chromatography on a silica column (eluent: 5% of ethanol in dichloromethane) in the form of a brown foam with a yield of 76%. MH+=319.29.

355.3) N-{[4-(3,5-ditert-butyl-4-hydroxyphenyl)-1,3-thiazol-2-yl]methyl}acetamide:

Intermediate 355.2 (2 mmol) is dissolved in dichloromethane (20 ml). Triethylamine (3 mmol) is added and the mixture is cooled down to 0° C. Acetyl chloride (3 mmol) is then added dropwise. Once the addition is complete, the mixture is taken to ambient temperature and stirred overnight at this temperature before being poured into ice-cold water. The aqueous phase is extracted with dichloromethane, and the organic phase obtained is washed with salt water before being dried over magnesium sulphate. After filtration and evaporation of the solvents, the expected product is obtained, after chromatography on a silica column (eluent: 3% ethanol in dichloromethane), with a yield of 79%. Dark cream foam. MH+=361.2.

Example 356 ethyl [4-(3,5-ditert-butyl-4-hydroxyphenyl)-1,3-thiazol-2-yl]methylcarbamate A solution containing intermediate 6.2 described above (5 mmol) and 5 ml of a 1N solution of sodium hydroxide is cooled down to 10° C. Ethyl chloroformate (5 mmol) and 2.5 ml of a 2N solution of sodium hydroxide are added simultaneously. After stirring for 16 hours at 23° C., approximately 0.5 ml of a solution of concentrated hydrochloric acid (approximately 11 N) is added in order to adjust the pH to 4-5. The oil obtained is extracted with ethyl acetate (2×5 ml), washed with water then dried over magnesium sulphate. The solvents are evaporated off and the expected product is recovered in the form of white crystals. MH+=391.2.

Example 357

2,6-ditert-butyl-4-[2-(morpholin-4-ylmethyl)-1,3-thiazol-4-yl]phenol 357.1) 4-[2-(bromomethyl)-1,3-thiazol-4-yl]-2,6-ditert-butylphenol:

1.5 g (4.70 mmol) of intermediate 353.2, (2,6-ditert-butyl-4-[2-(hydroxymethyl)-1,3-thiazol-4-yl]phenol are dissolved in dichloromethane (30 ml). After adding $CBr_4$ (2.02 g; 6.10 mmol), the reaction medium is cooled down to 0° C. $PPh_3$ (1.48 g; 5.63 mmol) is added by fractions then the mixture is allowed to return to ambient temperature. The reaction medium is then poured into ice-cold water before being extracted with dichloromethane. The organic phase is washed with salt water before being dried over magnesium sulphate, filtered and concentrated under vacuum. The expected product is obtained after chromatography on a silica column (eluent: 30% of ethyl acetate in heptane), in order to produce a brown oil with a yield of 92%. This product is sufficiently pure to be able to be used directly in the following stage.
MH+=382.20.

357.2) 2,6-ditert-butyl-4-[2-(morpholin-4-ylmethyl)-1,3-thiazol-4-yl]phenol:

1.57 mmol of morpholine and 0.4 ml (2.62 mmol) of triethylamine are dissolved in dimethylformamide (15 ml). 0.400 g (1.05 mmol) of intermediate 357.1 dissolved in dimethylformamide (5 ml) is added then the mixture is stirred at ambient temperature for 18 hours. The reaction medium is then poured into ice-cold water and extraction is carried out with ethyl acetate. The organic phase is washed with salt water before being dried over magnesium sulphate, filtered and concentrated under vacuum. The expected product is obtained after chromatography on a silica column (eluent: 50% ethyl acetate in heptane), in order to produce an orange oil with a yield of 92%. Light cream crystals are obtained. Melting point: 136.7-137.2° C.

Example 358

2,6-ditert-butyl-4-[2-(thiomorpholin-4-ylmethyl)-1,3-thiazol-4-yl]phenol

The experimental protocol used is the same as that described for Example 357, with thiomorpholine replacing the morpholine in the second stage. The expected product is obtained in the form of a light orange solid. Melting point: 153.4-154.6° C.

Example 359

4-[2-(anilinomethyl)-1,3-thiazol-4-yl]-2,6-ditert-butylphenol

The experimental protocol used is the same as that described for Example 357, with aniline replacing the morpholine in the second stage. The expected product is obtained in the form of brown crystals. Melting point: 147.2-148.0° C.

Example 360

2,6-ditert-butyl-4-(2-{[[2-(dimethylamino)ethyl]-(methyl)amino]methyl}-1,3-thiazol-4-yl)phenol 360.1) 4-[3,5-bis(1,1-dimethylethyl)-4-hydroxyphenyl]-N-methyl-2-thiazolemethanamine hydrochloride:

This compound is obtained using an experimental protocol identical to that in Stages 363.1 to 363.4 of Example 363 (see below).

360.2) 2,6-ditert-butyl-4-(2-{[[2-(dimethylamino)ethyl]-(methyl)amino]methyl}-1,3-thiazol-4-yl)phenol:

5 mmol of triethylamine and a slight excess (1.2 mmol) of N-dimethyl-N-(2-chloroethyl)amine are added dropwise at ambient temperature under an argon atmosphere to a solution of 1 mmol of intermediate 360.1 in 20 ml of dimethylformamide. After stirring for 24 hours at 80° C., the reaction mixture is poured into ice-cold water. Extraction is carried out with ethyl acetate followed by washing with a saturated solution of NaCl, drying over magnesium sulphate and concentrating the solution. The expected product is obtained after chromatography on a silica column (eluent: dichloromethane containing 5% of ethanol with traces of ammonium hydroxide to dichloromethane containing 5% of ethanol with traces of ammonium hydroxide). After evaporation, the pure fractions produce a viscous brown oil. MH+=404.26.

Example 361

2,6-ditert-butyl-4-{5-methyl-2-[(methylamino)methyl]-1,3-thiazol-4-yl}phenol hydrochloride 361.1) N-Boc-sarcosinamide:

15.0 g (0.120 mol) of sarcosinamide hydrochloride (N-Me-Gly-$NH_2$.HCl) are dissolved in dichloromethane containing 46.2 ml (0.265 mol) of diisopropylethylamine. The mixture is cooled down to 0° C. then Boc-O-Boc (28.8 g; 0.132 mol) is added by fractions and the mixture is stirred overnight at ambient temperature. The reaction medium is then poured into ice-cold water and extraction is carried out with dichloromethane. The organic phase is washed successively with a 10% aqueous solution of sodium bicarbonate and with water, then finally with a saturated solution of sodium chloride. The organic phase is then dried over magnesium sulphate, filtered and concentrated under vacuum. The product obtained is purified by crystallization from diisopropyl ether in order to produce a white solid with a yield of 72%. Melting point: 103° C.

361.2) 2-{[(1,1-dimethylethoxy)carbonyl]methyl}aminoethanethioamide:

16.0 g (0.085 mol) of intermediate 361.1 is dissolved in dimethoxyethane (500 ml) and the solution obtained is cooled down to 5° C. Sodium bicarbonate (28.5 g; 0.34 mol)

then, in small portions, (P$_2$S$_5$)$_2$ (38.76 g; 0.17 mol) are added. The reaction medium is left to return to ambient temperature while stirring over 24 hours. After evaporation under vacuum of the solvents, a 10% aqueous solution of sodium bicarbonate is added to the residue and the solution is extracted using ethyl acetate. The organic phase is washed successively with a 10% aqueous solution of sodium bicarbonate and with water, then finally with a saturated solution of sodium chloride. The organic phase is then dried over magnesium sulphate, filtered and concentrated under vacuum. The product obtained is purified by crystallization from ether in order to produce a white coloured solid with a yield of 65%. Melting point: 150-151° C.

361.3) bromo-1-(3,5-ditert-butyl-4-hydroxyphenyl)propan-1-one:

This compound is obtained simply by reacting 1-(3,5-ditert-butyl-4-hydroxyphenyl)propan-1-one (prepared from 2,6-ditertbutylphenol according to Russ. *J. Org. Chem.* (1997), 33, 1409-1416) with bromine in acetic acid or also according to a protocol described in one of the following references: *Biorg. Med. Chem. Lett.* (1996), 6(3), 253-258; *J. Med. Chem.* (1988), 31(10), 1910-1918; *J. Am. Chem. Soc.* (1999), 121, 24.

361.4) 5-methyl-4-[3,5-bis(1,1-dimethylethyl)-4-hydroxyphenyl]-N-[(1,1-dimethylethoxy)-carbonyl]-N-methyl-2-thiazolemethanamine:

Intermediate 361.2 (4.3 g; 2.11 mmol) and intermediate 361.3 (2.11 mmol) are dissolved in toluene (75 ml) under an argon atmosphere then the mixture is stirred at ambient temperature for 12 hours. The reaction medium is taken to reflux for 4 hours. After evaporation of the solvents, the residue is diluted with ethyl acetate and washed with a 10% NaHCO$_3$ solution then with a saturated solution of NaCl. The organic phase is separated followed by drying over magnesium sulphate, filtering and concentrating under vacuum. The expected product is obtained after chromatography on a silica column (eluent: 30% of ethyl acetate in heptane). The oil recovered is used as it is in the following stage.

361.5) 2,6-ditert-butyl-4-{5-methyl-2-[(methylamino)methyl]-1,3-thiazol-4-yl}phenol hydrochloride:

This compound is obtained in the form of a white powder using an experimental protocol similar to that in Stage 350.4 of Example 350. Melting point: 140-142° C.

Example 362

1-[4-(10H-phenothiazin-2-yl)-1,3-thiazol-2-yl]methanamine hydrochloride 362.1) 2-chloro-1-(10H-phenothiazin-2-yl)ethanone:

2-chloro-1-[10-(chloroacetyl)-10H-phenothiazin-2-yl]ethanone is prepared from phenothiazine according to a protocol described in the literature (*J. Heterocyclic. Chem.* (1978), 15, 175 and *Arzneimittel Forschung*, (1962), 12, 48), which is followed by a deprotection reaction in an acid medium (acetic acid and hydrochloric acid) of the chloroacetyl group (which was used to protect position 10 of the phenothiazine during the Friedel-Crafts reaction).

362.2) benzyl 2-amino-2-thioxoethylcarbamate:

85 mmol of Z-Gly-NH$_2$ is dissolved in dimethoxyethane (500 ml) and the solution obtained is cooled down to 5° C. Sodium bicarbonate (28.5 g; 0.34 mol) then, in small portions, (P$_2$S$_5$)$_2$ (38.76 g; 0.17 mol) are added. The reaction medium is left to return to ambient temperature while being stirred for 24 hours. After evaporation under vacuum of the solvents, a 10% aqueous solution of sodium bicarbonate is added to the residue and the solution is extracted using ethyl acetate. The organic phase is washed successively with a 10% aqueous solution of sodium bicarbonate and with water, then finally with a saturated solution of sodium chloride. The organic phase is then dried over magnesium sulphate, followed by filtering and concentrating under vacuum. The product obtained is then purified by crystallization from ether.

362.3) benzyl [4-(10H-phenothiazin-2-yl)-1,3-thiazol-2-yl]methylcarbamate:

Intermediates 362.1 and 362.2 are coupled according to a protocol similar to that described in Stage 350.3 of Example 350.

362.4) 1-[4-(10H-phenothiazin-2-yl)-1,3-thiazol-2-yl]methanamine hydrochloride

The experimental protocol used is the same as that described for Stage 350.4 of Example 350, with intermediate 362.3 replacing intermediate 350.3. After drying under vacuum, the expected product is obtained in the form of a dark green powder. Melting point: >275° C.

Example 363

N-{[4-(3,5-ditert-butyl-4-hydroxyphenyl)-1,3-thiazol-2-yl]methyl}-N-methylacetamide 363.1) N-Boc-sarcosinamide:

The preparation of this compound has already been described in Stage 361.1 of Example 361.

363.2) 2-{[(1,1-dimethylethoxy)carbonyl]methyl}aminoethanethioamide:

The preparation of this compound has already been described in Stage 361.2 of Example 361.

363.3) 4-[3,5-bis(1,1-dimethylethyl)-4-hydroxyphenyl]-N-[(1,1-dimethylethoxy)-carbonyl]-N-methyl-2-thiazolemethanamine:

Intermediate 363.2 (4.3 g; 2.11 mmol) and bromo-1-(3,5-ditert-butyl-4-hydroxyphenyl)ethanone (6.9 g; 2.11 mmol) are dissolved in benzene (75 ml) under an argon atmosphere then the mixture is stirred at ambient temperature for 12 hours. The reaction medium is taken to reflux for 4 hours. After evaporation of the solvents, the residue is diluted with dichloromethane and washed with a saturated solution of NaCl. The organic phase is separated, dried over magnesium sulphate followed by filtering and concentrating under vacuum. The expected product is obtained after chromatography on a silica column (eluent: 20% ethyl acetate in heptane) in the form of an oil which crystallizes very slowly in the refrigerator with a yield of 28%. Melting point: 126.5-127.3° C.

363.4) 4-[3,5-bis(1,1-dimethylethyl)-4-hydroxyphenyl]-N-methyl-2-thiazolemethanamine hydrochloride:

1.95 mmol of intermediate 363.3 is dissolved in ethyl acetate (20 ml). The solution is cooled down to 0° C. then HCl gas is bubbled through for 10 minutes. The mixture is left to return to ambient temperature while stirring. After filtering and drying under vacuum, the expected product is recovered (quantitative yield).

363.5) N-([4-(3,5-ditert-butyl-4-hydroxyphenyl)-1,3-thiazol-2-yl]methyl)-N-methylacetamide:

This compound is obtained according to a protocol identical to that described for Stage 355.3 of Example 355, intermediate 363.5 replacing intermediate 355.2. White crystals.

Melting point: 132.3-133.1° C.

Example 364

1-[4-(3,5-ditert-butyl-4-methoxyphenyl)-1,3-thiazol-2-yl]-N-methylmethanamine hydrochloride 364.1) 4-[3,5-bis(1,1-dimethylethyl)-4-methoxyphenyl]-N-[(1,1-dimethylethoxy)-carbonyl]-N-methyl-2-thiazolemethanamine:

Intermediate 363.3 is methylated by the action of methyl iodide in the presence of NaH in tetrahydrofuran in order to produce the expected product. The brown oil which is obtained is used as it is in the following stage.

364.2) 1-[4-(3,5-ditert-butyl-4-methoxyphenyl)-1,3-thiazol-2-yl]-N-methylmethanamine hydrochloride The operating method is similar to that of Stage 363.4 of Example 363, with intermediate 364.1 replacing intermediate 363.3 and the ethyl acetate being replaced by a mixture of ethyl acetate and ether. The expected product is recovered in the form of light cream crystals. Melting point: 218.4-219.6° C.

Example 365

2,6-ditert-butyl-4-{2-[(ethylamino)methyl]-1,3-thiazol-4-yl}phenol hydrochloride The experimental protocol is identical to that used in Stages 363.1 to 363.4 of Example 363, with N-ethylglycineamide (*J. Med. Chem.* (1995), 38(21), 4244-4256) replacing the N-sarcosinamide in the first stage. White crystals. Melting point: 232.4-234.6° C.

Example 366

2,6-ditert-butyl-4-{2-[(4-phenylpiperazin-1-yl)methyl]-1,3-thiazol-4-yl}phenol hydrochloride The experimental protocol used is the same as that described for Example 357, with 4-phenylpiperazine replacing the morpholine in the second stage. Light cream crystals. Melting point: 225.3-226.9° C.

Example 367

2,6-ditert-butyl-4-{2-[(4-methyl-1,4-diazepan-1-yl)methyl]-1,3-thiazol-4-yl}phenol hydrochloride The experimental protocol used is the same as that described for Example 357, with N-methylhomopiperazine replacing the morpholine in the second stage. White crystals. Melting point: 222.1-225.4° C.

Example 368

N-{1-[4-(4-anilinophenyl)-1,3-thiazol-2-yl]ethyl}-N-methylamine hydrochloride 368.1) 1-(4-anilinophenyl)ethanone 4-amino-acetophenone (4.87 g; 36.0 mmol) is dissolved in dimethylformamide (75 ml). 15 g (0.108 mol) of potassium carbonate (previously dried at 170° C. under an argon atmosphere), 7.236 g (36.0 mmol) of iodobenzene, 0.4 g of copper in powder form and a catalytic quantity of copper iodide are added. The reaction mixture is taken to reflux for 12 hours. After leaving the reaction medium to return to ambient temperature, it is filtered on celite and poured into ice-cold water. After extraction with ethyl acetate, the organic phase is washed with water before being dried over magnesium sulphate, filtered and concentrated under vacuum. The product obtained is purified by crystallization from heptane in order to produce a yellow solid with a yield of 53.4%.

Melting point: 105° C.

368.2) N-(4-acetylphenyl)-N-phenylacetamide:

This compound is obtained according to a method inspired by Tetrahedron (1980), 36, 3017-3019. Intermediate 368.1 (60 mmol) is suspended in 150 ml of acetic anhydride. 70% perchloric acid (0.5 ml) is added. After heating for 15 minutes at 70° C., the mixture is poured onto ice and the precipitate formed is filtered. After drying under vacuum, redissolving in dichloromethane and treatment with animal charcoal, the suspension is filtered on celite and the solvents are evaporated off. After crystallization from heptane, a yellow solid is obtained with a yield of 54.2%. Melting point: 118-120° C. (value in the literature: 122-123° C.).

368.3) N-[4-(bromoacetyl)phenyl]-N-phenylacetamide

Intermediate 368.2 (0.633 g; 2.5 mmol) is dissolved in methanol (20 ml) and 1 g (2.0 mmol) of bromination resin PVPHP (*J. Macromol. Sci. Chem.* (1977), A11, (3), 507-514) is added. After stirring under an argon atmosphere for 4 hours, the resins are filtered and rinsed with methanol. After evaporation of the filtrate solvents and crystallization from methanol, a white solid is obtained with a yield of 59%. Melting point: 152-153° C.

368.4) tert-butyl (4-(4-[acetyl(phenyl)amino]phenyl)-1,3-thiazol-2-yl)methyl(methyl)carbamate:

Intermediate 368.3 (2.11 mmol) and intermediate 3.2 (2.11 mmol) are dissolved in toluene (75 ml) under an argon atmosphere then the mixture is stirred at ambient temperature for 12 hours. The reaction medium is heated under reflux for 4 hours. After evaporation of the solvents, the residue is diluted with dichloromethane and washed with a saturated solution of NaCl. The organic phase is separated, dried over magnesium sulphate, filtered and concentrated under vacuum. The expected product is obtained and used as it is in the following stage.

368.5) N-(1-[4-(4-anilinophenyl)-1,3-thiazol-2-yl]ethyl)-N-methylamine hydrochloride Intermediate 368.4 (1.5 mmol) is treated with concentrated HCl (15 ml) and acetic acid (30 ml). After heating under reflux for 24 hours and evaporation of the solvents, the residue is taken up in toluene, the solvents are again evaporated then the product crystallizes from a little water. A grey powder is obtained. Melting point: >250° C.

Example 369

2,6-ditert-butyl-4-{2-[(isopropylamino)methyl]-1,3-thiazol-4-yl}phenol hydrochloride Intermediate 355.2 (2 mmol), in solution in methanol (20 ml), is reacted with acetone (2.2 mmol), NaBH$_4$ (2.2 mmol) in the presence of molecular sieves. The product of the reaction is then converted to a hydrochloride according to an operating method similar to that of Stage 350.4 of Example 350. White crystals. Melting point: 197.1-198.8° C.

Example 370

2,6-ditert-butyl-4-{2-[(cyclohexylamino)methyl]-1,3-thiazol-4-yl}phenol hydrochloride The experimental protocol used is the same as that described for Example 369, with cyclohexanone replacing the acetone. White crystals. Melting point: 202.1-203.4° C.

Example 371

2,6-ditert-butyl-4-{2-[(4-isopropylpiperazin-1-yl)methyl]-1,3-thiazol-4-yl}phenol hydrochloride The experimental protocol used is the same as that described for Example 357, with N-isopropylpiperazine replacing the morpholine in the second stage. White crystals. Melting point: 238.4-239.7° C.

Example 372

N-methyl-1-[4-(10H-phenothiazin-2-yl)-1,3-thiazol-2-yl]ethanamine hydrochloride

The experimental protocol used is the same as that described for Stage 368.4 of Example 368, with intermediate 362.1 replacing intermediate 368.3, this stage being followed by a stage similar to that of Stage 350.4 of Example 350 in order to obtain the hydrochloride. Dark green powder. Melting point: >250° C.

Example 373

2,6-ditert-butyl-4-{2-[(4-ethylpiperazin-1-yl)methyl]-1,3-thiazol-4-yl}phenol hydrochloride The experimental protocol used is the same as that described for Example 357, with N-ethylpiperazine replacing the morpholine in the second stage. White crystals. Melting point: 247.0-248.8° C.

Example 374

N-{[4-(4-anilinophenyl)-1,3-thiazol-2-yl]methyl}-N-ethylamine hydrochloride

The experimental protocol used is the same as that described for 363.1 to 363.4 of Example 363, with N-ethylglycineamide (*J. Med. Chem.* (1995), 38(21), 4244-56) replacing the sarcosinamide and intermediate 368.3 replacing the bromo-1-(3,5-ditert-butyl-4-hydroxyphenyl)ethanone. Dark green powder. Melting point: >250° C.

Example 375

N-{[4-(10H-phenothiazin-2-yl)-1,3-thiazol-2-yl]methyl}ethanamine hydrochloride

The experimental protocol used is the same as that described for 363.1 to 363.4 of Example 363, with N-ethylglycineamide (*J. Med. Chem.* (1995), 38(21), 4244-56) replacing the sarcosinamide and intermediate 362.1 replacing the bromo-1-(3,5-ditert-butyl-4-hydroxyphenyl)ethanone. Dark green powder. Melting point: >250° C.

Example 376

2,6-ditert-butyl-4-(2-{[4-(dimethylamino)piperidin-1-yl]methyl}-1,3-thiazol-4-yl)phenol hydrochloride The experimental protocol used is the same as that described for Example 357, with 4-dimethylaminopiperidine (*J. Med. Chem.* (1983), 26, 1218-1223 or *J. Chem. Soc.* (1957), 3165-3172) replacing the morpholine in the second stage. Dark green powder.
Melting point: 113.0-113.4° C.

Example 377

1-{[4-(3,5-ditert-butyl-4-hydroxyphenyl)-1,3-thiazol-2-yl]methyl}piperidin-4-ol hydrochloride 377.1) 1-{[4-(3,5-ditert-butyl-4-hydroxyphenyl)-1,3-thiazol-2-yl]methyl}piperidin-4-ol The experimental protocol used is the same as that described for Example 357, with piperidin-4-one hydrochloride (*J. Org. Chem.* (1949), 14, 530-535) replacing the morpholine and 2 additional equivalents of triethylamine being used in the second stage. The product obtained is used as it is in the following stage.

377.2) 1-{[4-(3,5-ditert-butyl-4-hydroxyphenyl)-1,3-thiazol-2-yl]methyl}piperidin-4-ol hydrochloride:

Intermediate 377.1 is reduced to alcohol by the action of NaBH$_4$ in methanol. Once the reaction is complete, dichloromethane and salt water are added to the reaction medium. The aqueous phase is extracted with dichloromethane followed by washing with salt water. The combined organic phases are dried over magnesium sulphate and the solvents are evaporated off.

The product obtained previously is dissolved in ethyl acetate and the solution is cooled down to 0° C. A 1N solution of HCl in ether (3 equivalents) is added slowly, the mixture being maintained at a temperature of 0° C. for the addition then left to return to ambient temperature, stirring being maintained in this way for 12 hours. The expected product is recovered in the form of a white solid. Melting point: 215.4-218.2° C.

Example 378

4-methylpentyl 2-[4-(1,1'-biphenyl-4-yl)-1H-imidazol-2-yl]ethylcarbamate 378.1) N-([(4-methylpentyl)oxy]carbonyl)-β-alanine:

Triphosgene at 23° C. (5.3 g; 0.019 mol) is added to a solution containing 4-methyl-1-pentanol (5 g; 0.049 mol) in 80 ml of dichloromethane. The mixture is cooled down to 0° C. then pyridine (3.8 g; 0.049 mol) is added dropwise. The mixture is taken to 23° C. and stirring is maintained for 2 hours. The solvents are evaporated off using a rotary evaporator. The white solid recovered is filtered on frit after triturating in ether. The ether of the filtrate is evaporated off.

A mixture containing β-alanine (4.4 g, 0.049 mol) and 50 ml of a 1N solution of sodium hydroxide is cooled down to 10° C. Freshly prepared 4-methylpentylcarbonate chloride and 50 ml of a 1N solution of sodium hydroxide at 5° C. are added simultaneously to the mixture of β-alanine and sodium hydroxide prepared above. After stirring for 16 hours at 23° C., approximately 80 ml of a solution of hydrochloric acid (approximately 1N) is added in order to adjust the pH to 4-5 until a light white precipitate is obtained. The reaction mixture is extracted with ethyl acetate (2×50 ml) and the extract is washed with water then dried over magnesium sulphate. A colourless oil is obtained (7.2 g; yield of 68%).

NMR H$^1$ (δ ppm, DMSO): 0.85 (dq, 6H); 1.15 (m, 2H); 1.49-1.53 (m, 3H); 2.35 (t, 2H); 3.14-3.19 (m, 2H); 3.88-3.91 (m, 2H); 7.04 (se, 1H).; 12 (se, 1H)

378.2) 4-methylpentyl 2-[4-(1,1'-biphenyl-4-yl)-1H-imidazol-2-yl]ethylcarbamate:

A mixture of intermediate 378.1 (4.52 g; 0.021 mol) and cesium carbonate (3.4 g; 0.0105 mol) in 35 ml of methanol is stirred at 23° C. for 1 hour. The methanol is eliminated by evaporation under reduced pressure in a rotary evaporator. The mixture obtained is dissolved in 70 ml of dimethylformamide then 2-bromo-4-phenylacetophenone (5.7 g; 0.021 mol) is added. After stirring for 16 hours, the solvent is evaporated under reduced pressure. The mixture obtained is taken up in ethyl acetate then the cesium bromide is filtered. The ethyl acetate of the filtrate is evaporated off and the reaction oil is taken up in a mixture of xylenes (300 ml) and ammonium acetate (32 g; 0.42 mol). The reaction medium is heated to reflux for approximately 1 hour 30 minutes while evacuating the water using a Dean-Stark then, after cooling down, a mixture of ice-cold water and ethyl acetate is poured into the reaction medium. After decanting, the organic phase is washed with a saturated solution of sodium bicarbonate followed by drying over magnesium sulphate then evaporating under vacuum. After purification on a silica column (eluent: ethyl acetate-heptane/5-5 to 10-0), a white-coloured powder is obtained (yield of 10%). Melting point: 128.3° C. MH+=392.3.

The Compounds of Examples 379 to 392 are Obtained According to Procedures Similar to that Described for Example 378 or Above in the Part Entitled "Preparation of the Compounds of General Formula (I)".

Example 379

3,3-dimethylbutyl 2-[4-(4-pyrrolidin-1-ylphenyl)-1H-imidazol-2-yl]ethylcarbamate Melting point: 119.2° C. MH+=385.3.

Example 380 isopentyl 2-[4-(1,1'-biphenyl-4-yl)-1H-imidazol-2-yl]ethylcarbamate

Melting point: 128-130° C. MH+=378.3.

Example 381 hexyl 2-[4-(4'-bromo-1,1'-biphenyl-4-yl)-1H-imidazol-2-yl]ethylcarbamate

Melting point: 138-140° C. MH+=470.2.

Example 382 benzyl 2-[4-(4-tert-butylphenyl)-1H-imidazol-2-yl]ethylcarbamate

Melting point: 173° C. MH+=378.2.

Example 383

3,3-dimethylbutyl 2-[4-(1,1'-biphenyl-4-yl)-1H-imidazol-2-yl]ethylcarbamate

Melting point: 98.4° C. MH+=392.15.

Example 384 hexyl 2-[4-(4-pyrrolidin-1-ylphenyl)-1H-imidazol-2-yl]ethylcarbamate

Melting point: 110-114° C. MH+=385.3.

Example 385

4,4,4-trifluorobutyl 2-[4-(4-pyrrolidin-1-ylphenyl)-1H-imidazol-2-yl]ethylcarbamate Melting point: 148.3° C. MH+=411.3.

Example 386 hexyl 2-[4-(3,5-ditert-butyl-4-hydroxyphenyl)-1H-imidazol-2-yl]ethylcarbamate

Melting point: 197.4° C. MH+=444.4.

Example 387

3,3-dimethylbutyl 2-[4-(3,5-ditert-butyl-4-hydroxyphenyl)-1H-imidazol-2-yl]ethylcarbamate Melting point: 118-120° C. MH+=441.3.

Example 388

3,3-dimethylbutyl 2-[4-(4-methoxyphenyl)-1H-imidazol-2-yl]ethylcarbamate

Melting point: 116.8° C. MH+=346.2.

Example 389 benzyl 2-[4-(3,5-ditert-butyl-4-hydroxyphenyl)-1H-imidazol-2-yl]ethylcarbamate

Melting point: 177.5° C. MH+=450.3.

Example 390 benzyl 2-[4-(4-pyrrolidin-1-ylphenyl)-1H-imidazol-2-yl]ethylcarbamate

Melting point: 122.4° C. MH+=391.2.

Example 391

2-phenylethyl 2-[4-(1,1'-biphenyl-4-yl)-1H-imidazol-2-yl]ethylcarbamate

Melting point: 142-143° C. MH+=412.2.

Example 392 butyl 2-[4-(4'-fluoro-1,1'-biphenyl-4-yl)-1H-imidazol-2-yl]ethylcarbamate

Melting point: 149.3° C. MH+=382.2.

Example 393 butyl 2-[4-(1,1'-biphenyl-4-yl)-5-methyl-1H-imidazol-2-yl]ethylcarbamate 393.1) 1-(1,1'-biphenyl-4-yl)propan-1-one:

A mixture containing phenylboric acid (6.1 g; 50 mmol), 4'-bromopropiophenone (10.65 g; 50 mmol), sodium carbonate (5.3 g; 50 mmol) and palladium chloride (500 mg, 2.8 mmol) in 300 ml of water is heated under reflux for 4 hours. Boric acid (1 g; 0.8 mmol) is then added followed by heating for 30 minutes. Once the mixture has been returned to 23° C., 250 ml of ethyl acetate is added followed by filtering on frit then on GFA paper. The filtrate is decanted and the organic phase is washed with a saturated solution of NaCl before being dried over $MgSO_4$ and concentrated using a rotary evaporator. The precipitate is stirred for 30 minutes in 100 ml of isopentane and 5 ml of dichloromethane. After filtration on frit, the solid is rinsed with isopentane. A cream coloured powder is obtained (8.7 g; 83%). Melting point: 98-99° C. MH+=211.1

393.2) 1-(1,1'-biphenyl-4-yl)-2-bromopropan-1-one:

Intermediate 393.1 prepared previously is stirred with a bromination resin PVPHP (30 g; 2 mmol $Br_3$/g) in 120 ml of toluene for 3 hours at a temperature of approximately 5° C. Approximately 15 g of bromination resin is added followed by stirring again for 3 hours at 23° C. Approximately 15 g of resin is added then the mixture is stirred for 16 hours. The resin is recovered by filtration on frit and rinsed with toluene then with dichloromethane. The filtrate is concentrated to dryness and the precipitate obtained is stirred in isopropyl acetate for 30 minutes. The reaction medium is filtered on frit and rinsed with isopentane. A cream-coloured powder is obtained (9.58 g; 87%). Melting point: 102-104° C. MH+=398.2.

393.3) N-(butoxycarbonyl)-β-alanine:

A solution containing β-alanine (8.9 g; 0.1 mol) and 100 ml of a 1N solution of sodium hydroxide is cooled down to 10° C. n-butyl chloroformate (13.66 g; 0.1 mol) and 50 ml of a 2N solution of sodium hydroxide are added simultaneously. After stirring for 16 hours at 23° C., approximately 10 ml of a solution of concentrated hydrochloric acid (approximately 11 N) is added in order to adjust the pH to 4-5. The oil obtained is extracted with ethyl acetate (2×50 ml), washed with water then dried over magnesium sulphate. The product crystallizes from isopentane in the form of a white powder (yield of 68%). Melting point: 50.5° C.

393.4) butyl 2-[4-(1,1'-biphenyl-4-yl)-5-methyl-1H-imidazol-2-yl]ethylcarbamate:

A mixture of N-(butoxycarbonyl)-β-alanine (prepared in Stage 393.3; 3.27 g; 0.0173 mol) and cesium carbonate (2.81 g; 0.0087 mol) in 50 ml of methanol is stirred at 23° C. for 1 hour. The methanol is eliminated by evaporation under reduced pressure in a rotary evaporator. The mixture obtained is dissolved in 50 ml of dimethylformamide then intermediate 393.2 (5 g; 0.0173 mol) is added. After stirring for 16 hours, the solvent is evaporated off under reduced pressure. The mixture obtained is taken up in ethyl acetate then the cesium bromide is filtered. The ethyl acetate of the filtrate is evaporated off and the reaction oil is taken up in a mixture of xylene (80 ml) and ammonium acetate (26.6 g; 0.35 mol). The reaction medium is heated under reflux for approximately 1 hour 30 minutes while eliminating the water using a Dean-Stark then, after cooling down, a mixture of ice-cold water and ethyl acetate is poured into the reaction medium. After decanting, the organic phase is washed with a saturated solution of sodium bicarbonate, dried over magnesium sulphate then evaporated under vacuum. After purification on a silica column (eluent: $CH_2Cl_2$-ethanol/9-1), a colourless oil is obtained which crystallizes from a mixture of isopentane and isopropyl ether. After filtration and drying a white coloured powder is obtained (3.31 g, yield of 50%). Melting point: 143-144° C. MH+=378.2.

The Compounds of Examples 394 to 398 are Obtained According to Procedures Similar to that Described for Example 393 or Above in the Part Entitled "Preparation of Compounds of General Formula (I)".

Example 394 butyl 2-[4-(4'-methyl-1,1'-biphenyl-4-yl)-1H-imidazol-2-yl]ethylcarbamate

Melting point: 168.4° C. MH+=378.2.

Example 395 butyl 2-[4-(4'-chloro-1,1'-biphenyl-4-yl)-1H-imidazol-2-yl]ethylcarbamate

Melting point: 164.2° C. MH+=398.2.

Example 396 butyl 2-[4-(2'-fluoro-1,1'-biphenyl-4-yl)-1H-imidazol-2-yl]ethylcarbamate

Melting point: 113.8° C. MH+=382.2.

Example 397 butyl 2-{4-[4'-(methylthio)-1,1'-biphenyl-4-yl]-1H-imidazol-2-yl}ethylcarbamate

Melting point: 167.9° C. MH+=410.3.

Example 398 butyl 2-[4-(2',4'-difluoro-1,1'-biphenyl-4-yl)-1H-imidazol-2-yl]ethylcarbamate

Melting point: 105.7° C. MH+=430.2.

Example 399

2,6-di-tert-butyl-4-{2-[(propylamino)methyl]-1,3-thiazol-4-yl}phenol hydrochloride 399.1) 2,6-di-tert-butyl-4-{2-[(propylamino)methyl]-1,3-thiazol-4-yl}phenol:

0.636 g (2.0 mmol) of intermediate 355.2, 0.16 ml (2.2 mmol) of propionaldehyde and 1 g of previously activated pulverulent 4 Å molecular sieve are added successively to a flask containing 20 ml of anhydrous MeOH, under an inert atmosphere. The reaction mixture is stirred vigorously for 18 hours before adding 0.083 g (2.2 mmol) of NaBH$_4$ in portions. Stirring is maintained for a further 4 hours then 5 ml of water is added. After 15 minutes, the sieve is filtered out and the reaction mixture is extracted twice with 100 ml of CH$_2$Cl$_2$. The organic phase is washed successively with 50 ml of water and 50 ml of salt water before being dried over sodium sulphate, filtered and concentrated under vacuum. The residue is purified on a silica column (eluent: 30% ethyl acetate in heptane). A yellow oil is obtained which is used as it is in the following stage.

399.2) 2,6-di-tert-butyl-4-{2-[(propylamino)methyl]-1,3-thiazol-4-yl}phenol hydrochloride Intermediate 399.1 is dissolved in anhydrous ether (15 ml). The solution is cooled down to 0° C. then an excess of a 1N solution of HCl in ether (0.6 ml) is added dropwise. The mixture is left to return to ambient temperature while stirring. After filtration, washing with ether then with isopentane and drying under vacuum, a white-grey solid is recovered with a yield of 4%. MH+=361.2.

Example 400

N-{[4-(10H-phenothiazin-2-yl)-1,3-thiazol-2-yl]methyl}-N-propylamine hydrochloride The experimental protocol used is the same as that described for Stage 399.1 of Example 399, with the compound of Example 362 replacing intermediate 355.2. A yellow-green solid is obtained with a yield of 32%. MH+=354.2.

Example 401

N-{[4-(10H-phenothiazin-2-yl)-1,3-thiazol-2-yl]methyl}butan-1-amine

The experimental protocol used is the same as that described for Example 357, with butylamine replacing the morpholine in Stage 357.2. A yellow solid is obtained with a yield of 25.6%. Melting point: 139.0-141.0° C.

Example 402

N-{[4-(10H-phenothiazin-2-yl)-1,3-thiazol-2-yl]methyl}pentan-1-amine hydrochloride The experimental protocol used is the same as that described for Stage 399.1 of Example 399, with the compound of Example 362 and valeraldehyde replacing intermediate 355.2 and propionaldehyde respectively. A dark-coloured solid is obtained with a yield of 38%. MH+=382.2.

Example 403

(R,S)-1-{[4-(3,5-di-tert-butyl-4-hydroxyphenyl)-1,3-thiazol-2-yl]methyl}piperidin-3-ol hydrochloride The experimental protocol used is the same as that described for Example 357, with (R,S)-3-hydroxypiperidine replacing the morpholine in Stage 357.2. The product obtained in the form of a base is salified according to the protocol described for Stage 399.2 in order to produce a light cream solid with a yield of 81%. Melting point: 126.9-130.1° C.

Example 404

(R,S)-1-{[4-(3,5-di-tert-butyl-4-hydroxyphenyl)-1,3-thiazol-2-yl]methyl}pyrrolidin-3-ol hydrochloride The experimental protocol used is the same as that described for Example 357, with (R,S)-3-hydroxypyrrolidine replacing the morpholine in Stage 357.2. The product obtained in the form of a base is salified according to the protocol described for Stage 399.2 in order to produce a light cream solid with a yield of 93%. Melting point: 79.8-83.3° C.

Example 405

[4-(10H-phenothiazin-2-yl)-1,3-thiazol-2-yl]methanol 405.1) [4-(10H-phenothiazin-2-yl)-1,3-thiazol-2-yl]methyl pivalate This compound is prepared according to a protocol identical to that described for Stage 350.3 of Example 350, respectively using 2-(tert-butylcarbonyloxy)thioacetamide and 2-bromo-1-[10-(chloroacetyl)-10H-phenothiazin-2-yl]ethanone instead of intermediate 1.2 and bromo-1-(3,5-ditert-butyl-4-hydroxyphenyl)ethanone. The expected compound is obtained in the form of a greenish solid with a yield of 63.2%. Melting point: 120.0-122.0° C.

405.2) [4-(10H-phenothiazin-2-yl)-1,3-thiazol-2-yl]methanol:

This compound is prepared from intermediate 405.1 according to a protocol identical to that described for Stage 353.2 of Example 353. The expected compound is obtained in the form of a greenish solid with a yield of 61%. Melting point: 145.0-147.0° C.

Example 406

N,N-dimethyl-N-{[4-(10H-phenothiazin-2-yl)-1,3-thiazol-2-yl]methyl}amine 406.1) 2-[2-(bromomethyl)-1,3-thiazol-4-yl]-10H-phenothiazine:

This compound is prepared according to a protocol identical to that described for Stage 357.1 of Example 357, using intermediate 405.2 instead of intermediate 353.2. The expected compound is obtained in the form of shiny golden yellow-green crystals with a yield of 42%. Melting point: 165-170° C. (decomp.).

406.2) N,N-dimethyl-N-{[4-(10H-phenothiazin-2-yl)-1,3-thiazol-2-yl]methyl}amine:

This compound is prepared according to a protocol identical to that described for Stage 357.2 of Example 357 using intermediate 406.1 and N,N-dimethylamine respectively instead of intermediate 357.1 and the morpholine. The expected compound is obtained in the form of a yellow solid with a yield of 41.8%. Melting point: 155.0-157.0° C.

Example 407

2-{2-[(4-methylpiperazin-1-yl)methyl]-1,3-thiazol-4-yl}-10H-phenothiazine hydrochloride The experimental protocol used is the same as that described for Example 357, with intermediate 406.1 and N-methylpiperazine respectively replacing intermediate 357.1 and the morpholine in Stage 357.2. The product obtained in the form of a base is salified according to the protocol described for Stage 399.2 in order to produce a grey solid with a yield of 67%. Melting point: 210.0-212.0° C.

Example 408

2-[2-(piperidin-1-ylmethyl)-1,3-thiazol-4-yl]-10H-phenothiazine

The experimental protocol used is the same as that described for Example 357, with intermediate 406.1 and piperidine respectively replacing intermediate 357.1 and the morpholine in Stage 357.2. The product obtained in the form of a base is salified according to the protocol described for Stage 50.2 in order to produce a grey-yellow solid with a yield of 67%. Melting point: 186.0-188.0° C.

Example 409

2-[2-(piperazin-1-ylmethyl)-1,3-thiazol-4-yl]-10H-phenothiazine hydrochloride 409.1) tert-butyl 4-{[4-(10H-phenothiazin-2-yl)-1,3-thiazol-2-yl]methyl}piperazine-1-carboxylate:

This compound is prepared according to a protocol identical to that described for Example 357, respectively using intermediate 406.1 and N-tert-butoxycarbonylpiperazine instead of intermediate 357.1 and morpholine. The expected compound is obtained with a yield of 81.2%. MH+=481.2.

409.2) 2-[2-(piperazin-1-ylmethyl)-1,3-thiazol-4-yl]-10H-phenothiazine hydrochloride:

This compound is prepared according to a protocol identical to that described for Stage 350.4 of Example 350, with intermediate 409.1 replacing intermediate 350.3. The expected compound is obtained in the form of a grey-green solid with a yield of 78.9%.
Melting point: 210.0-215.0° C.

Example 410

1-{[4-(3,5-di-tert-butyl-4-hydroxyphenyl)-1,3-thiazol-2-yl]methyl}azetidin-3-ol hydrochloride 410.1) 1-(diphenylmethyl)-3-hydroxyazetidine hydrochloride:

Aminodiphenylmethane (55 g; 0.3 mol) and epichlorhydrin (23.5 ml; 0.3 mol) are mixed in methanol (200 ml). The mixture is heated under reflux for 5 days. The methanol is then evaporated off in order to produce a beige solid. The latter is filtered and washed with ether in order to produce a white solid with a yield of 45%. Melting point: 186.0-186.4° C.

410.2) Azetidin-3-ol:

Intermediate 410.1 is dissolved in an ethanol/THF mixture (7:3) to which water is added in order to obtain a good level of solubilization. The atmosphere is purged with argon then hydrogen before placing the mixture at ambient temperature under a pressure of 3 bars of hydrogen. After filtration and washing with ethanol, the solvents are evaporated off and the residual paste is taken up in ether. The solid formed is filtered and rinsed with ether in order to produce a white solid (yield of 86%). Melting point: 74.0-76.8° C.

410.3) 1-{[4-(3,5-di-tert-butyl-4-hydroxyphenyl)-1,3-thiazol-2-yl]methyl}azetidin-3-ol hydrochloride:

This compound is prepared according to a protocol identical to that described for Example 357, with intermediate 410.2 replacing the morpholine in Stage 357.2. The product obtained in the form of a base is salified according to the protocol described for Stage 399.2 in order to produce a light cream solid with a yield of 74%. Melting point: 124.2-126.5° C.

Example 411

2-[2-(morpholin-4-ylmethyl)-1,3-thiazol-4-yl]-10H-phenothiazine

This compound is prepared according to a protocol identical to that described for Example 357, with intermediate 406.1 replacing intermediate 357.1 in Stage 357.2 in order to produce an off-white solid with a yield of 86.0%. Melting point: 203.0-205.0° C.

Example 412

2-[2-(thiomorpholin-4-ylmethyl)-1,3-thiazol-4-yl]-10H-phenothiazine

This compound is prepared according to a protocol identical to that described for Example 357, with intermediate 406.1 and thiomorpholine respectively replacing intermediate 357.1 and the morpholine in Stage 357.2. The expected product is obtained in the form of a yellow solid with a yield of 80.8%. Melting point: 229.0-231.0° C.

Example 413

2-{2-[(4-methyl-1,4-diazepan-1-yl)methyl]-1,3-thiazol-4-yl}-10H-phenothiazine

This compound is prepared according to a protocol identical to that described for Example 357, with intermediate 406.1 and homopiperazine respectively replacing intermediate 357.1 and the morpholine in Stage 357.2. The expected product is obtained in the form of a yellow solid with a yield of 27.0%. Melting point: 135-137° C.

Example 414

(3R)-1-{[4-(3,5-di-tert-butyl-4-hydroxyphenyl)-1,3-thiazol-2-yl]methyl}pyrrolidin-3-ol hydrochloride This compound is prepared according to a protocol identical to that described for Example 357, with (R)-3-pyrrolidinol replacing the morpholine in Stage 357.2. The product obtained in the form of a base is salified according to the protocol described for Stage 399.2 in order to produce a white solid with a yield of 93%. Melting point: 162.0-164.6° C.

Example 415

(3S)-1-{[4-(3,5-di-tert-butyl-4-hydroxyphenyl)-1,3-thiazol-2-yl]methyl}pyrrolidin-3-ol hydrochloride This compound is prepared according to a protocol identical to that described for Example 357, with (S)-3-pyrrolidinol replacing the morpholine in Stage 357.2. The product obtained in the form of a base is salified according to the protocol described for Stage 399.2 in order to produce a white solid with a yield of 93%. Melting point: 162.8-165.9° C.

Example 416

2,6-di-tert-butyl-4-[2-(pyrrolidin-1-ylmethyl)-1,3-thiazol-4-yl]phenol hydrochloride This compound is prepared according to a protocol identical to that described for Example 357, with pyrrolidine replacing the morpholine in Stage 357.2. The product obtained in the form of a base is salified according to the protocol described for Stage 399.2 in order to produce an off-white solid with a yield of 73%. Melting point: 188.0-195.0° C.

Example 417

2,6-di-tert-butyl-4-{2-[(butylamino)methyl]-1,3-thiazol-4-yl}phenol hydrochloride This compound is prepared according to a protocol identical to that described for Example 357, with butylamine replacing the morpholine in Stage 357.2. The product obtained in the form of a base is salified according to the protocol described for Stage 399.2 in order to produce an off-white solid with a yield of 72%. Melting point: 179.7-180.2° C.

Example 418

2-{2-[(4-ethylpiperazin-1-yl)methyl]-1,3-thiazol-4-yl}-10H-phenothiazine

This compound is prepared according to a protocol identical to that described for Example 357, with intermediate 406.1 and N-ethylpiperazine respectively replacing intermediate 357.1 and the morpholine in Stage 357.2. The expected product is obtained in the form of a white solid with a yield of 57.7%. Melting point: 182.0-184.0° C.

Example 419

N-methyl-N-{[4-(10H-phenothiazin-2-yl)-1H-imidazol-2-yl]methyl}amine hydrochloride 419.1) tert-butyl methyl{[4-(10H-phenothiazin-2-yl)-1H-imidazol-2-yl]methyl}carbamate:

This compound is prepared according to a protocol identical to that described for Stage 393.4 of Example 393, with Boc-Sar-OH and 2-chloro-1-[10-(chloroacetyl)-10H-phenothiazin-2-yl]ethanone (cf. Stage 362.1 of Example 362) respectively replacing the N-(butoxycarbonyl)-β-alanine and intermediate 393.2 whereas ethanol replaces the methanol in Stage 393.4. The expected product is obtained with a yield of 81.6% and used as it is in the following stage.

419.2) N-methyl-N-{[4-(10H-phenothiazin-2-yl)-1H-imidazol-2-yl]methyl}amine hydrochloride:

Intermediate 419.1 is deprotected before being converted to the hydrochloride according to an operating method similar to that of Stage 350.4 of Example 350. The expected product is obtained in the form of a brown powder with a yield of 53.7%. Melting point: 190.0-195.0° C.

Example 420 methyl [4-(10H-phenothiazin-2-yl)-1,3-thiazol-2-yl]methylcarbamate

The compound of Example 362 (0.622 g; 2.0 mmol) is dissolved in dioxane (100 ml) cooled down to 0° C. Triethylamine is added, then, dropwise, methylchloroformate (2.5 mmol). The reaction medium is then stirred for 3 hours at ambient temperature before being poured into ice-cold water and extracted with ethyl acetate. The organic phase is dried over magnesium sulphate, filtered and concentrated under vacuum. The expected product is purified on a silica column (eluent: 10% acetone in dichloromethane). The pure fractions are combined and the solvents are evaporated off in order to produce an off-white solid with a yield of 46.0%. Melting point: 151-153° C.

Example 421 butyl [4-(10H-phenothiazin-2-yl)-1,3-thiazol-2-yl]methylcarbamate

This compound is prepared according to a protocol identical to that described for Example 420, using n-butylchloroformate instead of methylchloroformate. The expected product is obtained in the form of a yellow solid with a yield of 61.0%.

Melting point: 186.0-188.0° C.

Example 422

N-neopentyl-N-{[4-(10H-phenothiazin-2-yl)-1,3-thiazol-2-yl]methyl}amine

This compound is prepared according to a protocol identical to that described for Stage 399.1 of Example 399, with the compound of Example 362 and pivaldehyde respectively replacing intermediate 355.2 and the propionaldehyde. The expected product is obtained in the form of an off-white solid with a yield of 40.6%. Melting point: 172.0-174.0° C.

Example 423

1-{[4-(10H-phenothiazin-2-yl)-1,3-thiazol-2-yl]methyl}piperidin-4-ol

This compound is prepared according to a protocol identical to that described for Example 357, with intermediate 406.1 and 4-hydroxy-piperidine respectively replacing intermediate 357.1 and the morpholine in Stage 357.2. The expected product is obtained in the form of a white solid with a yield of 52.5%. Melting point: 205.0-207.0° C.

Example 424

N-{[4-(10H-phenothiazin-2-yl)-1,3-thiazol-2-yl]methyl}acetamide

This compound is prepared according to a protocol identical to that described for Example 355, with the compound of Example 362 replacing intermediate 355.2 in Stage 355.3. The expected product is obtained in the form of a yellow solid with a yield of 25.0%. Melting point: 219.0-221.0° C.

Example 425

N-{[4-(10H-phenothiazin-2-yl)-1,3-thiazol-2-yl]methyl}butanamide

This compound is prepared according to a protocol identical to that described for Example 355, with the compound of Example 362 and butanoyl chloride respectively replacing intermediate 355.2 and the acetyl chloride in Stage 355.3. The expected product is obtained in the form of a yellow solid with a yield of 47.2%. Melting point: 218.0-220.0° C.

Example 426

2,6-di-tert-butyl-4-{2-[(4-propylpiperazin-1-yl)methyl]-1,3-thiazol-4-yl}phenol 426.1) hydrochloride of tert-butyl 4-{[4-(3,5-ditert-butyl-4-hydroxyphenyl)-1,3-thiazol-2-yl]methyl}piperazine-1-carboxylate:

This compound is prepared according to a protocol identical to that described for Example 357, with N-Boc-piperazine replacing the morpholine in Stage 357.2. A pale orange solid is obtained with a yield of 64%. Melting point: 108-109° C.

426.2) 2,6-ditert-butyl-4-[2-(piperazin-1-ylmethyl)-1,3-thiazol-4-yl]phenol hydrochloride:

This compound is prepared according to a protocol identical to that described for Stage 350.4, with intermediate 426.1 replacing intermediate 350.3. A white solid is obtained with a yield of 86%. Melting point: 255.4-257.7° C.

426.3) 2,6-di-tert-butyl-4-{2-[(4-propylpiperazin-1-yl)methyl]-1,3-thiazol-4-yl}phenol:

This compound is prepared according to a protocol identical to that described for Stage 399.1 of Example 399, with intermediate 426.2 replacing intermediate 355.2 and an excess of triethylamine being added initially in order to convert intermediate 426.2 to the corresponding base. The expected product is obtained in the form of an off-white solid with a yield of 45%. Melting point: 236.5-238.2° C.

Example 427

2,6-di-tert-butyl-4-{2-[2-methyl-1-(methylamino)propyl]-1,3-thiazol-4-yl}phenol hydrochloride 427.1) N-(tert-butoxycarbonyl)-N-methylvaline:

N-methyl-D,L-valine (10.0 g; 0.0763 mol) is solubilized in a dioxane-water mixture (9:1) (100 ml) containing triethylamine (13 ml). The mixture is cooled down to 0° C. then Boc-O-Boc (18.32 g; 0.0763 mol) is added by portions, and the mixture is stirred overnight at ambient temperature. The reaction medium is then poured into ice-cold water followed by extraction with ethyl acetate. The organic phase is washed successively with a 10% aqueous solution of sodium bicarbonate and with water, then finally with a saturated solution of sodium chloride. The organic phase is then dried over magnesium sulphate, filtered and concentrated under vacuum in order to produce an oily product which crystallizes from petroleum ether. The expected product is recovered with a yield of 67% before being used as it is in the following stage. Melting point: 83-85° C.

427.2) $N^2$-(tert-butoxycarbonyl)-$N^2$-methylvalinamide:

1-(3-dimethylaminopropyl)-3-ethyl-carbodiimide hydrochloride (9.777 g; 0.051 mol) and hydroxybenzotriazole (7.8 g; 0.051 mol) are added successively to intermediate 427.1 (11.8 g; 0.051 mol) in dichloromethane (200 ml). Triethylamine (13 ml) is then added dropwise then the mixture is stirred for 12 hours at ambient temperature. The reaction medium is then poured into a 10% aqueous solution of sodium bicarbonate. After decanting, the organic phase is washed with water then with a saturated solution of sodium chloride. The organic phase is then dried over magnesium sulphate, filtered and concentrated under vacuum. The residue is taken up in methanol previously saturated with ammonia gas (150 ml). The mixture is placed in an autoclave oven at 50° C. and stirred for 4 days at this temperature. The methanol is evaporated off and the product is taken up in dichloromethane before being washed with a saturated solution of sodium chloride. The organic phase is dried over magnesium sulphate, filtered and concentrated under vacuum. The product is purified by triturating in ether in order to produce a white solid with a yield of 23.5%. Melting point: 181-183° C.

427.3) tert-butyl 1-(aminocarbonothioyl)-2-methylpropyl(methyl)carbamate:

This compound is prepared by reacting intermediate 427.2 with $P_2S_5$ under the conditions described in Example 361, Stage 361.2. The expected product is purified by chromatography on a silica column (eluent=5% methanol in dichloromethane) in order to produce an off-white solid with a yield of 32.5%. Melting point: 199.0-201.0° C.

427.4) 2,6-di-tert-butyl-4-{2-[2-methyl-1-(methylamino)propyl]-1,3-thiazol-4-yl}phenol hydrochloride:

This compound is prepared according to a protocol identical to that described for Stage 350.3 of Example 350, with intermediate 427.3 replacing intermediate 350.2. The intermediate compound obtained is deprotected with hydrobromic acid released in situ in order to produce the expected product in the form of a free base, which is purified by chromatography on a silica column (eluent: 30% ethyl acetate in heptane). The free base is then salified by dissolving in ethyl acetate through which a stream of HCl gas is passed for 10 minutes. The mixture is stirred for an hour then evaporated to dryness, and the residue is taken up in ether. After filtration, a pale pink solid is recovered with a yield of 92%. Melting point: 248.6-250.0° C.

Example 428

N,2-dimethyl-1-[4-(10H-phenothiazin-2-yl)-1,3-thiazol-2-yl]propan-1-amine hydrochloride 428.1) tert-butyl methyl{2-methyl-1-[4-(10H-phenothiazin-2-yl)-1,3-thiazol-2-yl]propyl}carbamate:

Intermediates 427.3 and 362.1 are coupled according to a protocol similar to that described in Stage 350.3 of Example 350. The expected compound is obtained in the form of an oil which is purified by chromatography on a silica column (eluent: pure dichloromethane). The expected product is obtained in the form of a white solid with a yield of 72.4%. This is used as it is in the following stage.

428.2) N,2-dimethyl-1-[4-(10H-phenothiazin-2-yl)-1,3-thiazol-2-yl]propan-1-amine hydrochloride:

This compound is prepared according to a protocol identical to that described for Stage 350.4 of Example 350, with intermediate 428.1 replacing intermediate 350.3. After washing with ether and isopentane then drying, the expected compound is obtained in the form of a dark green powder with a yield of 62%. MH+=368.1.

Example 429

N-{[4-(10H-phenothiazin-2-yl)-1,3-thiazol-2-yl]methyl}hexanamide

This compound is prepared according to a protocol identical to that described for Example 355, with the compound of Example 362 and hexanoyl chloride respectively replacing intermediate 355.2 and acetyl chloride in Stage 355.3. The expected product is obtained in the form of a brown solid with a yield of 40.7%. Melting point: 192.0-194.0° C.

Example 430

(3R)-1-{[4-(10H-phenothiazin-2-yl)-1,3-thiazol-2-yl]methyl}pyrrolidin-3-ol

This compound is prepared according to a protocol identical to that described for Example 357, with intermediate 406.1 and (R)-3-pyrrolidinol respectively replacing intermediate 357.1 and the morpholine in Stage 357.2. The expected product is obtained in the form of a white solid with a yield of 49.5%. Melting point: 180.0-182.0° C.

Example 431

(3S)-1-{[4-(10H-phenothiazin-2-yl)-1,3-thiazol-2-yl]methyl}pyrrolidin-3-ol

This compound is prepared according to a protocol identical to that described for Example 357, with intermediate 406.1 and (S)-3-pyrrolidinol respectively replacing intermediate 357.1 and the morpholine in Stage 357.2. The expected product is obtained in the form of a white solid with a yield of 49.5%. Melting point: 178.0-180.0° C.

Example 432

1-{[4-(10H-phenothiazin-2-yl)-1,3-thiazol-2-yl]methyl}azetidin-3-ol

This compound is prepared according to a protocol identical to that described for Example 357, with intermediate 406.1 and azetidine-3-ol (intermediate 410.2) respectively replacing intermediate 357.1 and the morpholine in Stage 357.2. The expected product is obtained in the form of an off-white solid with a yield of 20.4%.

Melting point: 240.0-242.0° C.

Example 433

2-{2-[(4-propylpiperazin-1-yl)methyl]-1,3-thiazol-4-yl}-10H-phenothiazine

This compound is prepared according to a protocol identical to that described for Example 357, with intermediate 406.1 and N-propylpiperazine respectively replacing intermediate 357.1 and the morpholine in Stage 357.2. The expected product is obtained in the form of a white solid with a yield of 42.6%. Melting point: 189.0-190.0° C.

Example 434

2-{2-[(4-acetylpiperazin-1-yl)methyl]-1,3-thiazol-4-yl}-10H-phenothiazine

This compound is prepared according to a protocol identical to that described for Example 357, with intermediate 406.1 and N-acetyl-piperazine respectively replacing intermediate 357.1 and the morpholine in Stage 357.2. The expected product is obtained in the form of an off-white solid with a yield of 53.5%. Melting point: 218.0-220.0° C.

Example 435

2-{2-[(4-butylpiperazin-1-yl)methyl]-1,3-thiazol-4-yl}-10H-phenothiazine

This compound is prepared according to a protocol identical to that described for Example 357, with intermediate 406.1 and N-butylpiperazine respectively replacing intermediate 357.1 and the morpholine in Stage 357.2. The expected product is obtained in the form of a white solid with a yield of 69.3%. Melting point: 188.0-190.0° C.

Example 436 methyl 4-{[4-(10H-phenothiazin-2-yl)-1,3-thiazol-2-yl]methyl}piperazine-1-carboxylate Intermediate 409.2 (0.380 g; 1 mmol) is dissolved in THF. Triethylamine (1 ml) then, dropwise, methylchloroformate (0.1 ml) are added to the solution obtained in this way.

Once the reaction is complete, the reaction mixture is poured into ice-cold water followed by extraction with ethyl acetate. The organic phase recovered is filtered and the solvents are evaporated off. After crystallization from isopropanol, the expected product is obtained in the form of a white solid with a yield of 66.1%. Melting point: 180.0-182.0° C.

Example 437

4-[2-(aminomethyl)-1H-imidazol-4-yl]-2,6-di-tert-butylphenol hydrochloride 437.1) benzyl [4-(3,5-di-tert-butyl-4-hydroxyphenyl)-1H-imidazol-2-yl]methylcarbamate:

This compound is prepared according to a protocol similar to that described for Stage 393.4 of Example 393, with carbobenzyloxyglycine and bromo-1-(3,5-ditert-butyl-4-hydroxyphenyl)ethanone respectively replacing the N-(butoxycarbonyl)-β-alanine and intermediate 393.2. The expected product is obtained with a yield of 55%. Melting point: 212.1-213.4° C.

437.2) 4-[2-(aminomethyl)-]H-imidazol-4-yl]-2,6-di-tert-butylphenol hydrochloride:

Intermediate 437.1 (2.2 g; 5.05 mmol) is dissolved in a 50/50 mixture of ethanol and THF (70 ml). 0.7 g of palladium on carbon (10%) is added and the mixture is placed under a hydrogen atmosphere (3.5 bars of pressure). The catalyst is filtered out then the solvent is evaporated off under reduced pressure. The base obtained is solubilized in ether and the hydrochloride is prepared by adding a 1N solution of HCl in ether (20 ml). After filtration and drying under vacuum, the expected product is recovered in the form of a white to slightly grey solid which is washed with ether then with iso-pentane (yield of 56%). Melting point: 225-228.3° C.

Example 438

4-{2-[(benzylamino)methyl]-1,3-thiazol-4-yl}-2,6-di-tert-butylphenol hydrochloride This compound is prepared according to a protocol identical to that described for Example 357, with benzylamine replacing the morpholine in Stage 357.2. The expected product is obtained in the form of a white solid with a yield of 62%. Melting point: 166.4-167.8° C.

Example 439

4-{2-[(4-acetylpiperazin-1-yl)methyl]-1,3-thiazol-4-yl}-2,6-di-tert-butylphenol hydrochloride This compound is prepared according to a protocol identical to that described for Example 357, with N-acetyl-piperazine replacing the morpholine in Stage 357.2. The expected product is obtained in the form of a white solid with a yield of 64%. Melting point: 199.0-200.4° C.

Example 440

N-methyl-N-{[4-(10H-phenoxazin-2-yl)-1,3-thiazol-2-yl]methyl}amine hydrochloride This compound is prepared according to a protocol identical to that described for Example 361, with 2-chloro-1-(10H-phenoxazin-2-yl)ethanone replacing bromo-1-(3,5-di-tert-butyl-4-hydroxyphenyl)propan-1-one (2-chloro-1-(10H-phenoxazine-2-yl)ethanone being prepared in a similar manner to that used for intermediate 362.1—cf. *J. Org. Chem.* (1960), 25, 747-753). The expected product is obtained after coupling, deprotection and salification in the form of a green solid. Melting point: 218-220° C.

Example 441

4-[2-(azetidin-1-ylmethyl)-1,3-thiazol-4-yl]-2,6-di-tert-butylphenol hydrochloride This compound is prepared according to a protocol identical to that described for Example 357, with azetidine replacing the morpholine in Stage 357.2. The expected product is obtained in the form of a white solid with a yield of 90%. Melting point: 141.7-144.2° C.

Example 442

2,6-di-tert-butyl-4-{2-[(4-butylpiperazin-1-yl)methyl]-1,3-thiazol-4-yl}phenol hydrochloride This compound is prepared according to a protocol identical to that described for Example 357, with N-butyl-piperazine replacing the morpholine in Stage 357.2. The expected product is obtained in the form of an off-white solid with a yield of 68%.
Melting point: 229.9-230.5° C.

The Compounds of Examples 443 to 461 are Obtained According to Procedures Similar to that Described for Example 378 or Above in the Part Entitled "Preparation of the Compounds of General Formula (I)".

Example 443 butyl 2-[4-(3'-chloro-1,1'-biphenyl-4-yl)-1H-imidazol-2-yl]ethylcarbamate

Melting point: 142.6° C. MH+=398.3.

Example 444 butyl 2-[4-(3'-fluoro-1,1'-biphenyl-4-yl)-1H-imidazol-2-yl]ethylcarbamate

Melting point: 141.5° C. MH+=381.2.

Example 445 butyl 2-[4-(4-isobutylphenyl)-1H-imidazol-2-yl]ethylcarbamate

Melting point: 95.5° C. MH+=344.2.

Example 446 benzyl 2-[4-(4-isobutylphenyl)-1H-imidazol-2-yl]ethylcarbamate

Melting point: 125.2° C. MH+=378.4.

Example 447 butyl 2-[4-(3'-chloro-4'-fluoro-1,1'-biphenyl-4-yl)-1H-imidazol-2-yl]ethylcarbamate Melting point: 132.4° C. MH+=416.3.

Example 448 butyl 2-[4-(3',4'-dichloro-1,1'-biphenyl-4-yl)-1H-imidazol-2-yl]ethylcarbamate

Melting point: 137.5° C. MH+=432.2.

Example 449 butyl 2-[4-(4-propylphenyl)-1H-imidazol-2-yl]ethylcarbamate

Melting point: 83.2° C. MH+=330.4.

Example 450 butyl 2-[4-(4-ethylphenyl)-1H-imidazol-2-yl]ethylcarbamate

Melting point: 92.4° C. MH+=316.3.

Example 451 butyl 2-[4-(4'-cyano-1,1'-biphenyl-4-yl)-1H-imidazol-2-yl]ethylcarbamate

Melting point: 147° C. MH+=389.2.

Example 452 butyl 2-{4-[41-(trifluoromethyl)-1,1'-biphenyl-4-yl]-1H-imidazol-2-yl}ethylcarbamate Melting point: 168.5° C. MH+=432.3.

Example 453 butyl 2-[4-(1,1'-biphenyl-4-yl)-5-ethyl-1H-imidazol-2-yl]ethylcarbamate

Melting point: 127-128° C. MH+=392.2.

Example 454 butyl 2-[4-(2'-chloro-1,1'-biphenyl-4-yl)-1H-imidazol-2-yl]ethylcarbamate

Melting point: 99.7° C. MH+=398.1.

Example 455 butyl 2-[4-(2',3'-difluoro-1,1'-biphenyl-4-yl)-1H-imidazol-2-yl]ethylcarbamate

Melting point: 90° C. MH+=400.1.

Example 456 butyl 2-[4-(2'-bromo-1,1'-biphenyl-4-yl)-1H-imidazol-2-yl]ethylcarbamate

Melting point: 109.6° C. MH+=442.1.

Example 457: butyl 2-[4-(3',5'-difluoro-1,1'-biphenyl-4-yl)-1H-imidazol-2-yl]ethylcarbamate Melting point: 111.1° C. MH+=400.2.

Example 458 butyl 2-[4-(2'-methoxy-1,1'-biphenyl-4-yl)-1H-imidazol-2-yl]ethylcarbamate

Melting point: 116-121° C. MH+=394.3.

Example 459 butyl 2-[4-(3'-nitro-1,1'-biphenyl-4-yl)-1H-imidazol-2-yl]ethylcarbamate

Melting point: 100.5-101.5° C. MH+=409.2.

Example 460 butyl 2-[4-(2',5'-difluoro-1,1'-biphenyl-4-yl)-1H-imidazol-2-yl]ethylcarbamate

Melting point: 109.5° C. MH+=400.2.

Example 461 butyl 2-[4-(3'-methoxy-1,1'-biphenyl-4-yl)-1H-imidazol-2-yl]ethylcarbamate

Melting point: 112-113° C. MH+=394.2.

Example 462 methyl 4-{[4-(3,5-di-tert-butyl-4-hydroxyphenyl)-1,3-thiazol-2-yl]methyl}piperazine-1-carboxylate hydrochloride This compound is prepared according to a protocol identical to that described for Example 357, with the methyl ester of piperazine-1-carboxylic acid replacing the morpholine in Stage 357.2. The expected product is obtained in the form of white crystals with a yield of 51%. Melting point: 240.6-241.4° C.

Example 463 methyl [4-(3,5-di-tert-butyl-4-hydroxyphenyl)-1,3-thiazol-2-yl]methylcarbamate

This compound is prepared according to a protocol identical to that described for Example 420, intermediate 355.2 replacing the compound of Example 362. The expected product is obtained in the form of white crystals with a yield of 18%. Melting point: 94.0-95.9° C.

Example 464

N-{[4-(3,5-di-tert-butyl-4-hydroxyphenyl)-1,3-thiazol-2-yl]methyl}benzamide

This compound is prepared according to a protocol identical to that described for Example 420, intermediate 355.2 replacing the compound of Example 362 and benzoyl chloride replacing methylchloroformate. The expected product is obtained in the form of white crystals with a yield of 84%. Melting point: 200.4-201.2° C.

Example 465

N-{[4-(3,5-di-tert-butyl-4-hydroxyphenyl)-1,3-thiazol-2-yl]methyl}-2-phenylacetamide This compound is prepared according to a protocol identical to that described for Example 420, intermediate 355.2 replacing the compound of Example 362 and phenylacetyl chloride replacing methylchloroformate. The expected product is obtained in the form of white crystals with a yield of 45%. Melting point: 123.5-125.4° C.

Example 466

N-{[4-(3,5-di-tert-butyl-4-hydroxyphenyl)-1,3-thiazol-2-yl]methyl}propanamide

This compound is prepared according to a protocol identical to that described for Example 420, intermediate 355.2 replacing the compound of Example 362 and propionyl chloride replacing methylchloroformate. The expected product is obtained in the form of white crystals with a yield of 45%. Melting point: 82.0-83.5° C.

Example 467

1-{[4-(3,5-di-tert-butyl-4-hydroxyphenyl)-1,3-thiazol-2-yl]methyl}piperidin-4-yl acetate This compound is prepared according to a protocol identical to that described for Example 357, 1-acetyl-piperazine replacing morpholine in Stage 357.2. The expected product is obtained in the form of orange crystals with a yield of 50%. Melting point: 160.3-160.6° C.

Example 468

1-{[4-(3,5-di-tert-butyl-4-hydroxyphenyl)-1,3-thiazol-2-yl]methyl}pyrrolidine-3,4-diol This compound is prepared according to a protocol identical to that described for Example 357, 3,4-dihydroxypyrrolidine replacing morpholine in Stage 357.2. The expected product is obtained in the form of a chestnut foam with a yield of 29%.
MH+=405.20.

Example 469 butyl 2-[4-(4-aminophenyl)-1H-imidazol-2-yl]ethylcarbamate 469.1) butyl 2-[4-(4-nitrophenyl)-1H-imidazol-2-yl]ethylcarbamate
This compound is prepared according to a protocol identical to that described for Example 31, 4-nitrophenacylbromide replacing then 4-phenyl-bromoacetophenone in Stage 31.2. The expected product is obtained in the form of brown powder with a yield of 1%.
MH+=333.20.

469.2) butyl 2-[4-(4-aminophenyl)-1H-imidazol-2-yl]ethylcarbamate
Intermediate 469.1 (0.28 g, 0.84 mmol) is dissolved in a 20 ml of ethanol. 0.02 g of palladium on carbon (10%) is added and the mixture is placed under a hydrogen atmosphere (2 bars of pressure). The catalyst is filtered out then the solvent is evaporated off under reduced pressure. The expected product is purified by chromatography on a silica column (eluent=8% methanol and 0.5% ammoniaque in dichloromethane) in order to produce a brown powder with a yield of 24%. Melting point: 120° C.

Example 470

N,2-dimethyl-1-[4-(10H-phenothiazin-2-yl)-1,3-thiazol-2-yl]propan-1-amine 470.1) N-[(benzyloxy)carbonyl]-N-methylvaline:
10.0 g (0.0762 mol) of N-(Me)-(DL)-Valine-OH are dissolved in dioxane/water (90/10; 100 ml) and pH is ajusted to 11 using a 1N sodium hydroxide aqueous solution. Benzyloxysuccinimide (20.9 g; 0.0839 mol) in dioxane (40 ml) was added dropwise and the mixture stirred overnight at room temperature. The reaction medium is then poured into ice-cooled water and acidified using a 10% aqueous citric acid solution followed by extraction with ethyl acetate. The organic phase is washed with a saturated solution of sodium chloride. The organic phase is then dried over magnesium sulphate, filtered and concentrated under vacuum. The residue is purified on a silica column (eluent: 5% ethanol in dichloromethane) affording the title compound as a pale yellow oil in a yield of 64%.
MH+=266.10.

470.2) N-(Methyl)(CBZ)-(DL)-Valine-NH$_2$:
Hydroxybenzotriazole (100 g; 0.653 mol) is suspended in methanol (500 ml), aqueous ammonium hydroxide 28% (60 ml) is added dropwise at room temperature and the suspension slowly goes into solution followed by precipitation, stirring being continued for approximately 5 hours. Methanol is evaporated and the white solid triturated with isopropylether. The solid is filtered and washed with isopropylether to afford the HOBT.NH$_3$ complex as a white powder in a 76% yield.

Intermediate 470.1 (12.9 g; 0.0486 mol), HOBT.NH$_3$ (as prepared previously; 9.1 g; 0.0584 mol) and benzotriazol-1-yloxytris(dimethylamino)phosphonium-hexafluorophosphate (BOP) (21.5 g; 0.0486 mol) are dissolved in DMF (120 ml) under an argon atmosphere. The mixture is cooled to 0° C. and di-isopropylethylamine (18.7 ml) is added dropwise and left to rise to room temperature with stirring overnight. The reaction medium is then poured into ice-cooled water and extraction with ethyl acetate carried out. The organic phase is washed with a 10% aqueous sodium bicarbonate solution followed by a saturated solution of sodium chloride. The organic phase is then dried over magnesium sulphate, filtered and concentrated under vacuum.

The solid residue is triturated with ether, the solid is filtered to afford a white hygroscopic solid with a yield of 83% which was used directly in the next step.
MH+=265.20

470.3) benzyl 1-(aminocarbonothioyl)-2-methylpropyl(methyl)carbamate:
This compound is prepared according to a protocol identical to that described for intermediate 1.2, where intermediate 470.2 replaces intermediate 1.1 The expected product is obtained in the form of a white solid with a yield of 36%. Melting point: 130° C.

470.4) benzyl methyl{2-methyl-1-[4-(10H-phenothiazin-2-yl)-1,3-thiazol-2-yl]propyl}carbamate:
This compound is prepared according to a protocol identical to that described for intermediate 1.3, wherein intermediate 470.3 replaces intermediate 1.2, 2-chloro-1-[10-(chloroacetyl)-10H-phenothiazin-2-yl ethanone replaces bromo-1-(3,5-ditert-butyl-4-hydroxyphenyl)ethanone and toluene replaces benzene. The expected product is obtained in the form of a yellow-orange foam with a yield of 49%.
MH+=502.10

470.5) N,2-dimethyl-1-[4-(10H-phenothiazin-2-yl)-1,3-thiazol-2-yl]propan-1-amine:
Intermediate 470.4 (1.2 g; 0.00238 mol) is dissolved in glacial acetic (12 ml). Concentrated HCl (4 ml) is added dropwise and the mixture is then heated at 100° C. for 2 hours before being evaporated to dryness. The residue is taken up into dichloromethane and washed with a 10% aqueous sodium bicarbonate solution followed by saturated solutions of sodium chloride until the aqueous phase is neutral (pH paper). The organic phase is then dried over magnesium sulphate, filtered and concentrated under vacuum. The residue is purified on an inversed phase silica column RP 18 (eluent: 40% aqueous (0.1N) TFA in acetonitrile). The combined fractions were evaporated to dryness, a 10% aqueous sodium bicarbonate solution was added to the residue and extracted with dichloromethane followed by a saturated solution of sodium chloride. The organic phase is then dried over magnesium sulphate, filtered and concentrated under vacuum. The solid was triturated with isopentane to afford the title compound as yellow-orange solid in a yield of 14%. Melting point: 143.2-144.0° C.

Example 471

N,2-dimethyl-1-[4-(10H-phenoxazin-2-yl)-1,3-thiazol-2-yl]propan-1-amine

The experimental protocol used is identical to that described for Example 470, the 2-chloro-1-[10-(chloroacetyl)-10H-phenoxazine-2-yl)ethanone replacing 2-chloro-1-[10-(chloroacetyl)-10H-phenothiazin-2-yl)ethanone to finally afford the title compound as a chestnut foam. MH+=352.2.

Example 472

N,3-dimethyl-1-[4-(10H-phenoxazin-2-yl)-1,3-thiazol-2-yl]butan-1-amine

The experimental protocol used is identical to that described for Example 470, thioamide benzyl-1-(aminocarbonothioyl)-3-methylbutyl(methyl)carbamate (prepared in the same fashion as intermediate 470.3) replacing benzyl 1-(aminocarbonothioyl)-2-methylpropyl(methyl)carbamate and 2-chloro-1-[10-(chloroacetyl)-10H-phenoxazine-2-yl) ethanone replacing 2-chloro-1-[10-(chloroacetyl)-10H-phenothiazin-2-yl)ethanone in Stage 470.4 to finally afford the title compound as a beige solid. Melting point: 143.1-147.0° C.

Example 473

N,3-dimethyl-1-[4-(10H-phenothiazin-2-yl)-1,3-thiazol-2-yl]butan-1-amine

The experimental protocol used is identical to that described for Example 470, thioamide benzyl-1-(aminocarbonothioyl)-3-methylbutyl(methyl)carbamate (prepared in the same fashion as the intermediate 470.3) replacing benzyl 1-(aminocarbonothioyl)-2-methylpropyl(methyl)carbamate in Stage 470.4 to finally afford the title compound as yellow crystals. Melting point: 145.7-148.1° C.

Example 474 hydrochloride salt of 2,6-di-tert-butyl-4-{2-[3-methyl-1-(methylamino)butyl]-1,3-thiazol-4-yl}phenol The experimental protocol used is identical to that described for Example 470, thioamide benzyl-1-(aminocarbonothioyl)-3-methylbutyl(methyl)carbamate (prepared in the same fashion as intermediate 470.3) replacing benzyl 1-(aminocarbonothioyl)-2-methylpropyl(methyl)carbamate and 2-bromo-1-(3,5-ditert-butyl-4-hydroxyphenyl)ethanone replacing 2-chloro-1-[10-(chloroacetyl)-10H-phenothiazin-2-yl)ethanone in Stage 470.4 during which removal of the CBZ protecting group occured in situ. The resulting free base compound is purified by normal phase chromatography, silica-gel column (eluent: 30% ethyl acetate in heptane) followed by formation of the hydrochloride salt using 1N HCl in ether to afford the title compound as a creamy-white solid in a overall yield of 13%. Melting point: 148.1-149.0° C.

Example 475 hydrochloride salt of [4-(3,5-di-tert-butylphenyl)-1,3-thiazol-2-yl]methylamine

The experimental protocol used is identical to that described for Example 470, thioamide benzyl 2-amino-2-thioxoethylcarbamate (prepared in the same fashion as intermediate 470.3) replacing intermediate 470.3 and 2-bromo-1-(3,5-ditert-butyl-phenyl)ethanone replacing 2-chloro-1-[10-(chloroacetyl)-10H-phenothiazin-2-yl)ethanone in Stage 470.4.

The deprotection of the N-CBZ protecting group is carried out in the same fashion as intermediate 470.5 however the formed free base compound is purified by normal phase chromatography on a silica-gel column (eluent: 10% ethyl acetate in heptane) followed by formation of the hydrochloride salt using 1N HCl in ether to afford the title compound as a creamy-white solid. Melting point: 207.0-209.6° C.

Example 476 hydrochloride salt of 2,6-di-tert-butyl-4-{2-[(1S)-1-(methylamino)ethyl]-1,3-thiazol-4-yl}phenol The experimental protocol used is identical to that described for Example 470, thioamide benzyl (1S)-2-amino-1-methyl-2-thioxoethyl(methyl)carbamate replacing intermediate 470.3 and 2-bromo-1-(3,5-ditert-butyl-4-hydroxyphenyl)ethanone replacing 2-chloro-1-[10-(chloroacetyl)-10H-phenothiazin-2-yl)ethanone. The deprotection of the N-(CBZ) protecting group is carried out in the same fashion as intermediate 470.5 however the formed free base compound is purified by normal phase chromatography on a silica-gel column (eluent: 3% ethanol in dichloromethane) followed by formation of the hydrochloride salt using 1N HCl in ether to afford the title compound as a white crystalline solid. Melting point: 240.6-242.0° C.

Example 477

2,6-di-tert-butyl-4-{2-[(1R)-1-(methylamino)ethyl]-1,3-thiazol-4-yl}phenol

The experimental protocol used is identical to that described for Example 476, thioamide benzyl (1R)-2-amino-1-methyl-2-thioxoethyl(methyl)carbamate replacing thioamide benzyl (1S)-2-amino-1-methyl-2-thioxoethyl(methyl) carbamate to finally afford after salt formation the title compound as a white crystalline solid. Melting point: 242.8-243.6° C.

Example 478 hydrochloride salt of N-{[4-(3,5-di-tert-butylphenyl)-1,3-thiazol-2-yl]methyl}-N-methylamine The experimental protocol used is identical to that described for Example 1,2-bromo-1-(3,5-ditert-butyl-phenyl)ethanone replacing 2-bromo-1-(3,5-ditert-butyl-4-hydroxyphenyl)ethanone in Stage 1.3. Removal of the N-(Boc) protecting group and salt formation was carried out in one step using HCl gas according to a protocol similar to that described for intermediate 29.2 to afford the title compound as a creamy-white solid. Melting point: 212.2-213.9° C.

Example 479 hydrochloride salt of N-methyl-N-{[4-(3,4,5-trimethoxyphenyl)-1,3-thiazol-2-yl]methyl}amine 479.1) 2-bromo-1-(3,4,5-trimethoxyphenyl)ethanone:
The experimental protocol used is identical to that described for Example 331, Stage 331.2, the commercially available 3,4,5-trimethoxy-acetophenone replacing intermediate 331.1. Intermediate 479.1 is obtained after chromatography on a silica column (eluent: 50% ethyl acetate in heptane) as a yellow solid in a yield of 66%.

MH+=289.01

479.2) N-methyl-N-{[4-(3,4,5-trimethoxyphenyl)-1,3-thiazol-2-yl]methyl}amine:

Title compound is obtained as described for Example 1, intermediate 479.1 replacing 2-bromo-1-(3,5-ditert-butyl-4-hydroxyphenyl)ethanone in Stage 1.4. Removal of the Boc protecting group and salt formation was carried out in one step using HCl gas similar to that described for intermediate 29.2 to afford the title compound as a yellow crystalline solid. Melting point: 199.4-200.6° C.

Example 480 hydrochloride salt of ethyl N-{[4-(3,5-di-tert-butyl-4-hydroxyphenyl)-1,3-thiazol-2-yl]methyl}glycinate The experimental protocol used is identical to that described for Example 2, ethylbromoacetate replacing chloropropargyl and the compound of Example 11 replacing the compound of Example 1. Followed by formation of the hydrochloride salt using 1N HCl in ether to afford the title compound as a white crystalline solid in an overall yield of 69%. Melting point: 164.0-167.0° C.

Example 481 hydrochloride salt of N-{[4-(3,5-di-tert-butyl-4-hydroxyphenyl)-1,3-thiazol-2-yl]methyl}glycine 481.1) Ethyl N-(tert-butoxycarbonyl)-N-{[4-(3,5-di-tert-butyl-4-hydroxyphenyl)-1,3-thiazol-2-yl]methyl}glycinate:

The experimental protocol used is identical to that described for Example 350, Stage 350.1, the compound of Example 480 replacing N-methyl-B-alaninenitrile, triethylamine being used instead of diisopropylethylamine and a catalytic amount of dimethylaminopyridine (DMAP) being added to carry out the reaction. The title compound is obtained as a green oil which is used directly in the next step.

MH+=505.30.

481.2) N-(tert-butoxycarbonyl)-N-{[4-(3,5-di-tert-butyl-4-hydroxyphenyl)-1,3-thiazol-2-yl]methyl}glycine:

1.0 g (1.98 mmol) of intermediate 481.1 is dissolved in THF (20 ml). A solution of lithium hydroxide (1N in water) is added dropwise and left to stir at room temperature for 6 hours. The reaction medium is then poured into water followed by extraction with diethyl ether. The aqueous phase is acidified with aqueous HCl (1N) and extracted with diethyl ether. The organic phase is washed with a saturated solution of sodium chloride, then dried over magnesium sulphate, filtered and concentrated under vacuum and used directly in the next step. MH+=477.20.

481.3) N-{[4-(3,5-di-tert-butyl-4-hydroxyphenyl)-1,3-thiazol-2-yl]methyl}glycine:

The experimental protocol used is identical to that described for Example 29, Stage 29.2, intermediate 481.2 replacing intermediate 29.1. The title compound is obtained as a white crystalline solid in a yield of 27%.

MH+=377.2.

Example 482 hydrochloride salt of 2,6-di-tert-butyl-4-{2-[(4-methoxypiperidin-1-yl)methyl]-1,3-thiazol-4-yl}phenol The experimental protocol used is identical to that described for Example 357, Stage 357.2, 4-methoxy-piperidine replacing morpholine. The title compound is obtained as a white crystalline solid. Melting point: 198.0-201.0° C.

Example 483 hydrochloride salt of N-methyl-N-{(1S)-2-methyl-1-[4-(10H-phenothiazin-2-yl)-1,3-thiazol-2-yl]propyl}amine This compound is prepared in an analogous fashion to Example 470, however using optically pure starting material, i.e. N-(Me)-(L)-Valine-OH instead of N-(Me)-(DL)-Valine-OH).

Melting point: 270.0-270.8° C.

Example 484 hydrochloride salt of N,2-dimethyl-1-[4-(10-methyl-10H-phenothiazin-2-yl)-1,3-thiazol-2-yl]propan-1-amine 484.1) Benzylmethyl{2-methyl-1-[4-(10-methyl-10H-phenothiazin-2-yl)-1,3-thiazol-2-yl]propyl}carbamate:

The intermediate 470.4 was methylated according to the following procedure: 0.200 g (0.410 mmol) of intermediate 470.4 is dissolved in dioxane (10 ml). Sodium hydride (0.024 g; 0.598 mmol) was added in small portions and left to stir for 30 minutes. Iodomethane (0.04 ml) is added dropwise and heated at 45° C. for 18 hours. Ethanol (10 ml) is added dropwise and the reaction medium is then poured into water before being extracted with ethyl acetate. The organic phase is washed with a saturated solution of sodium chloride, then dried over magnesium sulphate, filtered and concentrated under vacuum. Intermediate 484.1 is obtained after chromatography on a silica column (eluent: 15% ethyl acetate in heptane) as a yellow gummy solid in a yield of 42%.

MH+=516.10

484.2) hydrochloride salt of N,2-dimethyl-1-[4-(10-methyl-10H-phenothiazin-2-yl)-1,3-thiazol-2-yl]propan-1-amine:

Intermediate 484.1 was dissolved in a glacial acetic acid/water/methanol (30 ml) mixture. A catalytic amount of Pd/C was added and hydrogenated at room temperature under a pressure of 5 bars for 12 hours. The exhausted catalyst was filtered off and the filtrate was evaporated to dryness and azeotroped with toluene several times. The hydrochloride salt, a grey solid, is obtained using a 1N HCl solution in ether with an overall yield of 45%.

MH+=382.10

Example 485 hydrochloride salt of N-methyl-N-{(1S)-2-methyl-1-[4-(10H-phenoxazin-2-yl)-1,3-thiazol-2-yl]propyl}amine This compound is prepared in an analogous fashion to Example 471, however using optically pure starting material, i.e. N-(Me)-(CBZ)-(L)-Valine-OH instead of N-(Me)-(DL)-Valine-OH, to afford a grey powder.
MH+=351.2.

Example 486 hydrochloride salt of 4-{2-[(1R)-1-aminoethyl]-1,3-thiazol-4-yl}-2,6-di-tert-butylphenol The experimental protocol used is identical to that described for Example 470, thioamide benzyl (1R)-2-amino-1-methyl-2-thioxoethylcarbamate (prepared in a similar fashion to the intermediate 470.3) replacing thioamide benzyl 1-(aminocarbonothioyl)-2-methylpropyl(methyl)carbamate and 2-bromo-1-(3,5-ditert-butyl-4-hydroxyphenyl)ethanone replacing 2-chloro-1-[10-(chloroacetyl)-10H-phenothiazin-2-yl)ethanone in the fourth step. The title hydrochloride salt is then obtained as a white solid using 1N HCl in ether. Melting point: 211.8-215.2° C.

Example 487 hydrochloride salt of 4-{2-[(1S)-1-aminoethyl]-1,3-thiazol-4-yl}-2,6-di-tert-butylphenol The experimental protocol used is identical to that described for Example 470, thioamide benzyl (1S)-2-amino-1-methyl-2-thioxoethylcarbamate (prepared in a similar fashion to the intermediate 470.3) replacing thioamide benzyl 1-(aminocarbonothioyl)-2-methylpropyl(methyl)carbamate and 2-bromo-1-(3,5-ditert-butyl-4-hydroxyphenyl)ethanone replacing 2-chloro-1-[10-(chloroacetyl)-10H-phenothiazin-2-yl)ethanone in the fourth step. The title hydrochloride salt is then obtained as a white solid using 1N HCl in ether. Melting point: 191.0-195.0° C.

Example 488 hydrochloride salt of 4-[2-(1-aminocyclopropyl)-1,3-thiazol-4-yl]-2,6-di-tert-butylphenol 488.1) Tert-butyl [1-(aminocarbonyl)cyclopropyl]carbamate:

The experimental protocol used is identical to that described for Example 470, stage 470.2 where 1-[(tert-butoxycarbonyl)amino]cyclopropanecarboxylic acid replaces intermediate 470.1. The title compound is obtained as a colourless oil and used directly in the next step.

488.2) Tert-butyl [1-(aminocarbonothioyl)cyclopropyl]carbamate:

This compound is prepared according to a protocol identical to that described for Example 1, stage 1.2, where intermediate 488.1 replaces intermediate 1.1. The expected product is obtained in the form of a yellow oil and used directly in the next step.

488.3) hydrochloride salt of 4-12-(]-aminocyclopropyl)-1,3-thiazol-4-yl]-2,6-di-tert-butylphenol:

This compound is prepared according to a protocol identical to that described for Example 1, stage 1.3 wherein intermediate 488.2 replaces intermediate 1.2 and toluene replaces benzene. Deprotection of the N-(Boc) protecting group occurred in-situ. The hydrochloride salt is then obtained as a white-creamy solid using 1N HCl in ether.
Melting point: 200.6-202.2° C.

Example 489 hydrochloride salt of 4-{2-[(methylamino)methyl]-1,3-thiazol-4-yl}benzene-1,2-diol The experimental protocol used is identical to that described for Example 1,2-chloro-3',4'-dihydroxyacetophenone replacing 2-bromo-1-(3,5-ditert-butyl-4-hydroxyphenyl)ethanone. The title compound is obtained as a white-creamy solid.
MH+=237.0.

Example 490 hydrochloride salt of N-methyl-N-{(1R)-2-methyl-1-[4-(10H-phenothiazin-2-yl)-1,3-thiazol-2-yl]propyl)amine This compound is prepared in an analogous fashion to Example 470, however using optically pure starting material, i.e. N-(Me)-(CBZ)-(D)-Valine-OH instead of N-(Me)-(DL)-Valine-OH to afford the title compound as a light green powder. Melting point: 265.6-268.9° C.

Example 491 hydrochloride salt of (1R)-2-methyl-1-[4-(10H-phenothiazin-2-yl)-1,3-thiazol-2-yl]propan-1-amine 491.1) Tert-butyl (1R)-1-[4-(10-acetyl-10H-phenothiazin-2-yl)-1,3-thiazol-2-yl]-2-methylpropylcarbamate:

The experimental protocol used is identical to that described for Example 1, 1-(10-acetyl-10H-phenothiazin-2-yl)-2-bromoethanone (*Arzneimittel Forschung* (1962), 12, 48-52) replacing 2-bromo-1-(3,5-ditert-butyl-4-hydroxyphenyl)ethanone and thioamide tert-butyl(1R)-1-(aminocarbonothioyl)-2-methylpropylcarbamate (prepared in a similar fashion to intermediate 1.2) replacing intermediate 1.2. Removal of the N-(Boc) protecting group and salt formation was carried out in one step using HCl gas according to a procedure similar to that described for Example 29, Stage 29.2 to afford the title compound as a grey solid.
MH+=396.1.

491.2) (1R)-2-methyl-1-[4-(10H-phenothiazin-2-yl)-1,3-thiazol-2-yl]propan-1-amine:

The hydrochloride salt intermediate 491.1 is dissolved in 2N HCl and refluxed for 18 hours. The solution is extracted with ethyl acetate and the aqueous phase was made basic using an aqueuse solution (10%) of sodium bicarbonate and extracted with ethyl acetate. The organic phase is washed with a 10% aqueous sodium bicarbonate solution followed by a saturated solution of sodium chloride before being dried over magnesium sulphate, filtered and concentrated under vacuum. The residue is purified on a silica column (eluent: 5% ethanol in dichloromethane), affording the free base as a pale brown oil. The hydrochloride salt was formed using 1N HCl in ether to afford the title compound as a green powder.
MH+=354.2.

Example 492 hydrochloride salt of N-methyl-N-{(1R)-2-methyl-1-[4-(10H-phenoxazin-2-yl)-1,3-thiazol-2-yl]propyl}amine This compound is prepared in an analogous fashion to Stages 470.2 to 470.5 of Example 470, however using optically pure starting material, i.e. N-(Me)-(CBZ)-(D)-Valine-OH instead of intermediate 470.2. The title hydrochloride salt is obtained as a deep yellow powder.

MH+=352.2.

Example 493 hydrochloride salt of N²-{[4-(3,5-di-tert-butyl-4-hydroxyphenyl)-1,3-thiazol-2-yl]methyl}glycinamide The experimental protocol used is identical to that described for Example 2, 2-bromoacetamide replacing chloropropargyl and the compound of Example 11 replacing the compound of Example 1. The hydrochloride salt is then obtained as a white powder using 1N HCl in ether.

MH+=376.2.

Example 494 hydrochloride salt of ethyl N-{[4-(3,5-di-tert-butyl-4-hydroxyphenyl)-1,3-thiazol-2-yl]methyl}-N-(2-ethoxy-2-oxoethyl)glycinate The experimental protocol used is identical to that described for Example 2, with however an excess of ethyl-bromoacetate replacing chloropropargyl and the compound of Example 11 replacing the compound of Example 1. The hydrochloride salt is then obtained as a white foam using 1N HCl in ether.

MH+=491.2.

Example 495 hydrochloride salt of 4-(3,5-di-tert-butyl-4-methoxyphenyl)-2-(methoxymethyl)-1,3-thiazole The experimental protocol used is identical to that described for Example 484, Stage 484.1 with intermediate 334.1 replacing intermediate 470.4 and THF replacing dioxane. The title compound is obtained as a white solid in 38% yield. Melting point: 94.0-94.8° C.

Example 496 hydrochloride salt of 4-[2-(1-aminocyclopentyl)-1,3-thiazol-4-yl]-2,6-di-tert-butylphenol 496.1) Tert-butyl [1-(aminocarbonyl)cyclopentyl]carbamate:

The experimental protocol used is identical to that described for Example 470, stage 470.2 wherein 1-[(tert-butoxycarbonyl)amino]cyclopentanecarboxylic acid replaces intermediate 470.1. The title compound is obtained as a white flaky solid which was used directly in the next step.

496.2) Tert-butyl [1-(aminocarbonothioyl)cyclopentyl]carbamate:

This compound is prepared according to a protocol identical to that described for Example 1, stage 1.2, wherein intermediate 496.1 replaces intermediate 1.1 The expected product is obtained in the form white flaky solid which was used directly in the next step.

MH+=245.2.

496.3) Tert-butyl (1-[4-(3,5-di-tert-butyl-4-hydroxyphenyl)-1,3-thiazol-2-yl]cyclopentyl}carbamate:

This compound is prepared according to a protocol identical to that described for Example 1, stage 1.3, wherein intermediate 496.2 replaces intermediate 1.2 and toluene replaces benzene. The expected product is obtained in the form of a colourless oil.

MH+=473.4.

496.4) hydrochloride salt of 4-[2-(1-aminocyclopentyl)-1,3-thiazol-4-yl]-2,6-di-tert-butylphenol:

Removal of the N-(Boc) protecting group from intermediate 496.3 and salt formation was carried out in one step using HCl gas according to a protocol similar to that described for Example 29, stage 29.2 to afford the title compound as a white crystalline solid. Melting point: 288.8-290.7° C.

Pharmacological Study of the Products of the Invention

Study of the Effects on the Bond of a Specific Ligand of MAO-B, [³H]Ro 19-6327

The inhibitory activity of the products of the invention is determined by measurement of their effects on the bond of a specific ligand of MAO-B, [³H]Ro 19-6327.

a) Mitochondrial Preparation of the Cortex of Rats

The mitochondrial preparation of the cortex of rats is carried out according to the method described in Cesura A M, Galva M D, Imhof R and Da Prada M, *J. Neurochem*. 48 (1987), 170-176. The rats are decapitated and their cortex is removed, homogenized in 9 volumes of a 0.32 M sucrose buffer, buffered to pH 7.4 with 5 mM of HEPES, then centrifuged at 800 g for 20 minutes. The supernatants are recovered and the pellets are washed twice with the 0.32 M sucrose buffer as previously. The collected supernatants are centrifuged at 10000 g for 20 minutes. The pellets obtained are suspended in a Tris buffer (50 mM Tris, 130 mM NaCl, 5 mM KCl, 0.5 mM EGTA, 1 mM $MgCl_2$, pH 7.4) and centrifuged at 10000 g for 20 minutes. This stage is repeated twice, and the final pellet, corresponding to the mitochondrial fraction, is stored at −80° C. in the Tris buffer. The proteinic content of the preparation is determined by the Lowry method.

b) Bond of [³H]Ro 19-6327

100 µl of the mitochondrial preparation (2 mg protein/ml) are incubated for 1 hour at 37° C. in an Eppendorf tube, in the presence of 100 µl of [³H]Ro 19-6327 (33 nM, final concentration) and 100 µl of Tris buffer containing or not containing the inhibitors. The reaction is stopped by the addition of 1 ml of unlabelled Tris buffer into each tube, then the samples are centrifuged for 2 minutes at 12000 g. The supernatants are removed by suction and the pellets washed with 1 ml of Tris buffer. The pellets are then solubilized in 200 µl of sodium dodecyl sulphate (20% weight/volume) for 2 hours at 70° C. The radioactivity is determined by counting the samples using liquid scintillation.

c) Results

The compounds of Examples 1, 3, 6, 22, 24, 26 to 29, 323, 332, 350, 352, 354, 360, 367 and 477 described above show an $IC_{50}$ lower than 10 µM.

Study of the Effects on Lipidic Peroxidation of the Cerebral Cortex of the Rat

The inhibitory activity of the products of the invention is determined by measuring their effects on the degree of lipidic peroxidation, determined by the concentration of malondialdehyde (MDA). The MDA produced by peroxidation of unsaturated fatty acids is a good indication of lipidic peroxidation (H Esterbauer and K H Cheeseman, *Meth. Enzymol.* (1990) 186: 407-421). Male Sprague Dawley rats weighing 200 to 250 g (Charles River) were sacrificed by decapitation. The cerebral cortex is removed, then homogenized using a Thomas potter in a 20 mM Tris-HCl buffer, pH=7.4. The homogenate is centrifuged twice at 50000 g for 10 minutes at 4° C. The pellet is stored at −80° C. On the day of the experiment, the pellet is resuspended at a concentration of 1 g/15 ml and centrifuged at 515 g for 10 minutes at 4° C. The supernatant is used immediately to determine the lipidic peroxidation. The homogenate of rat's cerebral cortex (500 μl) is incubated at 37° C. for 15 minutes in the presence of the compounds to be tested or of the solvent (10 μl). The lipidic peroxidation reaction is initiated by adding 50 μl of $FeCl_2$ at 1 mM, EDTA at 1 mM and ascorbic acid at 4 mM. After incubation for 30 minutes at 37° C., the reaction is stopped by adding 50 μl of a solution of hydroxylated di-tert-butyl toluene (BHT, 0.2%). The MDA is quantified using a calorimetric test, by reacting a chromogenic reagent (R), N-methyl-2-phenylindol (650 μl) with 200 μl of the homogenate for 1 hour at 450 C. The condensation of an MDA molecule with two molecules of reagent R produces a stable chromophore the maximum absorbence wavelength of which is equal to 586 nm (Caldwell et al., *European J. Pharmacol.* (1995), 285, 203-206). The compounds of Examples 1 to 3, 6 to 17, 20 to 30, 320, 321, 323, 331, 332, 350, 352 to 377, 399 to 411, 413 to 435, 437 to 442, 463 to 467, 470 to 474, 476, 477 and 480 to 489 described above show an $IC_{50}$ lower than 10 μM.

Bond Test on the Cerebral Sodium Channels of the Cortex of the Rat

The test consists in measuring the interaction of the compounds vis-à-vis the bond of tritiated batrachotoxin on the voltage-dependent sodium channels according to the protocol described by Brown (*J. Neurosci.* (1986), 6, 2064-2070).

Preparation of Homogenates of Cerebral Cortices of the Rat

The cerebral cortices of Sprague-Dawley rats weighing 230-250 g (Charles River, France) are removed, weighed and homogenized using a Potter homogenizer provided with a teflon piston (10 strokes) in 10 volumes of isolation buffer the composition of which is as follows (sucrose 0.32 M; $K_2HPO_4$ 5 mM; pH 7.4). The homogenate is subjected to a first centrifugation at 1000 g for 10 minutes. The supernatant is removed and centrifuged at 20000 g for 15 minutes. The pellet is taken up in the isolation buffer and centrifuged at 20000 g for 15 minutes. The pellet obtained is resuspended in incubation buffer (HEPES 50 mM; KCl 5.4 mM; $MgSO_4$ 0.8 mM; glucose 5.5 mM; choline chloride 130 mM pH 7.4) then aliquoted and stored at −80° C. until the day of assay. The final protein concentration is comprised between 4 and 8 mg/ml. The assay of proteins is carried out using a kit marketed by BioRad (France).

Measurement of the Bond of Tritiated Batrachotoxin

The bond reaction is carried out by incubating for 1 hour 30 minutes at 25° C. 100 μl of homogenate of rat cortex containing 75 μg of proteins with 100 μl of [$^3$H] batrachotoxin-A 20-alpha benzoate (37.5 Ci/mmol, NEN) at 5 nM (final concentration), 200 μl of tetrodotoxin at 1 μM (final concentration) and scorpion venom at 40 μg/ml (final concentration) and 100 μl of incubation buffer alone or in the presence of the products to tested at different concentrations. The non-specific bond is determined in the presence of 300 μM of veratridine and the value of this non-specific bond is subtracted from all the other values. The samples are then filtered using a Brandel (Gaithersburg, Md., USA) using Unifilter GF/C plates pre-incubated with 0.1% of polyethylene imine (20 μl/well) and rinsed twice with 2 ml of filtration buffer (HEPES 5 mM; $CaCl_2$ 1.8 mM; $MgSO_4$ 0.8 mM; choline chloride 130 mM; BSA 0.01%; pH 7.4). After having added 20 μl of Microscint 0®, the radioactivity is counted using a liquid scintillation counter (Topcount, Packard). The measurement is carried out in duplicate. The results are expressed as a % of the specific bond of tritiated batrachotoxin relative to the control.

Results

The compounds of Examples 1, 6, 7, 11, 13, 15, 17, 20, 24, 31 to 38, 42, 43, 46 to 48, 53, 56, 57, 59 to 61, 64 to 80, 82 to 88, 92 to 95, 97, 105, 106, 108, 110, 113, 117, 118, 121 to 123, 125, 128, 130 to 139, 142 to 145, 149, 151, 152, 154, 162 to 166, 168 to 178, 181, 183 to 186, 188, 190 to 196, 198 to 206, 208 to 210, 212 to 218, 220 to 231, 233 to 250, 252 to 259, 261 to 281, 283 to 288, 293 to 313, 324, 338 to 340, 350, 352, 354, 361, 364, 365, 367, 369, 377 to 396, 398, 401, 410, 414 to 418, 438, 443 to 461, 469 and 476 to 478 described above all show an $IC_{50}$ lower than or equal to 1 μM. Moreover, the compounds of Examples 3, 9, 10, 26, 28 to 30 and 321 described above show an $IC_{50}$ lower than or equal to 3.5 μM.

What is claimed is:

1. A compound selected from the group consisting of a compound of the formula

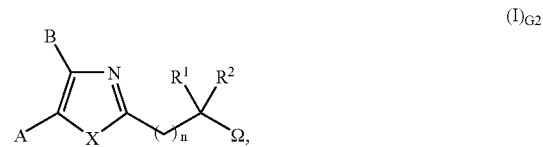

(I)$_{G2}$ in racemic, enantiomeric form or any combination of these forms wherein A is

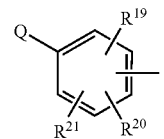

Q is phenyl optionally substituted with at least one member selected from the group consisting of halogen, —OH, —CN, —$NO_2$, alkyl and haloalkyl of 1 to 6 carbon atoms and alkoxy of 1 to 6 carbon atoms; $R_{19}$, $R_{20}$ and $R_{21}$ are individually selected from the group consisting of hydrogen, halogen, alkyl of 1 to 6 carbon atoms and alkoxy of 1 to 6 carbon atoms; X is NR38; $R_{38}$ is hydrogen or alkyl of 1 to 6 carbon atoms; $R_1$ and $R_2$ are individually hydrogen or alkyl of 1 to 6 carbon atoms; B is hydrogen or alkyl of 1 to 6 carbon atoms; Ω is

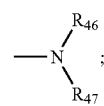

$R_{46}$ and $R_{47}$ are individually selected from the group consisting of hydrogen, alkyl of 1 to 6 carbon atoms and —(CH$_2$)$_k$—COOR$^{51}$; k and n are independently integers from 0 to 6; R$_{51}$ is hydrogen or alkyl of 1 to 8 carbon atoms or a pharmaceutically acceptable salt thereof.

2. The compound of claim 1, which is butyl 2-(4-[1,1'-biphenyl]-4-yl-1H-imidazol-2-yl)ethylcarbamate or a salt thereof.

3. The compound of claim 1 or its salt, which is selected from the group consisting of the following compounds:
  butyl 2-(4-[1,1'-biphenyl]-4-yl-1H-imidazol-2-yl)ethylcarbamate;
  4-[2-(2-{[butylamino)carbonyl]amino}ethyl)-1H-imidazol-4-yl]-1,1'-biphenyl;
  (R,S)-4-(2-{1-[(tert-butoxycarbonyl)amino]pentyl}-1H-imidazol-4-yl)-1,1'-biphenyl;
  butyl (4-[1,1'-biphenyl]-4-yl-1H-imidazol-2-yl)methylcarbamate;
  4-(2-{[(tert-butoxycarbonyl)amino]methyl}-1H-imidazol-4-yl)-1,1'-biphenyl;
  4-(2-{[(tert-butoxycarbonyl)amino]methyl}-1-methyl-1H-imidazol-4-yl)-1,1'-biphenyl;
  4-(2-{[(tert-butoxycarbonyl)(methyl)amino]methyl}-1H-imidazol-4-yl)-1,1'-biphenyl;
  4-(2-{2-[(tert-butoxycarbonyl)amino]ethyl}-1H-imidazol-4-yl)-1,1'-biphenyl;
  4-(2-{3-[(tert-butoxycarbonyl)amino]propyl}-1H-imidazol-4-yl)-1,1'-biphenyl;
  4-[2-(2-{[(tert-butylamino)carbonyl]amino}ethyl)-1H-imidazol-4-yl]-1,1'-biphenyl;
  (R,S)-4-(2-{1-[(tert-butoxycarbonyl)amino]heptyl}-1H-imidazol-4-yl)-1,1'-biphenyl;
  4-(2-{(1S)-1-[(tert-butoxycarbonyl)amino]propyl}-1H-imidazol-4-yl)-1,1'-biphenyl;
  4-[2-(2-{[(neopentyloxy)carbonyl]amino}ethyl)-1H-imidazol-4-yl]-1,1'-biphenyl;
  4-(2-{(1R)-1-[(tert-butoxycarbonyl)amino[butyl}-1H-imidazol-4-yl)-1,1'-biphenyl;
  4-(2-(1-[(butoxycarbonyl)amino]-1-methylethyl}-1H-imidazol-4-yl)-1,1'-biphenyl;
  4-(2-{2-[(isobutoxycarbonyl)amino]ethyl}-1H-imidazol-4-yl)-1,1'-biphenyl;
  4-(2-{(1S)-1-[(butoxycarbonyl)amino]ethyl}-1H-imidazol-4-yl)-1,1'-biphenyl;
  4-(2-{(1R)-1-[(butoxycarbonyl)amino]ethyl}-1H-imidazol-4-yl)-1,1'-biphenyl;
  4-(2-{2-[(methoxycarbonyl)amino]ethyl)-1H-imidazol-4-yl)-1,1'-biphenyl;
  4-(2-{2-[(propoxycarbonyl)amino]ethyl}-1H-imidazol-4-yl)-1,1'-biphenyl;
  4-(2-(2-[(ethoxycarbonyl)amino]ethyl}-1H-imidazol-4-yl)-1,1'-biphenyl;
  hexyl 2-(4-[1,1'-biphenyl]-4-yl-1H-imidazol-2-yl)ethylcarbamate;
  4-bromo-4'-(2-{2-[(butoxycarbonyl)amino]ethyl}-1H-imidazol-4-yl)-1,1'-biphenyl;
  4-[2-(2-{[(2-methoxyethoxy)carbonyl]amino}ethyl)-1H-imidazol-4-yl]-1,1'-biphenyl;
  isobutyl 2-[4-(4'-bromo-1,1'-biphenyl-4-yl)-1H-imidazol-2-yl]ethylcarbamate;
  4-methylpentyl 2-[4-(1,1'-biphenyl-4-yl)-1H-imidazol-2-yl]ethylcarbamate;
  isopentyl 2-[4-(1,1'-biphenyl-4-yl)-1H-imidazol-2-yl]ethylcarbamate;
  hexyl 2-[4-(4'-bromo-1,1'-biphenyl-4-yl)-1H-imidazol-2-yl]ethylcarbamate;
  3,3-dimethylbutyl 2-[4-(1,1'-biphenyl-4-yl)-1H-imidazol-2-yl]ethylcarbamate;
  2-phenylethyl 2-[4-(1,1'-biphenyl-4-yl)-1H-imidazol-2-yl]ethylcarbamate;
  butyl 2-[4-(4'-fluoro-1,1'-biphenyl-4-yl)-1H-imidazol-2-yl]ethylcarbamate;
  butyl 2-[4-(1,1'-biphenyl-4-yl)-5-methyl-1H-imidazol-2-yl]ethylcarbamate;
  butyl 2-[4-(4'-methyl-1,1'-biphenyl-4-yl)-1H-imidazol-2-yl]ethylcarbamate;
  butyl 2-[4-(4'-chloro-1,1'-biphenyl-4-yl)-1H-imidazol-2-yl]ethylcarbamate;
  butyl 2-[4-(2'-fluoro-1,1'-biphenyl-4-yl)-1H-imidazol-2-yl]ethylcarbamate;
  butyl 2-[4-(2',4'-difluoro-1,1-biphenyl-4-yl)-1H-imidazol-2-yl]ethylcarbamate;
  butyl 2-[4-(3'-chloro-1,1'-biphenyl-4-yl)-1H-imidazol-2-yl]ethylcarbamate;
  butyl 2-[4-(3'-fluoro-1,1'-biphenyl-4-yl)-1H-imidazol-2-yl]ethylcarbamate;
  butyl 2-[4-(3'-chloro-4'-fluoro-1,1'-biphenyl-4-yl)-1H-imidazol-2-yl]ethylcarbamate;
  butyl 2-[4-(3',4'-dichloro-1,1'-biphenyl-4-yl)-1H-imidazol-2-yl]ethylcarbamate;
  butyl 2-[4-(4'-cyano-1,1'-biphenyl-4-yl)-1H-imidazol-2-yl]ethylcarbamate;
  butyl 2-{4-[4'-(trifluoromethyl)-1,1'-biphenyl-4-yl]-1H-imidazol-2-yl}ethylcarbamate;
  butyl 2-[4-(1,1'-biphenyl-4-yl)-5-ethyl-1H-imidazol-2-yl]ethylcarbamate;
  butyl 2-[4-(2'-chloro-1,1'-biphenyl-4-yl)-1H-imidazol-2-yl]ethylcarbamate;
  butyl 2-[4-(2',3'-difluoro-1,1'-biphenyl-4-yl)-1H-imidazol-2-yl]ethylcarbamate;
  butyl 2-[4-(2'-bromo-1,1'-biphenyl-4-yl)-1H-imidazol-2-yl]ethylcarbamate;
  butyl 2-[4-(3',5'-difluoro-1,1'-biphenyl-4-yl)-1H-imidazol-2-yl]ethylcarbamate;
  butyl 2-[4-(2'-methoxy-1,1'-biphenyl-4-yl)-1H-imidazol-2-yl]ethylcarbamate;
  butyl 2-[4-(3'-nitro-1,1'-biphenyl-4-yl)-1H-imidazol-2-yl]ethylcarbamate;
  butyl 2-[4-(2',5'-difluoro-1,1'-biphenyl-4-yl)-1H-imidazol-2-yl]ethylcarbamate and
  butyl 2-[4-(3'-methoxy-1,1'-biphenyl-4-yl)-1H-imidazol-2-yl]ethylcarbamate; and the salts thereof.

4. A pharmaceutical composition containing, as active principle, a compound of formula (I)$_{G2}$ as defined in claim 1, or a pharmaceutically acceptable salt of such a compound, and at least one pharmaceutically acceptable excipient.

5. The pharmaceutically composition of claim 4 wherein the active principle is selected from the group consisting of the following compounds:
  butyl 2-(4-[1,1'-biphenyl]-4-yl-1H-imidazol-2-yl)ethylcarbamate;
  4-[2-(2-{[butylamino)carbonyl]amino}ethyl)-1H-imidazol-4-yl]-1,1'-biphenyl;
  (R,S)-4-(2-{1-(tert-butoxycarbonyl)amino]pentyl}-1H-imidazol-4-yl)-1,1'-biphenyl;
  butyl (4-[1,1'-biphenyl]-4-yl-1H-imidazol-2-yl)methylcarbamate;
  4-(2-{[(tert-butoxycarbonyl)amino]methyl}-1H-imidazol-4-yl)-1,1'-biphenyl;
  4-(2-{[(tert-butoxycarbonyl)amino]methyl}-1-methyl-1H-imidazol-4-yl)-1,1'-biphenyl;
  4-(2-{[(tert-butoxycarbonyl)(methyl)amino]methyl}-1H-imidazol-4-yl)-1,1'-biphenyl;
  4-(2-{2-[(tert-butoxycarbonyl)amino]ethyl}-1H-imidazol-4-yl)-1,1'-biphenyl;

4-(2-{3-[(tert-butoxycarbonyl)amino]propyl}-1H-imidazol-4-yl)-1,1'-biphenyl;
4-[2-(2-{[(tert-butylamino)carbonyl]amino}ethyl)-1H-imidazol-4-yl]-1,1'-biphenyl;
(R,S)-4-(2-(1-[(tert-butoxycarbonyl)amino]heptyl}-1H-imidazol-4-yl)-1,1'-biphenyl;
4-(2-{(1S)-1-[(tert-butoxycarbonyl)amino]propyl}-1H-imidazol-4-yl)-1,1'-biphenyl;
4-[2-(2-{[(neopentyloxy)carbonyl]amino}ethyl)-1H-imidazol-4-yl]-1,1'-biphenyl;
4-(2-{(1R)-1-[(tert-butoxycarbonyl)amino]butyl}-1H-imidazol-4-yl)-1,1'-biphenyl;
4-(2-{1-[(butoxycarbonyl)amino]-1-methylethyl}-1H-imidazol-4-yl)-1,1'-biphenyl;
4-(2-{2-[(isobutoxycarbonyl)amino]ethyl}-1H-imidazol-4-yl)-1,1'-biphenyl;
4-(2-{(1S)-1-[(butoxycarbonyl)amino]ethyl}-1H-imidazol-4-yl)-1,1'-biphenyl;
4-(2-{(1R)-1-[(butoxycarbonyl)amino]ethyl}-1H-imidazol-4-yl)-1,1'-biphenyl;
4-(2-{2-[(methoxycarbonyl)amino]ethyl}-1H-imidazol-4-yl)-1,1'-biphenyl;
4-(2-{2-[(propoxycarbonyl)amino]ethyl}-1H-imidazol-4-yl)-1,1'-biphenyl;
4-(2-{2-[(ethoxycarbonyl)amino]ethyl}-1H-imidazol-4-yl)-1,1'-biphenyl;
hexyl 2-(4-[1,1'-biphenyl]-4-yl-1H-imidazol-2-yl)ethylcarbamate;
4-bromo-4'-(2-{2-[(butoxycarbonyl)amino]ethyl}-1H-imidazol-4-yl)-1,1'-biphenyl;
4-[2-(2-{[(2-methoxyethoxy)carbonyl]amino}ethyl)-1H-imidazol-4-yl]-1,1'-biphenyl;
isobutyl 2-[4-(4'-bromo-1,1'-biphenyl-4-yl)-1H-imidazol-2-yl]ethylcarbamate;
4-methylpentyl 2-[4-(1,1'-biphenyl-4-yl)-1H-imidazol-2-yl]ethylcarbamate;
isopentyl 2-[4-(1,1'-biphenyl-4-yl)-1H-imidazol-2-yl]ethylcarbamate;
hexyl 2-[4-(4'-bromo-1,1'-biphenyl-4-yl)-1H-imidazol-2-yl]ethylcarbamate;
3,3-dimethylbutyl 2-[4-(1,1'-biphenyl-4-yl)-1H-imidazol-2-yl]ethylcarbamate;
2-phenylethyl 2-[4-(1,1'-biphenyl-4-yl)-1H-imidazol-2-yl]ethylcarbamate;
butyl 2-[4-(4'-fluoro-1,1'-biphenyl-4-yl)-1H-imidazol-2-yl]ethylcarbamate;
butyl 2-[4-(1,1'-biphenyl-4-yl)-5-methyl-1H-imidazol-2-yl]ethylcarbamate;
butyl 2-[4-(4'-methyl-1,1'-biphenyl-4-yl)-1H-imidazol-2-yl]ethylcarbamate;
butyl 2-[4-(4'-chloro-1,1'-biphenyl-4-yl)-1H-imidazol-2-yl]ethylcarbamate;
butyl 2-[4-(2'-fluoro-1,1'-biphenyl-4-yl)-1H-imidazol-2-yl]ethylcarbamate;
butyl 2-[4-(2',4'-difluoro-1,1'-biphenyl-4-yl)-1H-imidazol-2-yl]ethylcarbamate;
butyl 2-[4-(3'-chloro-1,1'-biphenyl-4-yl)-1H-imidazol-2-yl]ethylcarbamate;
butyl 2-[4-(3'-fluoro-1,1'-biphenyl-4-yl)-1H-imidazol-2-yl]ethylcarbamate;
butyl 2-[4-(3'-chloro-4'-fluoro-1,1'-biphenyl-4-yl)-1H-imidazol-2-yl]ethylcarbamate;
butyl 2-[4-(4'-cyano-1,1'-biphenyl-4yl)-1H-imidazol-2-yl]ethylcarbamate;
butyl 2-{4-[4'-(trifluoromethyl)-1,1'-biphenyl-4-yl]-1H-imidazol-2-yl}ethylcarbamate;
butyl 2-[4-(1,1'-biphenyl-4-yl)-5-ethyl-1H-imidazol-2-yl]ethylcarbamate;
butyl 2-[4-(2'-chloro-1,1'-biphenyl-4-yl)-1H-imidazol-2-yl]ethylcarbamate;
butyl 2-[4-(2',3'-difluoro-1,1'-biphenyl-4-yl)-1H-imidazol-2-yl]ethylcarbamate;
butyl 2-[4-(2'-bromo-1,1'-biphenyl-4-yl)-1H-imidazol-2-yl]ethylcarbamate;
butyl 2-[4-(3',5'-difluoro-1,1'-biphenyl-4-yl)-1H-imidazol-2-yl]ethylcarbamate;
butyl 2-[4-(2'-methoxy-1,1'-biphenyl-4-yl)-1H-imidazol-2-yl]ethylcarbamate;
butyl 2-[4-(3'-nitro-1,1'-biphenyl-4-yl)-1H-imidazol-2-yl]ethylcarbamate;
butyl 2-[4-(2',5'-difluoro-1,1'-biphenyl-4-yl)-1H-imidazol-2-yl]ethylcarbamate and
butyl 2-[4-(3'-methoxy-1,1'-biphenyl-4-yl)-1H-imidazol-2-yl]ethylcarbamate; and the salts thereof.

6. The pharmaceutical composition of claim 4 wherein the active principle is butyl 2-(4-[1,1'-biphenyl]-4-yl-1H-imidazol-2-yl)ethylcarbamate or one of its pharmaceutically acceptable salts.

* * * * *